US007919312B2

(12) United States Patent
Kukolj et al.

(10) Patent No.: US 7,919,312 B2
(45) Date of Patent: *Apr. 5, 2011

(54) SELF-REPLICATING RNA MOLECULE FROM HEPATITIS C VIRUS

(75) Inventors: George Kukolj, Laval (CA); Arnim Pause, Laval (CA)

(73) Assignee: Boehringer Ingelheim (Canada) Ltd., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/390,632

(22) Filed: Mar. 28, 2006

(65) Prior Publication Data

US 2006/0246424 A1 Nov. 2, 2006

Related U.S. Application Data

(63) Continuation of application No. 10/686,835, filed on Oct. 16, 2003, now abandoned, which is a continuation of application No. 10/029,907, filed on Dec. 21, 2001, now Pat. No. 6,706,874.

(60) Provisional application No. 60/257,857, filed on Dec. 22, 2000.

(51) Int. Cl.
*C12N 15/85* (2006.01)
*C12N 15/63* (2006.01)

(52) U.S. Cl. ....... 435/325; 435/320.1; 435/5; 424/228.1

(58) Field of Classification Search ................ 424/228.1
See application file for complete search history.

(56) References Cited

U.S. PATENT DOCUMENTS

| | | | |
|---|---|---|---|
| 6,630,343 B1 | 10/2003 | Bartenschlager | |
| 6,689,559 B2 | 2/2004 | Wimmer et al. | |
| 6,706,874 B2 * | 3/2004 | Kukolj et al. | 536/23.72 |
| 6,956,117 B2 * | 10/2005 | Kukolj et al. | 536/23.72 |
| 7,344,723 B2 * | 3/2008 | Kukolj et al. | 424/228.1 |
| 2002/0142350 A1 | 10/2002 | Kukolj et al. | |
| 2003/0148348 A1 | 8/2003 | Kukolj et al. | |

FOREIGN PATENT DOCUMENTS

| | | |
|---|---|---|
| CA | 2303526 | 3/2000 |
| EP | 1043399 | 3/2000 |
| WO | 9804008 | 1/1998 |
| WO | 9839031 | 9/1998 |
| WO | 0066623 | 11/2000 |
| WO | 0189364 | 11/2001 |

OTHER PUBLICATIONS

Fournier, Sureau, et al; In vitro infection of adult normal human hepatocytes in primary culture by hepatitis C virus; Journal of General Virology (1998); V. 79; pp. 2367-2374.
Grakoui, Wychowski, et al; Expression and identification of Hepatitis C Virus Polyprotein Cleavage Products; Journal of Virology (Mar. 993); V. 67, No. 3; pp. 1385-1395.
Hijikata, Mizushima, et al; Two Distinct Proteinase Activities Required for the Processing of a Putative Nonstructural Precursor Protein of Hepatitis C. Virus; Journal of Virology (Aug. 1993); V. 67, No. 8; pp. 4665-4675.
Bartenschlager, Ahlborn-Laake, et al; Nonstructural Protein 3 of the Hepatitis C. Virus Encodes a Serine-Type Proteinase Required for Cleavage at the NS3/4 and NS4/5 Junctions; Journal of Virology (Jul. 1993) V. 67, No. 7; pp. 3835-3844.
Reed, Xu, et al; Phosphorylation of the Hepatitis C. Virus NS5A Protein in Vitro and in Vivo: Properties of the NS5A-Associated Kinase; Journal of Virology (Oct. 1997); V. 71, No. 10; pp. 7187-7197.
Khromykh, Westaway; Subgenomic Replicons of the Flavivirus Kunjin: Construction and Applications; Journal of Virology (Feb. 1997); V. 71, No. 2; pp. 1497-1505.
Behrens, Grassmann, et al; Characterization of an Autonomous Subgenomic Pestivirus RNA Replicon; Journal of Virology (Mar. 1998); V. 72, No. 3; pp. 2364-2372.
Mizutani, Kato, et al; Characterization of Hepatitis C. Virus Replication in Cloned Cells Obtained from a Human T-Cell Leukemia Virus Type 1-Infected Cell Line, MT-2; Journal of Virology (Oct. 1996); V. 70, No. 10; pp. 7219-7223.
Moser, Tratschin, et al; A Recombinant Classical Swine Fever Virus Stably Expresses a Marker Gene; Journal of Virology (Jun. 1998); V. 72, No. 6; pp. 5318-5322.
Ikeda, Sugiyama, et al; Human hepatocyte clonal cell lines that support persistent replication of hepatitis C virus; Virus Research; 1998, V. 56; pp. 157-167; Elsevier.
Dash, Halim, et al; Transfection of HepG2 Cells with Infectious Hepatitis C. Virus Genome; American Journal of Pathology; 1997, V. 151; 363-373.
Gou, Ju-Tao, et al; Effect of Alpha Interferon on the Hepatitis C Virus Replicon; Journal of Virology (Sep. 2001); vol. 75, No. 18; pp. 8516-8523.
Hijikata, Makoto, et al; Gene Mapping of the Putative Structural Region of the Hepatitis C. Virus Genome by In Vitro Processing Analysis; Proc. Nat'l. Acad. Sci.; 1991; vol. 88; pp. 5547-5551.
Kim, Don Wook, et al; C-Terminal Domain of the Hepatitis C. Virus NS3 Protein Contains an RNA Helicase Activity; Biochemical and Biophysical Research Communications, Oct. 4, 1995, V. 215(1):160-166.

(Continued)

*Primary Examiner* — Bao Li
(74) *Attorney, Agent, or Firm* — Michael P. Morris; Mary-Ellen M. Devlin; Timothy X. Witkowski

(57) ABSTRACT

A unique HCV RNA molecule is provided having an enhanced efficiency of establishing cell culture replication. Novel adaptive mutations have been identified within the HCV non-structural region that improves the efficiency of establishing persistently replicating HCV RNA in cell culture. This self-replicating polynucleotide molecule contains, contrary to all previous reports, a 5'-NTR that can be either an A as an alternative to the G already disclosed and therefore provides an alternative to existing systems comprising a self-replicating HCV RNA molecule. The G→A mutation gives rise to HCV RNA molecules that, in conjunction with mutations in the HCV non-structural region, such as the G(2042) C/R mutations, possess greater efficiency of transduction and/or replication. These RNA molecules when transfected in a cell line are useful for evaluating potential inhibitors of HCV replication.

11 Claims, 9 Drawing Sheets

OTHER PUBLICATIONS

Figure 1:
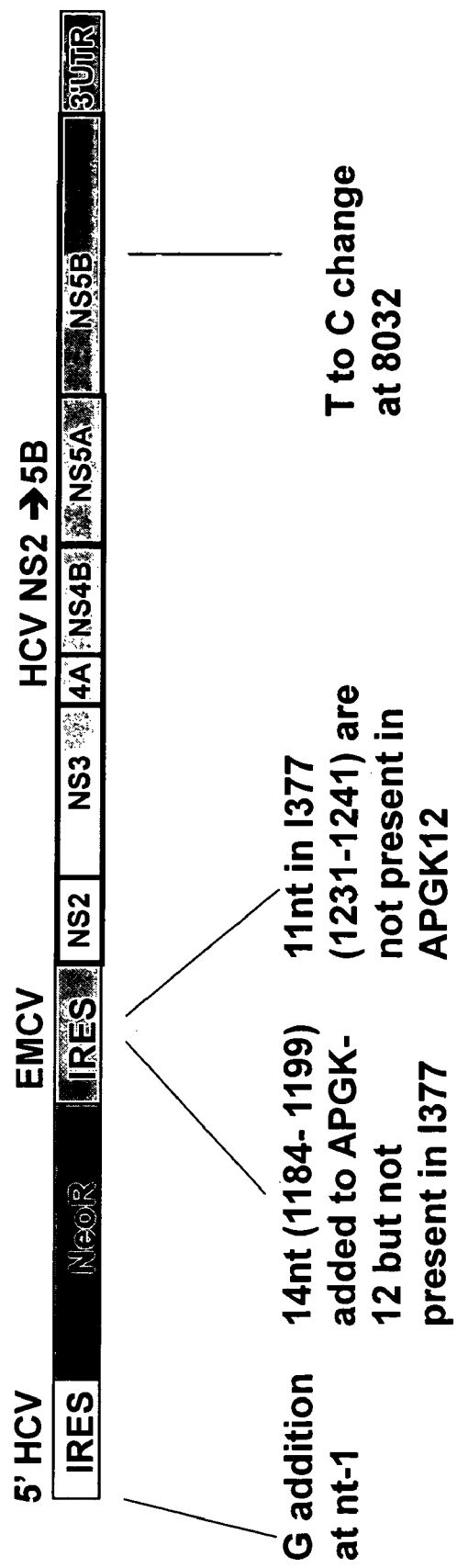

Kim, J-E, et al; Subcellular Localization of Hepatitis C Viral Proteins in Mammalian Cells; Archives of Virology (1999), 144; pp. 329-343.

Kim, J.L., et al; Crystal Structure of the Hepatitis C. Virus NS3 Protease Domain Complexed with a Synthetic NS4A Cofactor Peptide; Cell (Oct. 18, 1996) vol. 87; pp. 343-355.

Krieger, Nicole, et al; Enhancement of Hepatitis C Virus RNA Replication by Cell Culture-Adaptive Mutations; Journal of Virology (May 2001); V. 75, No. 10; pp. 4614-4624.

Kim, Morgenstern, et al; Hepatitis C virus NS3 RNA helicase domain with a bound oligonucleotide: the crystal structure provides insights into the mode of unwinding; Structure (1998), V. 6; pp. 89-100.

Yan, Li, et al; Complex of NS3 protease and NS4A peptide of BK strain hepatitis C virus; A 2.2 A resolution structure in a hexagonal crystal form; Protein Science (1998); V. 7; pp. 837-847.

Yao, Hesson, et al; Structure of the hepatitis C virus RNA helicase domain; Nature Structural Biology; 1997, V. 4, No. 6; pp. 463-467.

Ito, Mukaigawa, et al; Cultivation of hepatitis C virus in primary hepatocyte culture from patients with chronic hepatitis C results in release of high tire infectious virus; Journal of General Virology (1996); V. 77; pp. 1043-1054.

Yoo, Selby, et al; Transfection of a Differentiated Human Hepatoma Cell Line (Huh7) with In Vitro-Transcribed Hepatitis C Virus (HCV) RNA and Establishment of a Long-Term Culture Persistently Infected with HCV; Journal of Virology (Jan. 1995); V. 69, No. 1; pp. 32-38.

Ago, Adachi, et al; Crystal structure of the RNA-dependent RNA polymerase of hepatitis C virus; Structure; 1999, V. 7; pp. 1417-1426.

Blight, Kolykhalov, et al; Efficient Initiation of HCV RNA Replication in Call Culture; Science; 2000, V. 290; pp. 1972-1974.

Bressanelli, Tomei, et al; Crystal structure of the RNA-dependent RNA polymerase of hepatitis C virus; PNAS; 1999, V. 96, No. 23; pp. 13034-13039.

Cho, Ha, et al; Crystal Structure of RNA Helicase from Genotype 1b Hepatitis C Virus; The Journal of Biological Chemistry (1998); V. 273, No. 24; pp. 15045-15052.

Gale Jr., Korth, et al; Evidence that Hepatitis C Virus Resistance to Interferon is Mediated through Repression of the PKR Protein Kinase by the Nonstractural 5A Protein; Virology; 1997, V. 230; pp. 217-227.

Grakoui, McCourt, et al; A second hepatitis C virus-encoded proteinase, Proc. Natl. Acad. Sci. USA; 1993, V. 90; pp. 10583-10587.

Kwong, Kim, et al; Hepatitis C virus NS3/4A protease; Antiviral Research (1998); V. 40; pp. 1-18; Elsevier.

Landford, Sureau, et al; Demonstration of in Vitro Infection of Chimpanzee Hepatocytes with hepatitis C Virus Using Strand-Specific RT/PCR; Virology; 1994, V. 202; pp. 606-614.

Lesburg, Cable, et al; Crystal structure of the RNA-dependent RNA polymerase from hepatitis C virus reveals a fully encircled active site; Nature Structural Biology (1999); V. 6, No. 10; pp. 937-943.

Lohmann, Korner, et al; Replication of Subgenomic Hepatitis C Virus RNAs in a Hepatoma Cell Line; Science (1999); V. 285; pp. 110-113.

Lohmann, Korner, et al; Mutations in Hepatitis C Virus RNAs Conferring Cell Culture Adaptation; Journal of Virology (2001); V. 75, No. 3; pp. 1437-1449.

Love, Parge, et al; The Crystal Structure of Hepatitis C Virus NS3 Proteinase Reveals a Trypsin-like Fold and a Structural Zinc Binding Site; Cell (1996); V. 87, pp. 331-342.

Shimizu, Purcell, et al; Correlation between the infectivity of hepatitis C virus in vivo and its infectivity in vitro; Proc. Natl. Acad. Sci. USA (1993) V. 90, pp. 6037-6041.

Yanagi, St. Claire, et al; In vivo analysis of the 3' untranslated region of the hepatitis C virus after in vitro mutagenesis of an infectious cDNA clone; Proc. Nat'l. Acad. Sci. USA (1999) V. 96, pp. 2291-2295.

Bartenschlager, Lohmann; Replication of hepatitis C virus; Journal of General Virology (2000), V. 81, pp. 1631-1648.

International Search Report Issued Mar. 3, 2003 for PCT/CA 01/01843 the counterpart of U.S. Appl. No. 10/029,907.

Bartenschlager, Lohmann; Novel cell culture systems for hepatitis C virus; Antiviral Research (2001); V. 52; pp. 1-17; Elsevier.

Friebe, Lohmann, et al; Sequence in the 5' nontranslated region of hepatitis C Virus required for RNA replication; Journal of Virology, (Dec. 2001) V. 75, No. 24, pp. 12047-12057.

Ali, Pellerin, et al; Hepatitis C Virus subgenomic replicons in the human embryonic kidney 293 cell line; Journal of Virology (Jan. 2004) V. 78, No. 1, pp. 491-501.

* cited by examiner

C. Anti-HCV NS5B

B. Anti-HCV NS3

A. Anti-Neomycin Phosphotransferase

FIGURE 5A

| | S 22-3 SEQ ID NO 2 | R3 SEQ ID NO. 4 | R3-rep SEQ ID NO. 7 | R7 SEQ ID NO. 5 | R16 SEQ ID NO 6 |
|---|---|---|---|---|---|
| 5'end - FIRST nt (HCV IRES) | *G (nt 1) A | G (nt 1) A | - | - | G (nt 1) A |
| Neo | | A (nt 461) G | | | |
| EMCV IRES | | | | | |
| NS 2 | | A (nt 1739) G | | | |
| NS 3 | | G (nt 2778) A<br>A (nt 2840) C<br>A (nt 4052) G | T (nt 2509) C<br>G (nt 2778) A<br>A (nt 2840) C<br>T (nt 3574) C<br>A (nt 4052) G | A (nt 2935) G<br>A (nt 2979) G | A (nt 2816) G<br>A (nt 2979) G |
| NS 4A | A (nt 4446) R | A (nt 4446) G | C (nt 4387) T<br>A (nt 4446) G<br>C (nt 4507) T | | C (nt 4476) T |
| NS 4B | | T (nt 4855) C | T (nt 4855) C | | |
| NS 5A | G (nt 5498) T<br>A (nt 6268) R | A (nt 5351) G<br>G (nt 5498) T<br>G (nt 5659) A<br>C (nt 5871) T<br>A (nt 6268) G | A (nt 5351) G<br>G (nt 5498) T<br>G (nt 5659) A<br>T (nt 5838) C<br>C (nt 5871) T<br>A (nt 6115) G | A (nt 5324) G<br>G (nt 5498) T<br>T (nt 6001) C | G (nt 5498) C<br>T (nt 6320) C<br>T (nt 6584) C |
| NS 5B | | A (nt 6652) G | | C (nt 7252) T<br>T (nt 8349) C | |
| 3'end - last 98 nt | | | | | |

*first nt = G from HCV ires

FIGURE 5B

| | S 22-3 SEQ ID NO. 2 | R3 SEQ ID NO. 4 | R3 Rep SEQ ID NO. 7 | R7 SEQ ID NO. 5 | R16 SEQ ID NO. 6 |
|---|---|---|---|---|---|
| 5'end - FIRST nt (HCV IRES) | G (nt 1) A | G (nt 1) A | - | - | G (nt 1) A |
| NS 2 | - | - | - | - | - |
| NS 3 | - | R (1135) K<br>S (1560) G | R (1135) K<br>S (1560) G | E (1202) G | S (1148) G<br>E (1202) G |
| NS 4A | K (1691) mix K/R | K (1691) R | K (1691) R | - | L (1701) F |
| NS 4B | - | - | - | - | - |
| NS 5A | G (2042) C | T (1993) A<br>G (2042) C<br>P (2166) L | T (1993) A<br>G (2042) C<br>L (2155) P<br>P (2166) L | I (1984) V<br>G (2042) C | G (2042) R<br>S (2404) P |
| NS 5B | | | | M (2992) T | |
| 3'end - last 98 nt | | | | | | first a.a. of NS2 = 810

FIGURE 6

AMINO ACID SUBSTITUTIONS

| CLONE APGK-12 | 5' HCV IRES | NeoR | EMCV IRES | HCV NS2→5B ||||||| 3'HCV UTR |
|---|---|---|---|---|---|---|---|---|---|---|---|
| | | | | NS2 | NS3 | 4A | NS4B | NS5A | NS5B | | |
| G (nt1) SEQ ID NO 1 | | | | | | | | | | | |
| A (nt1) SEQ ID NO 24 | | | | - | - | - | - | - | - | | |
| R3 rep A(nt1) SEQ ID NO 25 | | | | | R(1135)K S(1560)G | K(1691)R | - | T(1993)A G(2042)C L(2155)P P(2166)L | | | |
| G (nt1) SEQ ID NO 7 | | | | | R(1135)K S(1560)G | K(1691)R | - | T(1993)A G(2042)C L(2155)P P(2166)L | | | |

77 cfu/μg
86 cfu/μg
1100000 cfu/μg
2000000 cfu/μg

HCV-Replicon: RNA Quantification

Ct = Threshold cycle $\alpha$ Starting RNA Quantity

SELF-REPLICATING RNA MOLECULE FROM HEPATITIS C VIRUS

RELATED APPLICATIONS

This application is a continuation of U.S. application Ser. No. 10/686,835, filed Oct. 16, 2003, which is a continuation of U.S. application Ser. No. 10/029,907, filed Dec. 21, 2001, which claims, as does the present application priority to U.S. Provisional Application Ser. No. 60/257,857 filed on Dec. 22, 2000, the disclosures of all of which are incorporated by reference in their entireties.

FIELD OF THE INVENTION

The present invention relates generally to a HCV RNA molecule that self-replicates in appropriate cell lines, particularly to a self-replicating HCV RNA construct having an enhanced efficiency of establishing cell culture replication.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so called chronic hepatitis C. This group is in turn at high risk for serious liver disease such as liver cirrhosis, hepatocellular carcinoma and terminal liver disease leading to death. The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established.

Various clinical studies have been conducted with the goal of identifying pharmaceutical compounds capable of effectively treating HCV infection in patients afflicted with chronic hepatitis C. These studies have involved the use of interferon-alpha, alone and in combination with other antiviral agents such as ribavirin. Such studies have shown that a substantial number of the participants do not respond to these therapies, and of those that do respond favorably, a large proportion were found to relapse after termination of treatment. To date there are no broadly effective antiviral compounds for treatment of HCV infection.

HCV is an enveloped positive strand RNA virus in the Flaviviridae family. The single strand HCV RNA genome is of positive polarity and comprises one open reading frame (ORF) of approximately 9600 nucleotides in length, which encodes a linear polyprotein of approx. 3010 amino acids. In infected cells, this polyprotein is cleaved at multiple sites by cellular and viral proteases to produce structural and non-structural (NS) proteins. The structural proteins (C, E1, E2 and E2-p7) comprise polypeptides that constitute the virus particle (Hijikata, M. et al., 1991, Proc. Natl. Acad. Sci. USA. 88, 5547-5551; Grakoui et al., 1993(a), J. Virol. 67, 1385-1395). The non-structural proteins (NS2, NS3, NS4A, NS4B, NS5A, NS5B) encode for enzymes or accessory factors that catalyze and regulate the replication of the HCV RNA genome. Processing of the structural proteins is catalyzed by host cell proteases (Hijikata, M. et al., 1991, Proc. Natl. Acad. Sci. USA. 88, 5547-5551). The generation of the mature non-structural proteins is catalyzed by two virally encoded proteases. The first is the NS2/3 zinc-dependent metalloprotease which auto-catalyses the release of the NS3 protein from the polyprotein. The released NS3 contains a N-terminal serine protease domain (Grakoui et al., 1993(b), Proc Natl Acad Sci USA, 90, 10583-7; Hijikata, M. et al., 1993, J. Virol. 67, 4665-4675) and catalyzes the remaining cleavages from the polyprotein. The released NS4A protein has at least two roles. First, forming a stable complex with NS3 protein and assisting in the membrane localization of the NS3/NS4A complex (Kim et al., Arch Virol. 1999, 144, 329-343) and second, acting as a cofactor for NS3 protease activity. This membrane-associated complex, in turn catalyzes the cleavage of the remaining sites on the polyprotein, thus effecting the release of NS4B, NS5A and NS5B (Bartenschlager, R. et al., 1993, J. Virol., 67, 3835-3844; Grakoui et al., 1993(a), J. Virol. 67, 1385-1395; Hijikata, M. et al., 1993, J. Virol. 67, 4665-4675; Love, R. A. et al., 1996, Cell, 87, 331-342; reviewed in Kwong et al., 1998 Antiviral Res., 40, 1-18). The C-terminal segment of the NS3 protein also harbors nucleoside triphosphatase and RNA helicase activity (Kim et al., 1995, Biochem. Biophys. Res. Comm., 215, 160-166.). The function of the protein NS4B is unknown. NS5A, a highly phosphorylated protein, seems to be responsible for the Interferon resistance of various HCV genotypes (Gale Jr. et al. 1997 Virology 230, 217; Reed et al., 1997 J. Virol. 71, 7187. NS5B is an RNA-dependent RNA polymerase (RdRp) that is involved in the replication of HCV.

The open reading frame of the HCV RNA genome is flanked on its 5' end by a non-translated region (NTR) of approx. 340 nucleotides that functions as the internal ribosome entry site (IRES), and on its 3' end by a NTR of approximately 230 nucleotides. Both the 5' and 3' NTRs are important for RNA genome replication. The genomic sequence variance is not evenly distributed over the genome and the 5'NTR and parts of the 3'NTR are the most highly conserved portions. The authentic, highly conserved 3'NTR is the object of U.S. Pat. No. 5,874,565 granted to Rice et al.

The cloned and characterized partial and complete sequences of the HCV genome have also been analyzed with regard to appropriate targets for a prospective antiviral therapy. Four viral enzyme activities provide possible targets such as (1) the NS2/3 protease; (2) the NS3/4A protease complex, (3) the NS3 Helicase and (4) the NS5B RNA-dependent RNA polymerase. The NS3/4A protease complex and the NS3 helicase have already been crystallized and their three-dimensional structure determined (Kim et al., 1996, Cell, 87, 343; Yem et al. Protein Science, 7, 837, 1998; Love, R. A. et al., 1996, Cell, 87, 331-342; Kim et al., 1998, Structure, 6, 89; Yao et al., 1997 Nature Structural Biology, 4, 463; Cho et al., 1998, J. Biol. Chem., 273, 15045). The NS5B RNA dependent RNA polymerase has also been crystallized to reveal a structure reminiscent of other nucleic acid polymerases (Bressanelli et al. 1999, Proc. Natl. Acad. Sci, USA 96, 13034-13039; Ago et al. 1999, Structure 7, 1417-1426; Lesburg et al. 1999, Nat. Struct. Biol. 6, 937-943).

Even though important targets for the development of a therapy for chronic HCV infection have been defined with these enzymes and even though a worldwide intensive search for suitable inhibitors is ongoing with the aid of rational drug design and HTS, the development of therapy has one major deficiency, namely the lack of cell culture systems or simple animal models, which allow direct and reliable propagation of HCV viruses. The lack of an efficient cell culture system is still the main reason to date that an understanding of HCV replication remains elusive.

Although flavi- and pestivirus self-replicating RNAs have been described and used for the replication in different cell lines with a relatively high yield, similar experiments with HCV have not been successful to date (Khromykh et al., 1997, J. Virol. 71, 1497; Behrens et al., 1998, J. Virol. 72, 2364; Moser et al., 1998 J. Virol. 72, 5318). It is known from different publications that cell lines or primary cell cultures can be infected with high-titer patient serum containing HCV (Lanford et al. 1994 Virology 202, 606; Shimizu et al. 1993 PNAS, USA 90, 6037-6041; Mizutani et al. 1996 J. Virol. 70, 7219-7223; Ikda, et al. 1998, Virus Res. 56, 157; Fourner et al. 1998, J. Gen. Virol. 79, 2376; Ito et al. 1996, J. Gen. Virol. 77, 1043-1054). However, these virus-infected cell lines or cell cultures do not allow the direct detection of HCV-RNA or HCV antigens.

It is also known from the publications of Yoo et al. 1995 J. Virol., 69, 32-38; and of Dash et al., 1997, Am. J. Pathol., 151, 363-373; that hepatoma cell lines can be transfected with synthetic HCV-RNA obtained through in vitro transcription of the cloned HCV genome. In both publications the authors started from the basic idea that the viral HCV genome is a plus-strand RNA functioning directly as mRNA after being transfected into the cell, permitting the synthesis of viral proteins in the course of the translation process, and so new HCV particles could form HCV viruses and their RNA detected through RT-PCR. However the published results of the RT-PCR experiments indicate that the HCV replication in the described HCV transfected hepatoma cells is not particularly efficient and not sufficient to measure the quality of replication, let alone measure the modulations in replication after exposure to potential antiviral drugs. Furthermore it is now known that the highly conserved 3' NTR is essential for the virus replication (Yanagi et al., 1999 Proc. Natl. Acad. Sci. USA, 96, 2291-95). This knowledge strictly contradicts the statements of Yoo et al. J. Virol., 69, 32-38(supra) and Dash et al., 1997, Am. J. Pathol., 151, 363-373. (supra), who used for their experiments only HCV genomes with shorter 3' NTRs and not the authentic 3' end of the HCV genome.

In WO 98/39031, Rice et al. disclosed authentic HCV genome RNA sequences, in particular containing: a) the highly conserved 5'-terminal sequence "GCCAGCC" (SEQ ID NO. 26); b) the HCV polyprotein coding region; and c) 3'-NTR authentic sequences.

In WO 99/04008, Purcell et al. disclosed an HCV infectious clone that also contained only the highly conserved 5'-terminal sequence "GCCAGC" (SEQ ID NO. 27).

Recently Lohman et al. 1999 (Science 285, 110-113) and Bartenschlager, R. et al., 1993, J. Virol., 67, 3835-3844(in CA 2,303,526, laid-open on Oct. 3, 2000) disclosed a HCV cell culture system where the viral RNA (I377/NS2-3') self-replicates in the transfected cells with such efficiency that the quality of replication can be measured with accuracy and reproducibility. The Lohman and Bartenschlager, R. et al., 1993, J. Virol., 67, 3835-3844 disclosures were the first demonstration of HCV RNA replication in cell culture that was substantiated through direct measurement by Northern blots. This replicon system and sequences disclosed therein highlight once again the conserved 5' sequence "GCCAGC" (SEQ ID NO. 27). A similar observation highlighting the conservation of the 5'NTR was made by Blight et al. 2000 (Science 290, 1972-1974) and WO 01/89364 published on Nov. 29, 2001.

In addition to the conservation of the 5' and 3' untranslated regions in cell culture replicating RNAs, three other publications by Lohman et al. 2001, J. Virol. 1437-1449 Krieger et al. 2001 J. Virol. 4614-4624 and Guo et al., (2001) J. Virol. 8516-8523 have recently disclosed distinct adaptive mutants within the HCV non-structural protein coding region. Specific nucleotide changes that alter the amino acids of the HCV non-structural proteins are shown to enhance the efficiency of establishing stable replicating HCV subgenomic replicons in culture cells.

Applicant has now found that, contrary to all previous reports, the highly conserved 5'-NTR can be mutated by adaptation to give rise to a HCV RNA sequence that, in conjunction with mutations in the HCV non-structural region, provides for a greater efficiency of transduction and/or replication.

Applicant has also identified novel adaptive mutations within the HCV non-structural region that improves the efficiency of establishing persistently replicating HCV RNA in cell culture.

One advantage of the present invention is to provide an alternative to these existing systems comprising a HCV RNA molecule that self-replicates. Moreover, the present invention demonstrates that the initiating nucleotide of the plus-strand genome can be either an A as an alternative to the G already disclosed.

A further advantage of the present invention is to provide a unique HCV RNA molecule that transduces and/or replicates with higher efficiency. The Applicant demonstrates the utility of this specific RNA molecule in a cell line and its use in evaluating a specific inhibitor of HCV replication.

SUMMARY OF THE INVENTION

In a first embodiment, the present invention provides a 5'-non translated region of the hepatitis C virus wherein its highly conserved guanine at position 1 is substituted for adenine.

Particularly, the present invention provides a hepatitis C virus polynucleotide comprising adenine at position 1 as numbered according to the I377/NS2-3' construct (Lohmann et al. 1999, Science 285, 110-113, Accession # AJ242651).

Particularly, the invention provides a HCV self-replicating polynucleotide comprising a 5'-terminus consisting of ACCAGC (SEQ ID NO. 8).

In a second embodiment, the present invention is directed to a HCV self-replicating polynucleotide encoding a polyprotein comprising one or more amino acid substitution selected from the group consisting of: R(1135)K; S(1148)G; S(1560)G; K(1691)R; L(1701)F; I(1984)V; T(1993)A; G(2042)C; G(2042)R; S(2404)P; L(2155)P; P(2166)L and M(2992)T.

Particularly, the invention is directed to a HCV self-replicating polynucleotide encoding a polyprotein comprising the any one of the amino acid substitutions as described above, further comprising the amino acid substitution E(1202)G.

More particularly, the invention provides a HCV self-replicating polynucleotide encoding a polyprotein comprising a G2042C or a G2042R mutation.

Most particularly, the invention provides for HCV self-replicating polynucleotide comprising a nucleotide substitution G→A at position 1, and said polynucleotide encodes a polyprotein further comprising a G2042C or a G2042R mutation.

Particularly, the polynucleotide of the present invention can be in the form of RNA or DNA that can be transcribed to RNA.

In a third embodiment, the invention also provides for an expression vector comprising a DNA form of the above polynucleotide, operably linked with a promoter.

According to a fourth embodiment, there is provided a host cell transfected with the self-replicating polynucleotide or the vector as described above.

In a fifth embodiment, the present invention provides a RNA replication assay comprising the steps of:
incubating the host cell as described above in the absence or presence of a potential hepatitis C virus inhibitor;
isolating the total cellular RNA from the cells;
analyzing the RNA so as to measure the amount of HCV RNA replicated;
comparing the levels of HCV RNA in cells in the absence and presence of the inhibitor.

In a sixth embodiment, the invention is directed to a method for testing a compound for inhibiting HCV replication, including the steps of:
a) treating the above described host cell with the compound;
b) evaluating the treated host cell for reduced replication, wherein reduced replication indicates the ability of the compound to inhibit replication.

DETAILED DESCRIPTION OF THE DRAWINGS

FIG. 1 is a schematic view of the bi-cistronic replicon RNA. The sequence deviations between the I377/NS2-3' replicon from Lohman et al., 1999 Science 285: 110-113 and the APGK12 replicon are indicated below the replicon. In place of a G nucleotide at the +1 position in the I377/NS2-3' replicon, the APGK12 contains an additional G resulting in GG at the 5' terminus (the first G being counted as position −1). In the linker region between the neo gene and the EMCV IRES sequence two areas deviate from I377/NS2-3':14 nucleotides (CGCGCCCAGATGTT) (SEQ ID NO. 28) which are not present in I377/NS2/3 are inserted at position 1184 in APGK12; 11 nucleotides (1231-1241) present in I377/NS2-3' are deleted to generate APGK-12. In the NS5B coding region, a T at position 8032 was mutated to C to eliminate a NcoI restriction site.

Figure 2:
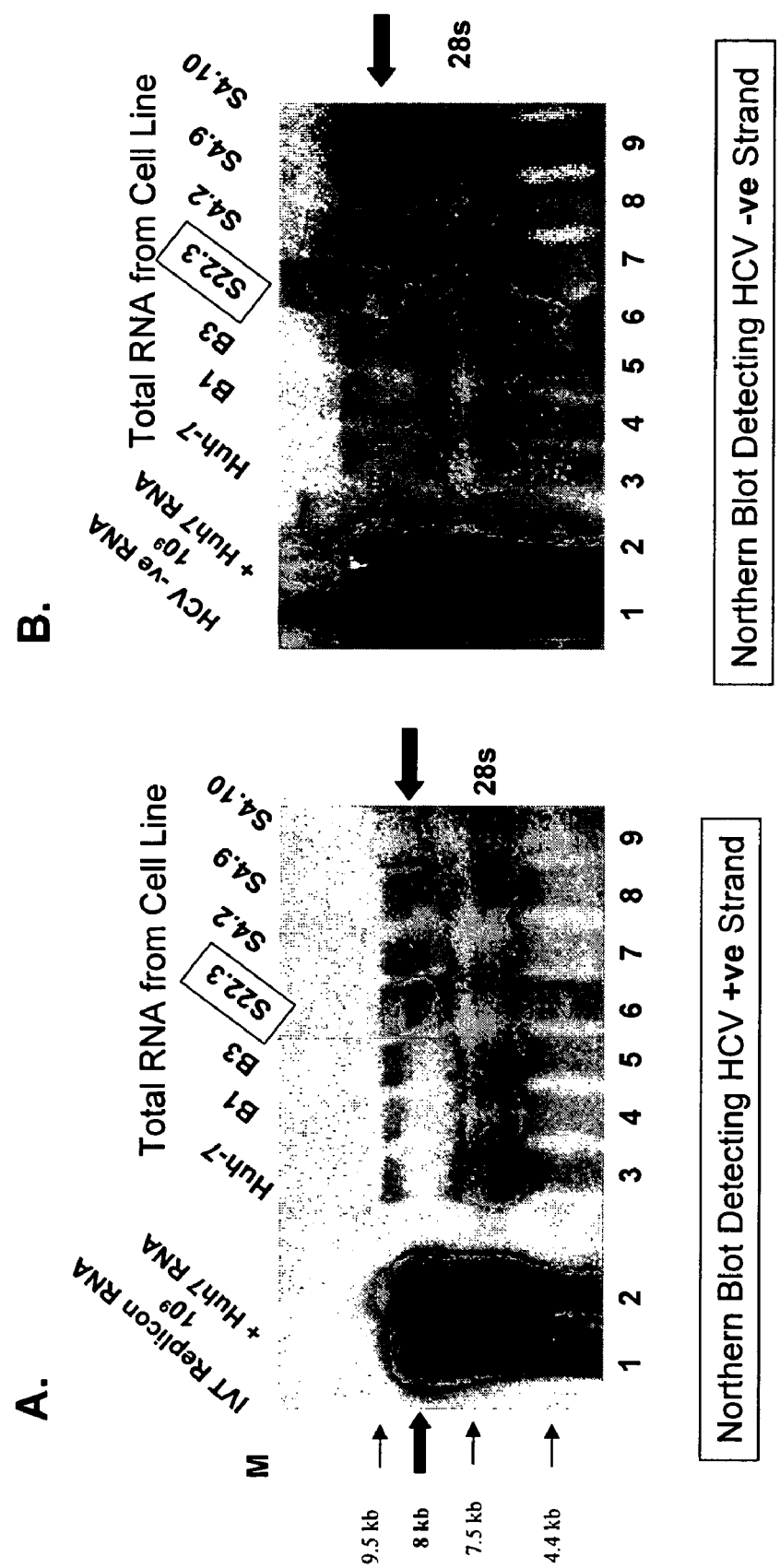

FIG. 2 shows Northern blots of RNA-transfected Huh-7 cell lines. 12 μg of total cellular RNA or control RNA was separated on 0.5% agarose-formaldehyde gels and transferred to Hybond N+ paper, fixed and (FIG. 2A) radioactively probed with HCV specific minus-strand RNA that detects the presence of plus-strand replicon RNA. Lanes 1 and 2: positive controls that contain $10^9$ copies of in vitro transcribed APGK12 RNA. Lane 3: negative control of total cellular RNA from untransfected Huh-7 cells. Lanes 4 and 5: cellular RNA from B1 and B3 cell lines that have integrated DNA copies of the neomycin phosphotransferase gene. Lane 6: total cellular RNA from a Huh-7 cell line, designated S22.3, that harbors high copy number HCV sub-genomic replicon RNA as highlighted by the arrow. Other cell lines have no detectable replicon RNA. FIG. 2B is identical to FIG. 2A with the exception that the blot was radioactively probed with HCV specific plus-strand RNA to detect the presence of HCV minus-strand RNA. Lanes 1 and 2 are positive control lanes that contain $10^9$ copies of full length HCV minus strand RNA. Lane 6, which contains 12 μg of total cellular RNA from cell line S22.3, harbors detectable minus-strand replicon RNA at the expected size of 8-9 kilobases. M represent the migration of non-radioactive molecular size markers on the agarose gel. 28s represents the migration of 28s ribosomal RNA and accounts for the detection of this species in a samples of total cellular RNA.

Figure 3:
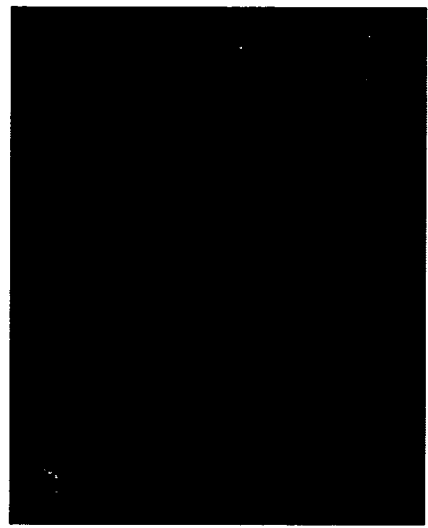
Figure 3:
Figure 3:

FIG. 3 shows indirect immunofluorescence of a HCV nonstructural protein in the S22.3 cell line. Indirect immunofluorescence was performed on cells that were cultured and fixed, permeabilized and exposed to a rabbit polyclonal antibody specific for a segment of the HCV NS4A protein. Secondary goat anti-rabbit antibody conjugated with red-fluor Alexa 594 (Molecular Probes) was used for detection. Top panels shows the results of immunofluorescence (40× objective) and the specific staining of the S22.3 cells. The bottom panels represent the identical field of cells viewed by diffractive interference contrast (DIC) microscopy. The majority of S22.3 (FIG. 3A) cells within the field stain positively for HCV NS4A protein that localizes in the cytoplasm, whereas the B1 cells (FIG. 3B) that fail to express any HCV proteins, only have background level of staining.

Figure 4:
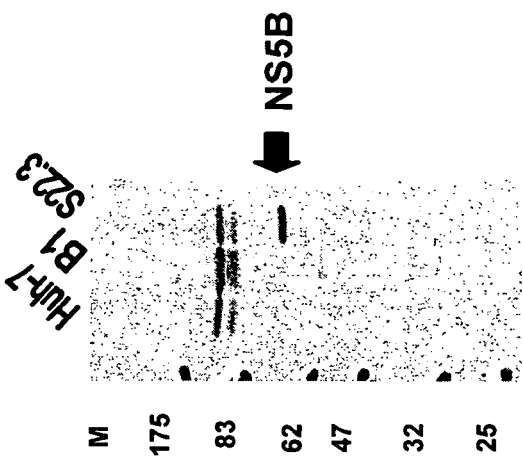
Figure 4:
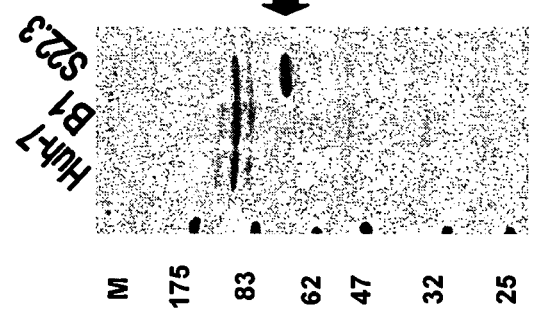
Figure 4:
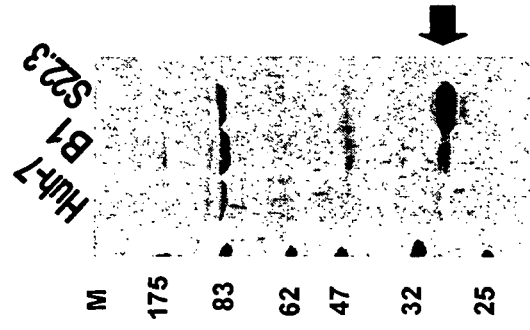

FIG. 4 shows Western-blots following SDS-PAGE separation of total proteins extracted from three cell lines: (i) naïve Huh-7 cell line, (ii) neomycin resistant Huh-7 cell line B1, and (iii) the S22.3 cell line. Panels A, B, and C, demonstrate the results of western blots probed with rabbit polyclonal antisera specific for neomycin phosphotransferase (NPT), HCV NS3, and HCV NS5B, respectively. Visualization was achieved through autoradiographic detection of a chemiluminescent reactive secondary goat anti-rabbit antibody. Panel A shows that the S22.3 RNA replicon cell line, expresses the NPT protein at levels higher than control B1 cells and that the naïve Huh-7 cell line does not produce the NPT protein. Panels B and C show that only the S22.3 cell line produces the mature HCV NS3 and NS5B proteins, respectively. M represents molecular weight (in kilodaltons) of pre-stained polypeptide markers.

FIGS. 5A and 5B identify the nucleotide and amino acid sequences respectively that differ from the APGK12 sequence in the different HCV bi-cistronic replicons. The S22.3 adapted replicon is a first generation replicon selected following the transfection of RNA transcribed from the APGK12 template. R3, R7, R16 are second generation replicons that were selected following the transfection of RNA isolated from the S22.3 first generation replicon cell line. FIG. 5A: Nucleotide mutations that were characterized in each of the adapted replicons are indicated adjacent to the respective segment of the replicon (IRES, NS3, NS4A, NS5A, and NS5B). FIG. 5B: Amino acid numbers are numbered according to the full length HCV poly-protein with the first amino acid in the second cistron corresponding to amino acid 810 in NS2 of I377/NS2-3' construct.

FIG. 6 depicts the colony formation efficiency of four in vitro transcribed HCV sub-genomic bi-cistronic replicon RNAs. The APGK12 serves as the reference sequence; highlighted are the initiating nucleotides of the HCV IRES in each of the constructs and the amino acid differences (from the APGK12 reference sequence) in the HCV non-structural region for the two R3-rep. Note that the in vitro transcribed APGK-12 RNAs that harbor either a 5'G or 5'A form colonies with the same efficiency (ca. 80 cfu/μg in panels A and B) following selection with 0.25 mg/ml G418. RNA isolated from the second generation R3 cell line was reverse transcribed into DNA and cloned into the pAPGK12 vector backbone to generate the R3-rep, which was sequenced and found to encode additional changes that included the L(2155)P substitution in the NS5A segment of the HCV polyprotein (compare R3-rep sequence with the R3 sequence in tables 2 and 3). Various quantities of in vitro transcribed R3-rep-5'A RNA, were transfected into naïve Huh-7 cells to determine a colony formation efficiency of $1.2 \times 10^6$ cfu/μg of RNA (panel C). Various quantities of R3-rep-5'G were also transfected resulting in a colony formation efficiency of $2 \times 10^6$ cfu/μg of RNA (panel D).

Figure 7:
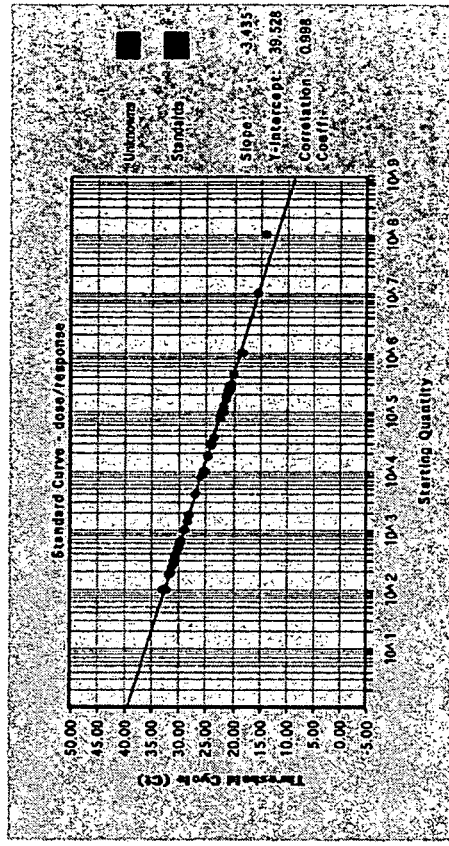
Figure 7:
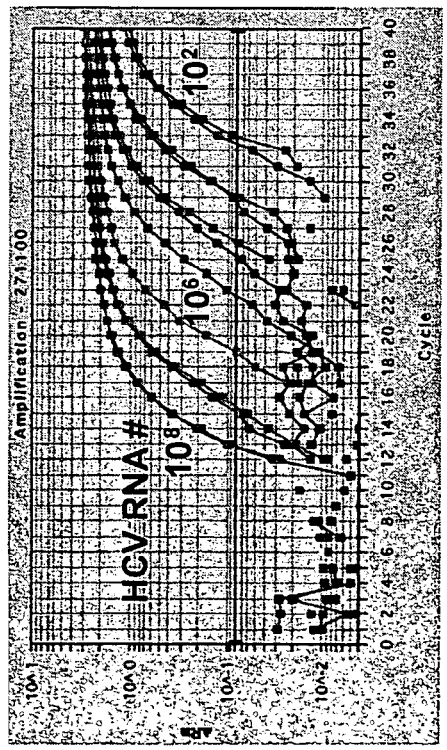

FIG. 7 displays a typical RT-PCR amplification plot (left panel) and the graphical representation of Ct values versus known HCV RNA quantity in a standard curve (right panel). Each of the plotted curves in the left panel, graph the increment of fluorescence reporter signal (delta-Rn) versus PCR cycle number for a predetermined quantity of HCV replicon RNA. The Ct value is obtained by determining the point at which the fluorescence exceeds an arbitrary value (horizontal line). The right panel demonstrates the linear relationship between starting RNA copy number of the predetermined standards (large black dots) and the Ct value. Smaller dots are the Ct values of RNA samples (containing unknown quantity of HCV replicon RNA) from S22.3 cells treated with various concentrations of a specific inhibitor of HCV replication.

Figure 8:
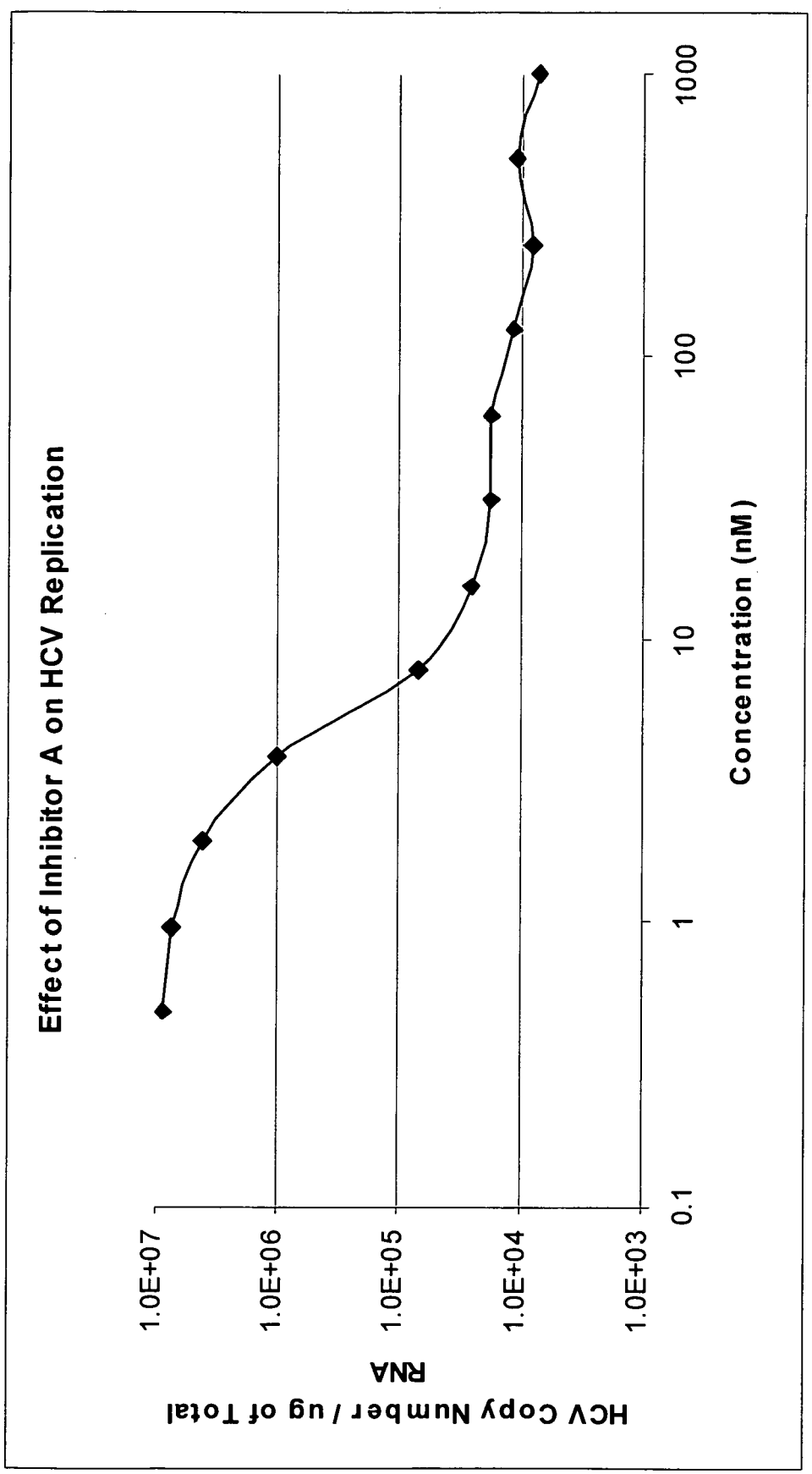

FIG. 8 shows the effect of increasing concentration of inhibitor A on HCV RNA replicon levels in Huh7 cells. S22.3 cells were grown in the presence of increasing concentrations of inhibitor A starting at 0.5 nM and ranging to 1024 nM. The inhibitor dose-response curve is the result of 11 concentrations from serial two-fold dilutions (1:1). One control well, without any inhibitor, was also included during the course of the experiment. The cells were incubated for 4 days in a 5% $CO_2$ incubator at 37° C. Total cellular RNA was extracted, quantified by optical density. HCV replicon RNA was evaluated by real time RT-PCR and plotted as genome equivalents/µg total RNA as a function of inhibitor concentration.

DEFINITIONS

Unless defined otherwise, the scientific and technological terms and nomenclature used herein have the same meaning as commonly understood by a person of ordinary skill to which this invention pertains. Generally, the procedures for cell culture, infection, molecular biology methods and the like are common methods used in the art. Such standard techniques can be found in reference manuals such as for example Sambrook et al. (1989) Molecular Cloning—A Laboratory Manual, Cold Spring Harbor Labs and Ausubel et al. (1994).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (1972) Biochemistry, 11, 1726-1732.

The present description refers to a number of routinely used recombinant DNA (rDNA) technology terms. Nevertheless, definitions of selected examples of such rDNA terms are provided for clarity and consistency.

The term "DNA segment or molecule or sequence", is used herein, to refer to molecules comprised of the deoxyribonucleotides adenine (A), guanine (G), thymine (T) and/or cytosine (C). These segments, molecules or sequences can be found in nature or synthetically derived. When read in accordance with the genetic code, these sequences can encode a linear stretch or sequence of amino acids which can be referred to as a polypeptide, protein, protein fragment and the like.

As used herein, the term "gene" is well known in the art and relates to a nucleic acid sequence defining a single protein or polypeptide. The polypeptide can be encoded by a full-length sequence or any portion of the coding sequence, so long as the functional activity of the protein is retained.

A "structural gene" defines a DNA sequence which is transcribed into RNA and translated into a protein having a specific structural function that constitute the viral particles. "Structural proteins" defines the HCV proteins incorporated into the virus particles namely, core "C", E1, E2, and E2-p7.

"Non-structural proteins", defines the HCV proteins that are not comprised in viral particles namely, NS2, NS3, NS4A, NS5A and NS5B.

"Restriction endonuclease or restriction enzyme" is an enzyme that has the capacity to recognize a specific base sequence (usually 4, 5 or 6 base pairs in length) in a DNA molecule, and to cleave the DNA molecule at every place where this sequence appears. An example of such an enzyme is EcoRI, which recognizes the base sequence G↓AATTC (SEQ ID NO. 29) and cleaves a DNA molecule at this recognition site.

"Restriction fragments" are DNA molecules produced by the digestion of DNA with a restriction endonuclease. Any given genome or DNA segment can be digested by a particular restriction endonuclease into at least two discrete molecules of restriction fragments.

"Agarose gel electrophoresis" is an analytical method for fractionating polynucleotide molecules based on their size. The method is based on the fact that nucleic acid molecules migrate through a gel as through a sieve, whereby the smallest molecule has the greatest mobility and travels the farthest through the gel. The sieving characteristics of the gel retards the largest molecules such that, these have the least mobility. The fractionated polynucleotides can be visualized by staining the gel using methods well known in the art, nucleic acid hybridization or by tagging the fractionated molecules with a detectable label. All these methods are well known in the art, specific methods can be found in Ausubel et al. (supra).

"Oligonucleotide or oligomer" is a molecule comprised of two or more deoxyribonucleotides or ribonucleotides, preferably more than three. The exact size of the molecule will depend on many factors, which in turn depend on the ultimate function or use of the oligonucleotide. An oligonucleotide can be derived synthetically, by cloning or by amplification.

"Sequence amplification" is a method for generating large amounts of a target sequence. In general, one or more amplification primers are annealed to a nucleic acid sequence. Using appropriate enzymes, sequences found adjacent to, or in between the primers are amplified. An amplification method used herein is the polymerase chain reaction (PCR) and can be used in conjunction with the reverse-transcriptase (RT) to produce amplified DNA copies of specific RNA sequences.

"Amplification primer" refers to an oligonucleotide, capable of annealing to a RNA or DNA region adjacent to a target sequence and serving as the initiation primer for DNA synthesis under suitable conditions well known in the art. The synthesized primer extension product is complementary to the target sequence.

The term "domain" or "region" refers to a specific amino acid sequence that defines either a specific function or structure within a protein. As an example herein, is the NS3 protease domain comprised within the HCV non-structural polyprotein.

The terms "plasmid" "vector" or "DNA construct" are commonly known in the art and refer to any genetic element, including, but not limited to, plasmid DNA, phage DNA, viral DNA and the like which can incorporate the oligonucleotide sequences, or sequences of the present invention and serve as DNA vehicle into which DNA of the present invention can be cloned. Numerous types of vectors exist and are well known in the art.

The terminology "expression vector" defines a vector as described above but designed to enable the expression of an inserted sequence following transformation or transfection into a host. The cloned gene (inserted sequence) is usually placed under the control of control element sequences such as promoter sequences. Such expression control sequences will vary depending on whether the vector is designed to express the operably linked gene in vitro or in vivo in a prokaryotic or eukaryotic host or both (shuttle vectors) and can additionally contain transcriptional elements such as enhancer elements, termination sequences, tissue-specificity elements, and/or translational initiation and termination sites.

A host cell or indicator cell has been "transfected" by exogenous or heterologous DNA (e.g. a DNA construct) or RNA, when such nucleic acid has been introduced inside the cell. The transfecting DNA may or may not be integrated (covalently linked) into chromosomal DNA making up the genome of the cell. In prokaryotes, yeast, and mammalian cells for example, the transfecting/transforming DNA may be maintained on an episomal element such as a plasmid. With respect to eukaryotic cells, an example of a stably transfected cell is one in which the transfecting DNA has become integrated into a chromosome and is inherited by daughter cells through chromosome replication. A host cell or indicator cell can be transfected with RNA. A cell can be stably transfected with RNA if the RNA replicates and copies of the RNA segregate to daughter cells upon cell division. This stability is demonstrated by the ability of the eukaryotic cell to establish cell lines or clones comprised of a population of daughter cells containing the transfecting DNA or RNA. Transfection methods are well known in the art (Sambrook et al., 1989, Molecular Cloning—A Laboratory Manual, Cold Spring Harbor Labs; Ausubel et al., 1994, Current Protocols in Molecular Biology, Wiley, N.Y.). If the RNA encodes for a genetic marker that imparts an observable phenotype, such as antibiotic resistance, then the stable transfection of replicating RNA can be monitored by the acquisition of such phenotype by the host cell.

As used herein the term "transduction" refers to the transfer of a genetic marker to host cells by the stable transfection of a replicating RNA.

The nucleotide sequences and polypeptides useful to practice the invention include without being limited thereto, mutants, homologs, subtypes, quasi-species, alleles, and the like. It is understood that generally, the sequences of the present invention encode a polyprotein. It will be clear to a person skilled in the art that the polyprotein of the present invention and any variant, derivative or fragment thereof, is auto-processed to an active protease.

As used herein, the designation "variant" denotes in the context of this invention a sequence whether a nucleic acid or amino acid, a molecule that retains a biological activity (either functional or structural) that is substantially similar to that of the original sequence. This variant may be from the same or different species and may be a natural variant or be prepared synthetically. Such variants include amino acid sequences having substitutions, deletions, or additions of one or more amino acids, provided the biological activity of the protein is conserved. The same applies to variants of nucleic acid sequences which can have substitutions, deletions, or additions of one or more nucleotides, provided that the biological activity of the sequence is generally maintained.

The term "derivative" is intended to include any of the above described variants when comprising additional chemical moiety not normally a part of these molecules. These chemical moieties can have varying purposes including, improving a molecule's solubility, absorption, biological half life, decreasing toxicity and eliminating or decreasing undesirable side effects. Furthermore, these moieties can be used for the purpose of labeling, binding, or they may be comprised in fusion product(s). Different moieties capable of mediating the above described effects can be found in Remington's The Science and Practice of Pharmacy (1995). Methodologies for coupling such moieties to a molecule are well known in the art.

The term "fragment" refers to any segment of an identified DNA, RNA or amino acid sequence and/or any segment of any of the variants or derivatives described herein above that substantially retains its biological activity (functional or structural) as required by the present invention.

The terms "variant", "derivative", and "fragment" of the present invention refer herein to proteins or nucleic acid molecules which can be isolated/purified, synthesized chemically or produced through recombinant DNA technology. All these methods are well known in the art. As exemplified herein below, the nucleotide sequences and polypeptides used in the present invention can be modified, for example by in vitro mutagenesis.

As used herein, the term "HCV polyprotein coding region" means the portion of a hepatitis C virus that codes for the polyprotein open reading frame (ORF). This ORF may encode proteins that are the same or different than wild-type HCV proteins. The ORF may also encode only some of the functional protein encoded by wild-type polyprotein coding region. The protein encoded therein may also be from different isolates of HCV, and non-HCV protein may also be encoded therein.

As used herein, the abbreviation "NTR" used in the context of a polynucleotide molecule means a non-translated region. The term "UTR" means untranslated region. Both are used interchangeably.

PREFERRED EMBODIMENTS

Particularly, the invention provides a HCV self-replicating polynucleotide molecule comprising a 5'-terminus consisting of ACCAGC (SEQ ID NO.8).

According to the first embodiment of this invention, there is particularly provided a HCV polynucleotide construct comprising:
  a 5'-non translated region (NTR) comprising the sequence ACCAGC (SEQ ID NO. 8) at, or proximal to, its 5'-terminus;
  a HCV polyprotein coding region; and
  a 3'-NTR region.

In a second embodiment, the present invention is directed to a HCV self-replicating polynucleotide encoding a polyprotein comprising one or more amino acid substitution selected from the group consisting of: R(1135)K; S(1148)G; S(1560)G; K(1691)R; L(1701)F; I(1984)V; T(1993)A; G(2042)C; G(2042)R; S(2404)P; L(2155)P; P(2166)L and M(2992)T.

Particularly, the invention is directed to a HCV self-replicating polynucleotide encoding a polyprotein comprising the any one of the amino acid substitutions as described above, further comprising the amino acid substitution E(1202)G.

Alternatively, the first embodiment of the present invention is directed to HCV self-replicating polynucleotide molecule comprising a G2042C/R mutation.

According to the second embodiment, the present invention particularly provides a HCV polynucleotide construct comprising:
  a 5'-NTR region comprising the sequence ACCAGC (SEQ ID NO. 8) at, or proximal to, its 5'-terminus;
  a HCV polyprotein region coding for a HCV polyprotein comprising a G(2042)C or a G(2042)R mutation; and
  a 3'-NTR region.

Preferably, the polynucleotide construct of the present invention is a DNA or RNA molecule. More preferably, the construct is a RNA molecule. Most preferably, the construct is a DNA molecule.

More particularly, the first embodiment of this invention is directed to a RNA molecule encoded by the DNA molecule selected from the group consisting of: SEQ ID NO. 2, 4, 5, 6, 7, 24 and 25.

Most particularly, the invention provides a DNA molecule selected from the group consisting of: SEQ ID NO. 2, 4, 5, 6, 7, 24 and 25.

In a third embodiment, the invention also is directed to an expression vector comprising DNA forms of the above polynucleotide, operably linked with a promoter.

Preferably, the promoter is selected from the group consisting of: T3, T7 and SP6.

According to a fourth embodiment, there is provided a host cell transfected with the self-replicating polynucleotide or vector as described above. Particularly, the host cell is a eukaryotic cell line. More particularly, the eukaryotic cell line is a hepatic cell line. Most particularly, the hepatic cell line is Huh-7.

In a fifth embodiment, the present invention provides a RNA replication assay comprising the steps of:
a) incubating the host cell as described above under conditions suitable for RNA replication;
b) isolating the total cellular RNA from the cells; and
c) analyzing the RNA so as to measure the amount of HCV RNA replicated.

Preferably, the analysis of RNA levels in step c) is carried out by amplifying the RNA by real-time RT-PCR analysis using HCV specific primers so as to measure the amount of HCV RNA replicated.

Alternatively in this fifth embodiment, the construct comprises a reporter gene, and the analysis of RNA levels in step c) is carried out by assessing the level of reporter expressed.

According to a preferred aspect of the sixth embodiment, the invention is directed to a method for testing a compound for inhibiting HCV replication, including the steps of:
a) carrying step a) as described in the above assay, in the presence or absence of the compound;
b) isolating the total cellular RNA from the cells; and
c) analyzing the RNA so as to measure the amount of HCV RNA replicated.
d) comparing the levels of HCV RNA in cells in the absence and presence of the inhibitor,
wherein reduced RNA levels is indicative of the ability of the compound to inhibit replication.

Preferably, the cell line is incubated with the test compound for about 3-4 days at a temperature of about 37° C.

EXAMPLES

Example 1

Replicon Constructs

APGK-12; FIG. 1 pET9a-EMCV was obtained by ligating an oligonucleotide linker 5' gaattccagatggcgcgcccagatgt-taaccagatccatggcacactctagagtactgtcgac 3' (SEQ ID NO.9) to pET-9a (Novagen) that was cut with EcoRI and SalI to form the vector pET-9a-mod. This linker contains the following restriction sites: EcoRI, AscI, HpaI, NcoI, XbaI, ScaI, SalI. The EMCV IRES was amplified by PCR from the vector pTM1 with primers 5' cggaatcgttaacagaccacaacggtttccctc 3' (SEQ ID NO.10) and 5' ggcgtacccatggtattatcgtgttttca 3' (SEQ ID NO.11) and ligated into pET-9a-mod via EcoRI and NcoI to form pET-9a-EMCV.

The sequence of HCV NS2 to NS5B followed by the 3'UTR of HCV was obtained from the replicon construct I377/NS2-3' (Lohman et al., 1999 Science 285:110-113; accession number: AJ242651) and synthesized by Operon Technologies Inc. with a T to C change at the NcoI site in NS5B at nucleotide 8032. This sequence was released from an GenOp® vector (Operon Technologies) with NcoI and ScaI and transferred into pET-9a-EMCV to form pET-9a-EMCV-NS2-5B-3'UTR.

pET-9a-HCV-neo was obtained by amplification of the HCV IRES from a HCV cDNA isolated from patient serum with primers 5' gcatatgaattctaatacgactcactat-aggccagcccccgattg 3' (SEQ ID NO.12) containing a T7 promoter and primer 5' ggcgcgcccttttggttttctttttgag-gtttaggattcgtgctcat 3' (SEQ ID NO.13) and amplification of the neomycin phosphotransferase gene from the vector pcDNA 3.1 (Invitrogen) with primers 5' aaagggcgcatgattgaa-caagatggattgcacgca 3' (SEQ ID NO.14) and 5' gcatatgttaact-cagaagaactcgtcaagaaggcgata 3' (SEQ ID NO.15). These two PCR fragments were mixed and amplified with primers 5' gcatatgaaftctaatacgactcactataggccagcccccgattg 3' (SEQ ID NO.16) and 5' gcatatgttaactcagaagaactcgtcaagaaggcgata 3' (SEQ ID NO.15), cut with Eco RI and HpaI and transferred into pET-9a-mod to form pet-9a-HCV-neo. The EMCV-NS2-5B-3'UTR was released from pET-9a-EMCV-NS2-5B-3'UTR with HpaI and ScaI and transferred into pet-9a-HCV-neo that was cut with HpaI to form pET-9a-APGK12. This insert was sequenced with specific successive primers using a ABI Prism® BigDye™ Terminator Cycle sequencing kit and analyzed on ABI Prism® 377 DNA Sequencer and is shown in SEQ ID NO 1.

RNA In Vitro Transcription pET-9a-APGK12 DNA was cut with ScaI for expression of the full-length replicon or with BglII for expression of a truncated negative control RNA. DNA was analyzed on a 1% agarose gel and purified by Phenol/Chloroform extraction. RNA was produced using a T7 Ribomax® kit (Promega) followed by extraction with phenol/chloroform and precipitation with 7.5 M LiCl$_2$. RNA was treated with DNAse I for 15 min to remove the DNA template and further purified with an RNeasy® column (Qiagen). RNA integrity was verified on a denaturing formaldehyde 1% agarose gel.

Example 2

Primary Transfection of Huh7 Cells and Selection of Replicon Cell Lines

Human hepatoma Huh7 cells (Health Science Research Resources Bank, Osaka, Japan) were grown in 10% FBS/DMEM. Cells were grown to 70% confluency, trypsinized, washed with phosphate buffered saline (PBS) and adjusted to $1 \times 10^7$ cells/ml of PBS. 800 µl of cells were transferred into 0.4 cm cuvettes and mixed with 15 µg of replicon RNA. Cells were electroporated using 960 µF, 300 volts for ~18 msec and evenly distributed into two 15 cm tissue culture plates and incubated in a tissue culture incubator for 24 hours. The selection of first and second generation replicon cell lines was with 10% FBS/DMEM medium supplemented with 1 mg/ml of G418. Cells were selected for 3-5 weeks until colonies were observed that were isolated and expanded.

Following the G418 selection and propagation of Huh-7 cells transfected with APGK12 (SEQ ID NO. 1) RNA, cells that formed a distinct colony were treated with trypsin and serially passed into larger culture flasks to establish cell lines. Approximately $10 \times 10^6$ cells were harvested from each cell line. The cells were lysed and the total cellular RNA extracted and purified as outlined in Qiagen RNAeasy® preparatory procedures. FIG. 2 shows the analysis of 12 µg of total cellular RNA from various cell lines as analyzed on a Northern blot of a denaturing agarose-formaldehyde gel.

FIG. 2A is a Northern blot (radioactively probed with HCV specific minus-strand RNA) that detects the presence of plus-strand replicon RNA. Lanes 1 and 2 are positive controls that contain $10^9$ copies of in vitro transcribed APGK12 RNA. Lane 2 contains the in vitro transcribed RNA mixed with 12 µg of total cellular from naïve Huh-7 cells. Lane 3 is a negative control of total cellular RNA from untreated Huh-7 cells. Lanes 4 and 5 contain cellular RNA from the B1 and B3 G418 resistant cell lines that have DNA integrated copies of the neomycin phosphotransferase gene. Lane 6 contains total cellular RNA from a Huh-7 cell line, designated S22.3, that harbors high copy number of HCV sub-genomic replicon RNA as detected by the positive signal in the 8 kilo-base range. Other cell lines have no detectable replicon RNA. FIG. 2B is a Northern blot of a duplicate of the gel presented in 2A with the exception that the blot was radioactively probed with HCV specific plus-strand RNA to detect the presence of HCV minus-strand RNA (lanes 1 and 2 are positive control lanes that contain $10^9$ copies of full length genomic HCV minus strand RNA); only lane 6, which contains 12 µg of total cellular RNA from cell line S22.3, harbors detectable minus-strand replicon RNA at the expected size of 8-9 kilobases. An quantitative estimation of RNA copy number, based on phosphorimager scanning of the Northern blots, is approximately $6 \times 10^7$ copies of plus-strand/µg of total RNA, and $6 \times 10^6$ copies of minus strand/µg of total RNA. The presence of the plus-strand and minus-strand intermediate confirms that the HCV sub-genomic RNA is actively replicating in the S22.3 cell line.

Example 3

S22.3 Cell Line Constitutively Expresses HCV Non-Structural Proteins

HCV non-structural protein expression was examined in the S22.3 cell line. FIG. 3 displays the result of indirect immunofluorescence that detects the HCV NS4A protein in the S22.3 cell line and not in the replicon negative B1 cell line (a G418 resistant Huh-7 cell line). Indirect immunofluorescence was performed on cells that were cultured and fixed (with 4% paraformaldehyde) onto Lab-tek chamber slides. Cells were permeabilized with 0.2% Triton X-100 for 10 minutes followed by a 1 hour treatment with 5% milk powder dissolved in phosphate-buffered saline (PBS). A rabbit serum containing polyclonal antibody raised against a peptide spanning the HCV NS4A region was the primary antibody used in detection. Following a 2 hour incubation with the primary antibody, cells were washed with PBS and a secondary goat anti-rabbit antibody conjugated with red-fluor Alexa® 594 (Molecular Probes) was added to cells for 3 hours. Unbound secondary antibody was removed with PBS washes and cells were sealed with a cover slip. FIG. 3 (top panels) shows the results of immunofluorescence as detected by a microscope with specific fluorescent filtering; the bottom panels represent the identical field of cells viewed by diffractive interference contrast (DIC) microscopy. The majority of S22.3 (FIG. 3A) cells within the field stain positively for HCV NS4A protein that localizes in the cytoplasm, whereas the B1 cells (FIG. 3B) that fail to express any HCV proteins, only have background level of staining. A small proportion of S22.3 cells express high levels of intensely stained HCV NS4A.

Expression of the proteins encoded by the bi-cistronic replicon RNA was also examined on Western-blots following SDS-PAGE separation of total proteins extracted from: (i) naïve Huh-7 cell line, (ii) neomycin resistant Huh-7 cell line B1, and (iii) the S22.3 cell line. FIG. 4 panels A, B, and C, demonstrate the results of western blots probed with rabbit polyclonal antisera specific for neomycin phosphotransferase (NPT), HCV NS3, and HCV NS5B, respectively. Visualization was achieved through autoradiographic detection of a chemiluminescent reactive secondary HRP-conjugated goat anti-rabbit antibody. FIG. 4 panel A shows that the S22.3 RNA replicon cell line, expresses the NPT protein at levels higher than B1 cells (which contain an integrated DNA copy of the npt gene) and that the naïve Huh-7 cell line does not produce the NPT protein. FIG. 4 panels B and C show that only the S22.3 cell line produces the mature HCV NS3 and NS5B proteins, respectively. The western blots demonstrate that the S22.3 cell line, which harbors actively replicating HCV sub-genomic replicon RNA, maintains replication of the RNA through the high level expression of the HCV non-structural proteins.

Example 4

Sequence Determination of Adapted Replicons

Total RNA was extracted from replicon containing Huh7 cells using a RNeasy Kit (Qiagen). Replicon RNA was reverse transcribed and amplified by PCR using a OneStep RT-PCR kit (Qiagen) and HCV specific primers (as selected from the full-length sequence disclosed in WO 00/66623). Ten distinct RT-PCR products, that covered the entire bi-cistronic replicon in a staggered fashion, were amplified using oligonucleotide primers. The PCR fragments were sequenced directly with ABI Prism® BigDye™ Terminator Cycle PCR Sequencing and analyzed on ABI Prism® 377 DNA Sequencer. To analyze the sequence of the HCV replicon 3' and 5' ends a RNA ligation/RT-PCR procedure described in Kolykhalov et al. 1996 J. of Virology, 7, p. 3363-3371 was followed. The nucleotide sequence of S22.3 is presented as SEQ ID NO. 2.

Example 5

Serial Passage of HCV Replicon RNA

The total cellular RNA from the S22.3 cell line was prepared as described above. HCV Replicon RNA copy number was determined by Taqman® RT-PCR analysis and 20 µg of total S22.3 cellular RNA (containing $1 \times 10^9$ copies of HCV RNA) was transfected by electroporation into $8 \times 10^6$ naïve Huh-7 cells. Transfected cells were subsequently cultured in 10 cm tissue culture plates containing DMEM supplemented with 10% fetal calf serum (10% FCS). Media was changed to DMEM (10% FCS) supplemented with 1 mg/ml G418 24 hours after transfection and then changed every three days. Twenty-three visible colonies formed three to four weeks post-transfection and G418 selection. G418 resistant colonies were expanded into second generation cell lines that represent the first cell lines harboring serially passaged HCV Replicon RNA. Three of these cell lines: R3, R7, and R16 were the subject of further analyses. First, the efficiency of transduction by each of the adapted replicons was determined by electroporation of the total cellular RNA (extracted from the R3, R7 and R16) into naïve Huh-7 cells; following electroporation, the transduction efficiency was determined as described above, by counting the visible G418 resistant colonies that arose following 3 to 5 weeks of G418 selection (Table 1). Second, the sequence of the serially passed adapted replicons was determined from the total cellular RNA that was extracted from each of the R3, R7 and R16 replicon cell lines as described in example 4 (SEQ ID NO. 4, 5, 6). Using the pAPGK12 as a reference sequence (SEQ ID NO. 1), the nucleotide changes that were selected in HCV segment of the adapted replicons are presented in FIG. 5A. Some of these nucleotide changes are silent and do not change the encoded amino acid whereas others result in an amino acid substitution. FIG. 5B summarizes the amino acid changes encoded by the adapted replicons with the amino acid sequence of pAPGK12 as the reference. It is important to note that the reference sequence APGK-12 (SEQ ID NO. 1) contains an extra G at the 5'-terminal (5'-GG) that is not maintained in the replicating RNA of the established cell lines. Also noteworthy is that, in addition to G→A at nucleotide 1, there is also an adapted mutation G→C/R at amino acid 2042 (shown as amino acid 1233 in the sequence listing since a.a. 810 of NS2 is numbered as a.a. 1 in SEQ ID) that can be found in all clones analyzed.

TABLE 1

Transfection of Huh-7 cells

| RNA | Copies of Replicon | # Colonies | SEQ ID |
|---|---|---|---|
| 5 ng APKG12 replicon in 20 μg total Huh-7 RNA | $1.2 \times 10^9$ | 0 | |
| 15 μg APKG12 replicon RNA 20 μg total: | $3 \times 10^{12}$ | 1 (S22.3) | 1 |
| S22.3 cellular RNA | $3 \times 10^9$ | 23 (3 clones analyzed) | 2 |
| R3 cellular RNA | $1 \times 10^9$ | 200 | 4 |
| R7 cellular RNA | $1 \times 10^9$ | 20 | 5 |
| R16 cellular RNA | $3 \times 10^8$ | 100 | 6 |
| cloned R3rep RNA | $2.3 \times 10^8$ | 2000 | 7 |

Example 6

Construction of APGK12 with 5'G→A Substitution (APGK12-5'A, SEQ ID NO.24)

The pAPGK12 DNA was modified to change the first nucleotide in the sequence to replace the 5'GG with a 5'A. The change in the pAPGK12 was introduced by replacing an EcoRI/AgeI portion of the sequence with a PCR-generated EcoRI/AgeI fragment that includes the mutation. The oligonucleotides used for the amplification were (SEQ ID. NO. 20): 5'-GTG GAC GAA TTC TAA TAC GAC TCA CTA TA A CCA GCC CCC GAT TGG-3' and (SEQ ID. NO. 21): 5'-GGA ACG CCC GTC GTG GCC AGC CAC GAT-3' and generated a 195 bp DNA fragment that was then digested with EcoRI and AgeI. The resulting 178 bp restriction fragment was used to replace the EcoRI/AgeI fragment in pAPGK12 to generate the pAPGK12-5'A plasmid.

Example 7 cDNA Cloning of the R3-Replicon (R3rep)

The cDNA clone of the R3 replicon was produced by RT-PCR of RNA extracted from the R3 cell line. The following two oligonucleotides were used: (SEQ ID. NO. 22): 5'-GTC GTC TTC TCT GAC ATG GAG AC-3' and (SEQ ID. NO. 23): 5'-GAG TTG CTC AGT GGA TTG ATG GGC AGC-3'. The ~4400 nt PCR fragment, starting within the NS2 coding region and extending to the 5'-end of the NS5B coding region, was cloned into the plasmid pCR3.1 by TA cloning (Invitrogen). The SacII/XhoI portion of this R3 sequence was then used to replace the SacII/XhoI fragment present in the pAPGK12 and the pAPGK12-5'A described above. Consequently, two R3 cDNA sequences were generated: (I) R3-Rep-5'G with an initiating 5'G (SEQ ID NO.7), and R3-Rep-5'A (SEQ ID NO.25) with an initiating 5'A. Sequencing of the R3 rep cDNA identified unique nucleotide changes that differ from the original pAPGK12 sequence (see FIG. 5A); some of these changes are silent and do not change the encoded amino acid, whereas others do result in an amino acid change (see FIG. 5B). The differences between R3 and the R3-rep reflect the isolation of a unique R3-rep cDNA clone encoding nucleotide changes that were not observed from the sequencing of the total RNA extracted from the R3 cell line.

Example 8

Efficiency of Colony Formation with Modified Constructs

RNA from pAPGK12, pAPGK12-5'A, pR3-Rep and pR3-Rep-5'A was generated by in vitro transcription using the T7 Ribomax® kit (Promega) as described in example 1 above. The reactions containing the pAPGK12-5'A and pR3-Rep-5'A templates were scaled-up 10-fold due to the limitation of commercial RNA polymerase in initiating transcripts with 5'-A. The full length RNAs and control truncated RNA for each clone were introduced into $8 \times 10^6$ naïve Huh-7 cells by electroporation as described in example 2. Replicon RNA was supplemented with total cellular Huh-7 carrier RNA to achieve a final 15-20 μg quantity. The cells were then cultured in DMEM medium supplemented with 10% fetal calf serum and 0.25 mg/ml G418 in two 150 mm plates. The lower concentration of G418 was sufficient to isolate and select replicon containing cell lines as none of the transfectants with the control truncated RNA produced any resistant colonies. In contrast, in vitro transcribed APGK-12 RNAs that harbor either a 5'G or 5'A form colonies with the same efficiency (ca. 80 cfu/μg in FIG. 6 panels A and B) following selection with G418. Various quantities (ranging from 0.1 ng to 1 μg) of the R3-rep-5'A RNA, were transfected into naïve Huh-7 cells to determine a colony formation efficiency of $1.2 \times 10^6$ cfu/μg of RNA (FIG. 6 panel C depicts transfection with 1 μg of RNA). Various quantities (ranging from 0.1 ng to 1 μg) of R3-rep [5'G] were similarly transfected resulting in a colony formation efficiency of $2 \times 10^6$ cfu/μg of RNA (FIG. 6 panel D depicts colony formation with 1 μg of RNA). Note that, shown for the first time, HCV subgenomic replicons replicate as efficiently with a 5'A nucleotide in place of the 5'G. APGK12 with a 5'A or 5'G RNA have similar transduction efficiencies. Similarly, R3-Rep RNAs with either the 5'A or 5'G both display the markedly increased transduction efficiency. Notably, the adaptive mutants within the HCV nonstructural segment encoded by the R3-Rep provides for a substantial increase in transduction efficiency as depicted by the dramatic increase in colony forming units per μg of transfected RNA.

Example 9

Quantification of HCV Replicon RNA Levels in Cell Lines

S22.3 cells, or cell lines harboring other adapted replicons, were seeded in DMEM supplemented with 10% FBS, Pen- Strep and 1 μg/mL Geneticin. At the end of the incubation period the replicon copy number is evaluated by real-time RT-PCR with the ABI Prism 7700 Sequence Detection System. The TAQMAN® EZ RT-PCR kit provides a system for the detection and analysis of HCV RNA (as first demonstrated by Martell et al. 1999 J. Clin. Microbiol. 37: 327-332). Direct detection of the reverse transcription polymerase chain reaction (RT-PCR) product with no downstream processing is accomplished by monitoring the increase in fluorescence of a dye-labeled DNA probe (FIG. 6). The nucleotide sequence of both primers (adapted from Ruster, B. Zeuzem, S. and Roth, W. K., 1995. Analytical Biochemistry 224:597-600) and probe (adapted from Hohne, M., Roeske, H. and Schreier, E. 1998, Poster Presentation: P297 at the Fifth International Meeting on Hepatitis C Virus and Related Viruses Molecular Virology and Pathogenesis, Venezia-Lido Italy, Jun. 25-28, 1998) located in the 5'-region of the HCV genome are the following:

```
HCV Forward primer:
                                            (SEQ ID NO.17)
5' ACG CAG AAA GCG TCT AGC CAT GGC GTT AGT 3'

HCV Reverse primer:
                                            (SEQ ID NO.18)
5' TCC CGG GGC ACT CGC AAG CAC CCT ATC AGG 3'

HCV Probe:
                                            (SEQ ID NO.19)
5' FAM-TGG TCT GCG GAA CGG GTG AGT ACA CC-TAMRA 3'
FAM: Fluorescence reporter dye.
TAMRA: Quencher dye.
```

Using The TAQMAN® EZ RT-PCR kit, the following reaction was set up:

| Component | Volume per sample (μL) | Final Concentration |
|---|---|---|
| RNase-Free Water | 16 | — |
| 5X Taqman EZ Buffer | 10 | 1X |
| Manganese Acetate 25 mM | 6 | 3 mM |
| dATP 10 mM | 1.5 | 300 μM |
| dCTP 10 mM | 1.5 | 300 μM |
| dGTP 10 mM | 1.5 | 300 μM |
| dUTP 20 mM | 1.5 | 300 μM |
| HCV Forward Primer 10 μM | 1 | 200 nM |
| HCV Reverse Primer 10 μM | 1 | 200 nM |
| HCV Probe 5 μM | 2 | 200 nM |
| rTth DNA Polymerase 2.5 U/μL | 2 | 0.1 U/μL |
| AmpErase UNG 1 U/μL | 0.5 | 0.01 U/μL |
| Total Mix | 45 | — |

To this reaction mix, 5 μL of total RNA extracted from S22.3 cells diluted at 10 ng/μL was added, for a total of 50 ng of RNA per reaction. The replicon copy number was evaluated with a standard curve made from known amounts of replicon copies (supplemented with 50 ng of wild type Huh-7 RNA) and assayed in an identical reaction mix (FIG. 7).

Thermal cycler parameters used for the RT-PCR reaction on the ABI Prism 7700 Sequence Detection System were optimized for HCV detection:

| Cycle | Temperature (° C.) | Time (Minutes) | Repeat | Reaction |
|---|---|---|---|---|
| Hold | 50 | 2 | | Initial Step |
| Hold | 60 | 30 | | Reverse Transcription |
| Hold | 95 | 5 | | UNG Deactivation |
| Cycle | 95 | 0:15 | 2 | Melt |
| | 60 | 1 | | Anneal/Extend |
| Cycle | 90 | 0:15 | 40 | Melt |
| | 60 | 1 | | Anneal/Extend |

Quantification is based on the threshold cycle, where the amplification plot crosses a defined fluorescence threshold. Comparison of the threshold cycles provides a highly sensitive measure of relative template concentration in different samples. Monitoring during early cycles, when PCR fidelity is at its highest, provides precise data for accurate quantification. The relative template concentration can be converted to RNA copy numbers by employing a standard curve of HCV RNA with known copy number (FIG. 7).

Example 10

A Specific HCV NS3 Protease Anti-Viral Compound Inhibits Replication of the HCV Replicon in S22.3 Cell Lines In order to determine the effect of a specific HCV NS3 protease anti-viral compound on replicon levels in S22.3 cells, the cells were seeded in 24 Well Cell Culture Cluster at $5 \times 10^4$ cells per well in 500 μL of DMEM complemented with 10% FBS, PenStrep and 1 μg/mL Geneticin. Cells were incubated until compound addition in a 5% $CO_2$ incubator at 37° C. The dose-response curve of the inhibitor displayed 11 concentrations resulting from serial two-fold dilutions (1:1). The starting concentration of compound A was 100 nM. One control well (without any compound) was also included in the course of the experiment. The 24 well plates were incubated for 4 days in a 5% $CO_2$ incubator at 37° C. Following a 4 day incubation period, the cells were washed once with PBS and RNA was extracted with the RNeasy® Mini Kit and Qiashredder® from Qiagen. RNA from each well was eluted in 50 uL of $H_2O$. The RNA was quantified by optical density at 260 nm on a Cary 1E UV-Visible Spectrophotometer. 50 ng of RNA from each well was used to quantify the HCV replicon RNA copy number as detailed in Example 6. The level of inhibition (% inhibition) of each well containing inhibitor was calculated with the following equation (CN=HCV Replicon copy number):

$$\% \cdot \text{inhibition} = \left( \frac{CN \cdot \text{control} - CN \cdot \text{well}}{CN \cdot \text{control}} \right) * 100$$

The calculated % inhibition values were then used to determine $IC_{50}$, slope factor (n) and maximum inhibition ($I_{max}$) by the non-linear regression routine NLIN procedure of SAS using the following equation:

$$\% \cdot \text{inhibition} = \frac{I_{max} \times [\text{inhibitor}]^n}{[\text{inhibitor}]^n + IC_{50}^n}$$

Compound A was tested in the assay at least 4 times. The $IC_{50}$ curves were analyzed individually by the SAS nonlinear regression analysis. FIG. 8 shows a typical curve and Table 2 shows the individual and average $IC_{50}$ values of compound A. The average $IC_{50}$ of compound A in the replication assay was 1.1 nM.

TABLE 2

$IC_{50}$ of compound A in the S22.3 Cell line Replicon Assay.

| Compound | $IC_{50}$ (nM) | Average $IC_{50}$ (nM) |
|---|---|---|
| A | 1.2 | |
|  | 1.2 | |
|  | 1.0 | |
|  | 0.9 | |
|  |  | 1.1 ± 0.2 |

Discussion

The reproducible and robust ex vivo propagation of hepatitis C virus, to levels required for the accurate testing of potential anti-viral compounds, has not been achieved with any system. As an alternative approach to studying the molecular mechanisms of hepatitis C virus RNA replication, selectable self-replicating bi-cistronic RNAs were developed (Lohman et al., 1999, Science 285, 110-113; Bartenschlager, R. et al., 1993, J. Virol., 67, 3835-3844 CA 2,303,526). Minimally, these replicons encode for some or all of the non-structural proteins and also carry a selectable marker such as the neomycin phosphotransferase. Though intracellular steady-state levels of these sub-genomic replicon RNAs among the selected clones is moderate to high, the frequency of generating G418-resistant colonies upon transfection of the consensus RNA described by Lohman et al. or Bartenschlager, R. et al., 1993, J. Virol., 67, 3835-3844 is very low. Less than 100 colonies are generated when 8 million cells are transfected with 1 µg of in vitro transcribed bi-cistronic replicon RNA. A low efficiency of colony formation was first noted by Lohmann et al (1999 et al, Science 285, 110-113). Since then, Lohmann et al. (2001) J. Virol. 1437-1449, Blight et al. 2000, Science 290, 1972-1974, and Guo et al., (2001) J. Virol. 8516-8523, have isolated sub-genomic RNAs with markedly improved efficiencies in the colony formation assay. Lohmann et al., 1999 Science 285, 110-113 originally reported that selection of sub genomic replicons may not involve the selection of adaptive mutants as serially passaged RNA did not demonstrate an improved transfection efficiency. Nevertheless, in an effort to characterize the function and fitness of replicating HCV RNA, we serially passaged the replicon RNA that was isolated from the first selected cell-line. Notably, a significant increase in colony forming efficiency was obtained from this experiment, even though the quantity of replicon RNA was orders of magnitude lower than originally used to transfect the in vitro transcribed RNA. Furthermore, a second round serial passage of replicon RNA from this first generation clone into naive Huh-7 cells provided for yet another increase in colony formation efficiency (Table 1).

Our analysis of replicating HCV RNAs identified several adaptive mutations that enhance the efficiency of colony formation by up to 4 orders of magnitude. Adaptive mutations were found in many non-structural proteins, as well as in the 5' non-translated region. The substitution of the 5'-GG doublet for a 5'-A as the inaugurating nucleotide of the HCV 5'-UTR is a variant of the HCV genome that has not been previously described, despite the sequencing of innumerable genotypes and subtypes from across the world. Our original replicon that carried a 5'-GG evolved to variants with either a single 5'-A or 5'-G, both of which showed equal transduction efficiency. We describe here the first report of a HCV genome that can tolerate and stably maintain a 5'A extremity. Moreover, we were successful in re-introducing this defined single nucleotide substitution into our cDNA clone and generate in vitro transcribed RNA harboring such an extremity to confirm that a 5'A functions as efficiently as a 5'G.

We have identified adaptive amino acid substitutions in the HCV non-structural proteins NS3, NS4A and NS5A in the R3 replicon, and a substitution in NS5B in the R7 clone (see FIG. 5B). These mutations, particularly the combination defined by the R3-rep (SEQ ID NO. 7), when reconstituted into a cDNA clone and transcribed onto a RNA replicon, result in a significantly enhanced transduction efficiency of up to 20,000 fold from the original wild type APGK12 replicon RNA. However, the steady state levels of intracellular replicon RNA were comparable from each of the different isolated clones. This result suggests that the increase in replication efficiency by the adaptive mutations does not result in higher stable intracellular RNA levels due to higher RNA replication, but rather confers increased permissivity for establishing the replicon in a greater number of Huh7 cells. Such a phenotype may be manifested transiently, through an initial increase of the amount of de novo replication, that is required to surpass a defined threshold to establish persistently replicating RNAs within a population of dividing cells.

Recently three other groups also identified other distinct adaptive mutants. Lohmann et al. (2000) reported enhanced transduction efficiencies of up to 10,000 fold with mutations in NS3, NS4B, NS5A and NS5B. Blight et al. 2000, Science 290:1972-1974 reported an augmentation of transduction efficiencies up to 20,000 fold with a single mutation in NS5A whereas Guo et al., (2001) J. Virol. 8516-8523 reported increases in transduction efficiencies of 5,000-10,000 fold with a deletion of a single amino acid in NS5A. The amino acid substitutions that we describe here have not previously been identified as adaptive mutants that enhance the efficiency of RNA transfection and/or replication. One exception is the mutation of E1202G in NS3 that we found in both the R7 and R16 replicons. This adaptation was previously described by Guo et al., (2001) J. Virol. 8516-8523 and Krieger et al (2001) J. Virol. 4614-4624. All other adaptive mutations, without exception, described herein are unpublished.

The development of selectable subgenomic HCV replicons has provided for potential avenues of exploration on HCV RNA replication, persistence, and pathogenesis in cultured cells. However, the low transduction efficiency with the HCV RNA-containing replicons as originally described (Lohmann et al., 1999 Science 285: 110-113) showed that it was not a practical system for reverse genetics studies. The adaptive mutants described herein overcome the low transduction efficiency. In light of the recent descriptions of adaptive mutants by other groups, we note that adaptation can be achieved by distinct mutations in different HCV NS proteins, although the level of adaptation can vary drastically. The replicons encoding adaptive mutants that are described herein are ideally suited for reverse genetic studies to identify novel HCV targets or host cell targets that may modulate HCV RNA replication or HCV replicon RNA colony formation. The adapted and highly efficient replicons are suitable tools for characterizing subtle genotypic or phenotypic changes that affect an easily quantifiable transduction efficiency.

Lastly, we have used our adapted HCV sub genomic replicon cell-line to demonstrate the proficient inhibition of HCV RNA replication by a specific small molecule inhibitor of the HCV NS3 protease. This is the first demonstration that an antiviral, designed to specifically inhibit one of the HCV non-structural proteins, inhibits HCV RNA replication in cell culture. Moreover, this compound and our S22.3 cell line validate the proposal that RNA replication is directed by the HCV non-structural proteins NS3 to NS5B. The assay that we have described and validated will be extremely useful in characterizing other inhibitors of HCV non-structural protein function in cell culture in a high throughput fashion.

All references found throughout the present disclosure are herein incorporated by reference whether they be found in the following list or not.

The invention claimed is:

1. An isolated host cell transfected with a self-replicating polynucleotide comprising:
(a) a 5'-Non Translated Region;
(b) a HCV polynucleotide coding region encoding an HCV polyprotein comprising: NS3, NS4A, NS4B, NS5A, and NS5B proteins, said polynucleotide coding region comprising SEQ ID NO. 4 or SEQ ID NO. 7, and
(c) a 3'-Non Translated Region.

2. The host cell according to claim 1, wherein the host cell is a eukaryotic cell line.

3. The host cell according to claim 2, wherein said eukaryotic cell line is a hepatic cell line.

4. The host cell according to claim 3, wherein said hepatic cell line is Huh-7.

5. The isolated host cell transfected with a self-replicating polynucleotide according to claim 1, wherein the 5'-Non Translated Region is ACCAGC (SEQ ID No. 8).

6. The isolated host cell transfected with a self-replicating polynucleotide according to claim 1, wherein the 5'-Non Translated Region is GCCAGC (SEQ ID No. 27).

7. A RNA replication assay comprising the steps of:
(a) incubating the host cell according to claim 1 under conditions suitable for RNA replication;
(b) isolating the total cellular RNA from the cells; and
(c) analyzing the RNA so as to measure the amount of HCV RNA replicated.

8. The assay according to claim 7, wherein the analysis of RNA levels in step (c) is carried out by amplifying the RNA by real-time RT-PCR analysis using HCV specific primers so as to measure the amount of HCV RNA replicated.

9. The assay according to claim 7, wherein said polynucleotide encodes for a reporter gene, and the analysis of RNA levels in step (c) is carried out by assessing the level of reporter expressed.

10. A method for testing a compound for inhibiting HCV replication, including the steps of:
(a) incubating the host cell according to claim 1 under conditions suitable for RNA replication in the presence or absence of the compound;
(b) isolating the total cellular RNA from the cells;
(c) analyzing the RNA so as to measure the amount of HCV RNA replicated; and
(d) comparing the levels of HCV RNA in cells in the absence and presence of the inhibitor,
wherein reduced RNA levels is indicative of the ability of the compound to inhibit replication.

11. The method according to claim 10, wherein said cell is incubated with the test compound for about 3-4 days at a temperature of about 37° C.

* * * * *

SEQUENCE LISTING

```
<160> NUMBER OF SEQ ID NOS: 29

<210> SEQ ID NO 1
<211> LENGTH: 8639
<212> TYPE: DNA
<213> ORGANISM: Hepatitis C virus
<220> FEATURE:
<221> NAME/KEY: CDS
<222> LOCATION: (1803)...(8408)

<400> SEQUENCE: 1
ggccagcccc cgattggggg cgacactcca ccatagatca ctccctgtg aggaactact        60 gtcttcacgc agaaagcgtc tagccatggc gttagtatga gtgtcgtgca gcctccagga      120 cccccctcc cgggagagcc atagtggtct gcggaaccgt gagtacacc ggaattgcca       180 ggacgaccgg gtcctttctt ggatcaaccc gctcaatgcc tggagatttg gcgtgcccc       240 cgcgagactc tagccgagt agtgttgggt cgcgaaaggc cttgtggtac tgcctgatag       300
ggtgcttgcg agtgccccgg gaggtctcgt agaccgtgca ccatgagcac gaatcctaaa      360
cctcaaagaa aaaccaaagg gcgcgccatg attgaacaag atggattgca cgcaggttct      420
ccggccgctt gggtggagag gctattcggc tatgactggg cacaacagac aatcggctgc      480
tctgatgccg ccgtgttccg gctgtcagcg caggggcgcc cggttctttt tgtcaagacc      540
gacctgtccg gtgccctgaa tgaactgcag gacgaggcag cgcggctatc gtggctggcc      600
acgacgggcg ttccttgcgc agctgtgctc gacgttgtca ctgaagcggg aagggactgg      660
ctgctattgg gcgaagtgcc ggggcaggat ctcctgtcat ctcaccttgc tcctgccgag      720
aaagtatcca tcatggctga tgcaatgcgg cggctgcata cgcttgatcc ggctacctgc      780
ccattcgacc accaagcgaa acatcgcatc gagcgagcac gtactcggat ggaagccggt      840
cttgtcgatc aggatgatct ggacgaagag catcaggggc tcgcgccagc cgaactgttc      900
gccaggctca aggcgcgcat gcccgacggc gaggatctcg tcgtgaccca tggcgatgcc      960
tgcttgccga atatcatggt ggaaaatggc cgcttttctg gattcatcga ctgtggccgg     1020
ctgggtgtgg cggaccgcta tcaggacata gcgttggcta cccgtgatat tgctgaagag     1080
cttggcggcg aatgggctga ccgcttcctc gtgctttacg gtatcgccgc tcccgattcg     1140
cagcgcatcg ccttctatcg ccttcttgac gagttcttct gagttcgcgc ccagatgtta     1200
acagaccaca acggtttccc tctagcggga tcaattccgc ccccccct aacgttactg      1260 gccgaagccg cttggaataa ggccggtgtg cgtttgtcta tatgttattt tccaccatat     1320
tgccgtcttt tggcaatgtg agggcccgga aacctggccc tgtcttcttg acgagcattc     1380
ctaggggtct ttcccctctc gccaaaggaa tgcaaggtct gttgaatgtc gtgaaggaag     1440
cagttcctct ggaagcttct tgaagacaaa caacgtctgt agcgaccctt gcaggcagc      1500 ggaacccccc acctggcgac aggtgcctct gcggccaaaa gccacgtgta taagatacac     1560
ctgcaaaggc ggcacaaccc cagtgccacg ttgtgagttg atagttgtg gaaagagtca      1620 aatggctctc ctcaagcgta ttcaacaagg gctgaagga tgcccagaag gtaccccatt      1680
gtatgggatc tgatctgggg cctcggtgca catgctttac atgtgtttag tcgaggttaa     1740
```

-continued

```
aaaacgtcta ggccccccga accacgggga cgtggttttc ctttgaaaaa cacgataata      1800
```

| | | | | | | | | | | | | | | | | |
|---|---|---|---|---|---|---|---|---|---|---|---|---|---|---|---|---|
| cc | atg | gac | cgg | gag | atg | gca | gca | tcg | tgc | gga | ggc | gcg | gtt | ttc | gta | 1847 |
| | Met | Asp | Arg | Glu | Met | Ala | Ala | Ser | Cys | Gly | Gly | Ala | Val | Phe | Val | |
| | 1 | | | | 5 | | | | | 10 | | | | | 15 | |

| | | | | | | | | | | | | | | | |
|---|---|---|---|---|---|---|---|---|---|---|---|---|---|---|---|
| ggt | ctg | ata | ctc | ttg | acc | ttg | tca | ccg | cac | tat | aag | ctg | ttc | ctc | gct | 1895 |
| Gly | Leu | Ile | Leu | Leu | Thr | Leu | Ser | Pro | His | Tyr | Lys | Leu | Phe | Leu | Ala | |
| | | | | 20 | | | | | 25 | | | | | 30 | | |

| | | | | | | | | | | | | | | | |
|---|---|---|---|---|---|---|---|---|---|---|---|---|---|---|---|
| agg | ctc | ata | tgg | tgg | tta | caa | tat | ttt | atc | acc | agg | gcc | gag | gca | cac | 1943 |
| Arg | Leu | Ile | Trp | Trp | Leu | Gln | Tyr | Phe | Ile | Thr | Arg | Ala | Glu | Ala | His | |
| | | | | 35 | | | | | 40 | | | | | 45 | | |

| | | | | | | | | | | | | | | | |
|---|---|---|---|---|---|---|---|---|---|---|---|---|---|---|---|
| ttg | caa | gtg | tgg | atc | ccc | ccc | ctc | aac | gtt | cgg | ggg | ggc | cgc | gat | gcc | 1991 |
| Leu | Gln | Val | Trp | Ile | Pro | Pro | Leu | Asn | Val | Arg | Gly | Gly | Arg | Asp | Ala | |
| | | 50 | | | | | 55 | | | | | 60 | | | | |

| | | | | | | | | | | | | | | | |
|---|---|---|---|---|---|---|---|---|---|---|---|---|---|---|---|
| gtc | atc | ctc | ctc | acg | tgc | gcg | atc | cac | cca | gag | cta | atc | ttt | acc | atc | 2039 |
| Val | Ile | Leu | Leu | Thr | Cys | Ala | Ile | His | Pro | Glu | Leu | Ile | Phe | Thr | Ile | |
| | 65 | | | | | 70 | | | | | 75 | | | | | |

| | | | | | | | | | | | | | | | |
|---|---|---|---|---|---|---|---|---|---|---|---|---|---|---|---|
| acc | aaa | atc | ttg | ctc | gcc | ata | ctc | ggt | cca | ctc | atg | gtg | ctc | cag | gct | 2087 |
| Thr | Lys | Ile | Leu | Leu | Ala | Ile | Leu | Gly | Pro | Leu | Met | Val | Leu | Gln | Ala | |
| 80 | | | | | 85 | | | | | 90 | | | | | 95 | |

| | | | | | | | | | | | | | | | |
|---|---|---|---|---|---|---|---|---|---|---|---|---|---|---|---|
| ggt | ata | acc | aaa | gtg | ccg | tac | ttc | gtg | cgc | gca | cac | ggg | ctc | att | cgt | 2135 |
| Gly | Ile | Thr | Lys | Val | Pro | Tyr | Phe | Val | Arg | Ala | His | Gly | Leu | Ile | Arg | |
| | | | 100 | | | | | 105 | | | | | 110 | | | |

| | | | | | | | | | | | | | | | |
|---|---|---|---|---|---|---|---|---|---|---|---|---|---|---|---|
| gca | tgc | atg | ctg | gtg | cgg | aag | gtt | gct | ggg | ggt | cat | tat | gtc | caa | atg | 2183 |
| Ala | Cys | Met | Leu | Val | Arg | Lys | Val | Ala | Gly | Gly | His | Tyr | Val | Gln | Met | |
| | | | 115 | | | | | 120 | | | | | 125 | | | |

| | | | | | | | | | | | | | | | |
|---|---|---|---|---|---|---|---|---|---|---|---|---|---|---|---|
| gct | ctc | atg | aag | ttg | gcc | gca | ctg | aca | ggt | acg | tac | gtt | tat | gac | cat | 2231 |
| Ala | Leu | Met | Lys | Leu | Ala | Ala | Leu | Thr | Gly | Thr | Tyr | Val | Tyr | Asp | His | |
| | 130 | | | | | 135 | | | | | 140 | | | | | |

| | | | | | | | | | | | | | | | |
|---|---|---|---|---|---|---|---|---|---|---|---|---|---|---|---|
| ctc | acc | cca | ctg | cgg | gac | tgg | gcc | cac | gcg | ggc | cta | cga | gac | ctt | gcg | 2279 |
| Leu | Thr | Pro | Leu | Arg | Asp | Trp | Ala | His | Ala | Gly | Leu | Arg | Asp | Leu | Ala | |
| 145 | | | | | 150 | | | | | 155 | | | | | | |

| | | | | | | | | | | | | | | | |
|---|---|---|---|---|---|---|---|---|---|---|---|---|---|---|---|
| gtg | gca | gtt | gag | ccc | gtc | gtc | ttc | tct | gat | atg | gag | acc | aag | gtt | atc | 2327 |
| Val | Ala | Val | Glu | Pro | Val | Val | Phe | Ser | Asp | Met | Glu | Thr | Lys | Val | Ile | |
| 160 | | | | 165 | | | | | 170 | | | | | 175 | | |

| | | | | | | | | | | | | | | | |
|---|---|---|---|---|---|---|---|---|---|---|---|---|---|---|---|
| acc | tgg | ggg | gca | gac | acc | gcg | gcg | tgt | ggg | gac | atc | atc | ttg | ggc | ctg | 2375 |
| Thr | Trp | Gly | Ala | Asp | Thr | Ala | Ala | Cys | Gly | Asp | Ile | Ile | Leu | Gly | Leu | |
| | | | | 180 | | | | | 185 | | | | | 190 | | |

| | | | | | | | | | | | | | | | |
|---|---|---|---|---|---|---|---|---|---|---|---|---|---|---|---|
| ccc | gtc | tcc | gcc | cgc | agg | ggg | agg | gag | ata | cat | ctg | gga | ccg | gca | gac | 2423 |
| Pro | Val | Ser | Ala | Arg | Arg | Gly | Arg | Glu | Ile | His | Leu | Gly | Pro | Ala | Asp | |
| | | | 195 | | | | | 200 | | | | | 205 | | | |

| | | | | | | | | | | | | | | | |
|---|---|---|---|---|---|---|---|---|---|---|---|---|---|---|---|
| agc | ctt | gaa | ggg | cag | ggg | tgg | cga | ctc | ctc | gcg | cct | att | acg | gcc | tac | 2471 |
| Ser | Leu | Glu | Gly | Gln | Gly | Trp | Arg | Leu | Leu | Ala | Pro | Ile | Thr | Ala | Tyr | |
| | | 210 | | | | | 215 | | | | | 220 | | | | |

| | | | | | | | | | | | | | | | |
|---|---|---|---|---|---|---|---|---|---|---|---|---|---|---|---|
| tcc | caa | cag | acg | cga | ggc | cta | ctt | ggc | tgc | atc | atc | act | agc | ctc | aca | 2519 |
| Ser | Gln | Gln | Thr | Arg | Gly | Leu | Leu | Gly | Cys | Ile | Ile | Thr | Ser | Leu | Thr | |
| | 225 | | | | | 230 | | | | | 235 | | | | | |

| | | | | | | | | | | | | | | | |
|---|---|---|---|---|---|---|---|---|---|---|---|---|---|---|---|
| ggc | cgg | gac | agg | aac | cag | gtc | gag | ggg | gag | gtc | caa | gtg | gtc | tcc | acc | 2567 |
| Gly | Arg | Asp | Arg | Asn | Gln | Val | Glu | Gly | Glu | Val | Gln | Val | Val | Ser | Thr | |
| 240 | | | | | 245 | | | | | 250 | | | | | 255 | |

| | | | | | | | | | | | | | | | |
|---|---|---|---|---|---|---|---|---|---|---|---|---|---|---|---|
| gca | aca | caa | tct | ttc | ctg | gcg | acc | tgc | gtc | aat | ggc | gtg | tgt | tgg | act | 2615 |
| Ala | Thr | Gln | Ser | Phe | Leu | Ala | Thr | Cys | Val | Asn | Gly | Val | Cys | Trp | Thr | |
| | | | | 260 | | | | | 265 | | | | | 270 | | |

| | | | | | | | | | | | | | | | |
|---|---|---|---|---|---|---|---|---|---|---|---|---|---|---|---|
| gtc | tat | cat | ggt | gcc | ggc | tca | aag | acc | ctt | gcc | ggc | cca | aag | ggc | cca | 2663 |
| Val | Tyr | His | Gly | Ala | Gly | Ser | Lys | Thr | Leu | Ala | Gly | Pro | Lys | Gly | Pro | |
| | | | 275 | | | | | 280 | | | | | 285 | | | |

| | | | | | | | | | | | | | | | |
|---|---|---|---|---|---|---|---|---|---|---|---|---|---|---|---|
| atc | acc | caa | atg | tac | acc | aat | gtg | gac | cag | gac | ctc | gtc | ggc | tgg | caa | 2711 |
| Ile | Thr | Gln | Met | Tyr | Thr | Asn | Val | Asp | Gln | Asp | Leu | Val | Gly | Trp | Gln | |
| | | 290 | | | | | 295 | | | | | 300 | | | | |

| | | | | | | | | | | | | | | | |
|---|---|---|---|---|---|---|---|---|---|---|---|---|---|---|---|
| gcg | ccc | ccc | ggg | gcg | cgt | tcc | ttg | aca | cca | tgc | acc | tgc | ggc | agc | tcg | 2759 |
| Ala | Pro | Pro | Gly | Ala | Arg | Ser | Leu | Thr | Pro | Cys | Thr | Cys | Gly | Ser | Ser | |

```
                                            305                         310                         315
gac  ctt  tac  ttg  gtc  acg  agg  cat  gcc  gat  gtc  att  ccg  gtg  cgc  cgg    2807
Asp  Leu  Tyr  Leu  Val  Thr  Arg  His  Ala  Asp  Val  Ile  Pro  Val  Arg  Arg
320                      325                         330                       335 cgg  ggc  gac  agc  agg  ggg  agc  cta  ctc  tcc  ccc  agg  ccc  gtc  tcc  tac    2855
Arg  Gly  Asp  Ser  Arg  Gly  Ser  Leu  Leu  Ser  Pro  Arg  Pro  Val  Ser  Tyr
                    340                      345                         350 ttg  aag  ggc  tct  tcg  ggc  ggt  cca  ctg  ctc  tgc  ccc  tcg  ggc  cac  gct    2903
Leu  Lys  Gly  Ser  Ser  Gly  Gly  Pro  Leu  Leu  Cys  Pro  Ser  Gly  His  Ala
                         355                      360                         365 gtg  ggc  atc  ttt  cgg  gct  gcc  gtg  tgc  acc  cga  ggg  gtt  gcg  aag  gcg    2951
Val  Gly  Ile  Phe  Arg  Ala  Ala  Val  Cys  Thr  Arg  Gly  Val  Ala  Lys  Ala
                              370                      375                         380 gtg  gac  ttt  gta  ccc  gtc  gag  tct  atg  gaa  acc  act  atg  cgg  tcc  ccg    2999
Val  Asp  Phe  Val  Pro  Val  Glu  Ser  Met  Glu  Thr  Thr  Met  Arg  Ser  Pro
385                      390                         395 gtc  ttc  acg  gac  aac  tcg  tcc  cct  ccg  gcc  gta  ccg  cag  aca  ttc  cag    3047
Val  Phe  Thr  Asp  Asn  Ser  Ser  Pro  Pro  Ala  Val  Pro  Gln  Thr  Phe  Gln
400                      405                         410                       415 gtg  gcc  cat  cta  cac  gcc  cct  act  ggt  agc  ggc  aag  agc  act  aag  gtg    3095
Val  Ala  His  Leu  His  Ala  Pro  Thr  Gly  Ser  Gly  Lys  Ser  Thr  Lys  Val
                    420                      425                         430 ccg  gct  gcg  tat  gca  gcc  caa  ggg  tat  aag  gtg  ctt  gtc  ctg  aac  ccg    3143
Pro  Ala  Ala  Tyr  Ala  Ala  Gln  Gly  Tyr  Lys  Val  Leu  Val  Leu  Asn  Pro
                         435                      440                         445 tcc  gtc  gcc  gcc  acc  cta  ggt  ttc  ggg  gcg  tat  atg  tct  aag  gca  cat    3191
Ser  Val  Ala  Ala  Thr  Leu  Gly  Phe  Gly  Ala  Tyr  Met  Ser  Lys  Ala  His
                              450                      455                         460 ggt  atc  gac  cct  aac  atc  aga  acc  ggg  gta  agg  acc  atc  acc  acg  ggt    3239
Gly  Ile  Asp  Pro  Asn  Ile  Arg  Thr  Gly  Val  Arg  Thr  Ile  Thr  Thr  Gly
465                      470                         475 gcc  ccc  atc  acg  tac  tcc  acc  tat  ggc  aag  ttt  ctt  gcc  gac  ggt  ggt    3287
Ala  Pro  Ile  Thr  Tyr  Ser  Thr  Tyr  Gly  Lys  Phe  Leu  Ala  Asp  Gly  Gly
480                      485                         490                       495 tgc  tct  ggg  ggc  gcc  tat  gac  atc  ata  ata  tgt  gat  gag  tgc  cac  tca    3335
Cys  Ser  Gly  Gly  Ala  Tyr  Asp  Ile  Ile  Ile  Cys  Asp  Glu  Cys  His  Ser
                    500                      505                         510 act  gac  tcg  acc  act  atc  ctg  ggc  atc  ggc  aca  gtc  ctg  gac  caa  gcg    3383
Thr  Asp  Ser  Thr  Thr  Ile  Leu  Gly  Ile  Gly  Thr  Val  Leu  Asp  Gln  Ala
                         515                      520                         525 gag  acg  gct  gga  gcg  cga  ctc  gtc  gtg  ctc  gcc  acc  gct  acg  cct  ccg    3431
Glu  Thr  Ala  Gly  Ala  Arg  Leu  Val  Val  Leu  Ala  Thr  Ala  Thr  Pro  Pro
                              530                      535                         540 gga  tcg  gtc  acc  gtg  cca  cat  cca  aac  atc  gag  gag  gtg  gct  ctg  tcc    3479
Gly  Ser  Val  Thr  Val  Pro  His  Pro  Asn  Ile  Glu  Glu  Val  Ala  Leu  Ser
545                      550                         555 agc  act  gga  gaa  atc  ccc  ttt  tat  ggc  aaa  gcc  atc  ccc  atc  gag  acc    3527
Ser  Thr  Gly  Glu  Ile  Pro  Phe  Tyr  Gly  Lys  Ala  Ile  Pro  Ile  Glu  Thr
560                      565                         570                       575 atc  aag  ggg  ggg  agg  cac  ctc  att  ttc  tgc  cat  tcc  aag  aag  aaa  tgt    3575
Ile  Lys  Gly  Gly  Arg  His  Leu  Ile  Phe  Cys  His  Ser  Lys  Lys  Lys  Cys
                         580                      585                         590 gat  gag  ctc  gcc  gcg  aag  ctg  tcc  ggc  ctc  gga  ctc  aat  gct  gta  gca    3623
Asp  Glu  Leu  Ala  Ala  Lys  Leu  Ser  Gly  Leu  Gly  Leu  Asn  Ala  Val  Ala
                              595                      600                         605 tat  tac  cgg  ggc  ctt  gat  gta  tcc  gtc  ata  cca  act  agc  gga  gac  gtc    3671
Tyr  Tyr  Arg  Gly  Leu  Asp  Val  Ser  Val  Ile  Pro  Thr  Ser  Gly  Asp  Val
                    610                      615                         620 att  gtc  gta  gca  acg  gac  gct  cta  atg  acg  ggc  ttt  acc  ggc  gat  ttc    3719
Ile  Val  Val  Ala  Thr  Asp  Ala  Leu  Met  Thr  Gly  Phe  Thr  Gly  Asp  Phe
```

```
              625                 630                 635
gac tca gtg atc gac tgc aat aca tgt gtc acc cag aca gtc gac ttc      3767
Asp Ser Val Ile Asp Cys Asn Thr Cys Val Thr Gln Thr Val Asp Phe
640                 645                 650                 655 agc ctg gac ccg acc ttc acc att gag acg acg acc gtg cca caa gac      3815
Ser Leu Asp Pro Thr Phe Thr Ile Glu Thr Thr Thr Val Pro Gln Asp
                    660                 665                 670 gcg gtg tca cgc tcg cag cgg cga ggc agg act ggt agg ggc agg atg      3863
Ala Val Ser Arg Ser Gln Arg Arg Gly Arg Thr Gly Arg Gly Arg Met
                675                 680                 685 ggc att tac agg ttt gtg act cca gga gaa cgg ccc tcg ggc atg ttc      3911
Gly Ile Tyr Arg Phe Val Thr Pro Gly Glu Arg Pro Ser Gly Met Phe
            690                 695                 700 gat tcc tcg gtt ctg tgc gag tgc tat gac gcg ggc tgt gct tgg tac      3959
Asp Ser Ser Val Leu Cys Glu Cys Tyr Asp Ala Gly Cys Ala Trp Tyr
        705                 710                 715 gag ctc acg ccc gcc gag acc tca gtt agg ttg cgg gct tac cta aac      4007
Glu Leu Thr Pro Ala Glu Thr Ser Val Arg Leu Arg Ala Tyr Leu Asn
720                 725                 730                 735 aca cca ggg ttg ccc gtc tgc cag gac cat ctg gag ttc tgg gag agc      4055
Thr Pro Gly Leu Pro Val Cys Gln Asp His Leu Glu Phe Trp Glu Ser
                    740                 745                 750 gtc ttt aca ggc ctc acc cac ata gac gcc cat ttc ttg tcc cag act      4103
Val Phe Thr Gly Leu Thr His Ile Asp Ala His Phe Leu Ser Gln Thr
                755                 760                 765 aag cag gca gga gac aac ttc ccc tac ctg gta gca tac cag gct acg      4151
Lys Gln Ala Gly Asp Asn Phe Pro Tyr Leu Val Ala Tyr Gln Ala Thr
            770                 775                 780 gtg tgc gcc agg gct cag gct cca cct cca tcg tgg gac caa atg tgg      4199
Val Cys Ala Arg Ala Gln Ala Pro Pro Pro Ser Trp Asp Gln Met Trp
        785                 790                 795 aag tgt ctc ata cgg cta aag cct acg ctg cac ggg cca acg ccc ctg      4247
Lys Cys Leu Ile Arg Leu Lys Pro Thr Leu His Gly Pro Thr Pro Leu
800                 805                 810                 815 ctg tat agg ctg gga gcc gtt caa aac gag gtt act acc aca cac ccc      4295
Leu Tyr Arg Leu Gly Ala Val Gln Asn Glu Val Thr Thr Thr His Pro
                    820                 825                 830 ata acc aaa tac atc atg gca tgc atg tcg gct gac ctg gag gtc gtc      4343
Ile Thr Lys Tyr Ile Met Ala Cys Met Ser Ala Asp Leu Glu Val Val
                835                 840                 845 acg agc acc tgg gtg ctg gta ggc gga gtc cta gca gct ctg gcc gcg      4391
Thr Ser Thr Trp Val Leu Val Gly Gly Val Leu Ala Ala Leu Ala Ala
            850                 855                 860 tat tgc ctg aca aca ggc agc gtg gtc att gtg ggc agg atc atc ttg      4439
Tyr Cys Leu Thr Thr Gly Ser Val Val Ile Val Gly Arg Ile Ile Leu
        865                 870                 875 tcc gga aag ccg gcc atc att ccc gac agg gaa gtc ctt tac cgg gag      4487
Ser Gly Lys Pro Ala Ile Ile Pro Asp Arg Glu Val Leu Tyr Arg Glu
880                 885                 890                 895 ttc gat gag atg gaa gag tgc gcc tca cac ctc cct tac atc gaa cag      4535
Phe Asp Glu Met Glu Glu Cys Ala Ser His Leu Pro Tyr Ile Glu Gln
                    900                 905                 910 gga atg cag ctc gcc gaa caa ttc aaa cag aag gca atc ggg ttg ctg      4583
Gly Met Gln Leu Ala Glu Gln Phe Lys Gln Lys Ala Ile Gly Leu Leu
                915                 920                 925 caa aca gcc acc aag caa gcg gag gct gct gct ccc gtg gtg gaa tcc      4631
Gln Thr Ala Thr Lys Gln Ala Glu Ala Ala Ala Pro Val Val Glu Ser
            930                 935                 940 aag tgg cgg acc ctc gaa gcc ttc tgg gcg aag cat atg tgg aat ttc      4679
Lys Trp Arg Thr Leu Glu Ala Phe Trp Ala Lys His Met Trp Asn Phe
```

```
                945                 950                 955
atc agc ggg ata caa tat tta gca ggc ttg tcc act ctg cct ggc aac      4727
Ile Ser Gly Ile Gln Tyr Leu Ala Gly Leu Ser Thr Leu Pro Gly Asn
960                 965                 970                 975 ccc gcg ata gca tca ctg atg gca ttc aca gcc tct atc acc agc ccg      4775
Pro Ala Ile Ala Ser Leu Met Ala Phe Thr Ala Ser Ile Thr Ser Pro
            980                 985                 990 ctc acc acc caa cat acc ctc ctg ttt aac atc ctg ggg gga tgg gtg      4823
Leu Thr Thr Gln His Thr Leu Leu Phe Asn Ile Leu Gly Gly Trp Val
                995                 1000                1005 gcc gcc caa ctt gct cct ccc agc gct gct tct gct ttc gta ggc gcc      4871
Ala Ala Gln Leu Ala Pro Pro Ser Ala Ala Ser Ala Phe Val Gly Ala
            1010                1015                1020 ggc atc gct gga gcg gct gtt ggc agc ata ggc ctt ggg aag gtg ctt      4919
Gly Ile Ala Gly Ala Ala Val Gly Ser Ile Gly Leu Gly Lys Val Leu
            1025                1030                1035 gtg gat att ttg gca ggt tat gga gca ggg gtg gca ggc gcg ctc gtg      4967
Val Asp Ile Leu Ala Gly Tyr Gly Ala Gly Val Ala Gly Ala Leu Val
1040                1045                1050                1055 gcc ttt aag gtc atg agc ggc gag atg ccc tcc acc gag gac ctg gtt      5015
Ala Phe Lys Val Met Ser Gly Glu Met Pro Ser Thr Glu Asp Leu Val
            1060                1065                1070 aac cta ctc cct gct atc ctc tcc cct ggc gcc cta gtc gtc ggg gtc      5063
Asn Leu Leu Pro Ala Ile Leu Ser Pro Gly Ala Leu Val Val Gly Val
                1075                1080                1085 gtg tgc gca gcg ata ctg cgt cgg cac gtg ggc cca ggg gag ggg gct      5111
Val Cys Ala Ala Ile Leu Arg Arg His Val Gly Pro Gly Glu Gly Ala
            1090                1095                1100 gtg cag tgg atg aac cgg ctg ata gcg ttc gct tcg cgg ggt aac cac      5159
Val Gln Trp Met Asn Arg Leu Ile Ala Phe Ala Ser Arg Gly Asn His
            1105                1110                1115 gtc tcc ccc acg cac tat gtg cct gag agc gac gct gca gca cgt gtc      5207
Val Ser Pro Thr His Tyr Val Pro Glu Ser Asp Ala Ala Ala Arg Val
1120                1125                1130                1135 act cag atc ctc tct agt ctt acc atc act cag ctg ctg aag agg ctt      5255
Thr Gln Ile Leu Ser Ser Leu Thr Ile Thr Gln Leu Leu Lys Arg Leu
                1140                1145                1150 cac cag tgg atc aac gag gac tgc tcc acg cca tgc tcc ggc tcg tgg      5303
His Gln Trp Ile Asn Glu Asp Cys Ser Thr Pro Cys Ser Gly Ser Trp
            1155                1160                1165 cta aga gat gtt tgg gat tgg ata tgc acg gtg ttg act gat ttc aag      5351
Leu Arg Asp Val Trp Asp Trp Ile Cys Thr Val Leu Thr Asp Phe Lys
            1170                1175                1180 acc tgg ctc cag tcc aag ctc ctg ccg cga ttg ccg gga gtc ccc ttc      5399
Thr Trp Leu Gln Ser Lys Leu Leu Pro Arg Leu Pro Gly Val Pro Phe
            1185                1190                1195 ttc tca tgt caa cgt ggg tac aag gga gtc tgg cgg ggc gac ggc atc      5447
Phe Ser Cys Gln Arg Gly Tyr Lys Gly Val Trp Arg Gly Asp Gly Ile
1200                1205                1210                1215 atg caa acc acc tgc cca tgt gga gca cag atc acc gga cat gtg aaa      5495
Met Gln Thr Thr Cys Pro Cys Gly Ala Gln Ile Thr Gly His Val Lys
            1220                1225                1230 aac ggt tcc atg agg atc gtg ggg cct agg acc tgt agt aac acg tgg      5543
Asn Gly Ser Met Arg Ile Val Gly Pro Arg Thr Cys Ser Asn Thr Trp
            1235                1240                1245 cat gga aca ttc ccc att aac gcg tac acc acg ggc ccc tgc acg ccc      5591
His Gly Thr Phe Pro Ile Asn Ala Tyr Thr Thr Gly Pro Cys Thr Pro
            1250                1255                1260 tcc ccg gcg cca aat tat tct agg gcg ctg tgg cgg gtg gct gct gag      5639
Ser Pro Ala Pro Asn Tyr Ser Arg Ala Leu Trp Arg Val Ala Ala Glu
```

-continued

```
                    1265                1270                1275
gag tac gtg gag gtt acg cgg gtg ggg gat ttc cac tac gtg acg ggc    5687
Glu Tyr Val Glu Val Thr Arg Val Gly Asp Phe His Tyr Val Thr Gly
1280                1285                1290                1295 atg acc act gac aac gta aag tgc ccg tgt cag gtt ccg gcc ccc gaa    5735
Met Thr Thr Asp Asn Val Lys Cys Pro Cys Gln Val Pro Ala Pro Glu
                    1300                1305                1310 ttc ttc aca gaa gtg gat ggg gtg cgg ttg cac agg tac gct cca gcg    5783
Phe Phe Thr Glu Val Asp Gly Val Arg Leu His Arg Tyr Ala Pro Ala
    1315                1320                1325 tgc aaa ccc ctc cta cgg gag gag gtc aca ttc ctg gtc ggg ctc aat    5831
Cys Lys Pro Leu Leu Arg Glu Glu Val Thr Phe Leu Val Gly Leu Asn
        1330                1335                1340 caa tac ctg gtt ggg tca cag ctc cca tgc gag ccc gaa ccg gac gta    5879
Gln Tyr Leu Val Gly Ser Gln Leu Pro Cys Glu Pro Glu Pro Asp Val
            1345                1350                1355 gca gtg ctc act tcc atg ctc acc gac ccc tcc cac att acg gcg gag    5927
Ala Val Leu Thr Ser Met Leu Thr Asp Pro Ser His Ile Thr Ala Glu
1360                1365                1370                1375 acg gct aag cgt agg ctg gcc agg gga tct ccc ccc tcc ttg gcc agc    5975
Thr Ala Lys Arg Arg Leu Ala Arg Gly Ser Pro Pro Ser Leu Ala Ser
                    1380                1385                1390 tca tca gct agc cag ctg tct gcg cct tcc ttg aag gca aca tgc act    6023
Ser Ser Ala Ser Gln Leu Ser Ala Pro Ser Leu Lys Ala Thr Cys Thr
    1395                1400                1405 acc cgt cat gac tcc ccg gac gct gac ctc atc gag gcc aac ctc ctg    6071
Thr Arg His Asp Ser Pro Asp Ala Asp Leu Ile Glu Ala Asn Leu Leu
        1410                1415                1420 tgg cgg cag gag atg ggc ggg aac atc acc cgc gtg gag tca gaa aat    6119
Trp Arg Gln Glu Met Gly Gly Asn Ile Thr Arg Val Glu Ser Glu Asn
            1425                1430                1435 aag gta gta att ttg gac tct ttc gag ccg ctc caa gcg gag gag gat    6167
Lys Val Val Ile Leu Asp Ser Phe Glu Pro Leu Gln Ala Glu Glu Asp
1440                1445                1450                1455 gag agg gaa gta tcc gtt ccg gcg gag atc ctg cgg agg tcc agg aaa    6215
Glu Arg Glu Val Ser Val Pro Ala Glu Ile Leu Arg Arg Ser Arg Lys
                    1460                1465                1470 ttc cct cga gcg atg ccc ata tgg gca cgc ccg gat tac aac cct cca    6263
Phe Pro Arg Ala Met Pro Ile Trp Ala Arg Pro Asp Tyr Asn Pro Pro
    1475                1480                1485 ctg tta gag tcc tgg aag gac ccg gac tac gtc cct cca gtg gta cac    6311
Leu Leu Glu Ser Trp Lys Asp Pro Asp Tyr Val Pro Pro Val Val His
        1490                1495                1500 ggg tgt cca ttg ccg cct gcc aag gcc cct ccg ata cca cct cca cgg    6359
Gly Cys Pro Leu Pro Pro Ala Lys Ala Pro Pro Ile Pro Pro Pro Arg
            1505                1510                1515 agg aag agg acg gtt gtc ctg tca gaa tct acc gtg tct tct gcc ttg    6407
Arg Lys Arg Thr Val Val Leu Ser Glu Ser Thr Val Ser Ser Ala Leu
1520                1525                1530                1535 gcg gag ctc gcc aca aag acc ttc ggc agc tcc gaa tcg tcg gcc gtc    6455
Ala Glu Leu Ala Thr Lys Thr Phe Gly Ser Ser Glu Ser Ser Ala Val
                    1540                1545                1550 gac agc ggc acg gca acg gcc tct cct gac cag ccc tcc gac gac ggc    6503
Asp Ser Gly Thr Ala Thr Ala Ser Pro Asp Gln Pro Ser Asp Asp Gly
    1555                1560                1565 gac gcg gga tcc gac gtt gag tcg tac tcc tcc atg ccc ccc ctt gag    6551
Asp Ala Gly Ser Asp Val Glu Ser Tyr Ser Ser Met Pro Pro Leu Glu
        1570                1575                1580 ggg gag ccg ggg gat ccc gat ctc agc gac ggg tct tgg tct acc gta    6599
Gly Glu Pro Gly Asp Pro Asp Leu Ser Asp Gly Ser Trp Ser Thr Val
```

-continued

|  |  |
|---|---|
| 1585 1590 1595 | |
| agc gag gag gct agt gag gac gtc gtc tgc tgc tcg atg tcc tac aca<br>Ser Glu Glu Ala Ser Glu Asp Val Val Cys Cys Ser Met Ser Tyr Thr<br>1600 1605 1610 1615 | 6647 |
| tgg aca ggc gcc ctg atc acg cca tgc gct gcg gag gaa acc aag ctg<br>Trp Thr Gly Ala Leu Ile Thr Pro Cys Ala Ala Glu Glu Thr Lys Leu<br>1620 1625 1630 | 6695 |
| ccc atc aat gca ctg agc aac tct ttg ctc cgt cac cac aac ttg gtc<br>Pro Ile Asn Ala Leu Ser Asn Ser Leu Leu Arg His His Asn Leu Val<br>1635 1640 1645 | 6743 |
| tat gct aca aca tct cgc agc gca agc ctg cgg cag aag aag gtc acc<br>Tyr Ala Thr Thr Ser Arg Ser Ala Ser Leu Arg Gln Lys Lys Val Thr<br>1650 1655 1660 | 6791 |
| ttt gac aga ctg cag gtc ctg gac gac cac tac cgg gac gtc ctc aag<br>Phe Asp Arg Leu Gln Val Leu Asp Asp His Tyr Arg Asp Val Leu Lys<br>1665 1670 1675 | 6839 |
| gag atg aag gcg aag gcg tcc aca gtt aag gct aaa ctt cta tcc gtg<br>Glu Met Lys Ala Lys Ala Ser Thr Val Lys Ala Lys Leu Leu Ser Val<br>1680 1685 1690 1695 | 6887 |
| gag gaa gcc tgt aag ctg acg ccc cca cat tcg gcc aga tct aaa ttt<br>Glu Glu Ala Cys Lys Leu Thr Pro Pro His Ser Ala Arg Ser Lys Phe<br>1700 1705 1710 | 6935 |
| ggc tat ggg gca aag gac gtc cgg aac cta tcc agc aag gcc gtt aac<br>Gly Tyr Gly Ala Lys Asp Val Arg Asn Leu Ser Ser Lys Ala Val Asn<br>1715 1720 1725 | 6983 |
| cac atc cgc tcc gtg tgg aag gac ttg ctg gaa gac act gag aca cca<br>His Ile Arg Ser Val Trp Lys Asp Leu Leu Glu Asp Thr Glu Thr Pro<br>1730 1735 1740 | 7031 |
| att gac acc acc atc atg gca aaa aat gag gtt ttc tgc gtc caa cca<br>Ile Asp Thr Thr Ile Met Ala Lys Asn Glu Val Phe Cys Val Gln Pro<br>1745 1750 1755 | 7079 |
| gag aag ggg ggc cgc aag cca gct cgc ctt atc gta ttc cca gat ttg<br>Glu Lys Gly Gly Arg Lys Pro Ala Arg Leu Ile Val Phe Pro Asp Leu<br>1760 1765 1770 1775 | 7127 |
| ggg gtt cgt gtg tgc gag aaa atg gcc ctt tac gat gtg gtc tcc acc<br>Gly Val Arg Val Cys Glu Lys Met Ala Leu Tyr Asp Val Val Ser Thr<br>1780 1785 1790 | 7175 |
| ctc cct cag gcc gtg atg ggc tct tca tac gga ttc caa tac tct cct<br>Leu Pro Gln Ala Val Met Gly Ser Ser Tyr Gly Phe Gln Tyr Ser Pro<br>1795 1800 1805 | 7223 |
| gga cag cgg gtc gag ttc ctg gtg aat gcc tgg aaa gcg aag aaa tgc<br>Gly Gln Arg Val Glu Phe Leu Val Asn Ala Trp Lys Ala Lys Lys Cys<br>1810 1815 1820 | 7271 |
| cct atg ggc ttc gca tat gac acc cgc tgt ttt gac tca acg gtc act<br>Pro Met Gly Phe Ala Tyr Asp Thr Arg Cys Phe Asp Ser Thr Val Thr<br>1825 1830 1835 | 7319 |
| gag aat gac atc cgt gtt gag gag tca atc tac caa tgt tgt gac ttg<br>Glu Asn Asp Ile Arg Val Glu Glu Ser Ile Tyr Gln Cys Cys Asp Leu<br>1840 1845 1850 1855 | 7367 |
| gcc ccc gaa gcc aga cag gcc ata agg tcg ctc aca gag cgg ctt tac<br>Ala Pro Glu Ala Arg Gln Ala Ile Arg Ser Leu Thr Glu Arg Leu Tyr<br>1860 1865 1870 | 7415 |
| atc ggg ggc ccc ctg act aat tct aaa ggg cag aac tgc ggc tat cgc<br>Ile Gly Gly Pro Leu Thr Asn Ser Lys Gly Gln Asn Cys Gly Tyr Arg<br>1875 1880 1885 | 7463 |
| cgg tgc cgc gcg agc ggt gta ctg acg acc agc tgc ggt aat acc ctc<br>Arg Cys Arg Ala Ser Gly Val Leu Thr Thr Ser Cys Gly Asn Thr Leu<br>1890 1895 1900 | 7511 |
| aca tgt tac ttg aag gcc gct gcg gcc tgt cga gct gcg aag ctc cag<br>Thr Cys Tyr Leu Lys Ala Ala Ala Ala Cys Arg Ala Ala Lys Leu Gln | 7559 |

|   |   |   |   |   |   |   |   |   |   |   |   |   |   |   |   |
|---|---|---|---|---|---|---|---|---|---|---|---|---|---|---|---|
|   |   | 1905 |   |   |   | 1910 |   |   |   | 1915 |   |   |   |   |   |
| gac | tgc | acg | atg | ctc | gta | tgc | gga | gac | gac | ctt | gtc | gtt | atc | tgt | gaa | 7607 |
| Asp | Cys | Thr | Met | Leu | Val | Cys | Gly | Asp | Asp | Leu | Val | Val | Ile | Cys | Glu |
| 1920 |   |   |   |   | 1925 |   |   |   | 1930 |   |   |   |   | 1935 |   |
| agc | gcg | ggg | acc | caa | gag | gac | gag | gcg | agc | cta | cgg | gcc | ttc | acg | gag | 7655 |
| Ser | Ala | Gly | Thr | Gln | Glu | Asp | Glu | Ala | Ser | Leu | Arg | Ala | Phe | Thr | Glu |
|   |   |   |   | 1940 |   |   |   |   | 1945 |   |   |   |   | 1950 |   |
| gct | atg | act | aga | tac | tct | gcc | ccc | cct | ggg | gac | ccg | ccc | aaa | cca | gaa | 7703 |
| Ala | Met | Thr | Arg | Tyr | Ser | Ala | Pro | Pro | Gly | Asp | Pro | Pro | Lys | Pro | Glu |
|   |   |   | 1955 |   |   |   |   | 1960 |   |   |   |   | 1965 |   |   |
| tac | gac | ttg | gag | ttg | ata | aca | tca | tgc | tcc | tcc | aat | gtg | tca | gtc | gcg | 7751 |
| Tyr | Asp | Leu | Glu | Leu | Ile | Thr | Ser | Cys | Ser | Ser | Asn | Val | Ser | Val | Ala |
|   |   | 1970 |   |   |   |   | 1975 |   |   |   |   | 1980 |   |   |   |
| cac | gat | gca | tct | ggc | aaa | agg | gtg | tac | tat | ctc | acc | cgt | gac | ccc | acc | 7799 |
| His | Asp | Ala | Ser | Gly | Lys | Arg | Val | Tyr | Tyr | Leu | Thr | Arg | Asp | Pro | Thr |
| 1985 |   |   |   |   | 1990 |   |   |   |   | 1995 |   |   |   |   |   |
| acc | ccc | ctt | gcg | cgg | gct | gcg | tgg | gag | aca | gct | aga | cac | act | cca | gtc | 7847 |
| Thr | Pro | Leu | Ala | Arg | Ala | Ala | Trp | Glu | Thr | Ala | Arg | His | Thr | Pro | Val |
| 2000 |   |   |   |   | 2005 |   |   |   |   | 2010 |   |   |   |   | 2015 |
| aat | tcc | tgg | cta | ggc | aac | atc | atc | atg | tat | gcg | ccc | acc | ttg | tgg | gca | 7895 |
| Asn | Ser | Trp | Leu | Gly | Asn | Ile | Ile | Met | Tyr | Ala | Pro | Thr | Leu | Trp | Ala |
|   |   |   |   | 2020 |   |   |   |   | 2025 |   |   |   |   | 2030 |   |
| agg | atg | atc | ctg | atg | act | cat | ttc | ttc | tcc | atc | ctt | cta | gct | cag | gaa | 7943 |
| Arg | Met | Ile | Leu | Met | Thr | His | Phe | Phe | Ser | Ile | Leu | Leu | Ala | Gln | Glu |
|   |   |   | 2035 |   |   |   |   | 2040 |   |   |   |   | 2045 |   |   |
| caa | ctt | gaa | aaa | gcc | cta | gat | tgt | cag | atc | tac | ggg | gcc | tgt | tac | tcc | 7991 |
| Gln | Leu | Glu | Lys | Ala | Leu | Asp | Cys | Gln | Ile | Tyr | Gly | Ala | Cys | Tyr | Ser |
|   |   | 2050 |   |   |   |   | 2055 |   |   |   |   | 2060 |   |   |   |
| att | gag | cca | ctt | gac | cta | cct | cag | atc | att | caa | cga | ctc | cac | ggc | ctt | 8039 |
| Ile | Glu | Pro | Leu | Asp | Leu | Pro | Gln | Ile | Ile | Gln | Arg | Leu | His | Gly | Leu |
| 2065 |   |   |   |   | 2070 |   |   |   |   | 2075 |   |   |   |   |   |
| agc | gca | ttt | tca | ctc | cat | agt | tac | tct | cca | ggt | gag | atc | aat | agg | gtg | 8087 |
| Ser | Ala | Phe | Ser | Leu | His | Ser | Tyr | Ser | Pro | Gly | Glu | Ile | Asn | Arg | Val |
| 2080 |   |   |   |   | 2085 |   |   |   |   | 2090 |   |   |   |   | 2095 |
| gct | tca | tgc | ctc | agg | aaa | ctt | ggg | gta | ccg | ccc | ttg | cga | gtc | tgg | aga | 8135 |
| Ala | Ser | Cys | Leu | Arg | Lys | Leu | Gly | Val | Pro | Pro | Leu | Arg | Val | Trp | Arg |
|   |   |   |   | 2100 |   |   |   |   | 2105 |   |   |   |   | 2110 |   |
| cat | cgg | gcc | aga | agt | gtc | cgc | gct | agg | cta | ctg | tcc | cag | ggg | ggg | agg | 8183 |
| His | Arg | Ala | Arg | Ser | Val | Arg | Ala | Arg | Leu | Leu | Ser | Gln | Gly | Gly | Arg |
|   |   |   | 2115 |   |   |   |   | 2120 |   |   |   |   | 2125 |   |   |
| gct | gcc | act | tgt | ggc | aag | tac | ctc | ttc | aac | tgg | gca | gta | agg | acc | aag | 8231 |
| Ala | Ala | Thr | Cys | Gly | Lys | Tyr | Leu | Phe | Asn | Trp | Ala | Val | Arg | Thr | Lys |
|   |   | 2130 |   |   |   |   | 2135 |   |   |   |   | 2140 |   |   |   |
| ctc | aaa | ctc | act | cca | atc | ccg | gct | gcg | tcc | cag | ttg | gat | tta | tcc | agc | 8279 |
| Leu | Lys | Leu | Thr | Pro | Ile | Pro | Ala | Ala | Ser | Gln | Leu | Asp | Leu | Ser | Ser |
|   | 2145 |   |   |   |   | 2150 |   |   |   |   | 2155 |   |   |   |   |
| tgg | ttc | gtt | gct | ggt | tac | agc | ggg | gga | gac | ata | tat | cac | agc | ctg | tct | 8327 |
| Trp | Phe | Val | Ala | Gly | Tyr | Ser | Gly | Gly | Asp | Ile | Tyr | His | Ser | Leu | Ser |
| 2160 |   |   |   |   | 2165 |   |   |   |   | 2170 |   |   |   |   | 2175 |
| cgt | gcc | cga | ccc | cgc | tgg | ttc | atg | tgg | tgc | cta | ctc | cta | ctt | tct | gta | 8375 |
| Arg | Ala | Arg | Pro | Arg | Trp | Phe | Met | Trp | Cys | Leu | Leu | Leu | Leu | Ser | Val |
|   |   |   | 2180 |   |   |   |   | 2185 |   |   |   |   | 2190 |   |   |
| ggg | gta | ggc | atc | tat | cta | ctc | ccc | aac | cga | tga | acggggagct | aaacactcca |   |   | 8428 |
| Gly | Val | Gly | Ile | Tyr | Leu | Leu | Pro | Asn | Arg |   |   |   |   |   |   |
|   |   |   | 2195 |   |   |   |   | 2200 |   |   |   |   |   |   |   |

```
ggccaatagg ccatcctgtt ttttcccctt tttttttttc tttttttttt tttttttttt    8488
tttttttttt ttttctcctt tttttttcct ctttttttcc ttttctttcc tttggtggct    8548
ccatcttagc cctagtcacg gctagctgtg aaaggtccgt gagccgcttg actgcagaga    8608
```

-continued

| gtgctgatac tggcctctct gcagatcaag t | 8639 |

```
<210> SEQ ID NO 2
<211> LENGTH: 8642
<212> TYPE: DNA
<213> ORGANISM: Hepatitis C virus
<220> FEATURE:
<221> NAME/KEY: CDS
<222> LOCATION: (1802)...(8407)
<221> NAME/KEY: variation
<222> LOCATION: 6268
<223> OTHER INFORMATION: r = a or g
<221> NAME/KEY: variation
<222> LOCATION: 4446
<223> OTHER INFORMATION: r = a or g
```

<400> SEQUENCE: 2

| accagccccc gattgggggc gacactccac catagatcac tccctgtga ggaactactg | 60 |
| tcttcacgca gaaagcgtct agccatggcg ttagtatgag tgtcgtgcag cctccaggac | 120 |
| cccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta ccgtgcac catgagcacg aatcctaaac | 360 |
| ctcaaagaaa aaccaaaggg cgcgccatga ttgaacaaga tggattgcac gcaggttctc | 420 |
| cggccgcttg ggtggagagg ctattcggct atgactgggc acaacagaca atcggctgct | 480 |
| ctgatgccgc cgtgttccgg ctgtcagcgc agggggcgccc ggttcttttt gtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg aagccggtc | 840 |
| ttgtcgatca ggatgatctg gacgaagagc atcaggggct cgcgccagcc gaactgttcg | 900 |
| ccaggctcaa ggcgcgcatg cccgacggcg aggatctcgt cgtgacccat ggcgatgcct | 960 |
| gcttgccgaa tatcatggtg gaaaatggcc gcttttctgg attcatcgac tgtggccggc | 1020 |
| tgggtgtggc ggaccgctat caggacatag cgttggctac ccgtgatatt gctgaagagc | 1080 |
| ttggcggcga atgggctgac cgcttcctcg tgctttacgg tatcgccgct cccgattcgc | 1140 |
| agcgcatcgc cttctatcgc cttcttgacg agttcttctg agttcgcgcc cagatgttaa | 1200 |
| cagaccacaa cggtttccct ctagcgggat caattccgcc cccccccta acgttactgg | 1260 |
| ccgaagccgc ttggaataag gccggtgtgc gtttgtctat atgttatttt ccaccatatt | 1320 |
| gccgtctttt ggcaatgtga gggcccggaa acctggccct gtcttcttga cgagcattcc | 1380 |
| tagggggtctt tcccctctcg ccaaaggaat gcaaggtctg ttgaatgtcg tgaaggaagc | 1440 |
| agttcctctg gaagcttctt gaagacaaac aacgtctgta gcgaccctt gcaggcagcg | 1500 |
| gaaccccca cctggcgaca ggtgcctctg cggccaaaag ccacgtgtat aagatacacc | 1560 |
| tgcaaaggcg gcacaacccc agtgccacgt tgtgagttgg atagttgtgg aaagagtcaa | 1620 |
| atggctctcc tcaagcgtat tcaacaaggg gctgaaggat gcccagaagg taccccattg | 1680 |
| tatgggatct gatctggggc ctcggtgcac atgctttaca tgtgtttagt cgaggttaaa | 1740 |
| aaacgtctag gccccccgaa ccacggggac gtggttttcc tttgaaaaac acgataatac | 1800 |
| c atg gac cgg gag atg gca gca tcg tgc gga ggc gcg gtt ttc gta ggt | 1849 |

```
    Met Asp Arg Glu Met Ala Ala Ser Cys Gly Gly Ala Val Phe Val Gly
    1               5                   10                  15 ctg ata ctc ttg acc ttg tca ccg cac tat aag ctg ttc ctc gct agg      1897
Leu Ile Leu Leu Thr Leu Ser Pro His Tyr Lys Leu Phe Leu Ala Arg
                20                  25                  30 ctc ata tgg tgg tta caa tat ttt atc acc agg gcc gag gca cac ttg      1945
Leu Ile Trp Trp Leu Gln Tyr Phe Ile Thr Arg Ala Glu Ala His Leu
            35                  40                  45 caa gtg tgg atc ccc ccc ctc aac gtt cgg ggg ggc cgc gat gcc gtc      1993
Gln Val Trp Ile Pro Pro Leu Asn Val Arg Gly Gly Arg Asp Ala Val
        50                  55                  60 atc ctc ctc acg tgc gcg atc cac cca gag cta atc ttt acc atc acc      2041
Ile Leu Leu Thr Cys Ala Ile His Pro Glu Leu Ile Phe Thr Ile Thr
65                  70                  75                  80 aaa atc ttg ctc gcc ata ctc ggt cca ctc atg gtg ctc cag gct ggt      2089
Lys Ile Leu Leu Ala Ile Leu Gly Pro Leu Met Val Leu Gln Ala Gly
                85                  90                  95 ata acc aaa gtg ccg tac ttc gtg cgc gca cac ggg ctc att cgt gca      2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct      2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc      2233
Leu Met Lys Leu Ala Ala Leu Thr Gly Thr Tyr Val Tyr Asp His Leu
    130                 135                 140 acc cca ctg cgg gac tgg gcc cac gcg ggc cta cga gac ctt gcg gtg      2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc      2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc      2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc      2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc      2473
Leu Glu Gly Gln Gly Trp Arg Leu Leu Ala Pro Ile Thr Ala Tyr Ser
    210                 215                 220 caa cag acg cga ggc cta ctt ggc tgc atc atc act agc ctc aca ggc      2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca      2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc      2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc      2665
Tyr His Gly Ala Gly Ser Lys Thr Leu Ala Gly Pro Lys Gly Pro Ile
        275                 280                 285 acc caa atg tac acc aat gtg gac cag gac ctc gtc ggc tgg caa gcg      2713
Thr Gln Met Tyr Thr Asn Val Asp Gln Asp Leu Val Gly Trp Gln Ala
    290                 295                 300 ccc ccc ggg gcg cgt tcc ttg aca cca tgc acc tgc ggc agc tcg gac      2761
Pro Pro Gly Ala Arg Ser Leu Thr Pro Cys Thr Cys Gly Ser Ser Asp
305                 310                 315                 320 ctt tac ttg gtc acg agg cat gcc gat gtc att ccg gtg cgc cgg cgg      2809
```

-continued

| | | | | | | | | | | | | |
|---|---|---|---|---|---|---|---|---|---|---|---|---|
| Leu | Tyr | Leu | Val | Thr | Arg | His | Ala | Asp | Val | Ile | Pro | Val | Arg | Arg | Arg |
| | | | | 325 | | | | 330 | | | | 335 | | | |

```
ggc gac agc agg ggg agc cta ctc tcc ccc agg ccc gtc tcc tac ttg    2857
Gly Asp Ser Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg    2905
Lys Gly Ser Ser Gly Gly Pro Leu Leu Cys Pro Ser Gly His Ala Val
            355                 360                 365 ggc atc ttt cgg gct gcc gtg tgc acc cga ggg gtt gcg aag gcg gtg    2953
Gly Ile Phe Arg Ala Ala Val Cys Thr Arg Gly Val Ala Lys Ala Val
        370                 375                 380 gac ttt gta ccc gtc gag tct atg gaa acc act atg cgg tcc ccg gtc    3001
Asp Phe Val Pro Val Glu Ser Met Glu Thr Thr Met Arg Ser Pro Val
385                 390                 395                 400 ttc acg gac aac tcg tcc cct ccg gcc gta ccg cag aca ttc cag gtg    3049
Phe Thr Asp Asn Ser Ser Pro Pro Ala Val Pro Gln Thr Phe Gln Val
            405                 410                 415 gcc cat cta cac gcc cct act ggt agc ggc aag agc act aag gtg ccg    3097
Ala His Leu His Ala Pro Thr Gly Ser Gly Lys Ser Thr Lys Val Pro
            420                 425                 430 gct gcg tat gca gcc caa ggg tat aag gtg ctt gtc ctg aac ccg tcc    3145
Ala Ala Tyr Ala Ala Gln Gly Tyr Lys Val Leu Val Leu Asn Pro Ser
            435                 440                 445 gtc gcc gcc acc cta ggt ttc ggg gcg tat atg tct aag gca cat ggt    3193
Val Ala Ala Thr Leu Gly Phe Gly Ala Tyr Met Ser Lys Ala His Gly
            450                 455                 460 atc gac cct aac atc aga acc ggg gta agg acc atc acc acg ggt gcc    3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc    3289
Pro Ile Thr Tyr Ser Thr Tyr Gly Lys Phe Leu Ala Asp Gly Gly Cys
            485                 490                 495 tct ggg ggc gcc tat gac atc ata ata tgt gat gag tgc cac tca act    3337
Ser Gly Gly Ala Tyr Asp Ile Ile Ile Cys Asp Glu Cys His Ser Thr
        500                 505                 510 gac tcg acc act atc ctg ggc atc ggc aca gtc ctg gac caa gcg gag    3385
Asp Ser Thr Thr Ile Leu Gly Ile Gly Thr Val Leu Asp Gln Ala Glu
        515                 520                 525 acg gct gga gcg cga ctc gtc gtg ctc gcc acc gct acg cct ccg gga    3433
Thr Ala Gly Ala Arg Leu Val Val Leu Ala Thr Ala Thr Pro Pro Gly
        530                 535                 540 tcg gtc acc gtg cca cat cca aac atc gag gag gtg gct ctg tcc agc    3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc    3529
Thr Gly Glu Ile Pro Phe Tyr Gly Lys Ala Ile Pro Ile Glu Thr Ile
            565                 570                 575 aag ggg ggg agg cac ctc att ttc tgc cat tcc aag aag aaa tgt gat    3577
Lys Gly Gly Arg His Leu Ile Phe Cys His Ser Lys Lys Lys Cys Asp
            580                 585                 590 gag ctc gcc gcg aag ctg tcc ggc ctc gga ctc aat gct gta gca tat    3625
Glu Leu Ala Ala Lys Leu Ser Gly Leu Gly Leu Asn Ala Val Ala Tyr
            595                 600                 605 tac cgg ggc ctt gat gta tcc gtc ata cca act agc gga gac gtc att    3673
Tyr Arg Gly Leu Asp Val Ser Val Ile Pro Thr Ser Gly Asp Val Ile
        610                 615                 620 gtc gta gca acg gac gct cta atg acg ggc ttt acc ggc gat ttc gac    3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc    3769
```

```
                Ser Val Ile Asp Cys Asn Thr Cys Val Thr Gln Thr Val Asp Phe Ser
                                645                 650                 655 ctg gac ccg acc ttc acc att gag acg acg acc gtg cca caa gac gcg            3817
Leu Asp Pro Thr Phe Thr Ile Glu Thr Thr Thr Val Pro Gln Asp Ala
            660                 665                 670 gtg tca cgc tcg cag cgg cga ggc agg act ggt agg ggc agg atg ggc            3865
Val Ser Arg Ser Gln Arg Arg Gly Arg Thr Gly Arg Gly Arg Met Gly
675                 680                 685 att tac agg ttt gtg act cca gga gaa cgg ccc tcg ggc atg ttc gat            3913
Ile Tyr Arg Phe Val Thr Pro Gly Glu Arg Pro Ser Gly Met Phe Asp
            690                 695                 700 tcc tcg gtt ctg tgc gag tgc tat gac gcg ggc tgt gct tgg tac gag            3961
Ser Ser Val Leu Cys Glu Cys Tyr Asp Ala Gly Cys Ala Trp Tyr Glu
705                 710                 715                 720 ctc acg ccc gcc gag acc tca gtt agg ttg cgg gct tac cta aac aca            4009
Leu Thr Pro Ala Glu Thr Ser Val Arg Leu Arg Ala Tyr Leu Asn Thr
                725                 730                 735 cca ggg ttg ccc gtc tgc cag gac cat ctg gag ttc tgg gag agc gtc            4057
Pro Gly Leu Pro Val Cys Gln Asp His Leu Glu Phe Trp Glu Ser Val
            740                 745                 750 ttt aca ggc ctc acc cac ata gac gcc cat ttc ttg tcc cag act aag            4105
Phe Thr Gly Leu Thr His Ile Asp Ala His Phe Leu Ser Gln Thr Lys
        755                 760                 765 cag gca gga gac aac ttc ccc tac ctg gta gca tac cag gct acg gtg            4153
Gln Ala Gly Asp Asn Phe Pro Tyr Leu Val Ala Tyr Gln Ala Thr Val
770                 775                 780 tgc gcc agg gct cag gct cca cct cca tcg tgg gac caa atg tgg aag            4201
Cys Ala Arg Ala Gln Ala Pro Pro Pro Ser Trp Asp Gln Met Trp Lys
785                 790                 795                 800 tgt ctc ata cgg cta aag cct acg ctg cac ggg cca acg ccc ctg ctg            4249
Cys Leu Ile Arg Leu Lys Pro Thr Leu His Gly Pro Thr Pro Leu Leu
                805                 810                 815 tat agg ctg gga gcc gtt caa aac gag gtt act acc aca cac ccc ata            4297
Tyr Arg Leu Gly Ala Val Gln Asn Glu Val Thr Thr Thr His Pro Ile
            820                 825                 830 acc aaa tac atc atg gca tgc atg tcg gct gac ctg gag gtc gtc acg            4345
Thr Lys Tyr Ile Met Ala Cys Met Ser Ala Asp Leu Glu Val Val Thr
        835                 840                 845 agc acc tgg gtg ctg gta ggc gga gtc cta gca gct ctg gcc gcg tat            4393
Ser Thr Trp Val Leu Val Gly Gly Val Leu Ala Ala Leu Ala Ala Tyr
850                 855                 860 tgc ctg aca aca ggc agc gtg gtc att gtg ggc agg atc atc ttg tcc            4441
Cys Leu Thr Thr Gly Ser Val Val Ile Val Gly Arg Ile Ile Leu Ser
865                 870                 875                 880 gga arg ccg gcc atc att ccc gac agg gaa gtc ctt tac cgg gag ttc            4489
Gly Xaa Pro Ala Ile Ile Pro Asp Arg Glu Val Leu Tyr Arg Glu Phe
                885                 890                 895 gat gag atg gaa gag tgc gcc tca cac ctc cct tac atc gaa cag gga            4537
Asp Glu Met Glu Glu Cys Ala Ser His Leu Pro Tyr Ile Glu Gln Gly
            900                 905                 910 atg cag ctc gcc gaa caa ttc aaa cag aag gca atc ggg ttg ctg caa            4585
Met Gln Leu Ala Glu Gln Phe Lys Gln Lys Ala Ile Gly Leu Leu Gln
        915                 920                 925 aca gcc acc aag caa gcg gag gct gct gct ccc gtg gtg gaa tcc aag            4633
Thr Ala Thr Lys Gln Ala Glu Ala Ala Ala Pro Val Val Glu Ser Lys
930                 935                 940 tgg cgg acc ctc gaa gcc ttc tgg gcg aag cat atg tgg aat ttc atc            4681
Trp Arg Thr Leu Glu Ala Phe Trp Ala Lys His Met Trp Asn Phe Ile
945                 950                 955                 960 agc ggg ata caa tat tta gca ggc ttg tcc act ctg cct ggc aac ccc            4729
```

```
Ser Gly Ile Gln Tyr Leu Ala Gly Leu Ser Thr Leu Pro Gly Asn Pro
            965                 970                 975 gcg ata gca tca ctg atg gca ttc aca gcc tct atc acc agc ccg ctc    4777
Ala Ile Ala Ser Leu Met Ala Phe Thr Ala Ser Ile Thr Ser Pro Leu
            980                 985                 990 acc acc caa cat acc ctc ctg ttt aac atc ctg ggg gga tgg gtg gcc    4825
Thr Thr Gln His Thr Leu Leu Phe Asn Ile Leu Gly Gly Trp Val Ala
            995                 1000                1005 gcc caa ctt gct cct ccc agc gct gct tct gct ttc gta ggc gcc ggc    4873
Ala Gln Leu Ala Pro Pro Ser Ala Ala Ser Ala Phe Val Gly Ala Gly
            1010                1015                1020 atc gct gga gcg gct gtt ggc agc ata ggc ctt ggg aag gtg ctt gtg    4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc    4969
Asp Ile Leu Ala Gly Tyr Gly Ala Gly Val Ala Gly Ala Leu Val Ala
            1045                1050                1055 ttt aag gtc atg agc ggc gag atg ccc tcc acc gag gac ctg gtt aac    5017
Phe Lys Val Met Ser Gly Glu Met Pro Ser Thr Glu Asp Leu Val Asn
            1060                1065                1070 cta ctc cct gct atc ctc tcc cct ggc gcc cta gtc gtc ggg gtc gtg    5065
Leu Leu Pro Ala Ile Leu Ser Pro Gly Ala Leu Val Val Gly Val Val
            1075                1080                1085 tgc gca gcg ata ctg cgt cgg cac gtg ggc cca ggg gag ggg gct gtg    5113
Cys Ala Ala Ile Leu Arg Arg His Val Gly Pro Gly Glu Gly Ala Val
            1090                1095                1100 cag tgg atg aac cgg ctg ata gcg ttc gct tcg cgg ggt aac cac gtc    5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act    5209
Ser Pro Thr His Tyr Val Pro Glu Ser Asp Ala Ala Ala Arg Val Thr
            1125                1130                1135 cag atc ctc tct agt ctt acc atc act cag ctg ctg aag agg ctt cac    5257
Gln Ile Leu Ser Ser Leu Thr Ile Thr Gln Leu Leu Lys Arg Leu His
            1140                1145                1150 cag tgg atc aac gag gac tgc tcc acg cca tgc tcc ggc tcg tgg cta    5305
Gln Trp Ile Asn Glu Asp Cys Ser Thr Pro Cys Ser Gly Ser Trp Leu
            1155                1160                1165 aga gat gtt tgg gat tgg ata tgc acg gtg ttg act gat ttc aag acc    5353
Arg Asp Val Trp Asp Trp Ile Cys Thr Val Leu Thr Asp Phe Lys Thr
            1170                1175                1180 tgg ctc cag tcc aag ctc ctg ccg cga ttg ccg gga gtc ccc ttc ttc    5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg    5449
Ser Cys Gln Arg Gly Tyr Lys Gly Val Trp Arg Gly Asp Gly Ile Met
            1205                1210                1215 caa acc acc tgc cca tgt gga gca cag atc acc gga cat gtg aaa aac    5497
Gln Thr Thr Cys Pro Cys Gly Ala Gln Ile Thr Gly His Val Lys Asn
            1220                1225                1230 tgt tcc atg agg atc gtg ggg cct agg acc tgt agt aac acg tgg cat    5545
Cys Ser Met Arg Ile Val Gly Pro Arg Thr Cys Ser Asn Thr Trp His
            1235                1240                1245 gga aca ttc ccc att aac gcg tac acc acg ggc ccc tgc acg ccc tcc    5593
Gly Thr Phe Pro Ile Asn Ala Tyr Thr Thr Gly Pro Cys Thr Pro Ser
            1250                1255                1260 ccg gcg cca aat tat tct agg gcg ctg tgg cgg gtg gct gct gag gag    5641
Pro Ala Pro Asn Tyr Ser Arg Ala Leu Trp Arg Val Ala Ala Glu Glu
1265                1270                1275                1280 tac gtg gag gtt acg cgg gtg ggg gat ttc cac tac gtg acg ggc atg    5689
```

```
Tyr Val Glu Val Thr Arg Val Gly Asp Phe His Tyr Val Thr Gly Met
            1285                1290                1295 acc act gac aac gta aag tgc ccg tgt cag gtt ccg gcc ccc gaa ttc      5737
Thr Thr Asp Asn Val Lys Cys Pro Cys Gln Val Pro Ala Pro Glu Phe
            1300                1305                1310 ttc aca gaa gtg gat ggg gtg cgg ttg cac agg tac gct cca gcg tgc      5785
Phe Thr Glu Val Asp Gly Val Arg Leu His Arg Tyr Ala Pro Ala Cys
            1315                1320                1325 aaa ccc ctc cta cgg gag gag gtc aca ttc ctg gtc ggg ctc aat caa      5833
Lys Pro Leu Leu Arg Glu Glu Val Thr Phe Leu Val Gly Leu Asn Gln
            1330                1335                1340 tac ctg gtt ggg tca cag ctc cca tgc gag ccc gaa ccg gac gta gca      5881
Tyr Leu Val Gly Ser Gln Leu Pro Cys Glu Pro Glu Pro Asp Val Ala
1345                1350                1355                1360 gtg ctc act tcc atg ctc acc gac ccc tcc cac att acg gcg gag acg      5929
Val Leu Thr Ser Met Leu Thr Asp Pro Ser His Ile Thr Ala Glu Thr
                1365                1370                1375 gct aag cgt agg ctg gcc agg gga tct ccc ccc tcc ttg gcc agc tca      5977
Ala Lys Arg Arg Leu Ala Arg Gly Ser Pro Pro Ser Leu Ala Ser Ser
            1380                1385                1390 tca gct agc cag ctg tct gcg cct tcc ttg aag gca aca tgc act acc      6025
Ser Ala Ser Gln Leu Ser Ala Pro Ser Leu Lys Ala Thr Cys Thr Thr
            1395                1400                1405 cgt cat gac tcc ccg gac gct gac ctc atc gag gcc aac ctc ctg tgg      6073
Arg His Asp Ser Pro Asp Ala Asp Leu Ile Glu Ala Asn Leu Leu Trp
            1410                1415                1420 cgg cag gag atg ggc ggg aac atc acc cgc gtg gag tca gaa aat aag      6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag      6169
Val Val Ile Leu Asp Ser Phe Glu Pro Leu Gln Ala Glu Glu Asp Glu
                1445                1450                1455 agg gaa gta tcc gtt ccg gcg gag atc ctg cgg agg tcc agg aaa ttc      6217
Arg Glu Val Ser Val Pro Ala Glu Ile Leu Arg Arg Ser Arg Lys Phe
            1460                1465                1470 cct cga gcg atg ccc ata tgg gca cgc ccg gat tac aac cct cca ctg      6265
Pro Arg Ala Met Pro Ile Trp Ala Arg Pro Asp Tyr Asn Pro Pro Leu
            1475                1480                1485 ttr gag tcc tgg aag gac ccg gac tac gtc cct cca gtg gta cac ggg      6313
Xaa Glu Ser Trp Lys Asp Pro Asp Tyr Val Pro Pro Val Val His Gly
            1490                1495                1500 tgt cca ttg ccg cct gcc aag gcc cct ccg ata cca cct cca cgg agg      6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg      6409
Lys Arg Thr Val Val Leu Ser Glu Ser Thr Val Ser Ser Ala Leu Ala
                1525                1530                1535 gag ctc gcc aca aag acc ttc ggc agc tcc gaa tcg tcg gcc gtc gac      6457
Glu Leu Ala Thr Lys Thr Phe Gly Ser Ser Glu Ser Ser Ala Val Asp
            1540                1545                1550 agc ggc acg gca acg gcc tct cct gac cag ccc tcc gac gac ggc gac      6505
Ser Gly Thr Ala Thr Ala Ser Pro Asp Gln Pro Ser Asp Asp Gly Asp
            1555                1560                1565 gcg gga tcc gac gtt gag tcg tac tcc tcc atg ccc ccc ctt gag ggg      6553
Ala Gly Ser Asp Val Glu Ser Tyr Ser Ser Met Pro Pro Leu Glu Gly
            1570                1575                1580 gag ccg ggg gat ccc gat ctc agc gac ggg tct tgg tct acc gta agc      6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg      6649
```

```
                Glu Glu Ala Ser Glu Asp Val Val Cys Cys Ser Met Ser Tyr Thr Trp
                            1605                1610                1615 aca ggc gcc ctg atc acg cca tgc gct gcg gag gaa acc aag ctg ccc              6697
Thr Gly Ala Leu Ile Thr Pro Cys Ala Ala Glu Glu Thr Lys Leu Pro
            1620                1625                1630 atc aat gca ctg agc aac tct ttg ctc cgt cac cac aac ttg gtc tat              6745
Ile Asn Ala Leu Ser Asn Ser Leu Leu Arg His His Asn Leu Val Tyr
            1635                1640                1645 gct aca aca tct cgc agc gca agc ctg cgg cag aag aag gtc acc ttt              6793
Ala Thr Thr Ser Arg Ser Ala Ser Leu Arg Gln Lys Lys Val Thr Phe
            1650                1655                1660 gac aga ctg cag gtc ctg gac gac cac tac cgg gac gtg ctc aag gag              6841
Asp Arg Leu Gln Val Leu Asp Asp His Tyr Arg Asp Val Leu Lys Glu
1665                1670                1675                1680 atg aag gcg aag gcg tcc aca gtt aag gct aaa ctt cta tcc gtg gag              6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc              6937
Glu Ala Cys Lys Leu Thr Pro Pro His Ser Ala Arg Ser Lys Phe Gly
            1700                1705                1710 tat ggg gca aag gac gtc cgg aac cta tcc agc aag gcc gtt aac cac              6985
Tyr Gly Ala Lys Asp Val Arg Asn Leu Ser Ser Lys Ala Val Asn His
            1715                1720                1725 atc cgc tcc gtg tgg aag gac ttg ctg gaa gac act gag aca cca att              7033
Ile Arg Ser Val Trp Lys Asp Leu Leu Glu Asp Thr Glu Thr Pro Ile
        1730                1735                1740 gac acc acc atc atg gca aaa aat gag gtt ttc tgc gtc caa cca gag              7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg              7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc              7177
Val Arg Val Cys Glu Lys Met Ala Leu Tyr Asp Val Val Ser Thr Leu
            1780                1785                1790 cct cag gcc gtg atg ggc tct tca tac gga ttc caa tac tct cct gga              7225
Pro Gln Ala Val Met Gly Ser Ser Tyr Gly Phe Gln Tyr Ser Pro Gly
            1795                1800                1805 cag cgg gtc gag ttc ctg gtg aat gcc tgg aaa gcg aag aaa tgc cct              7273
Gln Arg Val Glu Phe Leu Val Asn Ala Trp Lys Ala Lys Lys Cys Pro
            1810                1815                1820 atg ggc ttc gca tat gac acc cgc tgt ttt gac tca acg gtc act gag              7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc              7369
Asn Asp Ile Arg Val Glu Glu Ser Ile Tyr Gln Cys Cys Asp Leu Ala
                1845                1850                1855 ccc gaa gcc aga cag gcc ata agg tcg ctc aca gag cgg ctt tac atc              7417
Pro Glu Ala Arg Gln Ala Ile Arg Ser Leu Thr Glu Arg Leu Tyr Ile
            1860                1865                1870 ggg ggc ccc ctg act aat tct aaa ggg cag aac tgc ggc tat cgc cgg              7465
Gly Gly Pro Leu Thr Asn Ser Lys Gly Gln Asn Cys Gly Tyr Arg Arg
            1875                1880                1885 tgc cgc gcg agc ggt gta ctg acg acc agc tgc ggt aat acc ctc aca              7513
Cys Arg Ala Ser Gly Val Leu Thr Thr Ser Cys Gly Asn Thr Leu Thr
            1890                1895                1900 tgt tac ttg aag gcc gct gcg gcc tgt cga gct gcg aag ctc cag gac              7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc              7609
```

| | | |
|---|---|---|
| Cys Thr Met Leu Val Cys Gly Asp Asp Leu Val Ile Cys Glu Ser<br>              1925                         1930                  1935 | |
| gcg ggg acc caa gag gac gag gcg agc cta cgg gcc ttc acg gag gct<br>Ala Gly Thr Gln Glu Asp Glu Ala Ser Leu Arg Ala Phe Thr Glu Ala<br>              1940                      1945                 1950 | 7657 |
| atg act aga tac tct gcc ccc cct ggg gac ccg ccc aaa cca gaa tac<br>Met Thr Arg Tyr Ser Ala Pro Pro Gly Asp Pro Pro Lys Pro Glu Tyr<br>              1955                      1960                 1965 | 7705 |
| gac ttg gag ttg ata aca tca tgc tcc tcc aat gtg tca gtc gcg cac<br>Asp Leu Glu Leu Ile Thr Ser Cys Ser Ser Asn Val Ser Val Ala His<br>            1970                      1975                 1980 | 7753 |
| gat gca tct ggc aaa agg gtg tac tat ctc acc cgt gac ccc acc acc<br>Asp Ala Ser Gly Lys Arg Val Tyr Tyr Leu Thr Arg Asp Pro Thr Thr<br>1985                  1990                      1995                 2000 | 7801 |
| ccc ctt gcg cgg gct gcg tgg gag aca gct aga cac act cca gtc aat<br>Pro Leu Ala Arg Ala Ala Trp Glu Thr Ala Arg His Thr Pro Val Asn<br>                      2005                      2010                 2015 | 7849 |
| tcc tgg cta ggc aac atc atc atg tat gcg ccc acc ttg tgg gca agg<br>Ser Trp Leu Gly Asn Ile Ile Met Tyr Ala Pro Thr Leu Trp Ala Arg<br>            2020                      2025                 2030 | 7897 |
| atg atc ctg atg act cat ttc ttc tcc atc ctt cta gct cag gaa caa<br>Met Ile Leu Met Thr His Phe Phe Ser Ile Leu Leu Ala Gln Glu Gln<br>            2035                      2040                 2045 | 7945 |
| ctt gaa aaa gcc cta gat tgt cag atc tac ggg gcc tgt tac tcc att<br>Leu Glu Lys Ala Leu Asp Cys Gln Ile Tyr Gly Ala Cys Tyr Ser Ile<br>            2050                      2055                 2060 | 7993 |
| gag cca ctt gac cta cct cag atc att caa cga ctc cac ggc ctt agc<br>Glu Pro Leu Asp Leu Pro Gln Ile Ile Gln Arg Leu His Gly Leu Ser<br>2065                  2070                      2075                 2080 | 8041 |
| gca ttt tca ctc cat agt tac tct cca ggt gag atc aat agg gtg gct<br>Ala Phe Ser Leu His Ser Tyr Ser Pro Gly Glu Ile Asn Arg Val Ala<br>            2085                      2090                 2095 | 8089 |
| tca tgc ctc agg aaa ctt ggg gta ccg ccc ttg cga gtc tgg aga cat<br>Ser Cys Leu Arg Lys Leu Gly Val Pro Pro Leu Arg Val Trp Arg His<br>            2100                      2105                 2110 | 8137 |
| cgg gcc aga agt gtc cgc gct agg cta ctg tcc cag ggg ggg agg gct<br>Arg Ala Arg Ser Val Arg Ala Arg Leu Leu Ser Gln Gly Gly Arg Ala<br>            2115                      2120                 2125 | 8185 |
| gcc act tgt ggc aag tac ctc ttc aac tgg gca gta agg acc aag ctc<br>Ala Thr Cys Gly Lys Tyr Leu Phe Asn Trp Ala Val Arg Thr Lys Leu<br>            2130                      2135                 2140 | 8233 |
| aaa ctc act cca atc ccg gct gcg tcc cag ttg gat tta tcc agc tgg<br>Lys Leu Thr Pro Ile Pro Ala Ala Ser Gln Leu Asp Leu Ser Ser Trp<br>2145                  2150                      2155                 2160 | 8281 |
| ttc gtt gct ggt tac agc ggg gga gac ata tat cac agc ctg tct cgt<br>Phe Val Ala Gly Tyr Ser Gly Gly Asp Ile Tyr His Ser Leu Ser Arg<br>                      2165                      2170                 2175 | 8329 |
| gcc cga ccc cgc tgg ttc atg tgg tgc cta ctc cta ctt tct gta ggg<br>Ala Arg Pro Arg Trp Phe Met Trp Cys Leu Leu Leu Leu Ser Val Gly<br>            2180                      2185                 2190 | 8377 |
| gta ggc atc tat cta ctc ccc aac cga tga acggggagct aaacactcca<br>Val Gly Ile Tyr Leu Leu Pro Asn Arg<br>            2195                      2200 | 8427 |
| ggccaatagg ccatcctgtt ttttccccct tttttttttt tttttttttc ttttttttt | 8487 |
| tttttttttt ttttttttc tccttttttt tcctcttttt ttcctttttct ttcctttggt | 8547 |
| ggctccatct tagccctagt cacggctagc tgtgaaaggt ccgtgagccg cttgactgca | 8607 |
| gagagtgctg atactggcct ctctgcagat caagt | 8642 |

```
<210> SEQ ID NO 3
<211> LENGTH: 2201
<212> TYPE: PRT
<213> ORGANISM: Hepatitis C virus
<220> FEATURE:
<221> NAME/KEY: VARIANT
<222> LOCATION: 882
<223> OTHER INFORMATION: Xaa is Lys or Arg
<221> NAME/KEY: VARIANT
<222> LOCATION: 1489
<223> OTHER INFORMATION: Xaa is Leu

<400> SEQUENCE: 3

Met Asp Arg Glu Met Ala Ala Ser Cys Gly Gly Ala Val Phe Val Gly
 1               5                  10                  15

Leu Ile Leu Leu Thr Leu Ser Pro His Tyr Lys Leu Phe Leu Ala Arg
                20                  25                  30

Leu Ile Trp Trp Leu Gln Tyr Phe Ile Thr Arg Ala Glu Ala His Leu
            35                  40                  45

Gln Val Trp Ile Pro Pro Leu Asn Val Arg Gly Gly Arg Asp Ala Val
50                  55                  60

Ile Leu Leu Thr Cys Ala Ile His Pro Glu Leu Ile Phe Thr Ile Thr
65                  70                  75                  80

Lys Ile Leu Leu Ala Ile Leu Gly Pro Leu Met Val Leu Gln Ala Gly
                85                  90                  95

Ile Thr Lys Val Pro Tyr Phe Val Arg Ala His Gly Leu Ile Arg Ala
            100                 105                 110

Cys Met Leu Val Arg Lys Val Ala Gly Gly His Tyr Val Gln Met Ala
        115                 120                 125

Leu Met Lys Leu Ala Ala Leu Thr Gly Thr Tyr Val Tyr Asp His Leu
130                 135                 140

Thr Pro Leu Arg Asp Trp Ala His Ala Gly Leu Arg Asp Leu Ala Val
145                 150                 155                 160

Ala Val Glu Pro Val Val Phe Ser Asp Met Glu Thr Lys Val Ile Thr
                165                 170                 175

Trp Gly Ala Asp Thr Ala Ala Cys Gly Asp Ile Ile Leu Gly Leu Pro
            180                 185                 190

Val Ser Ala Arg Arg Gly Arg Glu Ile His Leu Gly Pro Ala Asp Ser
        195                 200                 205

Leu Glu Gly Gln Gly Trp Arg Leu Leu Ala Pro Ile Thr Ala Tyr Ser
210                 215                 220

Gln Gln Thr Arg Gly Leu Leu Gly Cys Ile Ile Thr Ser Leu Thr Gly
225                 230                 235                 240

Arg Asp Arg Asn Gln Val Glu Gly Glu Val Gln Val Val Ser Thr Ala
                245                 250                 255

Thr Gln Ser Phe Leu Ala Thr Cys Val Asn Gly Val Cys Trp Thr Val
            260                 265                 270

Tyr His Gly Ala Gly Ser Lys Thr Leu Ala Gly Pro Lys Gly Pro Ile
        275                 280                 285

Thr Gln Met Tyr Thr Asn Val Asp Gln Asp Leu Val Gly Trp Gln Ala
290                 295                 300

Pro Pro Gly Ala Arg Ser Leu Thr Pro Cys Thr Cys Gly Ser Ser Asp
305                 310                 315                 320

Leu Tyr Leu Val Thr Arg His Ala Asp Val Ile Pro Val Arg Arg Arg
                325                 330                 335

Gly Asp Ser Arg Gly Ser Leu Leu Ser Pro Arg Pro Val Ser Tyr Leu
            340                 345                 350
```

-continued

```
Lys Gly Ser Ser Gly Gly Pro Leu Leu Cys Pro Ser Gly His Ala Val
            355                 360                 365
Gly Ile Phe Arg Ala Ala Val Cys Thr Arg Gly Val Ala Lys Ala Val
        370                 375                 380
Asp Phe Val Pro Val Glu Ser Met Glu Thr Thr Met Arg Ser Pro Val
385                 390                 395                 400
Phe Thr Asp Asn Ser Ser Pro Pro Ala Val Pro Gln Thr Phe Gln Val
                405                 410                 415
Ala His Leu His Ala Pro Thr Gly Ser Gly Lys Ser Thr Lys Val Pro
                420                 425                 430
Ala Ala Tyr Ala Ala Gln Gly Tyr Lys Val Leu Val Leu Asn Pro Ser
            435                 440                 445
Val Ala Ala Thr Leu Gly Phe Gly Ala Tyr Met Ser Lys Ala His Gly
    450                 455                 460
Ile Asp Pro Asn Ile Arg Thr Gly Val Arg Thr Ile Thr Thr Gly Ala
465                 470                 475                 480
Pro Ile Thr Tyr Ser Thr Tyr Gly Lys Phe Leu Ala Asp Gly Gly Cys
                485                 490                 495
Ser Gly Gly Ala Tyr Asp Ile Ile Cys Asp Glu Cys His Ser Thr
            500                 505                 510
Asp Ser Thr Thr Ile Leu Gly Ile Gly Thr Val Leu Asp Gln Ala Glu
        515                 520                 525
Thr Ala Gly Ala Arg Leu Val Val Leu Ala Thr Ala Thr Pro Pro Gly
530                 535                 540
Ser Val Thr Val Pro His Pro Asn Ile Glu Glu Val Ala Leu Ser Ser
545                 550                 555                 560
Thr Gly Glu Ile Pro Phe Tyr Gly Lys Ala Ile Pro Ile Glu Thr Ile
                565                 570                 575
Lys Gly Gly Arg His Leu Ile Phe Cys His Ser Lys Lys Lys Cys Asp
            580                 585                 590
Glu Leu Ala Ala Lys Leu Ser Gly Leu Gly Leu Asn Ala Val Ala Tyr
        595                 600                 605
Tyr Arg Gly Leu Asp Val Ser Val Ile Pro Thr Ser Gly Asp Val Ile
610                 615                 620
Val Val Ala Thr Asp Ala Leu Met Thr Gly Phe Thr Gly Asp Phe Asp
625                 630                 635                 640
Ser Val Ile Asp Cys Asn Thr Cys Val Thr Gln Thr Val Asp Phe Ser
                645                 650                 655
Leu Asp Pro Thr Phe Thr Ile Glu Thr Thr Thr Val Pro Gln Asp Ala
            660                 665                 670
Val Ser Arg Ser Gln Arg Arg Gly Arg Thr Gly Arg Gly Arg Met Gly
        675                 680                 685
Ile Tyr Arg Phe Val Thr Pro Gly Glu Arg Pro Ser Gly Met Phe Asp
690                 695                 700
Ser Ser Val Leu Cys Glu Cys Tyr Asp Ala Gly Cys Ala Trp Tyr Glu
705                 710                 715                 720
Leu Thr Pro Ala Glu Thr Ser Val Arg Leu Arg Ala Tyr Leu Asn Thr
                725                 730                 735
Pro Gly Leu Pro Val Cys Gln Asp His Leu Glu Phe Trp Glu Ser Val
            740                 745                 750
Phe Thr Gly Leu Thr His Ile Asp Ala His Phe Leu Ser Gln Thr Lys
        755                 760                 765
Gln Ala Gly Asp Asn Phe Pro Tyr Leu Val Ala Tyr Gln Ala Thr Val
770                 775                 780
```

-continued

```
Cys Ala Arg Ala Gln Ala Pro Pro Ser Trp Asp Gln Met Trp Lys
785                 790                 795                 800

Cys Leu Ile Arg Leu Lys Pro Thr Leu His Gly Pro Thr Pro Leu Leu
            805                 810                 815

Tyr Arg Leu Gly Ala Val Gln Asn Glu Val Thr Thr His Pro Ile
        820                 825                 830

Thr Lys Tyr Ile Met Ala Cys Met Ser Ala Asp Leu Glu Val Val Thr
            835                 840                 845

Ser Thr Trp Val Leu Val Gly Gly Val Leu Ala Ala Leu Ala Ala Tyr
    850                 855                 860

Cys Leu Thr Thr Gly Ser Val Val Ile Val Gly Arg Ile Ile Leu Ser
865                 870                 875                 880

Gly Xaa Pro Ala Ile Ile Pro Asp Arg Glu Val Leu Tyr Arg Glu Phe
            885                 890                 895

Asp Glu Met Glu Glu Cys Ala Ser His Leu Pro Tyr Ile Glu Gln Gly
        900                 905                 910

Met Gln Leu Ala Glu Gln Phe Lys Gln Lys Ala Ile Gly Leu Leu Gln
    915                 920                 925

Thr Ala Thr Lys Gln Ala Glu Ala Ala Ala Pro Val Val Glu Ser Lys
    930                 935                 940

Trp Arg Thr Leu Glu Ala Phe Trp Ala Lys His Met Trp Asn Phe Ile
945                 950                 955                 960

Ser Gly Ile Gln Tyr Leu Ala Gly Leu Ser Thr Leu Pro Gly Asn Pro
            965                 970                 975

Ala Ile Ala Ser Leu Met Ala Phe Thr Ala Ser Ile Thr Ser Pro Leu
            980                 985                 990

Thr Thr Gln His Thr Leu Leu Phe Asn Ile Leu Gly Gly Trp Val Ala
        995                 1000                1005

Ala Gln Leu Ala Pro Pro Ser Ala Ala Ser Ala Phe Val Gly Ala Gly
    1010                1015                1020

Ile Ala Gly Ala Ala Val Gly Ser Ile Gly Leu Gly Lys Val Leu Val
1025                1030                1035                1040

Asp Ile Leu Ala Gly Tyr Gly Ala Gly Val Ala Gly Ala Leu Val Ala
            1045                1050                1055

Phe Lys Val Met Ser Gly Glu Met Pro Ser Thr Glu Asp Leu Val Asn
            1060                1065                1070

Leu Leu Pro Ala Ile Leu Ser Pro Gly Ala Leu Val Val Gly Val Val
    1075                1080                1085

Cys Ala Ala Ile Leu Arg Arg His Val Gly Pro Gly Glu Gly Ala Val
    1090                1095                1100

Gln Trp Met Asn Arg Leu Ile Ala Phe Ala Ser Arg Gly Asn His Val
1105                1110                1115                1120

Ser Pro Thr His Tyr Val Pro Glu Ser Asp Ala Ala Ala Arg Val Thr
            1125                1130                1135

Gln Ile Leu Ser Ser Leu Thr Ile Thr Gln Leu Leu Lys Arg Leu His
        1140                1145                1150

Gln Trp Ile Asn Glu Asp Cys Ser Thr Pro Cys Ser Gly Ser Trp Leu
    1155                1160                1165

Arg Asp Val Trp Asp Trp Ile Cys Thr Val Leu Thr Asp Phe Lys Thr
    1170                1175                1180

Trp Leu Gln Ser Lys Leu Leu Pro Arg Leu Pro Gly Val Pro Phe Phe
1185                1190                1195                1200

Ser Cys Gln Arg Gly Tyr Lys Gly Val Trp Arg Gly Asp Gly Ile Met
```

-continued

```
                1205                1210                1215
Gln Thr Thr Cys Pro Cys Gly Ala Gln Ile Thr Gly His Val Lys Asn
            1220                1225                1230
Cys Ser Met Arg Ile Val Gly Pro Arg Thr Cys Ser Asn Thr Trp His
            1235                1240                1245
Gly Thr Phe Pro Ile Asn Ala Tyr Thr Thr Gly Pro Cys Thr Pro Ser
            1250                1255                1260
Pro Ala Pro Asn Tyr Ser Arg Ala Leu Trp Arg Val Ala Ala Glu Glu
1265                1270                1275                1280
Tyr Val Glu Val Thr Arg Val Gly Asp Phe His Tyr Val Thr Gly Met
            1285                1290                1295
Thr Thr Asp Asn Val Lys Cys Pro Cys Gln Val Pro Ala Pro Glu Phe
            1300                1305                1310
Phe Thr Glu Val Asp Gly Val Arg Leu His Arg Tyr Ala Pro Ala Cys
            1315                1320                1325
Lys Pro Leu Leu Arg Glu Glu Val Thr Phe Leu Val Gly Leu Asn Gln
            1330                1335                1340
Tyr Leu Val Gly Ser Gln Leu Pro Cys Glu Pro Glu Pro Asp Val Ala
1345                1350                1355                1360
Val Leu Thr Ser Met Leu Thr Asp Pro Ser His Ile Thr Ala Glu Thr
            1365                1370                1375
Ala Lys Arg Arg Leu Ala Arg Gly Ser Pro Pro Ser Leu Ala Ser Ser
            1380                1385                1390
Ser Ala Ser Gln Leu Ser Ala Pro Ser Leu Lys Ala Thr Cys Thr Thr
            1395                1400                1405
Arg His Asp Ser Pro Asp Ala Asp Leu Ile Glu Ala Asn Leu Leu Trp
            1410                1415                1420
Arg Gln Glu Met Gly Gly Asn Ile Thr Arg Val Glu Ser Glu Asn Lys
1425                1430                1435                1440
Val Val Ile Leu Asp Ser Phe Glu Pro Leu Gln Ala Glu Glu Asp Glu
            1445                1450                1455
Arg Glu Val Ser Val Pro Ala Glu Ile Leu Arg Arg Ser Arg Lys Phe
            1460                1465                1470
Pro Arg Ala Met Pro Ile Trp Ala Arg Pro Asp Tyr Asn Pro Pro Leu
            1475                1480                1485
Xaa Glu Ser Trp Lys Asp Pro Asp Tyr Val Pro Pro Val Val His Gly
            1490                1495                1500
Cys Pro Leu Pro Pro Ala Lys Ala Pro Pro Ile Pro Pro Pro Arg Arg
1505                1510                1515                1520
Lys Arg Thr Val Val Leu Ser Glu Ser Thr Val Ser Ser Ala Leu Ala
            1525                1530                1535
Glu Leu Ala Thr Lys Thr Phe Gly Ser Ser Glu Ser Ser Ala Val Asp
            1540                1545                1550
Ser Gly Thr Ala Thr Ala Ser Pro Asp Gln Pro Ser Asp Asp Gly Asp
            1555                1560                1565
Ala Gly Ser Asp Val Glu Ser Tyr Ser Ser Met Pro Pro Leu Glu Gly
            1570                1575                1580
Glu Pro Gly Asp Pro Asp Leu Ser Asp Gly Ser Trp Ser Thr Val Ser
1585                1590                1595                1600
Glu Glu Ala Ser Glu Asp Val Val Cys Cys Ser Met Ser Tyr Thr Trp
            1605                1610                1615
Thr Gly Ala Leu Ile Thr Pro Cys Ala Ala Glu Glu Thr Lys Leu Pro
            1620                1625                1630
```

```
Ile Asn Ala Leu Ser Asn Ser Leu Leu Arg His His Asn Leu Val Tyr
        1635                1640                1645
Ala Thr Thr Ser Arg Ser Ala Ser Leu Arg Gln Lys Lys Val Thr Phe
        1650                1655                1660
Asp Arg Leu Gln Val Leu Asp Asp His Tyr Arg Asp Val Leu Lys Glu
1665                1670                1675                1680
Met Lys Ala Lys Ala Ser Thr Val Lys Ala Lys Leu Leu Ser Val Glu
        1685                1690                1695
Glu Ala Cys Lys Leu Thr Pro Pro His Ser Ala Arg Ser Lys Phe Gly
        1700                1705                1710
Tyr Gly Ala Lys Asp Val Arg Asn Leu Ser Ser Lys Ala Val Asn His
        1715                1720                1725
Ile Arg Ser Val Trp Lys Asp Leu Leu Glu Asp Thr Glu Thr Pro Ile
        1730                1735                1740
Asp Thr Thr Ile Met Ala Lys Asn Glu Val Phe Cys Val Gln Pro Glu
1745                1750                1755                1760
Lys Gly Gly Arg Lys Pro Ala Arg Leu Ile Val Phe Pro Asp Leu Gly
        1765                1770                1775
Val Arg Val Cys Glu Lys Met Ala Leu Tyr Asp Val Val Ser Thr Leu
        1780                1785                1790
Pro Gln Ala Val Met Gly Ser Ser Tyr Gly Phe Gln Tyr Ser Pro Gly
        1795                1800                1805
Gln Arg Val Glu Phe Leu Val Asn Ala Trp Lys Ala Lys Lys Cys Pro
        1810                1815                1820
Met Gly Phe Ala Tyr Asp Thr Arg Cys Phe Asp Ser Thr Val Thr Glu
1825                1830                1835                1840
Asn Asp Ile Arg Val Glu Glu Ser Ile Tyr Gln Cys Cys Asp Leu Ala
        1845                1850                1855
Pro Glu Ala Arg Gln Ala Ile Arg Ser Leu Thr Glu Arg Leu Tyr Ile
        1860                1865                1870
Gly Gly Pro Leu Thr Asn Ser Lys Gly Gln Asn Cys Gly Tyr Arg Arg
        1875                1880                1885
Cys Arg Ala Ser Gly Val Leu Thr Thr Ser Cys Gly Asn Thr Leu Thr
        1890                1895                1900
Cys Tyr Leu Lys Ala Ala Ala Ala Cys Arg Ala Ala Lys Leu Gln Asp
1905                1910                1915                1920
Cys Thr Met Leu Val Cys Gly Asp Asp Leu Val Val Ile Cys Glu Ser
        1925                1930                1935
Ala Gly Thr Gln Glu Asp Glu Ala Ser Leu Arg Ala Phe Thr Glu Ala
        1940                1945                1950
Met Thr Arg Tyr Ser Ala Pro Pro Gly Asp Pro Pro Lys Pro Glu Tyr
        1955                1960                1965
Asp Leu Glu Leu Ile Thr Ser Cys Ser Ser Asn Val Ser Val Ala His
        1970                1975                1980
Asp Ala Ser Gly Lys Arg Val Tyr Tyr Leu Thr Arg Asp Pro Thr Thr
1985                1990                1995                2000
Pro Leu Ala Arg Ala Ala Trp Glu Thr Ala Arg His Thr Pro Val Asn
        2005                2010                2015
Ser Trp Leu Gly Asn Ile Ile Met Tyr Ala Pro Thr Leu Trp Ala Arg
        2020                2025                2030
Met Ile Leu Met Thr His Phe Phe Ser Ile Leu Leu Ala Gln Glu Gln
        2035                2040                2045
Leu Glu Lys Ala Leu Asp Cys Gln Ile Tyr Gly Ala Cys Tyr Ser Ile
        2050                2055                2060
```

```
Glu Pro Leu Asp Leu Pro Gln Ile Ile Gln Arg Leu His Gly Leu Ser
2065                2070                2075                2080

Ala Phe Ser Leu His Ser Tyr Ser Pro Gly Glu Ile Asn Arg Val Ala
            2085                2090                2095

Ser Cys Leu Arg Lys Leu Gly Val Pro Pro Leu Arg Val Trp Arg His
            2100                2105                2110

Arg Ala Arg Ser Val Arg Ala Arg Leu Leu Ser Gln Gly Gly Arg Ala
            2115                2120                2125

Ala Thr Cys Gly Lys Tyr Leu Phe Asn Trp Ala Val Arg Thr Lys Leu
            2130                2135                2140

Lys Leu Thr Pro Ile Pro Ala Ala Ser Gln Leu Asp Leu Ser Ser Trp
2145                2150                2155                2160

Phe Val Ala Gly Tyr Ser Gly Gly Asp Ile Tyr His Ser Leu Ser Arg
                2165                2170                2175

Ala Arg Pro Arg Trp Phe Met Trp Cys Leu Leu Leu Ser Val Gly
            2180                2185                2190

Val Gly Ile Tyr Leu Leu Pro Asn Arg
            2195                2200

<210> SEQ ID NO 4
<211> LENGTH: 8643
<212> TYPE: DNA
<213> ORGANISM: Hepatitis C virus
<220> FEATURE:
<221> NAME/KEY: CDS
<222> LOCATION: (1802)...(8407)

<400> SEQUENCE: 4
accagccccc gattgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc gcaacagaca atcggctgct     480
ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg gaagccggtc     840
ttgtcgatca ggatgatctg gacgaagagc atcaggggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agttcgcgcc cagatgttaa    1200
cagaccacaa cggtttccct ctagcgggat caattccgcc ccccccccta acgttactgg    1260
```

```
ccgaagccgc ttggaataag gccggtgtgc gtttgtctat atgttatttt ccaccatatt   1320
gccgtctttt ggcaatgtga gggcccggaa acctggccct gtcttcttga cgagcattcc   1380 tagggggtctt tcccctctcg ccaaaggaat gcaaggtctg ttgaatgtcg tgaaggaagc   1440
agttcctctg gaagcttctt gaagacaaac aacgtctgta gcgacccttt gcaggcagcg   1500 gaaccccca cctggcgaca ggtgcctctg cggccaaaag ccacgtgtat aagatacacc    1560
tgcaaaggcg gcacaacccc agtgccacgt tgtgagttgg atagttgtgg aaagagtcaa   1620
atggctctcc tcaagcgtat tcaacaaggg gctgaaggat gcccagaagg tacccattg    1680 tatgggatct gatctggggc ctcggtgcac atgctttaca tgtgtttagt cgaggttaga   1740
aaacgtctag gccccccgaa ccacggggac gtggttttcc tttgaaaaac acgataatac   1800
```

```
c atg gac cgg gag atg gca gca tcg tgc gga ggc gcg gtt ttc gta ggt   1849
  Met Asp Arg Glu Met Ala Ala Ser Cys Gly Gly Ala Val Phe Val Gly
   1               5                  10                  15 ctg ata ctc ttg acc ttg tca ccg cac tat aag ctg ttc ctc gct agg     1897
Leu Ile Leu Leu Thr Leu Ser Pro His Tyr Lys Leu Phe Leu Ala Arg
            20                  25                  30 ctc ata tgg tgg tta caa tat ttt atc acc agg gcc gag gca cac ttg     1945
Leu Ile Trp Trp Leu Gln Tyr Phe Ile Thr Arg Ala Glu Ala His Leu
        35                  40                  45 caa gtg tgg atc ccc ccc ctc aac gtt cgg ggg ggc cgc gat gcc gtc     1993
Gln Val Trp Ile Pro Pro Leu Asn Val Arg Gly Gly Arg Asp Ala Val
    50                  55                  60 atc ctc ctc acg tgc gcg atc cac cca gag cta atc ttt acc atc acc     2041
Ile Leu Leu Thr Cys Ala Ile His Pro Glu Leu Ile Phe Thr Ile Thr
 65                  70                  75                  80 aaa atc ttg ctc gcc ata ctc ggt cca ctc atg gtg ctc cag gct ggt     2089
Lys Ile Leu Leu Ala Ile Leu Gly Pro Leu Met Val Leu Gln Ala Gly
                85                  90                  95 ata acc aaa gtg ccg tac ttc gtg cgc gca cac ggg ctc att cgt gca     2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct     2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc     2233
Leu Met Lys Leu Ala Ala Leu Thr Gly Thr Tyr Val Tyr Asp His Leu
    130                 135                 140 acc cca ctg cgg gac tgg gcc cac gcg ggc cta cga gac ctt gcg gtg     2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc     2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc     2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc     2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc     2473
Leu Glu Gly Gln Gly Trp Arg Leu Leu Ala Pro Ile Thr Ala Tyr Ser
    210                 215                 220 caa cag acg cga ggc cta ctt ggc tgc atc atc act agc ctc aca ggc     2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca     2569
```

```
                Arg Asp Arg Asn Gln Val Glu Gly Glu Val Gln Val Val Ser Thr Ala
                                245                 250                 255 aca caa tct ttc ctg gcg acc tgc gtc aat ggc gtg tgt tgg act gtc              2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc              2665
Tyr His Gly Ala Gly Ser Lys Thr Leu Ala Gly Pro Lys Gly Pro Ile
        275                 280                 285 acc caa atg tac acc aat gtg gac cag gac ctc gtc ggc tgg caa gcg              2713
Thr Gln Met Tyr Thr Asn Val Asp Gln Asp Leu Val Gly Trp Gln Ala
    290                 295                 300 ccc ccc ggg gcg cgt tcc ttg aca cca tgc acc tgc ggc agc tcg gac              2761
Pro Pro Gly Ala Arg Ser Leu Thr Pro Cys Thr Cys Gly Ser Ser Asp
305                 310                 315                 320 ctt tac ttg gtc acg aag cat gcc gat gtc att ccg gtg cgc gg cgg              2809
Leu Tyr Leu Val Thr Lys His Ala Asp Val Ile Pro Val Arg Arg Arg
                325                 330                 335 ggc gac agc agg ggg agc cta ctc tcc ccc cgg ccc gtc tcc tac ttg              2857
Gly Asp Ser Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg              2905
Lys Gly Ser Ser Gly Gly Pro Leu Leu Cys Pro Ser Gly His Ala Val
        355                 360                 365 ggc atc ttt cgg gct gcc gtg tgc acc cga ggg gtt gcg aag gcg gtg              2953
Gly Ile Phe Arg Ala Ala Val Cys Thr Arg Gly Val Ala Lys Ala Val
    370                 375                 380 gac ttt gta ccc gtc gag tct atg gaa acc act atg cgg tcc ccg gtc              3001
Asp Phe Val Pro Val Glu Ser Met Glu Thr Thr Met Arg Ser Pro Val
385                 390                 395                 400 ttc acg gac aac tcg tcc cct ccg gcc gta ccg cag aca ttc cag gtg              3049
Phe Thr Asp Asn Ser Ser Pro Pro Ala Val Pro Gln Thr Phe Gln Val
                405                 410                 415 gcc cat cta cac gcc cct act ggt agc ggc aag agc act aag gtg ccg              3097
Ala His Leu His Ala Pro Thr Gly Ser Gly Lys Ser Thr Lys Val Pro
            420                 425                 430 gct gcg tat gca gcc caa ggg tat aag gtg ctt gtc ctg aac ccg tcc              3145
Ala Ala Tyr Ala Ala Gln Gly Tyr Lys Val Leu Val Leu Asn Pro Ser
        435                 440                 445 gtc gcc gcc acc cta ggt ttc ggg gcg tat atg tct aag gca cat ggt              3193
Val Ala Ala Thr Leu Gly Phe Gly Ala Tyr Met Ser Lys Ala His Gly
    450                 455                 460 atc gac cct aac atc aga acc ggg gta agg acc atc acc acg ggt gcc              3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc              3289
Pro Ile Thr Tyr Ser Thr Tyr Gly Lys Phe Leu Ala Asp Gly Gly Cys
                485                 490                 495 tct ggg ggc gcc tat gac atc ata ata tgt gat gag tgc cac tca act              3337
Ser Gly Gly Ala Tyr Asp Ile Ile Ile Cys Asp Glu Cys His Ser Thr
            500                 505                 510 gac tcg acc act atc ctg ggc atc ggc aca gtc ctg gac caa gcg gag              3385
Asp Ser Thr Thr Ile Leu Gly Ile Gly Thr Val Leu Asp Gln Ala Glu
        515                 520                 525 acg gct gga gcg cga ctc gtc gtg ctc gcc acc gct acg cct ccg gga              3433
Thr Ala Gly Ala Arg Leu Val Val Leu Ala Thr Ala Thr Pro Pro Gly
    530                 535                 540 tcg gtc acc gtg cca cat cca aac atc gag gag gtg gct ctg tcc agc              3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc              3529
```

|   |   |   |   |   |   |   |   |   |   |   |   |   |   |   |   |
|---|---|---|---|---|---|---|---|---|---|---|---|---|---|---|---|
| Thr | Gly | Glu | Ile | Pro | Phe | Tyr | Gly | Lys | Ala | Ile | Pro | Ile | Glu | Thr | Ile |
|   |   |   |   | 565 |   |   |   | 570 |   |   |   | 575 |   |   |   |

```
aag ggg ggg agg cac ctc att ttc tgc cat tcc aag aag aaa tgt gat      3577
Lys Gly Gly Arg His Leu Ile Phe Cys His Ser Lys Lys Lys Cys Asp
                580                 585                 590 gag ctc gcc gcg aag ctg tcc ggc ctc gga ctc aat gct gta gca tat      3625
Glu Leu Ala Ala Lys Leu Ser Gly Leu Gly Leu Asn Ala Val Ala Tyr
                595                 600                 605 tac cgg ggc ctt gat gta tcc gtc ata cca act agc gga gac gtc att      3673
Tyr Arg Gly Leu Asp Val Ser Val Ile Pro Thr Ser Gly Asp Val Ile
            610                 615                 620 gtc gta gca acg gac gct cta atg acg ggc ttt acc ggc gat ttc gac      3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc      3769
Ser Val Ile Asp Cys Asn Thr Cys Val Thr Gln Thr Val Asp Phe Ser
                    645                 650                 655 ctg gac ccg acc ttc acc att gag acg acg acc gtg cca caa gac gcg      3817
Leu Asp Pro Thr Phe Thr Ile Glu Thr Thr Thr Val Pro Gln Asp Ala
                660                 665                 670 gtg tca cgc tcg cag cgg cga ggc agg act ggt agg ggc agg atg ggc      3865
Val Ser Arg Ser Gln Arg Arg Gly Arg Thr Gly Arg Gly Arg Met Gly
            675                 680                 685 att tac agg ttt gtg act cca gga gaa cgg ccc tcg ggc atg ttc gat      3913
Ile Tyr Arg Phe Val Thr Pro Gly Glu Arg Pro Ser Gly Met Phe Asp
        690                 695                 700 tcc tcg gtt ctg tgc gag tgc tat gac gcg ggc tgt gct tgg tac gag      3961
Ser Ser Val Leu Cys Glu Cys Tyr Asp Ala Gly Cys Ala Trp Tyr Glu
705                 710                 715                 720 ctc acg ccc gcc gag acc tca gtt agg ttg cgg gct tac cta aac aca      4009
Leu Thr Pro Ala Glu Thr Ser Val Arg Leu Arg Ala Tyr Leu Asn Thr
                    725                 730                 735 cca ggg ttg ccc gtc tgc cag gac cat ctg gag ttc tgg gag ggc gtc      4057
Pro Gly Leu Pro Val Cys Gln Asp His Leu Glu Phe Trp Glu Gly Val
                740                 745                 750 ttt aca ggc ctc acc cac ata gac gcc cat ttc ttg tcc cag act aag      4105
Phe Thr Gly Leu Thr His Ile Asp Ala His Phe Leu Ser Gln Thr Lys
            755                 760                 765 cag gca gga gac aac ttc ccc tac ctg gta gca tac cag gct acg gtg      4153
Gln Ala Gly Asp Asn Phe Pro Tyr Leu Val Ala Tyr Gln Ala Thr Val
        770                 775                 780 tgc gcc agg gct cag gct cca cct cca tcg tgg gac caa atg tgg aag      4201
Cys Ala Arg Ala Gln Ala Pro Pro Pro Ser Trp Asp Gln Met Trp Lys
785                 790                 795                 800 tgt ctc ata cgg cta aag cct acg ctg cac ggg cca acg ccc ctg ctg      4249
Cys Leu Ile Arg Leu Lys Pro Thr Leu His Gly Pro Thr Pro Leu Leu
                    805                 810                 815 tat agg ctg gga gcc gtt caa aac gag gtt act acc aca cac ccc ata      4297
Tyr Arg Leu Gly Ala Val Gln Asn Glu Val Thr Thr Thr His Pro Ile
                820                 825                 830 acc aaa tac atc atg gca tgc atg tcg gct gac ctg gag gtc gtc acg      4345
Thr Lys Tyr Ile Met Ala Cys Met Ser Ala Asp Leu Glu Val Val Thr
            835                 840                 845 agc acc tgg gtg ctg gta ggc gga gtc cta gca gct ctg gcc gcg tat      4393
Ser Thr Trp Val Leu Val Gly Gly Val Leu Ala Ala Leu Ala Ala Tyr
        850                 855                 860 tgc ctg aca aca ggc agc gtg gtc att gtg ggc agg atc atc ttg tcc      4441
Cys Leu Thr Thr Gly Ser Val Val Ile Val Gly Arg Ile Ile Leu Ser
865                 870                 875                 880 gga agg ccg gcc atc att ccc gac agg gaa gtc ctt tac cgg gag ttc      4489
```

```
Gly Arg Pro Ala Ile Ile Pro Asp Arg Glu Val Leu Tyr Arg Glu Phe
                885                 890                 895 gat gag atg gaa gag tgc gcc tca cac ctc cct tac atc gaa cag gga        4537
Asp Glu Met Glu Glu Cys Ala Ser His Leu Pro Tyr Ile Glu Gln Gly
        900                 905                 910 atg cag ctc gcc gaa caa ttc aaa cag aag gca atc ggg ttg ctg caa        4585
Met Gln Leu Ala Glu Gln Phe Lys Gln Lys Ala Ile Gly Leu Leu Gln
            915                 920                 925 aca gcc acc aag caa gcg gag gct gct gct ccc gtg gtg gaa tcc aag        4633
Thr Ala Thr Lys Gln Ala Glu Ala Ala Ala Pro Val Val Glu Ser Lys
        930                 935                 940 tgg cgg acc ctc gaa gcc ttc tgg gcg aag cat atg tgg aat ttc atc        4681
Trp Arg Thr Leu Glu Ala Phe Trp Ala Lys His Met Trp Asn Phe Ile
945                 950                 955                 960 agc ggg ata caa tat tta gca ggc ttg tcc act ctg cct ggc aac ccc        4729
Ser Gly Ile Gln Tyr Leu Ala Gly Leu Ser Thr Leu Pro Gly Asn Pro
                965                 970                 975 gcg ata gca tca ctg atg gca ttc aca gcc tct atc acc agc ccg ctc        4777
Ala Ile Ala Ser Leu Met Ala Phe Thr Ala Ser Ile Thr Ser Pro Leu
            980                 985                 990 acc acc caa cat acc ctc ctg ttt aac atc ctg ggg gga tgg gtg gcc        4825
Thr Thr Gln His Thr Leu Leu Phe Asn Ile Leu Gly Gly Trp Val Ala
        995                 1000                1005 gcc caa ctt gct cct ccc agc gct gct tcc gct ttc gta ggc gcc ggc        4873
Ala Gln Leu Ala Pro Pro Ser Ala Ala Ser Ala Phe Val Gly Ala Gly
    1010                1015                1020 atc gct gga gcg gct gtt ggc agc ata ggc ctt ggg aag gtg ctt gtg        4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc        4969
Asp Ile Leu Ala Gly Tyr Gly Ala Gly Val Ala Gly Ala Leu Val Ala
                1045                1050                1055 ttt aag gtc atg agc ggc gag atg ccc tcc acc gag gac ctg gtt aac        5017
Phe Lys Val Met Ser Gly Glu Met Pro Ser Thr Glu Asp Leu Val Asn
            1060                1065                1070 cta ctc cct gct atc ctc tcc cct ggc gcc cta gtc gtc ggg gtc gtg        5065
Leu Leu Pro Ala Ile Leu Ser Pro Gly Ala Leu Val Val Gly Val Val
        1075                1080                1085 tgc gca gcg ata ctg cgt cgg cac gtg ggc cca ggg gag ggg gct gtg        5113
Cys Ala Ala Ile Leu Arg Arg His Val Gly Pro Gly Glu Gly Ala Val
    1090                1095                1100 cag tgg atg aac cgg ctg ata gcg ttc gct tcg cgg ggt aac cac gtc        5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act        5209
Ser Pro Thr His Tyr Val Pro Glu Ser Asp Ala Ala Ala Arg Val Thr
                1125                1130                1135 cag atc ctc tct agt ctt acc atc act cag ctg ctg aag agg ctt cac        5257
Gln Ile Leu Ser Ser Leu Thr Ile Thr Gln Leu Leu Lys Arg Leu His
            1140                1145                1150 cag tgg atc aac gag gac tgc tcc acg cca tgc tcc ggc tcg tgg cta        5305
Gln Trp Ile Asn Glu Asp Cys Ser Thr Pro Cys Ser Gly Ser Trp Leu
        1155                1160                1165 aga gat gtt tgg gat tgg ata tgc acg gtg ttg act gat ttc aag gcc        5353
Arg Asp Val Trp Asp Trp Ile Cys Thr Val Leu Thr Asp Phe Lys Ala
    1170                1175                1180 tgg ctc cag tcc aag ctc ctg ccg cga ttg ccg gga gtc ccc ttc ttc        5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg        5449
```

|  |  |
|---|---:|
| Ser Cys Gln Arg Gly Tyr Lys Gly Val Trp Arg Gly Asp Gly Ile Met<br>　　　　　1205　　　　　　　　　1210　　　　　　　　　1215 |  |
| caa acc acc tgc cca tgt gga gca cag atc acc gga cat gtg aaa aac<br>Gln Thr Thr Cys Pro Cys Gly Ala Gln Ile Thr Gly His Val Lys Asn<br>　　　　　1220　　　　　　　　　1225　　　　　　　　　1230 | 5497 |
| tgt tcc atg agg atc gtg ggg cct agg acc tgt agt aac acg tgg cat<br>Cys Ser Met Arg Ile Val Gly Pro Arg Thr Cys Ser Asn Thr Trp His<br>　　　　　1235　　　　　　　　　1240　　　　　　　　　1245 | 5545 |
| gga aca ttc ccc att aac gcg tac acc acg ggc ccc tgc acg ccc tcc<br>Gly Thr Phe Pro Ile Asn Ala Tyr Thr Thr Gly Pro Cys Thr Pro Ser<br>　　　　　1250　　　　　　　　　1255　　　　　　　　　1260 | 5593 |
| ccg gcg cca aat tat tct agg gcg ctg tgg cgg gtg gct gct gag gag<br>Pro Ala Pro Asn Tyr Ser Arg Ala Leu Trp Arg Val Ala Ala Glu Glu<br>1265　　　　　　　　　1270　　　　　　　　　1275　　　　　　　　　1280 | 5641 |
| tac gtg gag gtt acg cga gtg ggg gat ttc cac tac gtg acg ggc atg<br>Tyr Val Glu Val Thr Arg Val Gly Asp Phe His Tyr Val Thr Gly Met<br>　　　　　1285　　　　　　　　　1290　　　　　　　　　1295 | 5689 |
| acc act gac aac gta aag tgc ccg tgt cag gtt ccg gcc ccc gaa ttc<br>Thr Thr Asp Asn Val Lys Cys Pro Cys Gln Val Pro Ala Pro Glu Phe<br>　　　　　1300　　　　　　　　　1305　　　　　　　　　1310 | 5737 |
| ttc aca gaa gtg gat ggg gtg cgg ttg cac agg tac gct cca gcg tgc<br>Phe Thr Glu Val Asp Gly Val Arg Leu His Arg Tyr Ala Pro Ala Cys<br>　　　　　1315　　　　　　　　　1320　　　　　　　　　1325 | 5785 |
| aaa ccc ctc cta cgg gag gag gtc aca ttc ctg gtc ggg ctc aat caa<br>Lys Pro Leu Leu Arg Glu Glu Val Thr Phe Leu Val Gly Leu Asn Gln<br>　　　　　1330　　　　　　　　　1335　　　　　　　　　1340 | 5833 |
| tac ctg gtt ggg tca cag ctc cca tgc gag ccc gaa ctg gac gta gca<br>Tyr Leu Val Gly Ser Gln Leu Pro Cys Glu Pro Glu Leu Asp Val Ala<br>1345　　　　　　　　　1350　　　　　　　　　1355　　　　　　　　　1360 | 5881 |
| gtg ctc act tcc atg ctc acc gac ccc tcc cac att acg gcg gag acg<br>Val Leu Thr Ser Met Leu Thr Asp Pro Ser His Ile Thr Ala Glu Thr<br>　　　　　1365　　　　　　　　　1370　　　　　　　　　1375 | 5929 |
| gct aag cgt agg ctg gcc agg gga tct ccc ccc tcc ttg gcc agc tca<br>Ala Lys Arg Arg Leu Ala Arg Gly Ser Pro Pro Ser Leu Ala Ser Ser<br>　　　　　1380　　　　　　　　　1385　　　　　　　　　1390 | 5977 |
| tca gct agc cag ctg tct gcg cct tcc ttg aag gca aca tgc act acc<br>Ser Ala Ser Gln Leu Ser Ala Pro Ser Leu Lys Ala Thr Cys Thr Thr<br>　　　　　1395　　　　　　　　　1400　　　　　　　　　1405 | 6025 |
| cgt cat gac tcc ccg gac gct gac ctc atc gag gcc aac ctc ctg tgg<br>Arg His Asp Ser Pro Asp Ala Asp Leu Ile Glu Ala Asn Leu Leu Trp<br>　　　　　1410　　　　　　　　　1415　　　　　　　　　1420 | 6073 |
| cgg cag gag atg ggc ggg aac atc acc cgc gtg gag tca gaa aat aag<br>Arg Gln Glu Met Gly Gly Asn Ile Thr Arg Val Glu Ser Glu Asn Lys<br>1425　　　　　　　　　1430　　　　　　　　　1435　　　　　　　　　1440 | 6121 |
| gta gta att ttg gac tct ttc gag ccg ctc caa gcg gag gag gat gag<br>Val Val Ile Leu Asp Ser Phe Glu Pro Leu Gln Ala Glu Glu Asp Glu<br>　　　　　1445　　　　　　　　　1450　　　　　　　　　1455 | 6169 |
| agg gaa gta tcc gtt ccg gcg gag atc ctg cgg agg tcc agg aaa ttc<br>Arg Glu Val Ser Val Pro Ala Glu Ile Leu Arg Arg Ser Arg Lys Phe<br>　　　　　1460　　　　　　　　　1465　　　　　　　　　1470 | 6217 |
| cct cga gcg atg ccc ata tgg gca cgc ccg gat tac aac cct cca ctg<br>Pro Arg Ala Met Pro Ile Trp Ala Arg Pro Asp Tyr Asn Pro Pro Leu<br>　　　　　1475　　　　　　　　　1480　　　　　　　　　1485 | 6265 |
| ttg gag tcc tgg aag gac ccg gac tac gtc cct cca gtg gta cac ggg<br>Leu Glu Ser Trp Lys Asp Pro Asp Tyr Val Pro Pro Val Val His Gly<br>　　　　　1490　　　　　　　　　1495　　　　　　　　　1500 | 6313 |
| tgt cca ttg ccg cct gcc aag gcc cct ccg ata cca cct cca cgg agg<br>Cys Pro Leu Pro Pro Ala Lys Ala Pro Pro Ile Pro Pro Pro Arg Arg<br>1505　　　　　　　　　1510　　　　　　　　　1515　　　　　　　　　1520 | 6361 |
| aag agg acg gtt gtc ctg tca gaa tct acc gtg tct tct gcc ttg gcg | 6409 |

```
                                           -continued

Lys Arg Thr Val Val Leu Ser Glu Ser Thr Val Ser Ser Ala Leu Ala
            1525                1530                1535 gag ctc gcc aca aag acc ttc ggc agc tcc gaa tcg tcg gcc gtc gac      6457
Glu Leu Ala Thr Lys Thr Phe Gly Ser Ser Glu Ser Ser Ala Val Asp
            1540                1545                1550 agc ggc acg gca acg gcc tct cct gac cag ccc tcc gac gac ggc gac      6505
Ser Gly Thr Ala Thr Ala Ser Pro Asp Gln Pro Ser Asp Asp Gly Asp
            1555                1560                1565 gcg gga tcc gac gtt gag tcg tac tcc tcc atg ccc ccc ctt gag ggg      6553
Ala Gly Ser Asp Val Glu Ser Tyr Ser Ser Met Pro Pro Leu Glu Gly
            1570                1575                1580 gag ccg ggg gat ccc gat ctc agc gac ggg tct tgg tct acc gta agc      6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg      6649
Glu Glu Ala Ser Glu Asp Val Val Cys Cys Ser Met Ser Tyr Thr Trp
                1605                1610                1615 acg ggc gcc ctg atc acg cca tgc gct gcg gag gaa acc aag ctg ccc      6697
Thr Gly Ala Leu Ile Thr Pro Cys Ala Ala Glu Glu Thr Lys Leu Pro
            1620                1625                1630 atc aat gca ctg agc aac tct ttg ctc cgt cac cac aac ttg gtc tat      6745
Ile Asn Ala Leu Ser Asn Ser Leu Leu Arg His His Asn Leu Val Tyr
            1635                1640                1645 gct aca aca tct cgc agc gca agc ctg cgg cag aag aag gtc acc ttt      6793
Ala Thr Thr Ser Arg Ser Ala Ser Leu Arg Gln Lys Lys Val Thr Phe
            1650                1655                1660 gac aga ctg cag gtc ctg gac gac cac tac cgg gac gtg ctc aag gag      6841
Asp Arg Leu Gln Val Leu Asp Asp His Tyr Arg Asp Val Leu Lys Glu
1665                1670                1675                1680 atg aag gcg aag gcg tcc aca gtt aag gct aaa ctt cta tcc gtg gag      6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc      6937
Glu Ala Cys Lys Leu Thr Pro Pro His Ser Ala Arg Ser Lys Phe Gly
            1700                1705                1710 tat ggg gca aag gac gtc cgg aac cta tcc agc aag gcc gtt aac cac      6985
Tyr Gly Ala Lys Asp Val Arg Asn Leu Ser Ser Lys Ala Val Asn His
            1715                1720                1725 atc cgc tcc gtg tgg aag gac ttg ctg gaa gac act gag aca cca att      7033
Ile Arg Ser Val Trp Lys Asp Leu Leu Glu Asp Thr Glu Thr Pro Ile
            1730                1735                1740 gac acc acc atc atg gca aaa aat gag gtt ttc tgc gtc caa cca gag      7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg      7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc      7177
Val Arg Val Cys Glu Lys Met Ala Leu Tyr Asp Val Val Ser Thr Leu
            1780                1785                1790 cct cag gcc gtg atg ggc tct tca tac gga ttc caa tac tct cct gga      7225
Pro Gln Ala Val Met Gly Ser Ser Tyr Gly Phe Gln Tyr Ser Pro Gly
            1795                1800                1805 cag cgg gtc gag ttc ctg gtg aat gcc tgg aaa gcg aag aaa tgc cct      7273
Gln Arg Val Glu Phe Leu Val Asn Ala Trp Lys Ala Lys Lys Cys Pro
            1810                1815                1820 atg ggc ttc gca tat gac acc cgc tgt ttt gac tca acg gtc act gag      7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc      7369
```

-continued

```
Asn Asp Ile Arg Val Glu Glu Ser Ile Tyr Gln Cys Cys Asp Leu Ala
            1845                1850                1855 ccc gaa gcc aga cag gcc ata agg tcg ctc aca gag cgg ctt tac atc    7417
Pro Glu Ala Arg Gln Ala Ile Arg Ser Leu Thr Glu Arg Leu Tyr Ile
        1860                1865                1870 ggg ggc ccc ctg act aat tct aaa ggg cag aac tgc ggc tat cgc cgg    7465
Gly Gly Pro Leu Thr Asn Ser Lys Gly Gln Asn Cys Gly Tyr Arg Arg
    1875                1880                1885 tgc cgc gcg agc ggt gta ctg acg acc agc tgc ggt aat acc ctc aca    7513
Cys Arg Ala Ser Gly Val Leu Thr Thr Ser Cys Gly Asn Thr Leu Thr
    1890                1895                1900 tgt tac ttg aag gcc gct gcg gcc tgt cga gct gcg aag ctc cag gac    7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc    7609
Cys Thr Met Leu Val Cys Gly Asp Asp Leu Val Val Ile Cys Glu Ser
            1925                1930                1935 gcg ggg acc caa gag gac gag gcg agc cta cgg gcc ttc acg gag gct    7657
Ala Gly Thr Gln Glu Asp Glu Ala Ser Leu Arg Ala Phe Thr Glu Ala
        1940                1945                1950 atg act aga tac tct gcc ccc cct ggg gac ccg ccc aaa cca gaa tac    7705
Met Thr Arg Tyr Ser Ala Pro Pro Gly Asp Pro Pro Lys Pro Glu Tyr
    1955                1960                1965 gac ttg gag ttg ata aca tca tgc tcc tcc aat gtg tca gtc gcg cac    7753
Asp Leu Glu Leu Ile Thr Ser Cys Ser Ser Asn Val Ser Val Ala His
    1970                1975                1980 gat gca tct ggc aaa agg gtg tac tat ctc acc cgt gac ccc acc acc    7801
Asp Ala Ser Gly Lys Arg Val Tyr Tyr Leu Thr Arg Asp Pro Thr Thr
1985                1990                1995                2000 ccc ctt gcg cgg gct gcg tgg gag aca gct aga cac act cca gtc aat    7849
Pro Leu Ala Arg Ala Ala Trp Glu Thr Ala Arg His Thr Pro Val Asn
            2005                2010                2015 tcc tgg cta ggc aac atc atc atg tat gcg ccc acc ttg tgg gca agg    7897
Ser Trp Leu Gly Asn Ile Ile Met Tyr Ala Pro Thr Leu Trp Ala Arg
        2020                2025                2030 atg atc ctg atg act cat ttc ttc tcc atc ctt cta gct cag gaa caa    7945
Met Ile Leu Met Thr His Phe Phe Ser Ile Leu Leu Ala Gln Glu Gln
    2035                2040                2045 ctt gaa aaa gcc cta gat tgt cag atc tac ggg gcc tgt tac tcc att    7993
Leu Glu Lys Ala Leu Asp Cys Gln Ile Tyr Gly Ala Cys Tyr Ser Ile
2050                2055                2060 gag cca ctt gac cta cct cag atc att caa cga ctc cac ggc ctt agc    8041
Glu Pro Leu Asp Leu Pro Gln Ile Ile Gln Arg Leu His Gly Leu Ser
2065                2070                2075                2080 gca ttt tca ctc cat agt tac tct cca ggt gag atc aat agg gtg gct    8089
Ala Phe Ser Leu His Ser Tyr Ser Pro Gly Glu Ile Asn Arg Val Ala
            2085                2090                2095 tca tgc ctc agg aaa ctt ggg gta ccg ccc ttg cga gtc tgg aga cat    8137
Ser Cys Leu Arg Lys Leu Gly Val Pro Pro Leu Arg Val Trp Arg His
        2100                2105                2110 cgg gcc aga agt gtc cgc gct agg cta ctg tcc cag ggg ggg agg gct    8185
Arg Ala Arg Ser Val Arg Ala Arg Leu Leu Ser Gln Gly Gly Arg Ala
    2115                2120                2125 gcc act tgt ggc aag tac ctc ttc aac tgg gca gta agg acc aag ctc    8233
Ala Thr Cys Gly Lys Tyr Leu Phe Asn Trp Ala Val Arg Thr Lys Leu
    2130                2135                2140 aaa ctc act cca atc ccg gct gcg tcc cag ttg gat tta tcc agc tgg    8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt    8329
```

-continued

| Phe | Val | Ala | Gly | Tyr | Ser | Gly | Gly | Asp | Ile | Tyr | His | Ser | Leu | Ser | Arg | |
|---|---|---|---|---|---|---|---|---|---|---|---|---|---|---|---|---|
| | | | | 2165 | | | | 2170 | | | | 2175 | | | | |

| gcc | cga | ccc | cgc | tgg | ttc | atg | tgg | tgc | cta | ctc | cta | ctt | tct | gta | ggg | 8377 |
|---|---|---|---|---|---|---|---|---|---|---|---|---|---|---|---|---|
| Ala | Arg | Pro | Arg | Trp | Phe | Met | Trp | Cys | Leu | Leu | Leu | Leu | Ser | Val | Gly | |
| | | 2180 | | | | | 2185 | | | | | 2190 | | | | |

| gta | ggc | atc | tat | cta | ctc | ccc | aac | cga | tga | acggggagct | aaacactcca | | | | | 8427 |
|---|---|---|---|---|---|---|---|---|---|---|---|---|---|---|---|---|
| Val | Gly | Ile | Tyr | Leu | Leu | Pro | Asn | Arg | | | | | | | | |
| | | 2195 | | | | 2200 | | | | | | | | | | |

| ggccaatagg ccatcctgtt ttttcccttt tttttttttt tttttttttt tttttttttt | 8487 |
|---|---|
| tttttttttt tttttttttt ttttcttttt tcccaattttt ttttcctttc tttcctttgg | 8547 |
| tggctccatc ttagccctag tcacggctag ctgtgaaagg tccgtgagcc gcttgactgc | 8607 |
| agagagtgct gatactggcc tctctgcaga tcaagt | 8643 |

<210> SEQ ID NO 5
<211> LENGTH: 8648
<212> TYPE: DNA
<213> ORGANISM: Hepatitis C virus
<220> FEATURE:
<221> NAME/KEY: CDS
<222> LOCATION: (1802)...(8407)

<400> SEQUENCE: 5

| gccagccccc gattggggc gacactccac catagatcac tcccctgtga ggaactactg | 60 |
|---|---|
| tcttcacgca gaaagcgtct agccatggcg ttagtatgag tgtcgtgcag cctccaggac | 120 |
| ccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaaggg cgcgccatga ttgaacaaga tggattgcac gcaggttctc | 420 |
| cggccgcttg ggtggagagg ctattcggct atgactgggc acaacagaca atcggctgct | 480 |
| ctgatgccgc cgtgttccgg ctgtcagcgc aggggcgccc ggttcttttt gtcaagaccg | 540 |
| acctgtccgg tgccctgaat gaactgcagg acgaggcagc gcggctatcg tggctggcca | 600 |
| cgacgggcgt tccttgcgca gctgtgctcg acgttgtcac tgaagcggga agggactggc | 660 |
| tgctattggg cgaagtgccg gggcaggatc tcctgtcatc tcaccttgct cctgccgaga | 720 |
| aagtatccat catggctgat gcaatgcggc ggctgcatac gcttgatccg gctacctgcc | 780 |
| cattcgacca ccaagcgaaa catcgcatcg agcgagcacg tactcggatg gaagccggtc | 840 |
| ttgtcgatca ggatgatctg gacgaagagc atcaggggct cgcgccagcc gaactgttcg | 900 |
| ccaggctcaa ggcgcgcatg cccgacgcg aggatctcgt cgtgacccat ggcgatgcct | 960 |
| gcttgccgaa tatcatggtg gaaaatggcc gcttttctgg attcatcgac tgtggccggc | 1020 |
| tgggtgtggc ggaccgctat caggacatag cgttggctac ccgtgatatt gctgaagagc | 1080 |
| ttggcggcga atgggctgac cgcttcctcg tgctttacgg tatcgccgct cccgattcgc | 1140 |
| agcgcatcgc cttctatcgc cttcttgacg agttcttctg agttcgcgcc cagatgttaa | 1200 |
| cagaccacaa cggtttccct ctagcgggat caattccgcc ccccccccta acgttactgg | 1260 |
| ccgaagccgc ttggaataag gccggtgtgc gtttgtctat atgttatttt ccaccatatt | 1320 |
| gccgtctttt ggcaatgtga gggcccggaa acctggccct gtcttcttga cgagcattcc | 1380 |
| taggggtctt tcccctctcg ccaaaggaat gcaaggtctg ttgaatgtcg tgaaggaagc | 1440 |
| agttcctctg gaagcttctt gaagacaaac aacgtctgta gcgaccctt gcaggcagcg | 1500 |

```
gaaccccccca cctggcgaca ggtgcctctg cggccaaaag ccacgtgtat aagatacacc    1560
tgcaaaggcg gcacaacccc agtgccacgt tgtgagttgg atagttgtgg aaagagtcaa    1620
atggctctcc tcaagcgtat tcaacaaggg gctgaaggat gcccagaagg taccccattg    1680
tatgggatct gatctggggc ctcggtgcac atgctttaca tgtgtttagt cgaggttaaa    1740
aaacgtctag gccccccgaa ccacggggac gtggttttcc tttgaaaaac acgataatac    1800
```

```
c atg gac cgg gag atg gca gca tcg tgc gga ggc gcg gtt ttc gta ggt    1849
  Met Asp Arg Glu Met Ala Ala Ser Cys Gly Gly Ala Val Phe Val Gly
   1               5                  10                  15 ctg ata ctc ttg acc ttg tca ccg cac tat aag ctg ttc ctc gct agg      1897
Leu Ile Leu Leu Thr Leu Ser Pro His Tyr Lys Leu Phe Leu Ala Arg
            20                  25                  30 ctc ata tgg tgg tta caa tat ttt atc acc agg gcc gag gca cac ttg      1945
Leu Ile Trp Trp Leu Gln Tyr Phe Ile Thr Arg Ala Glu Ala His Leu
        35                  40                  45 caa gtg tgg atc ccc ccc ctc aac gtt cgg ggg ggc cgc gat gcc gtc      1993
Gln Val Trp Ile Pro Pro Leu Asn Val Arg Gly Gly Arg Asp Ala Val
    50                  55                  60 atc ctc ctc acg tgc gcg atc cac cca gag cta atc ttt acc atc acc      2041
Ile Leu Leu Thr Cys Ala Ile His Pro Glu Leu Ile Phe Thr Ile Thr
65                  70                  75                  80 aaa atc ttg ctc gcc ata ctc ggt cca ctc atg gtg ctc cag gct ggt      2089
Lys Ile Leu Leu Ala Ile Leu Gly Pro Leu Met Val Leu Gln Ala Gly
                85                  90                  95 ata acc aaa gtg ccg tac ttc gtg cgc gca cac ggg ctc att cgt gca      2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct      2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc      2233
Leu Met Lys Leu Ala Ala Leu Thr Gly Thr Tyr Val Tyr Asp His Leu
    130                 135                 140 acc cca ctg cgg gac tgg gcc cac gcg ggc cta cga gac ctt gcg gtg      2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc      2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc      2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc      2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc      2473
Leu Glu Gly Gln Gly Trp Arg Leu Leu Ala Pro Ile Thr Ala Tyr Ser
    210                 215                 220 caa cag acg cga ggc cta ctt ggc tgc atc atc act agc ctc aca ggc      2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca      2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc      2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc      2665
Tyr His Gly Ala Gly Ser Lys Thr Leu Ala Gly Pro Lys Gly Pro Ile
```

```
                275                 280                 285
acc caa atg tac acc aat gtg gac cag gac ctc gtc ggc tgg caa gcg      2713
Thr Gln Met Tyr Thr Asn Val Asp Gln Asp Leu Val Gly Trp Gln Ala
290                 295                 300 ccc ccc ggg gcg cgt tcc ttg aca cca tgc acc tgc ggc agc tcg gac      2761
Pro Pro Gly Ala Arg Ser Leu Thr Pro Cys Thr Cys Gly Ser Ser Asp
305                 310                 315                 320 ctt tac ttg gtc acg agg cat gcc gat gtc att ccg gtg cgc cgg cgg      2809
Leu Tyr Leu Val Thr Arg His Ala Asp Val Ile Pro Val Arg Arg Arg
                325                 330                 335 ggc gac agc agg ggg agc cta ctc tcc ccc agg ccc gtc tcc tac ttg      2857
Gly Asp Ser Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg      2905
Lys Gly Ser Ser Gly Gly Pro Leu Leu Cys Pro Ser Gly His Ala Val
        355                 360                 365 ggc atc ttt cgg gct gcc gtg tgc acc cgg ggg gtt gcg aag gcg gtg      2953
Gly Ile Phe Arg Ala Ala Val Cys Thr Arg Gly Val Ala Lys Ala Val
370                 375                 380 gac ttt gta ccc gtc gag tct atg gga acc act atg cgg tcc ccg gtc      3001
Asp Phe Val Pro Val Glu Ser Met Gly Thr Thr Met Arg Ser Pro Val
385                 390                 395                 400 ttc acg gac aac tcg tcc cct ccg gcc gta ccg cag aca ttc cag gtg      3049
Phe Thr Asp Asn Ser Ser Pro Pro Ala Val Pro Gln Thr Phe Gln Val
                405                 410                 415 gcc cat cta cac gcc cct act ggt agc ggc aag agc act aag gtg ccg      3097
Ala His Leu His Ala Pro Thr Gly Ser Gly Lys Ser Thr Lys Val Pro
            420                 425                 430 gct gcg tat gca gcc caa ggg tat aag gtg ctt gtc ctg aac ccg tcc      3145
Ala Ala Tyr Ala Ala Gln Gly Tyr Lys Val Leu Val Leu Asn Pro Ser
        435                 440                 445 gtc gcc gcc acc cta ggt ttc ggg gcg tat atg tct aag gca cat ggt      3193
Val Ala Ala Thr Leu Gly Phe Gly Ala Tyr Met Ser Lys Ala His Gly
450                 455                 460 atc gac cct aac atc aga acc ggg gta agg acc atc acc acg ggt gcc      3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc      3289
Pro Ile Thr Tyr Ser Thr Tyr Gly Lys Phe Leu Ala Asp Gly Gly Cys
                485                 490                 495 tct ggg ggc gcc tat gac atc ata ata tgt gat gag tgc cac tca act      3337
Ser Gly Gly Ala Tyr Asp Ile Ile Ile Cys Asp Glu Cys His Ser Thr
            500                 505                 510 gac tcg acc act atc ctg ggc atc ggc aca gtc ctg gac caa gcg gag      3385
Asp Ser Thr Thr Ile Leu Gly Ile Gly Thr Val Leu Asp Gln Ala Glu
        515                 520                 525 acg gct gga gcg cga ctc gtc gtg ctc gcc acc gct acg cct ccg gga      3433
Thr Ala Gly Ala Arg Leu Val Val Leu Ala Thr Ala Thr Pro Pro Gly
530                 535                 540 tcg gtc acc gtg cca cat cca aac atc gag gag gtg gct ctg tcc agc      3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc      3529
Thr Gly Glu Ile Pro Phe Tyr Gly Lys Ala Ile Pro Ile Glu Thr Ile
                565                 570                 575 aag ggg ggg agg cac ctc att ttc tgc cat tcc aag aag aaa tgt gat      3577
Lys Gly Gly Arg His Leu Ile Phe Cys His Ser Lys Lys Lys Cys Asp
            580                 585                 590 gag ctc gcc gcg aag ctg tcc ggc ctc gga ctc aat gct gta gca tat      3625
Glu Leu Ala Ala Lys Leu Ser Gly Leu Gly Leu Asn Ala Val Ala Tyr
```

```
                  595                  600                  605
tac cgg ggc ctt gat gta tcc gtc ata cca act agc gga gac gtc att         3673
Tyr Arg Gly Leu Asp Val Ser Val Ile Pro Thr Ser Gly Asp Val Ile
610                 615                 620 gtc gta gca acg gac gct cta atg acg ggc ttt acc ggc gat ttc gac         3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc         3769
Ser Val Ile Asp Cys Asn Thr Cys Val Thr Gln Thr Val Asp Phe Ser
            645                 650                 655 ctg gac ccg acc ttc acc att gag acg acg acc gtg cca caa gac gcg         3817
Leu Asp Pro Thr Phe Thr Ile Glu Thr Thr Thr Val Pro Gln Asp Ala
        660                 665                 670 gtg tca cgc tcg cag cgg cga ggc agg act ggt agg ggc agg atg ggc         3865
Val Ser Arg Ser Gln Arg Arg Gly Arg Thr Gly Arg Gly Arg Met Gly
    675                 680                 685 att tac agg ttt gtg act cca gga gaa cgg ccc tcg ggc atg ttc gat         3913
Ile Tyr Arg Phe Val Thr Pro Gly Glu Arg Pro Ser Gly Met Phe Asp
690                 695                 700 tcc tcg gtt ctg tgc gag tgc tat gac gcg ggc tgt gct tgg tac gag         3961
Ser Ser Val Leu Cys Glu Cys Tyr Asp Ala Gly Cys Ala Trp Tyr Glu
705                 710                 715                 720 ctc acg ccc gcc gag acc tca gtt agg ttg cgg gct tac cta aac aca         4009
Leu Thr Pro Ala Glu Thr Ser Val Arg Leu Arg Ala Tyr Leu Asn Thr
            725                 730                 735 cca ggg ttg ccc gtc tgc cag gac cat ctg gag ttc tgg gag agc gtc         4057
Pro Gly Leu Pro Val Cys Gln Asp His Leu Glu Phe Trp Glu Ser Val
        740                 745                 750 ttt aca ggc ctc acc cac ata gac gcc cat ttc ttg tcc cag act aag         4105
Phe Thr Gly Leu Thr His Ile Asp Ala His Phe Leu Ser Gln Thr Lys
    755                 760                 765 cag gca gga gac aac ttc ccc tac ctg gta gca tac cag gct acg gtg         4153
Gln Ala Gly Asp Asn Phe Pro Tyr Leu Val Ala Tyr Gln Ala Thr Val
770                 775                 780 tgc gcc agg gct cag gct cca cct cca tcg tgg gac caa atg tgg aag         4201
Cys Ala Arg Ala Gln Ala Pro Pro Pro Ser Trp Asp Gln Met Trp Lys
785                 790                 795                 800 tgt ctc ata cgg cta aag cct acg ctg cac ggg cca acg ccc ctg ctg         4249
Cys Leu Ile Arg Leu Lys Pro Thr Leu His Gly Pro Thr Pro Leu Leu
            805                 810                 815 tat agg ctg gga gcc gtt caa aac gag gtt act acc aca cac ccc ata         4297
Tyr Arg Leu Gly Ala Val Gln Asn Glu Val Thr Thr Thr His Pro Ile
        820                 825                 830 acc aaa tac atc atg gca tgc atg tcg gct gac ctg gag gtc gtc acg         4345
Thr Lys Tyr Ile Met Ala Cys Met Ser Ala Asp Leu Glu Val Val Thr
    835                 840                 845 agc acc tgg gtg ctg gta ggc gga gtc cta gca gct ctg gcc gcg tat         4393
Ser Thr Trp Val Leu Val Gly Gly Val Leu Ala Ala Leu Ala Ala Tyr
850                 855                 860 tgc ctg aca aca ggc agc gtg gtc att gtg ggc agg atc atc ttg tcc         4441
Cys Leu Thr Thr Gly Ser Val Val Ile Val Gly Arg Ile Ile Leu Ser
865                 870                 875                 880 gga aag ccg gcc atc att ccc gac agg gaa gtc ctt tac cgg gag ttc         4489
Gly Lys Pro Ala Ile Ile Pro Asp Arg Glu Val Leu Tyr Arg Glu Phe
            885                 890                 895 gat gag atg gaa gag tgc gcc tca cac ctc cct tac atc gaa cag gga         4537
Asp Glu Met Glu Glu Cys Ala Ser His Leu Pro Tyr Ile Glu Gln Gly
        900                 905                 910 atg cag ctc gcc gaa caa ttc aaa cag aag gca atc ggg ttg ctg caa         4585
Met Gln Leu Ala Glu Gln Phe Lys Gln Lys Ala Ile Gly Leu Leu Gln
```

-continued

```
                 915                 920                 925
aca gcc acc aag caa gcg gag gct gct gct ccc gtg gtg gaa tcc aag    4633
Thr Ala Thr Lys Gln Ala Glu Ala Ala Ala Pro Val Val Glu Ser Lys
        930                 935                 940 tgg cgg acc ctc gaa gcc ttc tgg gcg aag cat atg tgg aat ttc atc    4681
Trp Arg Thr Leu Glu Ala Phe Trp Ala Lys His Met Trp Asn Phe Ile
945                 950                 955                 960 agc ggg ata caa tat tta gca ggc ttg tcc act ctg cct ggc aac ccc    4729
Ser Gly Ile Gln Tyr Leu Ala Gly Leu Ser Thr Leu Pro Gly Asn Pro
            965                 970                 975 gcg ata gca tca ctg atg gca ttc aca gcc tct atc acc agc ccg ctc    4777
Ala Ile Ala Ser Leu Met Ala Phe Thr Ala Ser Ile Thr Ser Pro Leu
    980                 985                 990 acc acc caa cat acc ctc ctg ttt aac atc ctg ggg gga tgg gtg gcc    4825
Thr Thr Gln His Thr Leu Leu Phe Asn Ile Leu Gly Gly Trp Val Ala
            995                 1000                1005 gcc caa ctt gct cct ccc agc gct gct tct gct ttc gta ggc gcc ggc    4873
Ala Gln Leu Ala Pro Pro Ser Ala Ala Ser Ala Phe Val Gly Ala Gly
    1010                1015                1020 atc gct gga gcg gct gtt ggc agc ata ggc ctt ggg aag gtg ctt gtg    4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc    4969
Asp Ile Leu Ala Gly Tyr Gly Ala Gly Val Ala Gly Ala Leu Val Ala
            1045                1050                1055 ttt aag gtc atg agc ggc gag atg ccc tcc acc gag gac ctg gtt aac    5017
Phe Lys Val Met Ser Gly Glu Met Pro Ser Thr Glu Asp Leu Val Asn
    1060                1065                1070 cta ctc cct gct atc ctc tcc cct ggc gcc cta gtc gtc ggg gtc gtg    5065
Leu Leu Pro Ala Ile Leu Ser Pro Gly Ala Leu Val Val Gly Val Val
            1075                1080                1085 tgc gca gcg ata ctg cgt cgg cac gtg ggc cca ggg gag ggg gct gtg    5113
Cys Ala Ala Ile Leu Arg Arg His Val Gly Pro Gly Glu Gly Ala Val
    1090                1095                1100 cag tgg atg aac cgg ctg ata gcg ttc gct tcg cgg ggt aac cac gtc    5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act    5209
Ser Pro Thr His Tyr Val Pro Glu Ser Asp Ala Ala Ala Arg Val Thr
            1125                1130                1135 cag atc ctc tct agt ctt acc atc act cag ctg ctg aag agg ctt cac    5257
Gln Ile Leu Ser Ser Leu Thr Ile Thr Gln Leu Leu Lys Arg Leu His
    1140                1145                1150 cag tgg atc aac gag gac tgc tcc acg cca tgc tcc ggc tcg tgg cta    5305
Gln Trp Ile Asn Glu Asp Cys Ser Thr Pro Cys Ser Gly Ser Trp Leu
            1155                1160                1165 aga gat gtt tgg gat tgg gta tgc acg gtg ttg act gat ttc aag acc    5353
Arg Asp Val Trp Asp Trp Val Cys Thr Val Leu Thr Asp Phe Lys Thr
    1170                1175                1180 tgg ctc cag tcc aag ctc ctg ccg cga ttg ccg gga gtc ccc ttc ttc    5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg    5449
Ser Cys Gln Arg Gly Tyr Lys Gly Val Trp Arg Gly Asp Gly Ile Met
            1205                1210                1215 caa acc acc tgc cca tgt gga gca cag atc acc gga cat gtg aaa aac    5497
Gln Thr Thr Cys Pro Cys Gly Ala Gln Ile Thr Gly His Val Lys Asn
    1220                1225                1230 tgt tcc atg agg atc gtg ggg cct agg acc tgt agt aac acg tgg cat    5545
Cys Ser Met Arg Ile Val Gly Pro Arg Thr Cys Ser Asn Thr Trp His
```

```
                    1235              1240              1245
gga aca ttc ccc att aac gcg tac acc acg ggc ccc tgc acg ccc tcc         5593
Gly Thr Phe Pro Ile Asn Ala Tyr Thr Thr Gly Pro Cys Thr Pro Ser
        1250              1255              1260 ccg gcg cca aat tat tct agg gcg ctg tgg cgg gtg gct gct gag gag         5641
Pro Ala Pro Asn Tyr Ser Arg Ala Leu Trp Arg Val Ala Ala Glu Glu
        1265              1270              1275              1280 tac gtg gag gtt acg cgg gtg ggg gat ttc cac tac gtg acg ggc atg         5689
Tyr Val Glu Val Thr Arg Val Gly Asp Phe His Tyr Val Thr Gly Met
                      1285              1290              1295 acc act gac aac gta aag tgc ccg tgt cag gtt ccg gcc ccc gaa ttc         5737
Thr Thr Asp Asn Val Lys Cys Pro Cys Gln Val Pro Ala Pro Glu Phe
                1300              1305              1310 ttc aca gaa gtg gat ggg gtg cgg ttg cac agg tac gct cca gcg tgc         5785
Phe Thr Glu Val Asp Gly Val Arg Leu His Arg Tyr Ala Pro Ala Cys
        1315              1320              1325 aaa ccc ctc cta cgg gag gag gtc aca ttc ctg gtc ggg ctc aat caa         5833
Lys Pro Leu Leu Arg Glu Glu Val Thr Phe Leu Val Gly Leu Asn Gln
        1330              1335              1340 tac ctg gtt ggg tca cag ctc cca tgc gag ccc gaa ccg gac gta gca         5881
Tyr Leu Val Gly Ser Gln Leu Pro Cys Glu Pro Glu Pro Asp Val Ala
1345              1350              1355              1360 gtg ctc act tcc atg ctc acc gac ccc tcc cac att acg gcg gag acg         5929
Val Leu Thr Ser Met Leu Thr Asp Pro Ser His Ile Thr Ala Glu Thr
                      1365              1370              1375 gct aag cgt agg ctg gcc agg gga tct ccc ccc tcc ttg gcc agc tca         5977
Ala Lys Arg Arg Leu Ala Arg Gly Ser Pro Pro Ser Leu Ala Ser Ser
                1380              1385              1390 tca gct agc cag ctg tct gcg ccc tcc ttg aag gca aca tgc act acc         6025
Ser Ala Ser Gln Leu Ser Ala Pro Ser Leu Lys Ala Thr Cys Thr Thr
        1395              1400              1405 cgt cat gac tcc ccg gac gct gac ctc atc gag gcc aac ctc ctg tgg         6073
Arg His Asp Ser Pro Asp Ala Asp Leu Ile Glu Ala Asn Leu Leu Trp
        1410              1415              1420 cgg cag gag atg ggc ggg aac atc acc cgc gtg gag tca gaa aat aag         6121
Arg Gln Glu Met Gly Gly Asn Ile Thr Arg Val Glu Ser Glu Asn Lys
1425              1430              1435              1440 gta gta att ttg gac tct ttc gag ccg ctc caa gcg gag gag gat gag         6169
Val Val Ile Leu Asp Ser Phe Glu Pro Leu Gln Ala Glu Glu Asp Glu
                      1445              1450              1455 agg gaa gta tcc gtt ccg gcg gag atc ctg cgg agg tcc agg aaa ttc         6217
Arg Glu Val Ser Val Pro Ala Glu Ile Leu Arg Arg Ser Arg Lys Phe
                1460              1465              1470 cct cga gcg atg ccc ata tgg gca cgc ccg gat tac aac cct cca ctg         6265
Pro Arg Ala Met Pro Ile Trp Ala Arg Pro Asp Tyr Asn Pro Pro Leu
        1475              1480              1485 tta gag tcc tgg aag gac ccg gac tac gtc cct cca gtg gta cac ggg         6313
Leu Glu Ser Trp Lys Asp Pro Asp Tyr Val Pro Pro Val Val His Gly
        1490              1495              1500 tgt cca ttg ccg cct gcc aag gcc cct ccg ata cca cct cca cgg agg         6361
Cys Pro Leu Pro Pro Ala Lys Ala Pro Pro Ile Pro Pro Pro Arg Arg
1505              1510              1515              1520 aag agg acg gtt gtc ctg tca gaa tct acc gtg tct tct gcc ttg gcg         6409
Lys Arg Thr Val Val Leu Ser Glu Ser Thr Val Ser Ser Ala Leu Ala
                      1525              1530              1535 gag ctc gcc aca aag acc ttc ggc agc tcc gaa tcg tcg gcc gtc gac         6457
Glu Leu Ala Thr Lys Thr Phe Gly Ser Ser Glu Ser Ser Ala Val Asp
                1540              1545              1550 agc ggc acg gca acg gcc tct cct gac cag ccc tcc gac gac ggc gac         6505
Ser Gly Thr Ala Thr Ala Ser Pro Asp Gln Pro Ser Asp Asp Gly Asp
```

-continued

```
                1555                1560                1565
gcg gga tcc gac gtt gag tcg tac tcc tcc atg ccc ccc ctt gag ggg    6553
Ala Gly Ser Asp Val Glu Ser Tyr Ser Ser Met Pro Pro Leu Glu Gly
1570                1575                1580 gag ccg ggg gat ccc gat ctc agc gac ggg tct tgg tct acc gta agc    6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg    6649
Glu Glu Ala Ser Glu Asp Val Val Cys Cys Ser Met Ser Tyr Thr Trp
                1605                1610                1615 aca ggc gcc ctg atc acg cca tgc gct gcg gag gaa acc aag ctg ccc    6697
Thr Gly Ala Leu Ile Thr Pro Cys Ala Ala Glu Glu Thr Lys Leu Pro
           1620                1625                1630 atc aat gca ctg agc aac tct ttg ctc cgt cac cac aac ttg gtc tat    6745
Ile Asn Ala Leu Ser Asn Ser Leu Leu Arg His His Asn Leu Val Tyr
      1635                1640                1645 gct aca aca tct cgc agc gca agc ctg cgg cag aag aag gtc acc ttt    6793
Ala Thr Thr Ser Arg Ser Ala Ser Leu Arg Gln Lys Lys Val Thr Phe
 1650                1655                1660 gac aga ctg cag gtc ctg gac gac cac tac cgg gac gtg ctc aag gag    6841
Asp Arg Leu Gln Val Leu Asp Asp His Tyr Arg Asp Val Leu Lys Glu
1665                1670                1675                1680 atg aag gcg aag gcg tcc aca gtt aag gct aaa ctt cta tcc gtg gag    6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc    6937
Glu Ala Cys Lys Leu Thr Pro Pro His Ser Ala Arg Ser Lys Phe Gly
           1700                1705                1710 tat ggg gca aag gac gtc cgg aac cta tcc agc aag gcc gtt aac cac    6985
Tyr Gly Ala Lys Asp Val Arg Asn Leu Ser Ser Lys Ala Val Asn His
      1715                1720                1725 atc cgc tcc gtg tgg aag gac ttg ctg gaa gac act gag aca cca att    7033
Ile Arg Ser Val Trp Lys Asp Leu Leu Glu Asp Thr Glu Thr Pro Ile
 1730                1735                1740 gac acc acc atc atg gca aaa aat gag gtt ttc tgc gtc caa cca gag    7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg    7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc    7177
Val Arg Val Cys Glu Lys Met Ala Leu Tyr Asp Val Val Ser Thr Leu
           1780                1785                1790 cct cag gcc gtg atg ggc tct tca tac gga ttc caa tac tct cct gga    7225
Pro Gln Ala Val Met Gly Ser Ser Tyr Gly Phe Gln Tyr Ser Pro Gly
      1795                1800                1805 cag cgg gtc gag ttc ctg gtg aat gct tgg aaa gcg aag aaa tgc cct    7273
Gln Arg Val Glu Phe Leu Val Asn Ala Trp Lys Ala Lys Lys Cys Pro
 1810                1815                1820 atg ggc ttc gca tat gac acc cgc tgt ttt gac tca acg gtc act gag    7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc    7369
Asn Asp Ile Arg Val Glu Glu Ser Ile Tyr Gln Cys Cys Asp Leu Ala
                1845                1850                1855 ccc gaa gcc aga cag gcc ata agg tcg ctc aca gag cgg ctt tac atc    7417
Pro Glu Ala Arg Gln Ala Ile Arg Ser Leu Thr Glu Arg Leu Tyr Ile
           1860                1865                1870 ggg ggc ccc ctg act aat tct aaa ggg cag aac tgc ggc tat cgc cgg    7465
Gly Gly Pro Leu Thr Asn Ser Lys Gly Gln Asn Cys Gly Tyr Arg Arg
```

| | | |
|---|---|---|
| 1875 | 1880 | 1885 |

```
tgc cgc gcg agc ggt gta ctg acg acc agc tgc ggt aat acc ctc aca      7513
Cys Arg Ala Ser Gly Val Leu Thr Thr Ser Cys Gly Asn Thr Leu Thr
    1890            1895            1900 tgt tac ttg aag gcc gct gcg gcc tgt cga gct gcg aag ctc cag gac      7561
Cys Tyr Leu Lys Ala Ala Ala Ala Cys Arg Ala Ala Lys Leu Gln Asp
1905            1910            1915            1920 tgc acg atg ctc gta tgc gga gac gac ctt gtc gtt atc tgt gaa agc      7609
Cys Thr Met Leu Val Cys Gly Asp Asp Leu Val Val Ile Cys Glu Ser
                1925            1930            1935 gcg ggg acc caa gag gac gag gcg agc cta cgg gcc ttc acg gag gct      7657
Ala Gly Thr Gln Glu Asp Glu Ala Ser Leu Arg Ala Phe Thr Glu Ala
            1940            1945            1950 atg act aga tac tct gcc ccc cct ggg gac ccg ccc aaa cca gaa tac      7705
Met Thr Arg Tyr Ser Ala Pro Pro Gly Asp Pro Pro Lys Pro Glu Tyr
        1955            1960            1965 gac ttg gag ttg ata aca tca tgc tcc tcc aat gtg tca gtc gcg cac      7753
Asp Leu Glu Leu Ile Thr Ser Cys Ser Ser Asn Val Ser Val Ala His
    1970            1975            1980 gat gca tct ggc aaa agg gtg tac tat ctc acc cgt gac ccc acc acc      7801
Asp Ala Ser Gly Lys Arg Val Tyr Tyr Leu Thr Arg Asp Pro Thr Thr
1985            1990            1995            2000 ccc ctt gcg cgg gct gcg tgg gag aca gct aga cac act cca gtc aat      7849
Pro Leu Ala Arg Ala Ala Trp Glu Thr Ala Arg His Thr Pro Val Asn
                2005            2010            2015 tcc tgg cta ggc aac atc atc atg tat gcg ccc acc ttg tgg gca agg      7897
Ser Trp Leu Gly Asn Ile Ile Met Tyr Ala Pro Thr Leu Trp Ala Arg
            2020            2025            2030 atg atc ctg atg act cat ttc ttc tcc atc ctt cta gct cag gaa caa      7945
Met Ile Leu Met Thr His Phe Phe Ser Ile Leu Leu Ala Gln Glu Gln
        2035            2040            2045 ctt gaa aaa gcc cta gat tgt cag atc tac ggg gcc tgt tac tcc att      7993
Leu Glu Lys Ala Leu Asp Cys Gln Ile Tyr Gly Ala Cys Tyr Ser Ile
    2050            2055            2060 gag cca ctt gac cta cct cag atc att caa cga ctc cac ggc ctt agc      8041
Glu Pro Leu Asp Leu Pro Gln Ile Ile Gln Arg Leu His Gly Leu Ser
2065            2070            2075            2080 gca ttt tca ctc cat agt tac tct cca ggt gag atc aat agg gtg gct      8089
Ala Phe Ser Leu His Ser Tyr Ser Pro Gly Glu Ile Asn Arg Val Ala
                2085            2090            2095 tca tgc ctc agg aaa ctt ggg gta ccg ccc ttg cga gtc tgg aga cat      8137
Ser Cys Leu Arg Lys Leu Gly Val Pro Pro Leu Arg Val Trp Arg His
            2100            2105            2110 cgg gcc aga agt gtc cgc gct agg cta ctg tcc cag ggg ggg agg gct      8185
Arg Ala Arg Ser Val Arg Ala Arg Leu Leu Ser Gln Gly Gly Arg Ala
        2115            2120            2125 gcc act tgt ggc aag tac ctc ttc aac tgg gca gta agg acc aag ctc      8233
Ala Thr Cys Gly Lys Tyr Leu Phe Asn Trp Ala Val Arg Thr Lys Leu
    2130            2135            2140 aaa ctc act cca atc ccg gct gcg tcc cag ttg gat tta tcc agc tgg      8281
Lys Leu Thr Pro Ile Pro Ala Ala Ser Gln Leu Asp Leu Ser Ser Trp
2145            2150            2155            2160 ttc gtt gct ggt tac agc ggg gga gac ata tat cac agc ctg tct cgt      8329
Phe Val Ala Gly Tyr Ser Gly Gly Asp Ile Tyr His Ser Leu Ser Arg
                2165            2170            2175 gcc cga ccc cgc tgg ttc acg tgg tgc cta ctc cta ctt tct gta ggg      8377
Ala Arg Pro Arg Trp Phe Thr Trp Cys Leu Leu Leu Ser Val Gly
            2180            2185            2190 gta ggc atc tat cta ctc ccc aac cga tga acggggagct aaacactcca        8427
Val Gly Ile Tyr Leu Leu Pro Asn Arg
```

```
                    2195            2200
ggccaatagg ccatcctgtt tttttccctt tttttccttt tttttttttt tttttttttt      8487
tttttttttt tttttttttt ttccccccct tttttcccct tttttttttcc ttttctttcc    8547 tttggtggct ccatcttagc cctagtcacg gctagctgtg aaaggtccgt gagccgcttg     8607
actgcagaga gtgctgatac tggcctctct gcagatcaag t                         8648

<210> SEQ ID NO 6
<211> LENGTH: 8638
<212> TYPE: DNA
<213> ORGANISM: Hepatitis C virus
<220> FEATURE:
<221> NAME/KEY: CDS
<222> LOCATION: (1802)...(8407)

<400> SEQUENCE: 6
accagccccc gattgggggc gacactccac catagatcac tccctgtga ggaactactg        60 tcttcacgca gaaagcgtct agccatggcg ttagtatgag tgtcgtgcag cctccaggac     120 ccccctccc gggagagcca tagtggtctg cggaaccggt gagtacaccg gaattgccag       180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg    300
gtgcttgcga gtgccccggg aggtctcgta ccgtgcac catgagcacg aatcctaaac       360
ctcaaagaaa aaccaaaggg cgcgccatga ttaacaaga tggattgcac gcaggttctc      420
cggccgcttg ggtggagagg ctattcggct atgactgggc acaacagaca atcggctgct    480
ctgatgccgc cgtgttccgg ctgtcagcgc aggggcgccc ggttcttttt gtcaagaccg   540
acctgtccgg tgccctgaat gaactgcagg acgaggcagc gcggctatcg tggctggcca    600
cgacgggcgt tccttgcgca gctgtgctcg acgttgtcac tgaagcggga agggactggc   660
tgctattggg cgaagtgccg gggcaggatc tcctgtcatc tcaccttgct cctgccgaga    720
aagtatccat catggctgat gcaatgcggc ggctgcatac gcttgatccg gctacctgcc    780
cattcgacca ccaagcgaaa catcgcatcg agcgagcacg tactcggatg aagccggtc     840 ttgtcgatca ggatgatctg gacgaagagc atcagggct cgcgccagcc gaactgttcg     900
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agttcgcgcc cagatgttaa    1200
cagaccacaa cggtttccct ctagcgggat caattccgcc cccccccta acgttactgg     1260 ccgaagccgc ttggaataag gccggtgtgc gtttgtctat atgttatttt ccaccatatt     1320
gccgtctttt ggcaatgtga gggcccggaa acctggccct gtcttcttga cgagcattcc   1380
taggggtctt tcccctctcg ccaaaggaat gcaaggtctg ttgaatgtcg tgaaggaagc    1440
agttcctctg gaagcttctt gaagacaaac aacgtctgta gcgaccctt gcaggcagcg     1500 gaaccccca cctggcgaca ggtgcctctg cggccaaaag ccacgtgtat aagatacacc    1560
tgcaaaggcg gcacaacccc agtgccacgt tgtgagttgg atagttgtgg aaaagagtcaa   1620 atggctctcc tcaagcgtat tcaacaaggg gctgaaggat gcccagaagg taccccattg    1680
tatgggatct gatctggggc ctcggtgcac atgctttaca tgtgtttagt cgaggttaaa    1740
aaacgtctag gccccccgaa ccacggggac gtggttttcc tttgaaaaac acgataatac    1800
```

```
c atg gac cgg gag atg gca gca tcg tgc gga ggc gcg gtt ttc gta ggt    1849
  Met Asp Arg Glu Met Ala Ala Ser Cys Gly Gly Ala Val Phe Val Gly
   1               5                  10                  15 ctg ata ctc ttg acc ttg tca ccg cac tat aag ctg ttc ctc gct agg      1897
Leu Ile Leu Leu Thr Leu Ser Pro His Tyr Lys Leu Phe Leu Ala Arg
             20                  25                  30 ctc ata tgg tgg tta caa tat ttt atc acc agg gcc gag gca cac ttg      1945
Leu Ile Trp Trp Leu Gln Tyr Phe Ile Thr Arg Ala Glu Ala His Leu
         35                  40                  45 caa gtg tgg atc ccc ccc ctc aac gtt cgg ggg ggc cgc gat gcc gtc      1993
Gln Val Trp Ile Pro Pro Leu Asn Val Arg Gly Gly Arg Asp Ala Val
 50                  55                  60 atc ctc ctc acg tgc gcg atc cac cca gag cta atc ttt acc atc acc      2041
Ile Leu Leu Thr Cys Ala Ile His Pro Glu Leu Ile Phe Thr Ile Thr
 65                  70                  75                  80 aaa atc ttg ctc gcc ata ctc ggt cca ctc atg gtg ctc cag gct ggt      2089
Lys Ile Leu Leu Ala Ile Leu Gly Pro Leu Met Val Leu Gln Ala Gly
                 85                  90                  95 ata acc aaa gtg ccg tac ttc gtg cgc gca cac ggg ctc att cgt gca      2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct      2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc      2233
Leu Met Lys Leu Ala Ala Leu Thr Gly Thr Tyr Val Tyr Asp His Leu
    130                 135                 140 acc cca ctg cgg gac tgg gcc cac gcg ggc cta cga gac ctt gcg gtg      2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc      2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc      2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc      2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc      2473
Leu Glu Gly Gln Gly Trp Arg Leu Leu Ala Pro Ile Thr Ala Tyr Ser
    210                 215                 220 caa cag acg cga ggc cta ctt ggc tgc atc atc act agc ctc aca ggc      2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca      2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc      2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc      2665
Tyr His Gly Ala Gly Ser Lys Thr Leu Ala Gly Pro Lys Gly Pro Ile
        275                 280                 285 acc caa atg tac acc aat gtg gac cag gac ctc gtc ggc tgg caa gcg      2713
Thr Gln Met Tyr Thr Asn Val Asp Gln Asp Leu Val Gly Trp Gln Ala
    290                 295                 300 ccc ccc ggg gcg cgt tcc ttg aca cca tgc acc tgc ggc agc tcg gac      2761
Pro Pro Gly Ala Arg Ser Leu Thr Pro Cys Thr Cys Gly Ser Ser Asp
305                 310                 315                 320
```

```
ctt tac ttg gtc acg agg cat gcc gat gtc att ccg gtg cgc cgg cgg      2809
Leu Tyr Leu Val Thr Arg His Ala Asp Val Ile Pro Val Arg Arg Arg
            325                 330                 335 ggc gac ggc agg ggg agc cta ctc tcc ccc agg ccc gtc tcc tac ttg      2857
Gly Asp Gly Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg      2905
Lys Gly Ser Ser Gly Gly Pro Leu Leu Cys Pro Ser Gly His Ala Val
            355                 360                 365 ggc atc ttt cgg gct gcc gtg tgc acc cga ggg gtt gcg aag gcg gtg      2953
Gly Ile Phe Arg Ala Ala Val Cys Thr Arg Gly Val Ala Lys Ala Val
            370                 375                 380 gac ttt gta ccc gtc gag tct atg gga acc act atg cgg tcc ccg gtc      3001
Asp Phe Val Pro Val Glu Ser Met Gly Thr Thr Met Arg Ser Pro Val
385                 390                 395                 400 ttc acg gac aac tcg tcc cct ccg gcc gta ccg cag aca ttc cag gtg      3049
Phe Thr Asp Asn Ser Ser Pro Pro Ala Val Pro Gln Thr Phe Gln Val
                    405                 410                 415 gcc cat cta cac gcc cct act ggt agc ggc aag agc act aag gtg ccg      3097
Ala His Leu His Ala Pro Thr Gly Ser Gly Lys Ser Thr Lys Val Pro
                420                 425                 430 gct gcg tat gca gcc caa ggg tat aag gtg ctt gtc ctg aac ccg tcc      3145
Ala Ala Tyr Ala Ala Gln Gly Tyr Lys Val Leu Val Leu Asn Pro Ser
            435                 440                 445 gtc gcc gcc acc cta ggt ttc ggg gcg tat atg tct aag gca cat ggt      3193
Val Ala Ala Thr Leu Gly Phe Gly Ala Tyr Met Ser Lys Ala His Gly
            450                 455                 460 atc gac cct aac atc aga acc ggg gta agg acc atc acg acg ggt gcc      3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc      3289
Pro Ile Thr Tyr Ser Thr Tyr Gly Lys Phe Leu Ala Asp Gly Gly Cys
                485                 490                 495 tct ggg ggc gcc tat gac atc ata ata tgt gat gag tgc cac tca act      3337
Ser Gly Gly Ala Tyr Asp Ile Ile Ile Cys Asp Glu Cys His Ser Thr
                500                 505                 510 gac tcg acc act atc ctg ggc atc ggc aca gtc ctg gac caa gcg gag      3385
Asp Ser Thr Thr Ile Leu Gly Ile Gly Thr Val Leu Asp Gln Ala Glu
            515                 520                 525 acg gct gga gcg cga ctc gtc gtg ctc gcc acc gct acg cct ccg gga      3433
Thr Ala Gly Ala Arg Leu Val Val Leu Ala Thr Ala Thr Pro Pro Gly
            530                 535                 540 tcg gtc acc gtg cca cat cca aac atc gag gag gtg gct ctg tcc agc      3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc      3529
Thr Gly Glu Ile Pro Phe Tyr Gly Lys Ala Ile Pro Ile Glu Thr Ile
                565                 570                 575 aag ggg ggg agg cac ctc att ttc tgc cat tcc aag aag aaa tgt gat      3577
Lys Gly Gly Arg His Leu Ile Phe Cys His Ser Lys Lys Lys Cys Asp
                580                 585                 590 gag ctc gcc gcg aag ctg tcc ggc ctc gga ctc aat gct gta gca tat      3625
Glu Leu Ala Ala Lys Leu Ser Gly Leu Gly Leu Asn Ala Val Ala Tyr
            595                 600                 605 tac cgg ggc ctt gat gta tcc gtc ata cca act agc gga gac gtc att      3673
Tyr Arg Gly Leu Asp Val Ser Val Ile Pro Thr Ser Gly Asp Val Ile
            610                 615                 620 gtc gta gca acg gac gct cta atg acg ggc ttt acc ggc gat ttc gac      3721
Val Val Ala Thr Asp Ala Leu Met Thr Gly Phe Thr Gly Asp Phe Asp
625                 630                 635                 640
```

| | | | | | | | | | | | | | | |
|---|---|---|---|---|---|---|---|---|---|---|---|---|---|---|
| tca | gtg | atc | gac | tgc | aat | aca | tgt | gtc | acc | cag | aca | gtc | gac | ttc | agc | 3769 |
| Ser | Val | Ile | Asp | Cys | Asn | Thr | Cys | Val | Thr | Gln | Thr | Val | Asp | Phe | Ser | |
| | | | 645 | | | | | 650 | | | | | 655 | | | |

| ctg | gac | ccg | acc | ttc | acc | att | gag | acg | acg | acc | gtg | cca | caa | gac | gcg | 3817 |
| Leu | Asp | Pro | Thr | Phe | Thr | Ile | Glu | Thr | Thr | Thr | Val | Pro | Gln | Asp | Ala |
| 660 | | | | | 665 | | | | | 670 | | | | | | |

| gtg | tca | cgc | tcg | cag | cgg | cga | ggc | agg | act | ggt | agg | ggc | agg | atg | ggc | 3865 |
| Val | Ser | Arg | Ser | Gln | Arg | Arg | Gly | Arg | Thr | Gly | Arg | Gly | Arg | Met | Gly |
| | | 675 | | | | | 680 | | | | | 685 | | | | |

| att | tac | agg | ttt | gtg | act | cca | gga | gaa | cgg | ccc | tcg | ggc | atg | ttc | gat | 3913 |
| Ile | Tyr | Arg | Phe | Val | Thr | Pro | Gly | Glu | Arg | Pro | Ser | Gly | Met | Phe | Asp |
| | 690 | | | | | 695 | | | | | 700 | | | | | |

| tcc | tcg | gtt | ctg | tgc | gag | tgc | tat | gac | gcg | ggc | tgt | gct | tgg | tac | gag | 3961 |
| Ser | Ser | Val | Leu | Cys | Glu | Cys | Tyr | Asp | Ala | Gly | Cys | Ala | Trp | Tyr | Glu |
| 705 | | | | 710 | | | | | 715 | | | | | 720 | | |

| ctc | acg | ccc | gcc | gag | acc | tca | gtt | agg | ttg | cgg | gct | tac | cta | aac | aca | 4009 |
| Leu | Thr | Pro | Ala | Glu | Thr | Ser | Val | Arg | Leu | Arg | Ala | Tyr | Leu | Asn | Thr |
| | | | | 725 | | | | | 730 | | | | | 735 | | |

| cca | ggg | ttg | ccc | gtc | tgc | cag | gac | cat | ctg | gag | ttc | tgg | gag | agc | gtc | 4057 |
| Pro | Gly | Leu | Pro | Val | Cys | Gln | Asp | His | Leu | Glu | Phe | Trp | Glu | Ser | Val |
| | | | 740 | | | | | 745 | | | | | 750 | | | |

| ttt | aca | ggc | ctc | acc | cac | ata | gac | gcc | cat | ttc | ttg | tcc | cag | act | aag | 4105 |
| Phe | Thr | Gly | Leu | Thr | His | Ile | Asp | Ala | His | Phe | Leu | Ser | Gln | Thr | Lys |
| | | 755 | | | | | 760 | | | | | 765 | | | | |

| cag | gca | gga | gac | aac | ttc | ccc | tac | ctg | gta | gca | tac | cag | gct | acg | gtg | 4153 |
| Gln | Ala | Gly | Asp | Asn | Phe | Pro | Tyr | Leu | Val | Ala | Tyr | Gln | Ala | Thr | Val |
| | 770 | | | | | 775 | | | | | 780 | | | | | |

| tgc | gcc | agg | gct | cag | gct | cca | cct | cca | tcg | tgg | gac | caa | atg | tgg | aag | 4201 |
| Cys | Ala | Arg | Ala | Gln | Ala | Pro | Pro | Pro | Ser | Trp | Asp | Gln | Met | Trp | Lys |
| 785 | | | | 790 | | | | | 795 | | | | | 800 | | |

| tgt | ctc | ata | cgg | cta | aag | cct | acg | ctg | cac | ggg | cca | acg | ccc | ctg | ctg | 4249 |
| Cys | Leu | Ile | Arg | Leu | Lys | Pro | Thr | Leu | His | Gly | Pro | Thr | Pro | Leu | Leu |
| | | | | 805 | | | | | 810 | | | | | 815 | | |

| tat | agg | ctg | gga | gcc | gtt | caa | aac | gag | gtt | act | acc | aca | cac | ccc | ata | 4297 |
| Tyr | Arg | Leu | Gly | Ala | Val | Gln | Asn | Glu | Val | Thr | Thr | Thr | His | Pro | Ile |
| | | | 820 | | | | | 825 | | | | | 830 | | | |

| acc | aaa | tac | atc | atg | gca | tgc | atg | tcg | gct | gac | ctg | gag | gtc | gtc | acg | 4345 |
| Thr | Lys | Tyr | Ile | Met | Ala | Cys | Met | Ser | Ala | Asp | Leu | Glu | Val | Val | Thr |
| | | 835 | | | | | 840 | | | | | 845 | | | | |

| agc | acc | tgg | gtg | ctg | gta | ggc | gga | gtc | cta | gca | gct | ctg | gcc | gcg | tat | 4393 |
| Ser | Thr | Trp | Val | Leu | Val | Gly | Gly | Val | Leu | Ala | Ala | Leu | Ala | Ala | Tyr |
| | 850 | | | | | 855 | | | | | 860 | | | | | |

| tgc | ctg | aca | aca | ggc | agc | gtg | gtc | att | gtg | ggc | agg | atc | atc | ttg | tcc | 4441 |
| Cys | Leu | Thr | Thr | Gly | Ser | Val | Val | Ile | Val | Gly | Arg | Ile | Ile | Leu | Ser |
| 865 | | | | 870 | | | | | 875 | | | | | 880 | | |

| gga | aag | ccg | gcc | atc | att | ccc | gac | agg | gaa | gtc | ttt | tac | cgg | gag | ttc | 4489 |
| Gly | Lys | Pro | Ala | Ile | Ile | Pro | Asp | Arg | Glu | Val | Phe | Tyr | Arg | Glu | Phe |
| | | | | 885 | | | | | 890 | | | | | 895 | | |

| gat | gag | atg | gaa | gag | tgc | gcc | tca | cac | ctc | cct | tac | atc | gaa | cag | gga | 4537 |
| Asp | Glu | Met | Glu | Glu | Cys | Ala | Ser | His | Leu | Pro | Tyr | Ile | Glu | Gln | Gly |
| | | | 900 | | | | | 905 | | | | | 910 | | | |

| atg | cag | ctc | gcc | gaa | caa | ttc | aaa | cag | aag | gca | atc | ggg | ttg | ctg | caa | 4585 |
| Met | Gln | Leu | Ala | Glu | Gln | Phe | Lys | Gln | Lys | Ala | Ile | Gly | Leu | Leu | Gln |
| | | 915 | | | | | 920 | | | | | 925 | | | | |

| aca | gcc | acc | aag | caa | gcg | gag | gct | gct | gct | ccc | gtg | gtg | gaa | tcc | aag | 4633 |
| Thr | Ala | Thr | Lys | Gln | Ala | Glu | Ala | Ala | Ala | Pro | Val | Val | Glu | Ser | Lys |
| | 930 | | | | | 935 | | | | | 940 | | | | | |

| tgg | cgg | acc | ctc | gaa | gcc | ttc | tgg | gcg | aag | cat | atg | tgg | aat | ttc | atc | 4681 |
| Trp | Arg | Thr | Leu | Glu | Ala | Phe | Trp | Ala | Lys | His | Met | Trp | Asn | Phe | Ile |
| 945 | | | | 950 | | | | | 955 | | | | | 960 | | |

```
agc ggg ata caa tat tta gca ggc ttg tcc act ctg cct ggc aac ccc      4729
Ser Gly Ile Gln Tyr Leu Ala Gly Leu Ser Thr Leu Pro Gly Asn Pro
            965                 970                 975 gcg ata gca tca ctg atg gca ttc aca gcc tct atc acc agc ccg ctc      4777
Ala Ile Ala Ser Leu Met Ala Phe Thr Ala Ser Ile Thr Ser Pro Leu
        980                 985                 990 acc acc caa cat acc ctc ctg ttt aac atc ctg ggg gga tgg gtg gcc      4825
Thr Thr Gln His Thr Leu Leu Phe Asn Ile Leu Gly Gly Trp Val Ala
                995                1000                1005 gcc caa ctt gct cct ccc agc gct gct tct gct ttc gta ggc gcc ggc      4873
Ala Gln Leu Ala Pro Pro Ser Ala Ala Ser Ala Phe Val Gly Ala Gly
            1010                1015                1020 atc gct gga gcg gct gtt ggc agc ata ggc ctt ggg aag gtg ctt gtg      4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc      4969
Asp Ile Leu Ala Gly Tyr Gly Ala Gly Val Ala Gly Ala Leu Val Ala
                1045                1050                1055 ttt aag gtc atg agc ggc gag atg ccc tcc acc gag gac ctg gtt aac      5017
Phe Lys Val Met Ser Gly Glu Met Pro Ser Thr Glu Asp Leu Val Asn
            1060                1065                1070 cta ctc cct gct atc ctc tcc cct ggc gcc cta gtc gtc ggg gtc gtg      5065
Leu Leu Pro Ala Ile Leu Ser Pro Gly Ala Leu Val Val Gly Val Val
            1075                1080                1085 tgc gca gcg ata ctg cgt cgg cac gtg ggc cca ggg gag ggg gct gtg      5113
Cys Ala Ala Ile Leu Arg Arg His Val Gly Pro Gly Glu Gly Ala Val
1090                1095                1100 cag tgg atg aac cgg ctg ata gcg ttc gct tcg cgg ggt aac cac gtc      5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act      5209
Ser Pro Thr His Tyr Val Pro Glu Ser Asp Ala Ala Ala Arg Val Thr
                1125                1130                1135 cag atc ctc tct agt ctt acc atc act cag ctg ctg aag agg ctt cac      5257
Gln Ile Leu Ser Ser Leu Thr Ile Thr Gln Leu Leu Lys Arg Leu His
            1140                1145                1150 cag tgg atc aac gag gac tgc tcc acg cca tgc tcc ggc tcg tgg cta      5305
Gln Trp Ile Asn Glu Asp Cys Ser Thr Pro Cys Ser Gly Ser Trp Leu
            1155                1160                1165 aga gat gtt tgg gat tgg ata tgc acg gtg ttg act gat ttc aag acc      5353
Arg Asp Val Trp Asp Trp Ile Cys Thr Val Leu Thr Asp Phe Lys Thr
            1170                1175                1180 tgg ctc cag tcc aag ctc ctg ccg cga ttg ccg gga gtc ccc ttc ttc      5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg      5449
Ser Cys Gln Arg Gly Tyr Lys Gly Val Trp Arg Gly Asp Gly Ile Met
                1205                1210                1215 caa acc acc tgc cca tgt gga gca cag atc acc gga cat gtg aaa aac      5497
Gln Thr Thr Cys Pro Cys Gly Ala Gln Ile Thr Gly His Val Lys Asn
            1220                1225                1230 cgt tcc atg agg atc gtg ggg cct agg acc tgt agt aac acg tgg cat      5545
Arg Ser Met Arg Ile Val Gly Pro Arg Thr Cys Ser Asn Thr Trp His
            1235                1240                1245 gga aca ttc ccc att aac gcg tac acc acg ggc ccc tgc acg ccc tcc      5593
Gly Thr Phe Pro Ile Asn Ala Tyr Thr Thr Gly Pro Cys Thr Pro Ser
            1250                1255                1260 ccg gcg cca aat tat tct agg gcg ctg tgg cgg gtg gct gct gag gag      5641
Pro Ala Pro Asn Tyr Ser Arg Ala Leu Trp Arg Val Ala Ala Glu Glu
1265                1270                1275                1280
```

```
tac gtg gag gtt acg cgg gtg ggg gat ttc cac tac gtg acg ggc atg      5689
Tyr Val Glu Val Thr Arg Val Gly Asp Phe His Tyr Val Thr Gly Met
            1285                1290                1295 acc act gac aac gta aag tgc ccg tgt cag gtt ccg gcc ccc gaa ttc      5737
Thr Thr Asp Asn Val Lys Cys Pro Cys Gln Val Pro Ala Pro Glu Phe
            1300                1305                1310 ttc aca gaa gtg gat ggg gtg cgg ttg cac agg tac gct cca gcg tgc      5785
Phe Thr Glu Val Asp Gly Val Arg Leu His Arg Tyr Ala Pro Ala Cys
            1315                1320                1325 aaa ccc ctc cta cgg gag gag gtc aca ttc ctg gtc ggg ctc aat caa      5833
Lys Pro Leu Leu Arg Glu Glu Val Thr Phe Leu Val Gly Leu Asn Gln
            1330                1335                1340 tac ctg gtt ggg tca cag ctc cca tgc gag ccc gaa ccg gac gta gca      5881
Tyr Leu Val Gly Ser Gln Leu Pro Cys Glu Pro Glu Pro Asp Val Ala
1345                1350                1355                1360 gtg ctc act tcc atg ctc acc gac ccc tcc cac att acg gcg gag acg      5929
Val Leu Thr Ser Met Leu Thr Asp Pro Ser His Ile Thr Ala Glu Thr
                1365                1370                1375 gct aag cgt agg ctg gcc agg gga tct ccc ccc tcc ttg gcc agc tca      5977
Ala Lys Arg Arg Leu Ala Arg Gly Ser Pro Pro Ser Leu Ala Ser Ser
            1380                1385                1390 tca gct agc cag ctg tct gcg cct tcc ttg aag gca aca tgc act acc      6025
Ser Ala Ser Gln Leu Ser Ala Pro Ser Leu Lys Ala Thr Cys Thr Thr
            1395                1400                1405 cgt cat gac tcc ccg gac gct gac ctc atc gag gcc aac ctc ctg tgg      6073
Arg His Asp Ser Pro Asp Ala Asp Leu Ile Glu Ala Asn Leu Leu Trp
            1410                1415                1420 cgg cag gag atg ggc ggg aac atc acc cgc gtg gag tca gaa aat aag      6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag      6169
Val Val Ile Leu Asp Ser Phe Glu Pro Leu Gln Ala Glu Glu Asp Glu
                1445                1450                1455 agg gaa gta tcc gtt ccg gcg gag atc ctg cgg agg tcc agg aaa ttc      6217
Arg Glu Val Ser Val Pro Ala Glu Ile Leu Arg Arg Ser Arg Lys Phe
            1460                1465                1470 cct cga gcg atg ccc ata tgg gca cgc ccg gat tac aac cct cca ctg      6265
Pro Arg Ala Met Pro Ile Trp Ala Arg Pro Asp Tyr Asn Pro Pro Leu
            1475                1480                1485 tta gag tcc tgg aag gac ccg gac tac gtc cct cca gtg gta cac ggg      6313
Leu Glu Ser Trp Lys Asp Pro Asp Tyr Val Pro Pro Val Val His Gly
            1490                1495                1500 tgt cca ctg ccg cct gcc aag gcc cct ccg ata cca cct cca cgg agg      6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg      6409
Lys Arg Thr Val Val Leu Ser Glu Ser Thr Val Ser Ser Ala Leu Ala
            1525                1530                1535 gag ctc gcc aca aag acc ttc ggc agc tcc gaa tcg tcg gcc gtc gac      6457
Glu Leu Ala Thr Lys Thr Phe Gly Ser Ser Glu Ser Ser Ala Val Asp
            1540                1545                1550 agc ggc acg gca acg gcc tct cct gac cag ccc tcc gac gac ggc gac      6505
Ser Gly Thr Ala Thr Ala Ser Pro Asp Gln Pro Ser Asp Asp Gly Asp
            1555                1560                1565 gcg gga tcc gac gtt gag tcg tac tcc tcc atg ccc ccc ctt gag ggg      6553
Ala Gly Ser Asp Val Glu Ser Tyr Ser Ser Met Pro Pro Leu Glu Gly
            1570                1575                1580 gag ccg ggg gat ccc gat ctc agc gac ggg cct tgg tct acc gta agc      6601
Glu Pro Gly Asp Pro Asp Leu Ser Asp Gly Pro Trp Ser Thr Val Ser
1585                1590                1595                1600
```

| | | |
|---|---|---|
| gag gag gct agt gag gac gtc gtc tgc tgc tcg atg tcc tac aca tgg<br>Glu Glu Ala Ser Glu Asp Val Val Cys Cys Ser Met Ser Tyr Thr Trp<br>　　　　　　1605　　　　　　　　1610　　　　　　　　1615 | | 6649 |
| aca ggc gcc ctg atc acg cca tgc gct gcg gag gaa acc aag ctg ccc<br>Thr Gly Ala Leu Ile Thr Pro Cys Ala Ala Glu Glu Thr Lys Leu Pro<br>1620　　　　　　　　1625　　　　　　　　1630 | | 6697 |
| atc aat gca ctg agc aac tct ttg ctc cgt cac cac aac ttg gtc tat<br>Ile Asn Ala Leu Ser Asn Ser Leu Leu Arg His His Asn Leu Val Tyr<br>　　1635　　　　　　　　1640　　　　　　　　1645 | | 6745 |
| gct aca aca tct cgc agc gca agc ctg cgg cag aag aag gtc acc ttt<br>Ala Thr Thr Ser Arg Ser Ala Ser Leu Arg Gln Lys Lys Val Thr Phe<br>　　　1650　　　　　　　　1655　　　　　　　　1660 | | 6793 |
| gac aga ctg cag gtc ctg gac gac cac tac cgg gac gtg ctc aag gag<br>Asp Arg Leu Gln Val Leu Asp Asp His Tyr Arg Asp Val Leu Lys Glu<br>1665　　　　　　　　1670　　　　　　　　1675　　　　　　　　1680 | | 6841 |
| atg aag gcg aag gcg tcc aca gtt aag gct aaa ctt cta tcc gtg gag<br>Met Lys Ala Lys Ala Ser Thr Val Lys Ala Lys Leu Leu Ser Val Glu<br>　　　　　　　　1685　　　　　　　　1690　　　　　　　　1695 | | 6889 |
| gaa gcc tgt aag ctg acg ccc cca cat tcg gcc aga tct aaa ttt ggc<br>Glu Ala Cys Lys Leu Thr Pro Pro His Ser Ala Arg Ser Lys Phe Gly<br>　　　　1700　　　　　　　　1705　　　　　　　　1710 | | 6937 |
| tat ggg gca aag gac gtc cgg aac cta tcc agc aag gcc gtt aac cac<br>Tyr Gly Ala Lys Asp Val Arg Asn Leu Ser Ser Lys Ala Val Asn His<br>　　　　　　1715　　　　　　　　1720　　　　　　　　1725 | | 6985 |
| atc cgc tcc gtg tgg aag gac ttg ctg gaa gac act gag aca cca att<br>Ile Arg Ser Val Trp Lys Asp Leu Leu Glu Asp Thr Glu Thr Pro Ile<br>　　　　　　　　1730　　　　　　　　1735　　　　　　　　1740 | | 7033 |
| gac acc acc atc atg gca aaa aat gag gtt ttc tgc gtc caa cca gag<br>Asp Thr Thr Ile Met Ala Lys Asn Glu Val Phe Cys Val Gln Pro Glu<br>1745　　　　　　　　1750　　　　　　　　1755　　　　　　　　1760 | | 7081 |
| aag ggg ggc cgc aag cca gct cgc ctt atc gta ttc cca gat ttg ggg<br>Lys Gly Gly Arg Lys Pro Ala Arg Leu Ile Val Phe Pro Asp Leu Gly<br>　　　　　　　　1765　　　　　　　　1770　　　　　　　　1775 | | 7129 |
| gtt cgt gtg tgc gag aaa atg gcc ctt tac gat gtg gtc tcc acc ctc<br>Val Arg Val Cys Glu Lys Met Ala Leu Tyr Asp Val Val Ser Thr Leu<br>　　　　1780　　　　　　　　1785　　　　　　　　1790 | | 7177 |
| cct cag gcc gtg atg ggc tct tca tac gga ttc caa tac tct cct gga<br>Pro Gln Ala Val Met Gly Ser Ser Tyr Gly Phe Gln Tyr Ser Pro Gly<br>　　　　　　1795　　　　　　　　1800　　　　　　　　1805 | | 7225 |
| cag cgg gtc gag ttc ctg gtg aat gcc tgg aaa gcg aag aaa tgc cct<br>Gln Arg Val Glu Phe Leu Val Asn Ala Trp Lys Ala Lys Lys Cys Pro<br>1810　　　　　　　　1815　　　　　　　　1820 | | 7273 |
| atg ggc ttc gca tat gac acc cgc tgt ttt gac tca acg gtc act gag<br>Met Gly Phe Ala Tyr Asp Thr Arg Cys Phe Asp Ser Thr Val Thr Glu<br>1825　　　　　　　　1830　　　　　　　　1835　　　　　　　　1840 | | 7321 |
| aat gac atc cgt gtt gag gag tca atc tac caa tgt tgt gac ttg gcc<br>Asn Asp Ile Arg Val Glu Glu Ser Ile Tyr Gln Cys Cys Asp Leu Ala<br>　　　　　　　　1845　　　　　　　　1850　　　　　　　　1855 | | 7369 |
| ccc gaa gcc aga cag gcc ata agg tcg ctc aca gag cgg ctt tac atc<br>Pro Glu Ala Arg Gln Ala Ile Arg Ser Leu Thr Glu Arg Leu Tyr Ile<br>　　　　　　　　1860　　　　　　　　1865　　　　　　　　1870 | | 7417 |
| ggg ggc ccc ctg act aat tct aaa ggg cag aac tgc ggc tat cgc cgg<br>Gly Gly Pro Leu Thr Asn Ser Lys Gly Gln Asn Cys Gly Tyr Arg Arg<br>　　　　　1875　　　　　　　　1880　　　　　　　　1885 | | 7465 |
| tgc cgc gcg agc ggt gta ctg acg acc agc tgc ggt aat acc ctc aca<br>Cys Arg Ala Ser Gly Val Leu Thr Thr Ser Cys Gly Asn Thr Leu Thr<br>　　　　1890　　　　　　　　1895　　　　　　　　1900 | | 7513 |
| tgt tac ttg aag gcc gct gcg gcc tgt cga gct gcg aag ctc cag gac<br>Cys Tyr Leu Lys Ala Ala Ala Ala Cys Arg Ala Ala Lys Leu Gln Asp<br>1905　　　　　　　　1910　　　　　　　　1915　　　　　　　　1920 | | 7561 |

```
tgc acg atg ctc gta tgc gga gac gac ctt gtc gtt atc tgt gaa agc    7609
Cys Thr Met Leu Val Cys Gly Asp Asp Leu Val Val Ile Cys Glu Ser
            1925                1930                1935 gcg ggg acc caa gag gac gag gcg agc cta cgg gcc ttc acg gag gct    7657
Ala Gly Thr Gln Glu Asp Glu Ala Ser Leu Arg Ala Phe Thr Glu Ala
        1940                1945                1950 atg act aga tac tct gcc ccc cct ggg gac ccg ccc aaa cca gaa tac    7705
Met Thr Arg Tyr Ser Ala Pro Pro Gly Asp Pro Pro Lys Pro Glu Tyr
    1955                1960                1965 gac ttg gag ttg ata aca tca tgc tcc tcc aat gtg tca gtc gcg cac    7753
Asp Leu Glu Leu Ile Thr Ser Cys Ser Ser Asn Val Ser Val Ala His
1970                1975                1980 gat gca tct ggc aaa agg gtg tac tat ctc acc cgt gac ccc acc acc    7801
Asp Ala Ser Gly Lys Arg Val Tyr Tyr Leu Thr Arg Asp Pro Thr Thr
1985                1990                1995                2000 ccc ctt gcg cgg gct gcg tgg gag aca gct aga cac act cca gtc aat    7849
Pro Leu Ala Arg Ala Ala Trp Glu Thr Ala Arg His Thr Pro Val Asn
            2005                2010                2015 tcc tgg cta ggc aac atc atc atg tat gcg ccc acc ttg tgg gca agg    7897
Ser Trp Leu Gly Asn Ile Ile Met Tyr Ala Pro Thr Leu Trp Ala Arg
        2020                2025                2030 atg atc ctg atg act cat ttc ttc tcc atc ctt cta gct cag gaa caa    7945
Met Ile Leu Met Thr His Phe Phe Ser Ile Leu Leu Ala Gln Glu Gln
    2035                2040                2045 ctt gaa aaa gcc cta gat tgt cag atc tac ggg gcc tgt tac tcc att    7993
Leu Glu Lys Ala Leu Asp Cys Gln Ile Tyr Gly Ala Cys Tyr Ser Ile
2050                2055                2060 gag cca ctt gac cta cct cag atc att caa cga ctc cac ggc ctt agc    8041
Glu Pro Leu Asp Leu Pro Gln Ile Ile Gln Arg Leu His Gly Leu Ser
2065                2070                2075                2080 gca ttt tca ctc cat agt tac tct cca ggt gag atc aat agg gtg gct    8089
Ala Phe Ser Leu His Ser Tyr Ser Pro Gly Glu Ile Asn Arg Val Ala
            2085                2090                2095 tca tgc ctc agg aaa ctt ggg gta ccg ccc ttg cga gtc tgg aga cat    8137
Ser Cys Leu Arg Lys Leu Gly Val Pro Pro Leu Arg Val Trp Arg His
        2100                2105                2110 cgg gcc aga agt gtc cgc gct agg cta ctg tcc cag ggg ggg agg gct    8185
Arg Ala Arg Ser Val Arg Ala Arg Leu Leu Ser Gln Gly Gly Arg Ala
    2115                2120                2125 gcc act tgt ggc aag tac ctc ttc aac tgg gca gta agg acc aag ctc    8233
Ala Thr Cys Gly Lys Tyr Leu Phe Asn Trp Ala Val Arg Thr Lys Leu
2130                2135                2140 aaa ctc act cca atc ccg gct gcg tcc cag ttg gat tta tcc agc tgg    8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt    8329
Phe Val Ala Gly Tyr Ser Gly Gly Asp Ile Tyr His Ser Leu Ser Arg
            2165                2170                2175 gcc cga ccc cgc tgg ttc atg tgg tgc cta ctc cta ctt tct gta ggg    8377
Ala Arg Pro Arg Trp Phe Met Trp Cys Leu Leu Leu Leu Ser Val Gly
        2180                2185                2190 gta ggc atc tat cta ctc ccc aac cga tga acggggagct aaacactcca      8427
Val Gly Ile Tyr Leu Leu Pro Asn Arg
    2195                2200 ggccaatagg ccatcctgtt tttttttttt tttttttttt tttttttttt tttttttttt  8487
tttttttttt tttttttttt ttttttcctc tttttttttcc ttttctttcc tttggtggct 8547 ccatcttagc cctagtcacg gctagctgtg aaaggtccgt gagccgcttg actgcagaga  8607
gtgctgatac tggcctctct gcagatcaag t                                 8638
```

<210> SEQ ID NO 7
<211> LENGTH: 8638
<212> TYPE: DNA
<213> ORGANISM: Hepatitis C virus
<220> FEATURE:
<221> NAME/KEY: CDS
<222> LOCATION: (1802)...(8407)

<400> SEQUENCE: 7

```
gccagccccc gattgggggc gacactccac catagatcac tcccctgtga ggaactactg      60
tcttcacgca gaaagcgtct agccatggcg ttagtatgag tgtcgtgcag cctccaggac     120
ccccctccc gggagagcca tagtggtctg cggaaccggt gagtacaccg gaattgccag      180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc agggcgcccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg gaagccggtc     840
ttgtcgatca ggatgatctg gacgaagagc atcagggct cgcgccagcc gaactgttcg     900
ccaggctcaa ggcgcgcatg cccgacggcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agttcgcgcc cagatgttaa    1200
cagaccacaa cggtttccct ctagcgggat caattccgcc ccccccccta acgttactgg    1260
ccgaagccgc ttggaataag gccggtgtgc gtttgtctat atgttatttt ccaccatatt    1320
gccgtctttt ggcaatgtga gggcccggaa acctggccct gtcttcttga cgagcattcc    1380
taggggtctt tcccctctcg ccaaaggaat gcaaggtctg ttgaatgtcg tgaaggaagc    1440
agttcctctg gaagcttctt gaagacaaac aacgtctgta cgacccttt gcaggcagcg    1500
gaaccccca cctggcgaca ggtgcctctg cggccaaaag ccacgtgtat aagatacacc    1560
tgcaaaggcg gcacaacccc agtgccacgt tgtgagttgg atagttgtgg aaagagtcaa    1620
atggctctcc tcaagcgtat tcaacaaggg gctgaaggat gcccagaagg taccccattg    1680
tatgggatct gatctggggc ctcggtgcac atgctttaca tgtgtttagt cgaggttaaa    1740
aaacgtctag gccccccgaa ccacggggac gtggttttcc tttgaaaaac acgataatac    1800
c atg gac cgg gag atg gca gca tcg tgc gga ggc gcg gtt ttc gta ggt    1849
  Met Asp Arg Glu Met Ala Ala Ser Cys Gly Gly Ala Val Phe Val Gly
   1               5                   10                  15 ctg ata ctc ttg acc ttg tca ccg cac tat aag ctg ttc ctc gct agg     1897
Leu Ile Leu Leu Thr Leu Ser Pro His Tyr Lys Leu Phe Leu Ala Arg
           20                  25                  30
```

| | |
|---|---|
| ctc ata tgg tgg tta caa tat ttt atc acc agg gcc gag gca cac ttg<br>Leu Ile Trp Trp Leu Gln Tyr Phe Ile Thr Arg Ala Glu Ala His Leu<br>35    40    45 | 1945 |
| caa gtg tgg atc ccc ccc ctc aac gtt cgg ggg ggc cgc gat gcc gtc<br>Gln Val Trp Ile Pro Pro Leu Asn Val Arg Gly Gly Arg Asp Ala Val<br>50    55    60 | 1993 |
| atc ctc ctc acg tgc gcg atc cac cca gag cta atc ttt acc atc acc<br>Ile Leu Leu Thr Cys Ala Ile His Pro Glu Leu Ile Phe Thr Ile Thr<br>65   70    75    80 | 2041 |
| aaa atc ttg ctc gcc ata ctc ggt cca ctc atg gtc ctc cag gct ggt<br>Lys Ile Leu Leu Ala Ile Leu Gly Pro Leu Met Val Leu Gln Ala Gly<br>    85    90    95 | 2089 |
| ata acc aaa gtg ccg tac ttc gtg cgc gca cac ggg ctc att cgt gca<br>Ile Thr Lys Val Pro Tyr Phe Val Arg Ala His Gly Leu Ile Arg Ala<br>  100    105    110 | 2137 |
| tgc atg ctg gtg cgg aag gtt gct ggg ggt cat tat gtc caa atg gct<br>Cys Met Leu Val Arg Lys Val Ala Gly Gly His Tyr Val Gln Met Ala<br>115    120    125 | 2185 |
| ctc atg aag ttg gcc gca ctg aca ggt acg tac gtt tat gac cat ctc<br>Leu Met Lys Leu Ala Ala Leu Thr Gly Thr Tyr Val Tyr Asp His Leu<br>130    135    140 | 2233 |
| acc cca ctg cgg gac tgg gcc cac gcg ggc cta cga gac ctt gcg gtg<br>Thr Pro Leu Arg Asp Trp Ala His Ala Gly Leu Arg Asp Leu Ala Val<br>145   150    155    160 | 2281 |
| gca gtt gag ccc gtc gtc ttc tct gat atg gag acc aag gtt atc acc<br>Ala Val Glu Pro Val Val Phe Ser Asp Met Glu Thr Lys Val Ile Thr<br>    165    170    175 | 2329 |
| tgg ggg gca gac acc gcg gcg tgt ggg gac atc atc ttg ggc ctg ccc<br>Trp Gly Ala Asp Thr Ala Ala Cys Gly Asp Ile Ile Leu Gly Leu Pro<br>  180    185    190 | 2377 |
| gtc tcc gcc cgc agg ggg agg gag ata cat ctg gga ccg gca gac agc<br>Val Ser Ala Arg Arg Gly Arg Glu Ile His Leu Gly Pro Ala Asp Ser<br>195    200    205 | 2425 |
| ctt gaa ggg cag ggg tgg cga ctc ctc gcg cct att acg gcc tac tcc<br>Leu Glu Gly Gln Gly Trp Arg Leu Leu Ala Pro Ile Thr Ala Tyr Ser<br>210    215    220 | 2473 |
| caa cag acg cga ggc cta ctt ggc tgc atc atc acc agc ctc aca ggc<br>Gln Gln Thr Arg Gly Leu Leu Gly Cys Ile Ile Thr Ser Leu Thr Gly<br>225   230    235    240 | 2521 |
| cgg gac agg aac cag gtc gag ggg gag gtc caa gtg gtc tcc acc gca<br>Arg Asp Arg Asn Gln Val Glu Gly Glu Val Gln Val Val Ser Thr Ala<br>    245    250    255 | 2569 |
| aca caa tct ttc ctg gcg acc tgc gtc aat ggc gtg tgt tgg act gtc<br>Thr Gln Ser Phe Leu Ala Thr Cys Val Asn Gly Val Cys Trp Thr Val<br>  260    265    270 | 2617 |
| tat cat ggt gcc ggc tca aag acc ctt gcc ggc cca aag ggc cca atc<br>Tyr His Gly Ala Gly Ser Lys Thr Leu Ala Gly Pro Lys Gly Pro Ile<br>275    280    285 | 2665 |
| acc caa atg tac acc aat gtg gac cag gac ctc gtc ggc tgg caa gcg<br>Thr Gln Met Tyr Thr Asn Val Asp Gln Asp Leu Val Gly Trp Gln Ala<br>290    295    300 | 2713 |
| ccc ccc ggg gcg cgt tcc ttg aca cca tgc acc tgc ggc agc tcg gac<br>Pro Pro Gly Ala Arg Ser Leu Thr Pro Cys Thr Cys Gly Ser Ser Asp<br>305   310    315    320 | 2761 |
| ctt tac ttg gtc acg aag cat gcc gat gtc att ccg gtg cgc cgg cgg<br>Leu Tyr Leu Val Thr Lys His Ala Asp Val Ile Pro Val Arg Arg Arg<br>    325    330    335 | 2809 |
| ggc gac agc agg ggg agc cta ctc tcc ccc cgg ccc gtc tcc tac ttg<br>Gly Asp Ser Arg Gly Ser Leu Leu Ser Pro Arg Pro Val Ser Tyr Leu<br>  340    345    350 | 2857 |

```
aag ggc tct tcg ggc ggt cca ctg ctc tgc ccc tcg ggc cac gct gtg        2905
Lys Gly Ser Ser Gly Gly Pro Leu Leu Cys Pro Ser Gly His Ala Val
        355                 360                 365 ggc atc ttt cgg gct gcc gtg tgc acc cga ggg gtt gcg aag gcg gtg        2953
Gly Ile Phe Arg Ala Ala Val Cys Thr Arg Gly Val Ala Lys Ala Val
    370                 375                 380 gac ttt gta ccc gtc gag tct atg gaa acc act atg cgg tcc ccg gtc        3001
Asp Phe Val Pro Val Glu Ser Met Glu Thr Thr Met Arg Ser Pro Val
385                 390                 395                 400 ttc acg gac aac tcg tcc cct ccg gcc gta ccg cag aca ttc cag gtg        3049
Phe Thr Asp Asn Ser Ser Pro Pro Ala Val Pro Gln Thr Phe Gln Val
                405                 410                 415 gcc cat cta cac gcc cct act ggt agc ggc aag agc act aag gtg ccg        3097
Ala His Leu His Ala Pro Thr Gly Ser Gly Lys Ser Thr Lys Val Pro
420                 425                 430 gct gcg tat gca gcc caa ggg tat aag gtg ctt gtc ctg aac ccg tcc        3145
Ala Ala Tyr Ala Ala Gln Gly Tyr Lys Val Leu Val Leu Asn Pro Ser
        435                 440                 445 gtc gcc gcc acc cta ggt ttc ggg gcg tat atg tct aag gca cat ggt        3193
Val Ala Ala Thr Leu Gly Phe Gly Ala Tyr Met Ser Lys Ala His Gly
    450                 455                 460 atc gac cct aac atc aga acc ggg gta agg acc atc acg acg ggt gcc        3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc        3289
Pro Ile Thr Tyr Ser Thr Tyr Gly Lys Phe Leu Ala Asp Gly Gly Cys
                485                 490                 495 tct ggg ggc gcc tat gac atc ata ata tgt gat gag tgc cac tca act        3337
Ser Gly Gly Ala Tyr Asp Ile Ile Ile Cys Asp Glu Cys His Ser Thr
            500                 505                 510 gac tcg acc act atc ctg ggc atc ggc aca gtc ctg gac caa gcg gag        3385
Asp Ser Thr Thr Ile Leu Gly Ile Gly Thr Val Leu Asp Gln Ala Glu
        515                 520                 525 acg gct gga gcg cga ctc gtc gtg ctc gcc acc gct acg cct ccg gga        3433
Thr Ala Gly Ala Arg Leu Val Val Leu Ala Thr Ala Thr Pro Pro Gly
    530                 535                 540 tcg gtc acc gtg cca cat cca aac atc gag gag gtg gct ctg tcc agc        3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc        3529
Thr Gly Glu Ile Pro Phe Tyr Gly Lys Ala Ile Pro Ile Glu Thr Ile
                565                 570                 575 aag ggg ggg agg cac ctc att ttc tgc cat tcc aag aag aaa tgc gat        3577
Lys Gly Gly Arg His Leu Ile Phe Cys His Ser Lys Lys Lys Cys Asp
            580                 585                 590 gag ctc gcc gcg aag ctg tcc ggc ctc gga ctc aat gct gta gca tat        3625
Glu Leu Ala Ala Lys Leu Ser Gly Leu Gly Leu Asn Ala Val Ala Tyr
        595                 600                 605 tac cgg ggc ctt gat gta tcc gtc ata cca act agc gga gac gtc att        3673
Tyr Arg Gly Leu Asp Val Ser Val Ile Pro Thr Ser Gly Asp Val Ile
    610                 615                 620 gtc gta gca acg gac gct cta atg acg ggc ttt acc ggc gat ttc gac        3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc        3769
Ser Val Ile Asp Cys Asn Thr Cys Val Thr Gln Thr Val Asp Phe Ser
                645                 650                 655 ctg gac ccg acc ttc acc att gag acg acg acc gtg cca caa gac gcg        3817
Leu Asp Pro Thr Phe Thr Ile Glu Thr Thr Thr Val Pro Gln Asp Ala
            660                 665                 670
```

-continued

| | |
|---|---|
| gtg tca cgc tcg cag cgg cga ggc agg act ggt agg ggc agg atg ggc<br>Val Ser Arg Ser Gln Arg Arg Gly Arg Thr Gly Arg Gly Arg Met Gly<br>     675                    680                    685 | 3865 |
| att tac agg ttt gtg act cca gga gaa cgg ccc tcg ggc atg ttc gat<br>Ile Tyr Arg Phe Val Thr Pro Gly Glu Arg Pro Ser Gly Met Phe Asp<br>    690                    695                    700 | 3913 |
| tcc tcg gtt ctg tgc gag tgc tat gac gcg ggc tgt gct tgg tac gag<br>Ser Ser Val Leu Cys Glu Cys Tyr Asp Ala Gly Cys Ala Trp Tyr Glu<br>705                    710                    715                    720 | 3961 |
| ctc acg ccc gcc gag acc tca gtt agg ttg cgg gct tac cta aac aca<br>Leu Thr Pro Ala Glu Thr Ser Val Arg Leu Arg Ala Tyr Leu Asn Thr<br>                    725                    730                    735 | 4009 |
| cca ggg ttg ccc gtc tgc cag gac cat ctg gag ttc tgg gag ggc gtc<br>Pro Gly Leu Pro Val Cys Gln Asp His Leu Glu Phe Trp Glu Gly Val<br>              740                    745                    750 | 4057 |
| ttt aca ggc ctc acc cac ata gac gcc cat ttc ttg tcc cag act aag<br>Phe Thr Gly Leu Thr His Ile Asp Ala His Phe Leu Ser Gln Thr Lys<br>           755                    760                    765 | 4105 |
| cag gca gga gac aac ttc ccc tac ctg gta gca tac cag gct acg gtg<br>Gln Ala Gly Asp Asn Phe Pro Tyr Leu Val Ala Tyr Gln Ala Thr Val<br>770                    775                    780 | 4153 |
| tgc gcc agg gct cag gct cca cct cca tcg tgg gac caa atg tgg aag<br>Cys Ala Arg Ala Gln Ala Pro Pro Pro Ser Trp Asp Gln Met Trp Lys<br>785                    790                    795                    800 | 4201 |
| tgt ctc ata cgg cta aag cct acg ctg cac ggg cca acg ccc ctg ctg<br>Cys Leu Ile Arg Leu Lys Pro Thr Leu His Gly Pro Thr Pro Leu Leu<br>                    805                    810                    815 | 4249 |
| tat agg ctg gga gcc gtt caa aac gag gtt act acc aca cac ccc ata<br>Tyr Arg Leu Gly Ala Val Gln Asn Glu Val Thr Thr Thr His Pro Ile<br>              820                    825                    830 | 4297 |
| acc aaa tac atc atg gca tgc atg tcg gct gac ctg gag gtc gtc acg<br>Thr Lys Tyr Ile Met Ala Cys Met Ser Ala Asp Leu Glu Val Val Thr<br>           835                    840                    845 | 4345 |
| agc acc tgg gtg ctg gta ggc gga gtc cta gca gct ctg gct gcg tat<br>Ser Thr Trp Val Leu Val Gly Gly Val Leu Ala Ala Leu Ala Ala Tyr<br>850                    855                    860 | 4393 |
| tgc ctg aca aca ggc agc gtg gtc att gtg ggc agg atc atc ttg tcc<br>Cys Leu Thr Thr Gly Ser Val Val Ile Val Gly Arg Ile Ile Leu Ser<br>865                    870                    875                    880 | 4441 |
| gga agg ccg gcc atc att ccc gac agg gaa gtc ctt tac cgg gag ttc<br>Gly Arg Pro Ala Ile Ile Pro Asp Arg Glu Val Leu Tyr Arg Glu Phe<br>                    885                    890                    895 | 4489 |
| gat gag atg gaa gag tgt gcc tca cac ctc cct tac atc gaa cag gga<br>Asp Glu Met Glu Glu Cys Ala Ser His Leu Pro Tyr Ile Glu Gln Gly<br>              900                    905                    910 | 4537 |
| atg cag ctc gcc gaa caa ttc aaa cag aag gca atc ggg ttg ctg caa<br>Met Gln Leu Ala Glu Gln Phe Lys Gln Lys Ala Ile Gly Leu Leu Gln<br>           915                    920                    925 | 4585 |
| aca gcc acc aag caa gcg gag gct gct gct ccc gtg gtg gaa tcc aag<br>Thr Ala Thr Lys Gln Ala Glu Ala Ala Ala Pro Val Val Glu Ser Lys<br>930                    935                    940 | 4633 |
| tgg cgg acc ctc gaa gcc ttc tgg gcg aag cat atg tgg aat ttc atc<br>Trp Arg Thr Leu Glu Ala Phe Trp Ala Lys His Met Trp Asn Phe Ile<br>945                    950                    955                    960 | 4681 |
| agc ggg ata caa tat tta gca ggc ttg tcc act ctg cct ggc aac ccc<br>Ser Gly Ile Gln Tyr Leu Ala Gly Leu Ser Thr Leu Pro Gly Asn Pro<br>              965                    970                    975 | 4729 |
| gcg ata gca tca ctg atg gca ttc aca gcc tct atc acc agc ccg ctc<br>Ala Ile Ala Ser Leu Met Ala Phe Thr Ala Ser Ile Thr Ser Pro Leu<br>           980                    985                    990 | 4777 |

-continued

```
acc acc caa cat acc ctc ctg ttt aac atc ctg ggg gga tgg gtg gcc        4825
Thr Thr Gln His Thr Leu Leu Phe Asn Ile Leu Gly Gly Trp Val Ala
        995                 1000                1005 gcc caa ctt gct cct ccc agc gct gct tcc gct ttc gta ggc gcc ggc        4873
Ala Gln Leu Ala Pro Pro Ser Ala Ala Ser Ala Phe Val Gly Ala Gly
        1010                1015                1020 atc gct gga gcg gct gtt ggc agc ata ggc ctt ggg aag gtg ctt gtg        4921
Ile Ala Gly Ala Ala Val Gly Ser Ile Gly Leu Gly Lys Val Leu Val
1025                1030                1035                1040 gat att ttg gca ggt tat gga gca ggg gtg gca ggc gcg ctc gtg gcc        4969
Asp Ile Leu Ala Gly Tyr Gly Ala Gly Val Ala Gly Ala Leu Val Ala
                1045                1050                1055 ttt aag gtc atg agc ggc gag atg ccc tcc acc gag gac ctg gtt aac        5017
Phe Lys Val Met Ser Gly Glu Met Pro Ser Thr Glu Asp Leu Val Asn
        1060                1065                1070 cta ctc cct gct atc ctc tcc cct ggc gcc cta gtc gtc ggg gtc gtg        5065
Leu Leu Pro Ala Ile Leu Ser Pro Gly Ala Leu Val Val Gly Val Val
        1075                1080                1085 tgc gca gcg ata ctg cgt cgg cac gtg ggc cca ggg gag ggg gct gtg        5113
Cys Ala Ala Ile Leu Arg Arg His Val Gly Pro Gly Glu Gly Ala Val
        1090                1095                1100 cag tgg atg aac cgg ctg ata gcg ttc gct tcg cgg ggt aac cac gtc        5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act        5209
Ser Pro Thr His Tyr Val Pro Glu Ser Asp Ala Ala Ala Arg Val Thr
                1125                1130                1135 cag atc ctc tct agt ctt acc atc act cag ctg ctg aag agg ctt cac        5257
Gln Ile Leu Ser Ser Leu Thr Ile Thr Gln Leu Leu Lys Arg Leu His
        1140                1145                1150 cag tgg atc aac gag gac tgc tcc acg cca tgc tcc ggc tcg tgg cta        5305
Gln Trp Ile Asn Glu Asp Cys Ser Thr Pro Cys Ser Gly Ser Trp Leu
        1155                1160                1165 aga gat gtt tgg gat tgg ata tgc acg gtg ttg act gat ttc aag gcc        5353
Arg Asp Val Trp Asp Trp Ile Cys Thr Val Leu Thr Asp Phe Lys Ala
        1170                1175                1180 tgg ctc cag tcc aag ctc ctg ccg cga ttg ccg gga gtc ccc ttc ttc        5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg        5449
Ser Cys Gln Arg Gly Tyr Lys Gly Val Trp Arg Gly Asp Gly Ile Met
                1205                1210                1215 caa acc acc tgc cca tgt gga gca cag atc acc gga cat gtg aaa aac        5497
Gln Thr Thr Cys Pro Cys Gly Ala Gln Ile Thr Gly His Val Lys Asn
        1220                1225                1230 tgt tcc atg agg atc gtg ggg cct agg acc tgt agt aac acg tgg cat        5545
Cys Ser Met Arg Ile Val Gly Pro Arg Thr Cys Ser Asn Thr Trp His
        1235                1240                1245 gga aca ttc ccc att aac gcg tac acc acg ggc ccc tgc acg ccc tcc        5593
Gly Thr Phe Pro Ile Asn Ala Tyr Thr Thr Gly Pro Cys Thr Pro Ser
        1250                1255                1260 ccg gcg cca aat tat tct agg gcg ctg tgg cgg gtg gct gct gag gag        5641
Pro Ala Pro Asn Tyr Ser Arg Ala Leu Trp Arg Val Ala Ala Glu Glu
1265                1270                1275                1280 tac gtg gag gtt acg cga gtg ggg gat ttc cac tac gtg acg ggc atg        5689
Tyr Val Glu Val Thr Arg Val Gly Asp Phe His Tyr Val Thr Gly Met
                1285                1290                1295 acc act gac aac gta aag tgc ccg tgt cag gtt ccg gcc ccc gaa ttc        5737
Thr Thr Asp Asn Val Lys Cys Pro Cys Gln Val Pro Ala Pro Glu Phe
        1300                1305                1310
```

```
ttc aca gaa gtg gat ggg gtg cgg ttg cac agg tac gct cca gcg tgc    5785
Phe Thr Glu Val Asp Gly Val Arg Leu His Arg Tyr Ala Pro Ala Cys
        1315                1320                1325 aaa ccc ctc cta cgg gag gag gtc aca ttc ctg gtc ggg ctc aat caa    5833
Lys Pro Leu Leu Arg Glu Glu Val Thr Phe Leu Val Gly Leu Asn Gln
    1330                1335                1340 tac ccg gtt ggg tca cag ctc cca tgc gag ccc gaa ctg gac gta gca    5881
Tyr Pro Val Gly Ser Gln Leu Pro Cys Glu Pro Glu Leu Asp Val Ala
1345                1350                1355                1360 gtg ctc act tcc atg ctc acc gac ccc tcc cac att acg gcg gag acg    5929
Val Leu Thr Ser Met Leu Thr Asp Pro Ser His Ile Thr Ala Glu Thr
            1365                1370                1375 gct aag cgt agg ctg gcc agg gga tct ccc ccc tcc ttg gcc agc tca    5977
Ala Lys Arg Arg Leu Ala Arg Gly Ser Pro Pro Ser Leu Ala Ser Ser
        1380                1385                1390 tca gct agc cag ctg tct gcg cct tcc ttg aag gca aca tgc act acc    6025
Ser Ala Ser Gln Leu Ser Ala Pro Ser Leu Lys Ala Thr Cys Thr Thr
    1395                1400                1405 cgt cat gac tcc ccg gac gct gac ctc atc gag gcc aac ctc ctg tgg    6073
Arg His Asp Ser Pro Asp Ala Asp Leu Ile Glu Ala Asn Leu Leu Trp
1410                1415                1420 cgg cag gag atg ggc ggg aac atc acc cgc gtg gag tca gag aat aag    6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag    6169
Val Val Ile Leu Asp Ser Phe Glu Pro Leu Gln Ala Glu Glu Asp Glu
        1445                1450                1455 agg gaa gta tcc gtt ccg gcg gag atc ctg cgg agg tcc agg aaa ttc    6217
Arg Glu Val Ser Val Pro Ala Glu Ile Leu Arg Arg Ser Arg Lys Phe
    1460                1465                1470 cct cga gcg atg ccc ata tgg gca cgc ccg gat tac aac cct cca ctg    6265
Pro Arg Ala Met Pro Ile Trp Ala Arg Pro Asp Tyr Asn Pro Pro Leu
1475                1480                1485 tta gag tcc tgg aag gac ccg gac tac gtc cct cca gtg gta cac ggg    6313
Leu Glu Ser Trp Lys Asp Pro Asp Tyr Val Pro Pro Val Val His Gly
        1490                1495                1500 tgt cca ttg ccg cct gcc aag gcc cct ccg ata cca cct cca cgg agg    6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg    6409
Lys Arg Thr Val Val Leu Ser Glu Ser Thr Val Ser Ser Ala Leu Ala
            1525                1530                1535 gag ctc gcc aca aag acc ttc ggc agc tcc gaa tcg tcg gcc gtc gac    6457
Glu Leu Ala Thr Lys Thr Phe Gly Ser Ser Glu Ser Ser Ala Val Asp
        1540                1545                1550 agc ggc acg gca acg gcc tct cct gac cag ccc tcc gac gac ggc gac    6505
Ser Gly Thr Ala Thr Ala Ser Pro Asp Gln Pro Ser Asp Asp Gly Asp
    1555                1560                1565 gcg gga tcc gac gtt gag tcg tac tcc tcc atg ccc ccc ctt gag ggg    6553
Ala Gly Ser Asp Val Glu Ser Tyr Ser Ser Met Pro Pro Leu Glu Gly
1570                1575                1580 gag ccg ggg gat ccc gat ctc agc gac ggg tct tgg tct acc gta agc    6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg    6649
Glu Glu Ala Ser Glu Asp Val Val Cys Cys Ser Met Ser Tyr Thr Trp
            1605                1610                1615 aca ggc gcc ctg atc acg cca tgc gct gcg gag gaa acc aag ctg ccc    6697
Thr Gly Ala Leu Ile Thr Pro Cys Ala Ala Glu Glu Thr Lys Leu Pro
        1620                1625                1630
```

```
atc aat gca ctg agc aac tct ttg ctc cgt cac cac aac ttg gtc tat          6745
Ile Asn Ala Leu Ser Asn Ser Leu Leu Arg His His Asn Leu Val Tyr
        1635                1640                1645 gct aca aca tct cgc agc gca agc ctg cgg cag aag aag gtc acc ttt          6793
Ala Thr Thr Ser Arg Ser Ala Ser Leu Arg Gln Lys Lys Val Thr Phe
1650                1655                1660 gac aga ctg cag gtc ctg gac gac cac tac cgg gac gtg ctc aag gag          6841
Asp Arg Leu Gln Val Leu Asp Asp His Tyr Arg Asp Val Leu Lys Glu
1665                1670                1675                1680 atg aag gcg aag gcg tcc aca gtt aag gct aaa ctt cta tcc gtg gag          6889
Met Lys Ala Lys Ala Ser Thr Val Lys Ala Lys Leu Leu Ser Val Glu
                1685                1690                1695 gaa gcc tgt aag ctg acg ccc cca cat tcg gcc aga tct aaa ttt ggc          6937
Glu Ala Cys Lys Leu Thr Pro Pro His Ser Ala Arg Ser Lys Phe Gly
        1700                1705                1710 tat ggg gca aag gac gtc cgg aac cta tcc agc aag gcc gtt aac cac          6985
Tyr Gly Ala Lys Asp Val Arg Asn Leu Ser Ser Lys Ala Val Asn His
1715                1720                1725 atc cgc tcc gtg tgg aag gac ttg ctg gaa gac act gag aca cca att          7033
Ile Arg Ser Val Trp Lys Asp Leu Leu Glu Asp Thr Glu Thr Pro Ile
1730                1735                1740 gac acc acc atc atg gca aaa aat gag gtt ttc tgc gtc caa cca gag          7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg          7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc          7177
Val Arg Val Cys Glu Lys Met Ala Leu Tyr Asp Val Val Ser Thr Leu
        1780                1785                1790 cct cag gcc gtg atg ggc tct tca tac gga ttc caa tac tct cct gga          7225
Pro Gln Ala Val Met Gly Ser Ser Tyr Gly Phe Gln Tyr Ser Pro Gly
1795                1800                1805 cag cgg gtc gag ttc ctg gtg aat gcc tgg aaa gcg aag aaa tgc cct          7273
Gln Arg Val Glu Phe Leu Val Asn Ala Trp Lys Ala Lys Lys Cys Pro
        1810                1815                1820 atg ggc ttc gca tat gac acc cgc tgt ttt gac tca acg gtc act gag          7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc          7369
Asn Asp Ile Arg Val Glu Glu Ser Ile Tyr Gln Cys Cys Asp Leu Ala
                1845                1850                1855 ccc gaa gcc aga cag gcc ata agg tcg ctc aca gag cgg ctt tac atc          7417
Pro Glu Ala Arg Gln Ala Ile Arg Ser Leu Thr Glu Arg Leu Tyr Ile
        1860                1865                1870 ggg ggc ccc ctg act aat tct aaa ggg cag aac tgc ggc tat cgc cgg          7465
Gly Gly Pro Leu Thr Asn Ser Lys Gly Gln Asn Cys Gly Tyr Arg Arg
1875                1880                1885 tgc cgc gcg agc ggt gta ctg acg acc agc tgc ggt aat acc ctc aca          7513
Cys Arg Ala Ser Gly Val Leu Thr Thr Ser Cys Gly Asn Thr Leu Thr
        1890                1895                1900 tgt tac ttg aag gcc gct gcg gcc tgt cga gct gcg aag ctc cag gac          7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc          7609
Cys Thr Met Leu Val Cys Gly Asp Asp Leu Val Val Ile Cys Glu Ser
                1925                1930                1935 gcg ggg acc caa gag gac gag gcg agc cta cgg gcc ttc acg gag gct          7657
Ala Gly Thr Gln Glu Asp Glu Ala Ser Leu Arg Ala Phe Thr Glu Ala
        1940                1945                1950
```

| | | |
|---|---|---|
| atg act aga tac tct gcc ccc cct ggg gac ccg ccc aaa cca gaa tac<br>Met Thr Arg Tyr Ser Ala Pro Pro Gly Asp Pro Pro Lys Pro Glu Tyr<br>        1955                     1960               1965 | 7705 | |
| gac ttg gag ttg ata aca tca tgc tcc tcc aat gtg tca gtc gcg cac<br>Asp Leu Glu Leu Ile Thr Ser Cys Ser Ser Asn Val Ser Val Ala His<br>1970                   1975               1980 | 7753 | |
| gat gca tct ggc aaa agg gtg tac tat ctc acc cgt gac ccc acc acc<br>Asp Ala Ser Gly Lys Arg Val Tyr Tyr Leu Thr Arg Asp Pro Thr Thr<br>1985                   1990               1995               2000 | 7801 | |
| ccc ctt gcg cgg gct gcg tgg gag aca gct aga cac act cca gtc aat<br>Pro Leu Ala Arg Ala Ala Trp Glu Thr Ala Arg His Thr Pro Val Asn<br>        2005                     2010               2015 | 7849 | |
| tcc tgg cta ggc aac atc atc atg tat gcg ccc acc ttg tgg gca agg<br>Ser Trp Leu Gly Asn Ile Ile Met Tyr Ala Pro Thr Leu Trp Ala Arg<br>                2020               2025               2030 | 7897 | |
| atg atc ctg atg act cat ttc ttc tcc atc ctt cta gct cag gaa caa<br>Met Ile Leu Met Thr His Phe Phe Ser Ile Leu Leu Ala Gln Glu Gln<br>        2035                     2040               2045 | 7945 | |
| ctt gaa aaa gcc cta gat tgt cag atc tac ggg gcc tgt tac tcc att<br>Leu Glu Lys Ala Leu Asp Cys Gln Ile Tyr Gly Ala Cys Tyr Ser Ile<br>2050                   2055               2060 | 7993 | |
| gag cca ctt gac cta cct cag atc att caa cga ctc cac ggc ctt agc<br>Glu Pro Leu Asp Leu Pro Gln Ile Ile Gln Arg Leu His Gly Leu Ser<br>2065                   2070               2075               2080 | 8041 | |
| gca ttt tca ctc cat agt tac tct cca ggt gag atc aat agg gtg gct<br>Ala Phe Ser Leu His Ser Tyr Ser Pro Gly Glu Ile Asn Arg Val Ala<br>                2085               2090               2095 | 8089 | |
| tca tgc ctc agg aaa ctt ggg gta ccg ccc ttg cga gtc tgg aga cat<br>Ser Cys Leu Arg Lys Leu Gly Val Pro Pro Leu Arg Val Trp Arg His<br>        2100                     2105               2110 | 8137 | |
| cgg gcc aga agt gtc cgc gct agg cta ctg tcc cag ggg ggg agg gct<br>Arg Ala Arg Ser Val Arg Ala Arg Leu Leu Ser Gln Gly Gly Arg Ala<br>                2115               2120               2125 | 8185 | |
| gcc act tgt ggc aag tac ctc ttc aac tgg gca gta agg acc aag ctc<br>Ala Thr Cys Gly Lys Tyr Leu Phe Asn Trp Ala Val Arg Thr Lys Leu<br>        2130                     2135               2140 | 8233 | |
| aaa ctc act cca atc ccg gct gcg tcc cag ttg gat tta tcc agc tgg<br>Lys Leu Thr Pro Ile Pro Ala Ala Ser Gln Leu Asp Leu Ser Ser Trp<br>2145                   2150               2155               2160 | 8281 | |
| ttc gtt gct ggt tac agc ggg gga gac ata tat cac agc ctg tct cgt<br>Phe Val Ala Gly Tyr Ser Gly Gly Asp Ile Tyr His Ser Leu Ser Arg<br>                2165               2170               2175 | 8329 | |
| gcc cga ccc cgc tgg ttc atg tgg tgc cta ctc cta ctt tct gta ggg<br>Ala Arg Pro Arg Trp Phe Met Trp Cys Leu Leu Leu Leu Ser Val Gly<br>        2180                     2185               2190 | 8377 | |
| gta ggc atc tat cta ctc ccc aac cga tga acggggagct aaacactcca<br>Val Gly Ile Tyr Leu Leu Pro Asn Arg<br>                2195               2200 | 8427 | |
| ggccaatagg ccatcctgtt tttttcccct tttttttttc tttttttttt tttttttttt | 8487 | |
| tttttttttt ttttctcctt ttttttttcct cttttttttcc tttttctttcc tttggtggct | 8547 | |
| ccatcttagc cctagtcacg gctagctgtg aaaggtccgt gagccgcttg actgcagaga | 8607 | |
| gtgctgatac tggcctctct gcagatcaag t | 8638 | |

<210> SEQ ID NO 8
<211> LENGTH: 6
<212> TYPE: DNA
<213> ORGANISM: Hepatitis C virus
<400> SEQUENCE: 8

```
accagc                                                          6

<210> SEQ ID NO 9
<211> LENGTH: 63
<212> TYPE: DNA
<213> ORGANISM: Hepatitis C virus

<400> SEQUENCE: 9
gaattccaga tggcgcgccc agatgttaac cagatccatg gcacactcta gagtactgtc    60
gac                                                                 63

<210> SEQ ID NO 10
<211> LENGTH: 33
<212> TYPE: DNA
<213> ORGANISM: Hepatitis C virus

<400> SEQUENCE: 10
cggaatcgtt aacagaccac aacggtttcc ctc                                 33

<210> SEQ ID NO 11
<211> LENGTH: 30
<212> TYPE: DNA
<213> ORGANISM: Hepatitis C virus

<400> SEQUENCE: 11
ggcgtaccca tggtattatc gtgttttca                                      30

<210> SEQ ID NO 12
<211> LENGTH: 45
<212> TYPE: DNA
<213> ORGANISM: Hepatitis C virus

<400> SEQUENCE: 12
gcatatgaat tctaatacga ctcactatag gccagccccc gattg                    45

<210> SEQ ID NO 13
<211> LENGTH: 45
<212> TYPE: DNA
<213> ORGANISM: Hepatitis C virus

<400> SEQUENCE: 13
ggcgcgccct tggtttttc tttgaggttt aggattcgtg ctcat                     45

<210> SEQ ID NO 14
<211> LENGTH: 36
<212> TYPE: DNA
<213> ORGANISM: Hepatitis C virus

<400> SEQUENCE: 14
aaagggcgca tgattgaaca agatggattg cacgca                              36

<210> SEQ ID NO 15
<211> LENGTH: 39
<212> TYPE: DNA
<213> ORGANISM: Hepatitis C virus

<400> SEQUENCE: 15
gcatatgtta actcagaaga actcgtcaag aaggcgata                           39

<210> SEQ ID NO 16
<211> LENGTH: 45
<212> TYPE: DNA
<213> ORGANISM: Hepatitis C virus
```

```
<400> SEQUENCE: 16
gcatatgaat tctaatacga ctcactatag gccagccccc gattg            45

<210> SEQ ID NO 17
<211> LENGTH: 30
<212> TYPE: DNA
<213> ORGANISM: Hepatitis C virus

<400> SEQUENCE: 17
acgcagaaag cgtctagcca tggcgttagt                             30

<210> SEQ ID NO 18
<211> LENGTH: 30
<212> TYPE: DNA
<213> ORGANISM: Hepatitis C virus

<400> SEQUENCE: 18
tcccggggca ctcgcaagca ccctatcagg                             30

<210> SEQ ID NO 19
<211> LENGTH: 26
<212> TYPE: DNA
<213> ORGANISM: Hepatitis C virus
<220> FEATURE:
<223> OTHER INFORMATION: Label with FAM: fluorescence reporter dye
<220> FEATURE:
<223> OTHER INFORMATION: Label with TAMRA: Quencher dye

<400> SEQUENCE: 19
tggtctgcgg aacgggtgag tacacc                                 26

<210> SEQ ID NO 20
<211> LENGTH: 45
<212> TYPE: DNA
<213> ORGANISM: Hepatitis C virus

<400> SEQUENCE: 20
gtggacgaat tctaatacga ctcactataa ccagcccccg attgg            45

<210> SEQ ID NO 21
<211> LENGTH: 27
<212> TYPE: DNA
<213> ORGANISM: Hepatitis C virus

<400> SEQUENCE: 21
ggaacgcccg tcgtggccag ccacgat                                27

<210> SEQ ID NO 22
<211> LENGTH: 23
<212> TYPE: DNA
<213> ORGANISM: Hepatitis C virus

<400> SEQUENCE: 22
gtcgtcttct ctgacatgga gac                                    23

<210> SEQ ID NO 23
<211> LENGTH: 27
<212> TYPE: DNA
<213> ORGANISM: Hepatitis C virus

<400> SEQUENCE: 23
gagttgctca gtggattgat gggcagc                                27

<210> SEQ ID NO 24
```

-continued

```
<211> LENGTH: 8638
<212> TYPE: DNA
<213> ORGANISM: Hepatitis C virus
<220> FEATURE:
<221> NAME/KEY: CDS
<222> LOCATION: (1802)...(8407)

<400> SEQUENCE: 24
accagccccc gattgggggc gacactccac catagatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag      180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactggga caacagaca atcggctgct      480 ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720 agtatccat catggctgat gcaatgcggc ggctgcatac gcttgatccg gctacctgcc      780
cattcgacca ccaagcgaaa catcgcatcg agcgagcacg tactcggatg aagccggtc     840 tgtcgatca ggatgatctg gacgaagagc atcagggct cgcgccagcc gaactgttcg       900
ccaggctcaa ggcgcgcatg cccgacgcg aggatctcgt cgtgacccat ggcgatgcct      960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agttcgcgcc agatgttaa     1200 cagaccacaa cggtttccct ctagcgggat caattccgcc ccccccta acgttactgg      1260 ccgaagccgc ttggaataag gccggtgtgc gtttgtctat atgttatttt ccaccatatt    1320
gccgtctttt ggcaatgtga gggcccggaa acctggcct gtcttcttga cgagcattcc    1380 tagggggtctt tcccctctcg ccaaaggaat gcaaggtctg ttgaatgtcg tgaaggaagc    1440
agttcctctg gaagcttctt gaagacaaac aacgtctgta gcgacccttt gcaggcagcg    1500 gaaccccca cctggcgaca ggtgcctctg cggccaaaag ccacgtgtat aagatacacc     1560
tgcaaaggcg gcacaacccc agtgccacgt tgtgagttgg atagttgtgg aaagagtcaa    1620
atggctctcc tcaagcgtat tcaacaaggg gctgaaggat gcccagaagg tacccccattg   1680 tatgggatct gatctggggc ctcggtgcac atgctttaca tgtgtttagt cgaggttaaa    1740
aaacgtctag gccccccgaa ccacggggac gtggttttcc tttgaaaaac acgataatac    1800
```

```
 c atg gac cgg gag atg gca gca tcg tgc gga ggc gcg gtt ttc gta ggt   1849
   Met Asp Arg Glu Met Ala Ala Ser Cys Gly Gly Ala Val Phe Val Gly
    1               5                   10                  15 ctg ata ctc ttg acc ttg tca ccg cac tat aag ctg ttc ctc gct agg      1897
Leu Ile Leu Leu Thr Leu Ser Pro His Tyr Lys Leu Phe Leu Ala Arg
             20                  25                  30 ctc ata tgg tgg tta caa tat ttt atc acc agg gcc gag gca cac ttg      1945
Leu Ile Trp Trp Leu Gln Tyr Phe Ile Thr Arg Ala Glu Ala His Leu
         35                  40                  45
```

```
caa gtg tgg atc ccc ccc ctc aac gtt cgg ggg ggc cgc gat gcc gtc       1993
Gln Val Trp Ile Pro Pro Leu Asn Val Arg Gly Gly Arg Asp Ala Val
 50                  55                  60 atc ctc ctc acg tgc gcg atc cac cca gag cta atc ttt acc atc acc       2041
Ile Leu Leu Thr Cys Ala Ile His Pro Glu Leu Ile Phe Thr Ile Thr
 65                  70                  75                  80 aaa atc ttg ctc gcc ata ctc ggt cca ctc atg gtg ctc cag gct ggt       2089
Lys Ile Leu Leu Ala Ile Leu Gly Pro Leu Met Val Leu Gln Ala Gly
                 85                  90                  95 ata acc aaa gtg ccg tac ttc gtg cgc gca cac ggg ctc att cgt gca       2137
Ile Thr Lys Val Pro Tyr Phe Val Arg Ala His Gly Leu Ile Arg Ala
            100                 105                 110 tgc atg ctg gtg cgg aag gtt gct ggg ggt cat tat gtc caa atg gct       2185
Cys Met Leu Val Arg Lys Val Ala Gly Gly His Tyr Val Gln Met Ala
            115                 120                 125 ctc atg aag ttg gcc gca ctg aca ggt acg tac gtt tat gac cat ctc       2233
Leu Met Lys Leu Ala Ala Leu Thr Gly Thr Tyr Val Tyr Asp His Leu
130                 135                 140 acc cca ctg cgg gac tgg gcc cac gcg ggc cta cga gac ctt gcg gtg       2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc       2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc       2377
Trp Gly Ala Asp Thr Ala Ala Cys Gly Asp Ile Ile Leu Gly Leu Pro
            180                 185                 190 gtc tcc gcc cgc agg ggg agg gag ata cat ctg gga ccg gca gac agc       2425
Val Ser Ala Arg Arg Gly Arg Glu Ile His Leu Gly Pro Ala Asp Ser
            195                 200                 205 ctt gaa ggg cag ggg tgg cga ctc ctc gcg cct att acg gcc tac tcc       2473
Leu Glu Gly Gln Gly Trp Arg Leu Leu Ala Pro Ile Thr Ala Tyr Ser
210                 215                 220 caa cag acg cga ggc cta ctt ggc tgc atc atc act agc ctc aca ggc       2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca       2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc       2617
Thr Gln Ser Phe Leu Ala Thr Cys Val Asn Gly Val Cys Trp Thr Val
            260                 265                 270 tat cat ggt gcc ggc tca aag acc ctt gcc ggc cca aag ggc cca atc       2665
Tyr His Gly Ala Gly Ser Lys Thr Leu Ala Gly Pro Lys Gly Pro Ile
            275                 280                 285 acc caa atg tac acc aat gtg gac cag gac ctc gtc ggc tgg caa gcg       2713
Thr Gln Met Tyr Thr Asn Val Asp Gln Asp Leu Val Gly Trp Gln Ala
            290                 295                 300 ccc ccc ggg gcg cgt tcc ttg aca cca tgc acc tgc ggc agc tcg gac       2761
Pro Pro Gly Ala Arg Ser Leu Thr Pro Cys Thr Cys Gly Ser Ser Asp
305                 310                 315                 320 ctt tac ttg gtc acg agg cat gcc gat gtc att ccg gtg cgc cgg cgg       2809
Leu Tyr Leu Val Thr Arg His Ala Asp Val Ile Pro Val Arg Arg Arg
                325                 330                 335 ggc gac agc agg ggc agc cta ctc tcc ccc agg ccc gtc tcc tac ttg       2857
Gly Asp Ser Arg Gly Ser Leu Leu Ser Pro Arg Pro Val Ser Tyr Leu
            340                 345                 350 aag ggc tct tcg ggc ggt cca ctg ctc tgc ccc tcg ggg cac gct gtg       2905
Lys Gly Ser Ser Gly Gly Pro Leu Leu Cys Pro Ser Gly His Ala Val
            355                 360                 365
```

| | | |
|---|---|---|
| ggc atc ttt cgg gct gcc gtg tgc acc cga ggg gtt gcg aag gcg gtg<br>Gly Ile Phe Arg Ala Ala Val Cys Thr Arg Gly Val Ala Lys Ala Val<br>370                            375                    380 | | 2953 |
| gac ttt gta ccc gtc gag tct atg gaa acc act atg cgg tcc ccg gtc<br>Asp Phe Val Pro Val Glu Ser Met Glu Thr Thr Met Arg Ser Pro Val<br>385                            390                    395                    400 | | 3001 |
| ttc acg gac aac tcg tcc cct ccg gcc gta ccg cag aca ttc cag gtg<br>Phe Thr Asp Asn Ser Ser Pro Pro Ala Val Pro Gln Thr Phe Gln Val<br>                      405                          410                          415 | | 3049 |
| gcc cat cta cac gcc cct act ggt agc ggc aag agc act aag gtg ccg<br>Ala His Leu His Ala Pro Thr Gly Ser Gly Lys Ser Thr Lys Val Pro<br>            420                          425                          430 | | 3097 |
| gct gcg tat gca gcc caa ggg tat aag gtg ctt gtc ctg aac ccg tcc<br>Ala Ala Tyr Ala Ala Gln Gly Tyr Lys Val Leu Val Leu Asn Pro Ser<br>                435                          440                    445 | | 3145 |
| gtc gcc gcc acc cta ggt ttc ggg gcg tat atg tct aag gca cat ggt<br>Val Ala Ala Thr Leu Gly Phe Gly Ala Tyr Met Ser Lys Ala His Gly<br>450                            455                    460 | | 3193 |
| atc gac cct aac atc aga acc ggg gta agg acc atc acc acg ggt gcc<br>Ile Asp Pro Asn Ile Arg Thr Gly Val Arg Thr Ile Thr Thr Gly Ala<br>465                            470                    475                    480 | | 3241 |
| ccc atc acg tac tcc acc tat ggc aag ttt ctt gcc gac ggt ggt tgc<br>Pro Ile Thr Tyr Ser Thr Tyr Gly Lys Phe Leu Ala Asp Gly Gly Cys<br>                485                          490                    495 | | 3289 |
| tct ggg ggc gcc tat gac atc ata ata tgt gat gag tgc cac tca act<br>Ser Gly Gly Ala Tyr Asp Ile Ile Ile Cys Asp Glu Cys His Ser Thr<br>            500                          505                    510 | | 3337 |
| gac tcg acc act atc ctg ggc atc ggc aca gtc ctg gac caa gcg gag<br>Asp Ser Thr Thr Ile Leu Gly Ile Gly Thr Val Leu Asp Gln Ala Glu<br>                515                          520                    525 | | 3385 |
| acg gct gga gcg cga ctc gtc gtg ctc gcc acc gct acg cct ccg gga<br>Thr Ala Gly Ala Arg Leu Val Val Leu Ala Thr Ala Thr Pro Pro Gly<br>530                            535                    540 | | 3433 |
| tcg gtc acc gtg cca cat cca aac atc gag gag gtg gct ctg tcc agc<br>Ser Val Thr Val Pro His Pro Asn Ile Glu Glu Val Ala Leu Ser Ser<br>545                            550                    555                    560 | | 3481 |
| act gga gaa atc ccc ttt tat ggc aaa gcc atc ccc atc gag acc atc<br>Thr Gly Glu Ile Pro Phe Tyr Gly Lys Ala Ile Pro Ile Glu Thr Ile<br>                      565                          570                          575 | | 3529 |
| aag ggg ggg agg cac ctc att ttc tgc cat tcc aag aag aaa tgt gat<br>Lys Gly Gly Arg His Leu Ile Phe Cys His Ser Lys Lys Lys Cys Asp<br>            580                          585                    590 | | 3577 |
| gag ctc gcc gcg aag ctg tcc ggc ctc gga ctc aat gct gta gca tat<br>Glu Leu Ala Ala Lys Leu Ser Gly Leu Gly Leu Asn Ala Val Ala Tyr<br>                595                          600                    605 | | 3625 |
| tac cgg ggc ctt gat gta tcc gtc ata cca act agc gga gac gtc att<br>Tyr Arg Gly Leu Asp Val Ser Val Ile Pro Thr Ser Gly Asp Val Ile<br>            610                          615                    620 | | 3673 |
| gtc gta gca acg gac gct cta atg acg ggc ttt acc ggc gat ttc gac<br>Val Val Ala Thr Asp Ala Leu Met Thr Gly Phe Thr Gly Asp Phe Asp<br>625                            630                    635                    640 | | 3721 |
| tca gtg atc gac tgc aat aca tgt gtc acc cag aca gtc gac ttc agc<br>Ser Val Ile Asp Cys Asn Thr Cys Val Thr Gln Thr Val Asp Phe Ser<br>                      645                          650                    655 | | 3769 |
| ctg gac ccg acc ttc acc att gag acg acg acc gtg cca caa gac gcg<br>Leu Asp Pro Thr Phe Thr Ile Glu Thr Thr Thr Val Pro Gln Asp Ala<br>            660                          665                    670 | | 3817 |
| gtg tca cgc tcg cag cgg cga ggc agg act ggt agg ggc agg atg ggc<br>Val Ser Arg Ser Gln Arg Arg Gly Arg Thr Gly Arg Gly Arg Met Gly<br>675                            680                    685 | | 3865 |

```
att tac agg ttt gtg act cca gga gaa cgg ccc tcg ggc atg ttc gat      3913
Ile Tyr Arg Phe Val Thr Pro Gly Glu Arg Pro Ser Gly Met Phe Asp
690                 695                 700 tcc tcg gtt ctg tgc gag tgc tat gac gcg ggc tgt gct tgg tac gag      3961
Ser Ser Val Leu Cys Glu Cys Tyr Asp Ala Gly Cys Ala Trp Tyr Glu
705                 710                 715                 720 ctc acg ccc gcc gag acc tca gtt agg ttg cgg gct tac cta aac aca      4009
Leu Thr Pro Ala Glu Thr Ser Val Arg Leu Arg Ala Tyr Leu Asn Thr
                725                 730                 735 cca ggg ttg ccc gtc tgc cag gac cat ctg gag ttc tgg gag agc gtc      4057
Pro Gly Leu Pro Val Cys Gln Asp His Leu Glu Phe Trp Glu Ser Val
        740                 745                 750 ttt aca ggc ctc acc cac ata gac gcc cat ttc ttg tcc cag act aag      4105
Phe Thr Gly Leu Thr His Ile Asp Ala His Phe Leu Ser Gln Thr Lys
    755                 760                 765 cag gca gga gac aac ttc ccc tac ctg gta gca tac cag gct acg gtg      4153
Gln Ala Gly Asp Asn Phe Pro Tyr Leu Val Ala Tyr Gln Ala Thr Val
770                 775                 780 tgc gcc agg gct cag gct cca cct cca tcg tgg gac caa atg tgg aag      4201
Cys Ala Arg Ala Gln Ala Pro Pro Pro Ser Trp Asp Gln Met Trp Lys
785                 790                 795                 800 tgt ctc ata cgg cta aag cct acg ctg cac ggg cca acg ccc ctg ctg      4249
Cys Leu Ile Arg Leu Lys Pro Thr Leu His Gly Pro Thr Pro Leu Leu
                805                 810                 815 tat agg ctg gga gcc gtt caa aac gag gtt act acc aca cac ccc ata      4297
Tyr Arg Leu Gly Ala Val Gln Asn Glu Val Thr Thr Thr His Pro Ile
        820                 825                 830 acc aaa tac atc atg gca tgc atg tcg gct gac ctg gag gtc gtc acg      4345
Thr Lys Tyr Ile Met Ala Cys Met Ser Ala Asp Leu Glu Val Val Thr
    835                 840                 845 agc acc tgg gtg ctg gta ggc gga gtc cta gca gct ctg gcc gcg tat      4393
Ser Thr Trp Val Leu Val Gly Gly Val Leu Ala Ala Leu Ala Ala Tyr
850                 855                 860 tgc ctg aca aca ggc agc gtg gtc att gtg ggc agg atc atc ttg tcc      4441
Cys Leu Thr Thr Gly Ser Val Val Ile Val Gly Arg Ile Ile Leu Ser
865                 870                 875                 880 gga aag ccg gcc atc att ccc gac agg gaa gtc ctt tac cgg gag ttc      4489
Gly Lys Pro Ala Ile Ile Pro Asp Arg Glu Val Leu Tyr Arg Glu Phe
                885                 890                 895 gat gag atg gaa gag tgc gcc tca cac ctc cct tac atc gaa cag gga      4537
Asp Glu Met Glu Glu Cys Ala Ser His Leu Pro Tyr Ile Glu Gln Gly
        900                 905                 910 atg cag ctc gcc gaa caa ttc aaa cag aag gca atc ggg ttg ctg caa      4585
Met Gln Leu Ala Glu Gln Phe Lys Gln Lys Ala Ile Gly Leu Leu Gln
    915                 920                 925 aca gcc acc aag caa gcg gag gct gct gct ccc gtg gtg gaa tcc aag      4633
Thr Ala Thr Lys Gln Ala Glu Ala Ala Ala Pro Val Val Glu Ser Lys
930                 935                 940 tgg cgg acc ctc gaa gcc ttc tgg gcg aag cat atg tgg aat ttc atc      4681
Trp Arg Thr Leu Glu Ala Phe Trp Ala Lys His Met Trp Asn Phe Ile
945                 950                 955                 960 agc ggg ata caa tat tta gca ggc ttg tcc act ctg cct ggc aac ccc      4729
Ser Gly Ile Gln Tyr Leu Ala Gly Leu Ser Thr Leu Pro Gly Asn Pro
                965                 970                 975 gcg ata gca tca ctg atg gca ttc aca gcc tct atc acc agc ccg ctc      4777
Ala Ile Ala Ser Leu Met Ala Phe Thr Ala Ser Ile Thr Ser Pro Leu
        980                 985                 990 acc acc caa cat acc ctc ctg ttt aac atc ctg ggg gga tgg gtg gcc      4825
Thr Thr Gln His Thr Leu Leu Phe Asn Ile Leu Gly Gly Trp Val Ala
    995                 1000                1005
```

| | | |
|---|---|---|
| gcc caa ctt gct cct ccc agc gct gct tct gct ttc gta ggc gcc ggc<br>Ala Gln Leu Ala Pro Pro Ser Ala Ala Ser Ala Phe Val Gly Ala Gly<br>      1010                      1015                      1020 | 4873 |
| atc gct gga gcg gct gtt ggc agc ata ggc ctt ggg aag gtg ctt gtg<br>Ile Ala Gly Ala Ala Val Gly Ser Ile Gly Leu Gly Lys Val Leu Val<br>1025                      1030                      1035                      1040 | 4921 |
| gat att ttg gca ggt tat gga gca ggg gtg gca ggc gcg ctc gtg gcc<br>Asp Ile Leu Ala Gly Tyr Gly Ala Gly Val Ala Gly Ala Leu Val Ala<br>                1045                      1050                      1055 | 4969 |
| ttt aag gtc atg agc ggc gag atg ccc tcc acc gag gac ctg gtt aac<br>Phe Lys Val Met Ser Gly Glu Met Pro Ser Thr Glu Asp Leu Val Asn<br>            1060                      1065                      1070 | 5017 |
| cta ctc cct gct atc ctc tcc cct ggc gcc cta gtc gtc ggg gtc gtg<br>Leu Leu Pro Ala Ile Leu Ser Pro Gly Ala Leu Val Val Gly Val Val<br>                1075                      1080                      1085 | 5065 |
| tgc gca gcg ata ctg cgt cgg cac gtg ggc cca ggg gag ggg gct gtg<br>Cys Ala Ala Ile Leu Arg Arg His Val Gly Pro Gly Glu Gly Ala Val<br>1090                      1095                      1100 | 5113 |
| cag tgg atg aac cgg ctg ata gcg ttc gct tcg cgg ggt aac cac gtc<br>Gln Trp Met Asn Arg Leu Ile Ala Phe Ala Ser Arg Gly Asn His Val<br>1105                      1110                      1115                      1120 | 5161 |
| tcc ccc acg cac tat gtg cct gag agc gac gct gca gca cgt gtc act<br>Ser Pro Thr His Tyr Val Pro Glu Ser Asp Ala Ala Ala Arg Val Thr<br>                1125                      1130                      1135 | 5209 |
| cag atc ctc tct agt ctt acc atc act cag ctg ctg aag agg ctt cac<br>Gln Ile Leu Ser Ser Leu Thr Ile Thr Gln Leu Leu Lys Arg Leu His<br>            1140                      1145                      1150 | 5257 |
| cag tgg atc aac gag gac tgc tcc acg cca tgc tcc ggc tcg tgg cta<br>Gln Trp Ile Asn Glu Asp Cys Ser Thr Pro Cys Ser Gly Ser Trp Leu<br>                1155                      1160                      1165 | 5305 |
| aga gat gtt tgg gat tgg ata tgc acg gtg ttg act gat ttc aag acc<br>Arg Asp Val Trp Asp Trp Ile Cys Thr Val Leu Thr Asp Phe Lys Thr<br>1170                      1175                      1180 | 5353 |
| tgg ctc cag tcc aag ctc ctg ccg cga ttg ccg gga gtc ccc ttc ttc<br>Trp Leu Gln Ser Lys Leu Leu Pro Arg Leu Pro Gly Val Pro Phe Phe<br>1185                      1190                      1195                      1200 | 5401 |
| tca tgt caa cgt ggg tac aag gga gtc tgg cgg ggc gac ggc atc atg<br>Ser Cys Gln Arg Gly Tyr Lys Gly Val Trp Arg Gly Asp Gly Ile Met<br>                1205                      1210                      1215 | 5449 |
| caa acc acc tgc cca tgt gga gca cag atc acc gga cat gtg aaa aac<br>Gln Thr Thr Cys Pro Cys Gly Ala Gln Ile Thr Gly His Val Lys Asn<br>            1220                      1225                      1230 | 5497 |
| ggt tcc atg agg atc gtg ggg cct agg acc tgt agt aac acg tgg cat<br>Gly Ser Met Arg Ile Val Gly Pro Arg Thr Cys Ser Asn Thr Trp His<br>                1235                      1240                      1245 | 5545 |
| gga aca ttc ccc att aac gcg tac acc acg ggc ccc tgc acg ccc tcc<br>Gly Thr Phe Pro Ile Asn Ala Tyr Thr Thr Gly Pro Cys Thr Pro Ser<br>1250                      1255                      1260 | 5593 |
| ccg gcg cca aat tat tct agg gcg ctg tgg cgg gtg gct gct gag gag<br>Pro Ala Pro Asn Tyr Ser Arg Ala Leu Trp Arg Val Ala Ala Glu Glu<br>1265                      1270                      1275                      1280 | 5641 |
| tac gtg gag gtt acg cgg gtg ggg gat ttc cac tac gtg acg ggc atg<br>Tyr Val Glu Val Thr Arg Val Gly Asp Phe His Tyr Val Thr Gly Met<br>                1285                      1290                      1295 | 5689 |
| acc act gac aac gta aag tgc ccg tgt cag gtt ccg gcc ccc gaa ttc<br>Thr Thr Asp Asn Val Lys Cys Pro Cys Gln Val Pro Ala Pro Glu Phe<br>            1300                      1305                      1310 | 5737 |
| ttc aca gaa gtg gat ggg gtg cgg ttg cac agg tac gct cca gcg tgc<br>Phe Thr Glu Val Asp Gly Val Arg Leu His Arg Tyr Ala Pro Ala Cys<br>                1315                      1320                      1325 | 5785 |

```
aaa ccc ctc cta cgg gag gag gtc aca ttc ctg gtc ggg ctc aat caa    5833
Lys Pro Leu Leu Arg Glu Glu Val Thr Phe Leu Val Gly Leu Asn Gln
    1330                1335                1340 tac ctg gtt ggg tca cag ctc cca tgc gag ccc gaa ccg gac gta gca    5881
Tyr Leu Val Gly Ser Gln Leu Pro Cys Glu Pro Glu Pro Asp Val Ala
1345                1350                1355                1360 gtg ctc act tcc atg ctc acc gac ccc tcc cac att acg gcg gag acg    5929
Val Leu Thr Ser Met Leu Thr Asp Pro Ser His Ile Thr Ala Glu Thr
                1365                1370                1375 gct aag cgt agg ctg gcc agg gga tct ccc ccc tcc ttg gcc agc tca    5977
Ala Lys Arg Arg Leu Ala Arg Gly Ser Pro Pro Ser Leu Ala Ser Ser
        1380                1385                1390 tca gct agc cag ctg tct gcg cct tcc ttg aag gca aca tgc act acc    6025
Ser Ala Ser Gln Leu Ser Ala Pro Ser Leu Lys Ala Thr Cys Thr Thr
            1395                1400                1405 cgt cat gac tcc ccg gac gct gac ctc atc gag gcc aac ctc ctg tgg    6073
Arg His Asp Ser Pro Asp Ala Asp Leu Ile Glu Ala Asn Leu Leu Trp
                1410                1415                1420 cgg cag gag atg ggc ggg aac atc acc cgc gtg gag tca gaa aat aag    6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag    6169
Val Val Ile Leu Asp Ser Phe Glu Pro Leu Gln Ala Glu Glu Asp Glu
                1445                1450                1455 agg gaa gta tcc gtt ccg gcg gag atc ctg cgg agg tcc agg aaa ttc    6217
Arg Glu Val Ser Val Pro Ala Glu Ile Leu Arg Arg Ser Arg Lys Phe
        1460                1465                1470 cct cga gcg atg ccc ata tgg gca cgc ccg gat tac aac cct cca ctg    6265
Pro Arg Ala Met Pro Ile Trp Ala Arg Pro Asp Tyr Asn Pro Pro Leu
            1475                1480                1485 tta gag tcc tgg aag gac ccg gac tac gtc cct cca gtg gta cac ggg    6313
Leu Glu Ser Trp Lys Asp Pro Asp Tyr Val Pro Pro Val Val His Gly
                1490                1495                1500 tgt cca ttg ccg cct gcc aag gcc cct ccg ata cca cct cca cgg agg    6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg    6409
Lys Arg Thr Val Val Leu Ser Glu Ser Thr Val Ser Ser Ala Leu Ala
                1525                1530                1535 gag ctc gcc aca aag acc ttc ggc agc tcc gaa tcg tcg gcc gtc gac    6457
Glu Leu Ala Thr Lys Thr Phe Gly Ser Ser Glu Ser Ser Ala Val Asp
        1540                1545                1550 agc ggc acg gca acg gcc tct cct gac cag ccc tcc gac gac ggc gac    6505
Ser Gly Thr Ala Thr Ala Ser Pro Asp Gln Pro Ser Asp Asp Gly Asp
            1555                1560                1565 gcg gga tcc gac gtt gag tcg tac tcc tcc atg ccc ccc ctt gag ggg    6553
Ala Gly Ser Asp Val Glu Ser Tyr Ser Ser Met Pro Pro Leu Glu Gly
                1570                1575                1580 gag ccg ggg gat ccc gat ctc agc gac ggg tct tgg tct acc gta agc    6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg    6649
Glu Glu Ala Ser Glu Asp Val Val Cys Cys Ser Met Ser Tyr Thr Trp
                1605                1610                1615 aca ggc gcc ctg atc acg cca tgc gct gcg gag gaa acc aag ctg ccc    6697
Thr Gly Ala Leu Ile Thr Pro Cys Ala Ala Glu Glu Thr Lys Leu Pro
        1620                1625                1630 atc aat gca ctg agc aac tct ttg ctc cgt cac cac aac ttg gtc tat    6745
Ile Asn Ala Leu Ser Asn Ser Leu Leu Arg His His Asn Leu Val Tyr
            1635                1640                1645
```

-continued

| | |
|---|---|
| gct aca aca tct cgc agc gca agc ctg cgg cag aag aag gtc acc ttt<br>Ala Thr Thr Ser Arg Ser Ala Ser Leu Arg Gln Lys Lys Val Thr Phe<br>　　　1650　　　　　　　1655　　　　　　　1660 | 6793 |
| gac aga ctg cag gtc ctg gac gac cac tac cgg gac gtg ctc aag gag<br>Asp Arg Leu Gln Val Leu Asp Asp His Tyr Arg Asp Val Leu Lys Glu<br>1665　　　　　　　1670　　　　　　　1675　　　　　　　1680 | 6841 |
| atg aag gcg aag gcg tcc aca gtt aag gct aaa ctt cta tcc gtg gag<br>Met Lys Ala Lys Ala Ser Thr Val Lys Ala Lys Leu Leu Ser Val Glu<br>　　　　　　　1685　　　　　　　1690　　　　　　　1695 | 6889 |
| gaa gcc tgt aag ctg acg ccc cca cat tcg gcc aga tct aaa ttt ggc<br>Glu Ala Cys Lys Leu Thr Pro Pro His Ser Ala Arg Ser Lys Phe Gly<br>1700　　　　　　　1705　　　　　　　1710 | 6937 |
| tat ggg gca aag gac gtc cgg aac cta tcc agc aag gcc gtt aac cac<br>Tyr Gly Ala Lys Asp Val Arg Asn Leu Ser Ser Lys Ala Val Asn His<br>　　　1715　　　　　　　1720　　　　　　　1725 | 6985 |
| atc cgc tcc gtg tgg aag gac ttg ctg gaa gac act gag aca cca att<br>Ile Arg Ser Val Trp Lys Asp Leu Leu Glu Asp Thr Glu Thr Pro Ile<br>1730　　　　　　　1735　　　　　　　1740 | 7033 |
| gac acc acc atc atg gca aaa aat gag gtt ttc tgc gtc caa cca gag<br>Asp Thr Thr Ile Met Ala Lys Asn Glu Val Phe Cys Val Gln Pro Glu<br>1745　　　　　　　1750　　　　　　　1755　　　　　　　1760 | 7081 |
| aag ggg ggc cgc aag cca gct cgc ctt atc gta ttc cca gat ttg ggg<br>Lys Gly Gly Arg Lys Pro Ala Arg Leu Ile Val Phe Pro Asp Leu Gly<br>　　　　　　　1765　　　　　　　1770　　　　　　　1775 | 7129 |
| gtt cgt gtg tgc gag aaa atg gcc ctt tac gat gtg gtc tcc acc ctc<br>Val Arg Val Cys Glu Lys Met Ala Leu Tyr Asp Val Val Ser Thr Leu<br>1780　　　　　　　1785　　　　　　　1790 | 7177 |
| cct cag gcc gtg atg ggc tct tca tac gga ttc caa tac tct cct gga<br>Pro Gln Ala Val Met Gly Ser Ser Tyr Gly Phe Gln Tyr Ser Pro Gly<br>　　　1795　　　　　　　1800　　　　　　　1805 | 7225 |
| cag cgg gtc gag ttc ctg gtg aat gcc tgg aaa gcg aag aaa tgc cct<br>Gln Arg Val Glu Phe Leu Val Asn Ala Trp Lys Ala Lys Lys Cys Pro<br>1810　　　　　　　1815　　　　　　　1820 | 7273 |
| atg ggc ttc gca tat gac acc cgc tgt ttt gac tca acg gtc act gag<br>Met Gly Phe Ala Tyr Asp Thr Arg Cys Phe Asp Ser Thr Val Thr Glu<br>1825　　　　　　　1830　　　　　　　1835　　　　　　　1840 | 7321 |
| aat gac atc cgt gtt gag gag tca atc tac caa tgt tgt gac ttg gcc<br>Asn Asp Ile Arg Val Glu Glu Ser Ile Tyr Gln Cys Cys Asp Leu Ala<br>　　　　　　　1845　　　　　　　1850　　　　　　　1855 | 7369 |
| ccc gaa gcc aga cag gcc ata agg tcg ctc aca gag cgg ctt tac atc<br>Pro Glu Ala Arg Gln Ala Ile Arg Ser Leu Thr Glu Arg Leu Tyr Ile<br>　　　　　　　1860　　　　　　　1865　　　　　　　1870 | 7417 |
| ggg ggc ccc ctg act aat tct aaa ggg cag aac tgc ggc tat cgc cgg<br>Gly Gly Pro Leu Thr Asn Ser Lys Gly Gln Asn Cys Gly Tyr Arg Arg<br>　　　1875　　　　　　　1880　　　　　　　1885 | 7465 |
| tgc cgc gcg agc ggt gta ctg acg acc agc tgc ggt aat acc ctc aca<br>Cys Arg Ala Ser Gly Val Leu Thr Thr Ser Cys Gly Asn Thr Leu Thr<br>1890　　　　　　　1895　　　　　　　1900 | 7513 |
| tgt tac ttg aag gcc gct gcg gcc tgt cga gct gcg aag ctc cag gac<br>Cys Tyr Leu Lys Ala Ala Ala Ala Cys Arg Ala Ala Lys Leu Gln Asp<br>1905　　　　　　　1910　　　　　　　1915　　　　　　　1920 | 7561 |
| tgc acg atg ctc gta tgc gga gac gac ctt gtc gtt atc tgt gaa agc<br>Cys Thr Met Leu Val Cys Gly Asp Asp Leu Val Val Ile Cys Glu Ser<br>　　　　　　　1925　　　　　　　1930　　　　　　　1935 | 7609 |
| gcg ggg acc caa gag gac gag gcg agc cta cgg gcc ttc acg gag gct<br>Ala Gly Thr Gln Glu Asp Glu Ala Ser Leu Arg Ala Phe Thr Glu Ala<br>　　　　　　　1940　　　　　　　1945　　　　　　　1950 | 7657 |
| atg act aga tac tct gcc ccc cct ggg gac ccg ccc aaa cca gaa tac<br>Met Thr Arg Tyr Ser Ala Pro Pro Gly Asp Pro Pro Lys Pro Glu Tyr<br>1955　　　　　　　1960　　　　　　　1965 | 7705 |

```
gac ttg gag ttg ata aca tca tgc tcc tcc aat gtg tca gtc gcg cac     7753
Asp Leu Glu Leu Ile Thr Ser Cys Ser Ser Asn Val Ser Val Ala His
    1970                1975                1980 gat gca tct ggc aaa agg gtg tac tat ctc acc cgt gac ccc acc acc     7801
Asp Ala Ser Gly Lys Arg Val Tyr Tyr Leu Thr Arg Asp Pro Thr Thr
1985                1990                1995                2000 ccc ctt gcg cgg gct gcg tgg gag aca gct aga cac act cca gtc aat     7849
Pro Leu Ala Arg Ala Ala Trp Glu Thr Ala Arg His Thr Pro Val Asn
                2005                2010                2015 tcc tgg cta ggc aac atc atc atg tat gcg ccc acc ttg tgg gca agg     7897
Ser Trp Leu Gly Asn Ile Ile Met Tyr Ala Pro Thr Leu Trp Ala Arg
            2020                2025                2030 atg atc ctg atg act cat ttc ttc tcc atc ctt cta gct cag gaa caa     7945
Met Ile Leu Met Thr His Phe Phe Ser Ile Leu Leu Ala Gln Glu Gln
        2035                2040                2045 ctt gaa aaa gcc cta gat tgt cag atc tac ggg gcc tgt tac tcc att     7993
Leu Glu Lys Ala Leu Asp Cys Gln Ile Tyr Gly Ala Cys Tyr Ser Ile
    2050                2055                2060 gag cca ctt gac cta cct cag atc att caa cga ctc cac ggc ctt agc     8041
Glu Pro Leu Asp Leu Pro Gln Ile Ile Gln Arg Leu His Gly Leu Ser
2065                2070                2075                2080 gca ttt tca ctc cat agt tac tct cca ggt gag atc aat agg gtg gct     8089
Ala Phe Ser Leu His Ser Tyr Ser Pro Gly Glu Ile Asn Arg Val Ala
                2085                2090                2095 tca tgc ctc agg aaa ctt ggg gta ccg ccc ttg cga gtc tgg aga cat     8137
Ser Cys Leu Arg Lys Leu Gly Val Pro Pro Leu Arg Val Trp Arg His
            2100                2105                2110 cgg gcc aga agt gtc cgc gct agg cta ctg tcc cag ggg ggg agg gct     8185
Arg Ala Arg Ser Val Arg Ala Arg Leu Leu Ser Gln Gly Gly Arg Ala
        2115                2120                2125 gcc act tgt ggc aag tac ctc ttc aac tgg gca gta agg acc aag ctc     8233
Ala Thr Cys Gly Lys Tyr Leu Phe Asn Trp Ala Val Arg Thr Lys Leu
    2130                2135                2140 aaa ctc act cca atc ccg gct gcg tcc cag ttg gat tta tcc agc tgg     8281
Lys Leu Thr Pro Ile Pro Ala Ala Ser Gln Leu Asp Leu Ser Ser Trp
2145                2150                2155                2160 ttc gtt gct ggt tac agc ggg gga gac ata tat cac agc ctg tct cgt     8329
Phe Val Ala Gly Tyr Ser Gly Gly Asp Ile Tyr His Ser Leu Ser Arg
                2165                2170                2175 gcc cga ccc cgc tgg ttc atg tgg tgc cta ctc cta ctt tct gta ggg     8377
Ala Arg Pro Arg Trp Phe Met Trp Cys Leu Leu Leu Leu Ser Val Gly
            2180                2185                2190 gta ggc atc tat cta ctc ccc aac cga tga acggggagct aaacactcca       8427
Val Gly Ile Tyr Leu Leu Pro Asn Arg
        2195                2200 ggccaatagg ccatcctgtt tttttccctt tttttttttc ttttttttt ttttttttt     8487 ttttttttt ttttctcctt ttttttcct cttttttttcc ttttctttcc tttggtggct     8547
ccatcttagc cctagtcacg gctagctgtg aaaggtccgt gagccgcttg actgcagaga   8607
gtgctgatac tggcctctct gcagatcaag t                                  8638
```

<210> SEQ ID NO 25
<211> LENGTH: 8638
<212> TYPE: DNA
<213> ORGANISM: Hepatitis C virus
<220> FEATURE:
<221> NAME/KEY: CDS
<222> LOCATION: (1802)...(8407)

<400> SEQUENCE: 25

-continued

```
accagccccc gattgggggc gacactccac catagatcac tcccctgtga ggaactactg      60
tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
cggccgcttg ggtggagagg ctattcggct atgactgggc acaacagaca atcggctgct     480
ctgatgccgc cgtgttccgg ctgtcagcgc aggggcgccc ggttcttttt gtcaagaccg     540
acctgtccgg tgccctgaat gaactgcagg acgaggcagc gcggctatcg tggctggcca     600
cgacgggcgt tccttgcgca gctgtgctcg acgttgtcac tgaagcggga agggactggc     660
tgctattggg cgaagtgccg gggcaggatc tcctgtcatc tcaccttgct cctgccgaga     720
aagtatccat catggctgat gcaatgcggc ggctgcatac gcttgatccg gctacctgcc     780
cattcgacca ccaagcgaaa catcgcatcg agcgagcacg tactcggatg gaagccggtc     840
ttgtcgatca ggatgatctg gacgaagagc atcaggggct cgcgccagcc gaactgttcg     900
ccaggctcaa ggcgcgcatg cccgacgcg aggatctcgt cgtgacccat ggcgatgcct     960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agttcgcgcc agatgttaa     1200
cagaccacaa cggtttccct ctagcgggat caattccgcc cccccccta acgttactgg    1260
ccgaagccgc ttggaataag gccggtgtgc gtttgtctat atgttatttt ccaccatatt    1320
gccgtctttt ggcaatgtga gggcccggaa acctggccct gtcttcttga cgagcattcc    1380
taggggtctt tcccctctcg ccaaaggaat gcaaggtctg ttgaatgtcg tgaaggaagc    1440
agttcctctg gaagcttctt gaagacaaac aacgtctgta gcgacccttt gcaggcagcg    1500
gaacccccca cctggcgaca ggtgcctctg cggccaaaag ccacgtgtat aagatacacc    1560
tgcaaaggcg gcacaacccc agtgccacgt tgtgagttgg atagttgtgg aaagagtcaa    1620
atggctctcc tcaagcgtat tcaacaaggg gctgaaggat gcccagaagg taccccattg    1680
tatgggatct gatctggggc ctcggtgcac atgctttaca tgtgtttagt cgaggttaaa    1740
aaacgtctag gccccccgaa ccacggggac gtggttttcc tttgaaaaac acgataatac    1800
```

```
c atg gac cgg gag atg gca gca tcg tgc gga ggc gcg gtt ttc gta ggt   1849
  Met Asp Arg Glu Met Ala Ala Ser Cys Gly Gly Ala Val Phe Val Gly
  1               5                   10                  15 ctg ata ctc ttg acc ttg tca ccg cac tat aag ctg ttc ctc gct agg     1897
Leu Ile Leu Leu Thr Leu Ser Pro His Tyr Lys Leu Phe Leu Ala Arg
            20                  25                  30 ctc ata tgg tgg tta caa tat ttt atc acc agg gcc gag gca cac ttg     1945
Leu Ile Trp Trp Leu Gln Tyr Phe Ile Thr Arg Ala Glu Ala His Leu
        35                  40                  45 caa gtg tgg atc ccc ccc ctc aac gtt cgg ggg ggc cgc gat gcc gtc     1993
Gln Val Trp Ile Pro Pro Leu Asn Val Arg Gly Gly Arg Asp Ala Val
    50                  55                  60 atc ctc ctc acg tgc gcg atc cac cca gag cta atc ttt acc atc acc     2041
Ile Leu Leu Thr Cys Ala Ile His Pro Glu Leu Ile Phe Thr Ile Thr
65                  70                  75                  80
```

```
aaa atc ttg ctc gcc ata ctc ggt cca ctc atg gtg ctc cag gct ggt   2089
Lys Ile Leu Leu Ala Ile Leu Gly Pro Leu Met Val Leu Gln Ala Gly
             85                  90                  95 ata acc aaa gtg ccg tac ttc gtg cgc gca cac ggg ctc att cgt gca   2137
Ile Thr Lys Val Pro Tyr Phe Val Arg Ala His Gly Leu Ile Arg Ala
        100                 105                 110 tgc atg ctg gtg cgg aag gtt gct ggg ggt cat tat gtc caa atg gct   2185
Cys Met Leu Val Arg Lys Val Ala Gly Gly His Tyr Val Gln Met Ala
        115                 120                 125 ctc atg aag ttg gcc gca ctg aca ggt acg tac gtt tat gac cat ctc   2233
Leu Met Lys Leu Ala Ala Leu Thr Gly Thr Tyr Val Tyr Asp His Leu
130                 135                 140 acc cca ctg cgg gac tgg gcc cac gcg ggc cta cga gac ctt gcg gtg   2281
Thr Pro Leu Arg Asp Trp Ala His Ala Gly Leu Arg Asp Leu Ala Val
145                 150                 155                 160 gca gtt gag ccc gtc gtc ttc tct gat atg gag acc aag gtt atc acc   2329
Ala Val Glu Pro Val Val Phe Ser Asp Met Glu Thr Lys Val Ile Thr
                165                 170                 175 tgg ggg gca gac acc gcg gcg tgt ggg gac atc atc ttg ggc ctg ccc   2377
Trp Gly Ala Asp Thr Ala Ala Cys Gly Asp Ile Ile Leu Gly Leu Pro
                180                 185                 190 gtc tcc gcc cgc agg ggg agg gag ata cat ctg gga ccg gca gac agc   2425
Val Ser Ala Arg Arg Gly Arg Glu Ile His Leu Gly Pro Ala Asp Ser
        195                 200                 205 ctt gaa ggg cag ggg tgg cga ctc ctc gcg cct att acg gcc tac tcc   2473
Leu Glu Gly Gln Gly Trp Arg Leu Leu Ala Pro Ile Thr Ala Tyr Ser
        210                 215                 220 caa cag acg cga ggc cta ctt ggc tgc atc atc acc agc ctc aca ggc   2521
Gln Gln Thr Arg Gly Leu Leu Gly Cys Ile Ile Thr Ser Leu Thr Gly
225                 230                 235                 240 cgg gac agg aac cag gtc gag ggg gag gtc caa gtg gtc tcc acc gca   2569
Arg Asp Arg Asn Gln Val Glu Gly Glu Val Gln Val Val Ser Thr Ala
                245                 250                 255 aca caa tct ttc ctg gcg acc tgc gtc aat ggc gtg tgt tgg act gtc   2617
Thr Gln Ser Phe Leu Ala Thr Cys Val Asn Gly Val Cys Trp Thr Val
                260                 265                 270 tat cat ggt gcc ggc tca aag acc ctt gcc ggc cca aag ggc cca atc   2665
Tyr His Gly Ala Gly Ser Lys Thr Leu Ala Gly Pro Lys Gly Pro Ile
        275                 280                 285 acc caa atg tac acc aat gtg gac cag gac ctc gtc ggc tgg caa gcg   2713
Thr Gln Met Tyr Thr Asn Val Asp Gln Asp Leu Val Gly Trp Gln Ala
        290                 295                 300 ccc ccc ggg gcg cgt tcc ttg aca cca tgc acc tgc ggc agc tcg gac   2761
Pro Pro Gly Ala Arg Ser Leu Thr Pro Cys Thr Cys Gly Ser Ser Asp
305                 310                 315                 320 ctt tac ttg gtc acg aag cat gcc gat gtc att ccg gtg cgc cgg cgg   2809
Leu Tyr Leu Val Thr Lys His Ala Asp Val Ile Pro Val Arg Arg Arg
                325                 330                 335 ggc gac agc agg ggg agc cta ctc tcc ccc cgg ccc gtc tcc tac ttg   2857
Gly Asp Ser Arg Gly Ser Leu Leu Ser Pro Arg Pro Val Ser Tyr Leu
                340                 345                 350 aag ggc tct tcg ggc ggt cca ctg ctc tgc ccc tcg ggg cac gct gtg   2905
Lys Gly Ser Ser Gly Gly Pro Leu Leu Cys Pro Ser Gly His Ala Val
        355                 360                 365 ggc atc ttt cgg gct gcc gtg tgc acc cga ggg gtt gcg aag gcg gtg   2953
Gly Ile Phe Arg Ala Ala Val Cys Thr Arg Gly Val Ala Lys Ala Val
        370                 375                 380 gac ttt gta ccc gtc gag tct atg gaa acc act atg cgg tcc ccg gtc   3001
Asp Phe Val Pro Val Glu Ser Met Glu Thr Thr Met Arg Ser Pro Val
385                 390                 395                 400
```

```
ttc acg gac aac tcg tcc cct ccg gcc gta ccg cag aca ttc cag gtg    3049
Phe Thr Asp Asn Ser Ser Pro Pro Ala Val Pro Gln Thr Phe Gln Val
                405             410                 415 gcc cat cta cac gcc cct act ggt agc ggc aag agc act aag gtg ccg    3097
Ala His Leu His Ala Pro Thr Gly Ser Gly Lys Ser Thr Lys Val Pro
            420                 425                 430 gct gcg tat gca gcc caa ggg tat aag gtg ctt gtc ctg aac ccg tcc    3145
Ala Ala Tyr Ala Ala Gln Gly Tyr Lys Val Leu Val Leu Asn Pro Ser
            435                 440                 445 gtc gcc gcc acc cta ggt ttc ggg gcg tat atg tct aag gca cat ggt    3193
Val Ala Ala Thr Leu Gly Phe Gly Ala Tyr Met Ser Lys Ala His Gly
        450                 455                 460 atc gac cct aac atc aga acc ggg gta agg acc atc acc acg ggt gcc    3241
Ile Asp Pro Asn Ile Arg Thr Gly Val Arg Thr Ile Thr Thr Gly Ala
465                 470                 475                 480 ccc atc acg tac tcc acc tat ggc aag ttt ctt gcc gac ggt ggt tgc    3289
Pro Ile Thr Tyr Ser Thr Tyr Gly Lys Phe Leu Ala Asp Gly Gly Cys
                485                 490                 495 tct ggg ggc gcc tat gac atc ata ata tgt gat gag tgc cac tca act    3337
Ser Gly Gly Ala Tyr Asp Ile Ile Ile Cys Asp Glu Cys His Ser Thr
                500                 505                 510 gac tcg acc act atc ctg ggc atc ggc aca gtc ctg gac caa gcg gag    3385
Asp Ser Thr Thr Ile Leu Gly Ile Gly Thr Val Leu Asp Gln Ala Glu
            515                 520                 525 acg gct gga gcg cga ctc gtg gtc ctc gcc acc gct acg cct ccg gga    3433
Thr Ala Gly Ala Arg Leu Val Val Leu Ala Thr Ala Thr Pro Pro Gly
            530                 535                 540 tcg gtc acc gtg cca cat cca aac atc gag gag gtg gct ctg tcc agc    3481
Ser Val Thr Val Pro His Pro Asn Ile Glu Glu Val Ala Leu Ser Ser
545                 550                 555                 560 act gga gaa atc ccc ttt tat ggc aaa gcc atc ccc atc gag acc atc    3529
Thr Gly Glu Ile Pro Phe Tyr Gly Lys Ala Ile Pro Ile Glu Thr Ile
                565                 570                 575 aag ggg ggg agg cac ctc att ttc tgc cat tcc aag aag aaa tgc gat    3577
Lys Gly Gly Arg His Leu Ile Phe Cys His Ser Lys Lys Lys Cys Asp
                580                 585                 590 gag ctc gcc gcg aag ctg tcc ggc ctc gga ctc aat gct gta gca tat    3625
Glu Leu Ala Ala Lys Leu Ser Gly Leu Gly Leu Asn Ala Val Ala Tyr
            595                 600                 605 tac cgg ggc ctt gat gta tcc gtc ata cca act agc gga gac gtc att    3673
Tyr Arg Gly Leu Asp Val Ser Val Ile Pro Thr Ser Gly Asp Val Ile
            610                 615                 620 gtc gta gca acg gac gct cta atg acg ggc ttt acc ggc gat ttc gac    3721
Val Val Ala Thr Asp Ala Leu Met Thr Gly Phe Thr Gly Asp Phe Asp
625                 630                 635                 640 tca gtg atc gac tgc aat aca tgt gtc acc cag aca gtc gac ttc agc    3769
Ser Val Ile Asp Cys Asn Thr Cys Val Thr Gln Thr Val Asp Phe Ser
                645                 650                 655 ctg gac ccg acc ttc acc att gag acg acg acc gtg cca caa gac gcg    3817
Leu Asp Pro Thr Phe Thr Ile Glu Thr Thr Thr Val Pro Gln Asp Ala
                660                 665                 670 gtg tca cgc tcg cag cgg cga ggc agg act ggt agg ggc agg atg ggc    3865
Val Ser Arg Ser Gln Arg Arg Gly Arg Thr Gly Arg Gly Arg Met Gly
            675                 680                 685 att tac agg ttt gtg act cca gga gaa cgg ccc tcg ggc atg ttc gat    3913
Ile Tyr Arg Phe Val Thr Pro Gly Glu Arg Pro Ser Gly Met Phe Asp
            690                 695                 700 tcc tcg gtt ctg tgc gag tgc tat gac gcg ggc tgt gct tgg tac gag    3961
Ser Ser Val Leu Cys Glu Cys Tyr Asp Ala Gly Cys Ala Trp Tyr Glu
705                 710                 715                 720
```

```
ctc acg ccc gcc gag acc tca gtt agg ttg cgg gct tac cta aac aca      4009
Leu Thr Pro Ala Glu Thr Ser Val Arg Leu Arg Ala Tyr Leu Asn Thr
            725                 730                 735 cca ggg ttg ccc gtc tgc cag gac cat ctg gag ttc tgg gag ggc gtc      4057
Pro Gly Leu Pro Val Cys Gln Asp His Leu Glu Phe Trp Glu Gly Val
    740                 745                 750 ttt aca ggc ctc acc cac ata gac gcc cat ttc ttg tcc cag act aag      4105
Phe Thr Gly Leu Thr His Ile Asp Ala His Phe Leu Ser Gln Thr Lys
            755                 760                 765 cag gca gga gac aac ttc ccc tac ctg gta gca tac cag gct acg gtg      4153
Gln Ala Gly Asp Asn Phe Pro Tyr Leu Val Ala Tyr Gln Ala Thr Val
    770                 775                 780 tgc gcc agg gct cag gct cca cct cca tcg tgg gac caa atg tgg aag      4201
Cys Ala Arg Ala Gln Ala Pro Pro Pro Ser Trp Asp Gln Met Trp Lys
785                 790                 795                 800 tgt ctc ata cgg cta aag cct acg ctg cac ggg cca acg ccc ctg ctg      4249
Cys Leu Ile Arg Leu Lys Pro Thr Leu His Gly Pro Thr Pro Leu Leu
            805                 810                 815 tat agg ctg gga gcc gtt caa aac gag gtt act acc aca cac ccc ata      4297
Tyr Arg Leu Gly Ala Val Gln Asn Glu Val Thr Thr Thr His Pro Ile
    820                 825                 830 acc aaa tac atc atg gca tgc atg tcg gct gac ctg gag gtc gtc acg      4345
Thr Lys Tyr Ile Met Ala Cys Met Ser Ala Asp Leu Glu Val Val Thr
            835                 840                 845 agc acc tgg gtg ctg gta ggc gga gtc cta gca gct ctg gct gcg tat      4393
Ser Thr Trp Val Leu Val Gly Gly Val Leu Ala Ala Leu Ala Ala Tyr
    850                 855                 860 tgc ctg aca aca ggc agc gtg gtc att gtg ggc agg atc atc ttg tcc      4441
Cys Leu Thr Thr Gly Ser Val Val Ile Val Gly Arg Ile Ile Leu Ser
865                 870                 875                 880 gga agg ccg gcc atc att ccc gac agg gaa gtc ctt tac cgg gag ttc      4489
Gly Arg Pro Ala Ile Ile Pro Asp Arg Glu Val Leu Tyr Arg Glu Phe
            885                 890                 895 gat gag atg gaa gag tgt gcc tca cac ctc cct tac atc gaa cag gga      4537
Asp Glu Met Glu Glu Cys Ala Ser His Leu Pro Tyr Ile Glu Gln Gly
    900                 905                 910 atg cag ctc gcc gaa caa ttc aaa cag aag gca atc ggg ttg ctg caa      4585
Met Gln Leu Ala Glu Gln Phe Lys Gln Lys Ala Ile Gly Leu Leu Gln
            915                 920                 925 aca gcc acc aag caa gcg gag gct gct gct ccc gtg gtg gaa tcc aag      4633
Thr Ala Thr Lys Gln Ala Glu Ala Ala Ala Pro Val Val Glu Ser Lys
    930                 935                 940 tgg cgg acc ctc gaa gcc ttc tgg gcg aag cat atg tgg aat ttc atc      4681
Trp Arg Thr Leu Glu Ala Phe Trp Ala Lys His Met Trp Asn Phe Ile
945                 950                 955                 960 agc ggg ata caa tat tta gca ggc ttg tcc act ctg cct ggc aac ccc      4729
Ser Gly Ile Gln Tyr Leu Ala Gly Leu Ser Thr Leu Pro Gly Asn Pro
            965                 970                 975 gcg ata gca tca ctg atg gca ttc aca gcc tct atc acc agc ccg ctc      4777
Ala Ile Ala Ser Leu Met Ala Phe Thr Ala Ser Ile Thr Ser Pro Leu
    980                 985                 990 acc acc caa cat acc ctc ctg ttt aac atc ctg ggg gga tgg gtg gcc      4825
Thr Thr Gln His Thr Leu Leu Phe Asn Ile Leu Gly Gly Trp Val Ala
            995                 1000                1005 gcc caa ctt gct cct ccc agc gct gct tcc gct ttc gta ggc gcc ggc      4873
Ala Gln Leu Ala Pro Pro Ser Ala Ala Ser Ala Phe Val Gly Ala Gly
    1010                1015                1020 atc gct gga gcg gct gtt ggc agc ata ggc ctt ggg aag gtg ctt gtg      4921
Ile Ala Gly Ala Ala Val Gly Ser Ile Gly Leu Gly Lys Val Leu Val
1025                1030                1035                1040
```

```
gat att ttg gca ggt tat gga gca ggg gtg gca ggc gcg ctc gtg gcc      4969
Asp Ile Leu Ala Gly Tyr Gly Ala Gly Val Ala Gly Ala Leu Val Ala
                1045                1050                1055 ttt aag gtc atg agc ggc gag atg ccc tcc acc gag gac ctg gtt aac      5017
Phe Lys Val Met Ser Gly Glu Met Pro Ser Thr Glu Asp Leu Val Asn
                1060                1065                1070 cta ctc cct gct atc ctc tcc cct ggc gcc cta gtc gtc ggg gtc gtg      5065
Leu Leu Pro Ala Ile Leu Ser Pro Gly Ala Leu Val Val Gly Val Val
                1075                1080                1085 tgc gca gcg ata ctg cgt cgg cac gtg ggc cca ggg gag ggg gct gtg      5113
Cys Ala Ala Ile Leu Arg Arg His Val Gly Pro Gly Glu Gly Ala Val
                1090                1095                1100 cag tgg atg aac cgg ctg ata gcg ttc gct tcg cgg ggt aac cac gtc      5161
Gln Trp Met Asn Arg Leu Ile Ala Phe Ala Ser Arg Gly Asn His Val
1105                1110                1115                1120 tcc ccc acg cac tat gtg cct gag agc gac gct gca gca cgt gtc act      5209
Ser Pro Thr His Tyr Val Pro Glu Ser Asp Ala Ala Ala Arg Val Thr
                1125                1130                1135 cag atc ctc tct agt ctt acc atc act cag ctg ctg aag agg ctt cac      5257
Gln Ile Leu Ser Ser Leu Thr Ile Thr Gln Leu Leu Lys Arg Leu His
                1140                1145                1150 cag tgg atc aac gag gac tgc tcc acg cca tgc tcc ggc tcg tgg cta      5305
Gln Trp Ile Asn Glu Asp Cys Ser Thr Pro Cys Ser Gly Ser Trp Leu
                1155                1160                1165 aga gat gtt tgg gat tgg ata tgc acg gtg ttg act gat ttc aag gcc      5353
Arg Asp Val Trp Asp Trp Ile Cys Thr Val Leu Thr Asp Phe Lys Ala
                1170                1175                1180 tgg ctc cag tcc aag ctc ctg ccg cga ttg ccg gga gtc ccc ttc ttc      5401
Trp Leu Gln Ser Lys Leu Leu Pro Arg Leu Pro Gly Val Pro Phe Phe
1185                1190                1195                1200 tca tgt caa cgt ggg tac aag gga gtc tgg cgg ggc gac ggc atc atg      5449
Ser Cys Gln Arg Gly Tyr Lys Gly Val Trp Arg Gly Asp Gly Ile Met
                1205                1210                1215 caa acc acc tgc cca tgt gga gca cag atc acc gga cat gtg aaa aac      5497
Gln Thr Thr Cys Pro Cys Gly Ala Gln Ile Thr Gly His Val Lys Asn
                1220                1225                1230 tgt tcc atg agg atc gtg ggg cct agg acc tgt agt aac acg tgg cat      5545
Cys Ser Met Arg Ile Val Gly Pro Arg Thr Cys Ser Asn Thr Trp His
                1235                1240                1245 gga aca ttc ccc att aac gcg tac acc acg ggc ccc tgc acg ccc tcc      5593
Gly Thr Phe Pro Ile Asn Ala Tyr Thr Thr Gly Pro Cys Thr Pro Ser
                1250                1255                1260 ccg gcg cca aat tat tct agg gcg ctg tgg cgg gtg gct gct gag gag      5641
Pro Ala Pro Asn Tyr Ser Arg Ala Leu Trp Arg Val Ala Ala Glu Glu
1265                1270                1275                1280 tac gtg gag gtt acg cga gtg ggg gat ttc cac tac gtg acg ggc atg      5689
Tyr Val Glu Val Thr Arg Val Gly Asp Phe His Tyr Val Thr Gly Met
                1285                1290                1295 acc act gac aac gta aag tgc ccg tgt cag gtt ccg gcc ccc gaa ttc      5737
Thr Thr Asp Asn Val Lys Cys Pro Cys Gln Val Pro Ala Pro Glu Phe
                1300                1305                1310 ttc aca gaa gtg gat ggg gtg cgg ttg cac agg tac gct cca gcg tgc      5785
Phe Thr Glu Val Asp Gly Val Arg Leu His Arg Tyr Ala Pro Ala Cys
                1315                1320                1325 aaa ccc ctc cta cgg gag gag gtc aca ttc ctg gtc ggg ctc aat caa      5833
Lys Pro Leu Leu Arg Glu Glu Val Thr Phe Leu Val Gly Leu Asn Gln
                1330                1335                1340 tac ccg gtt ggg tca cag ctc cca tgc gag ccc gaa ctg gac gta gca      5881
Tyr Pro Val Gly Ser Gln Leu Pro Cys Glu Pro Glu Leu Asp Val Ala
1345                1350                1355                1360
```

```
gtg ctc act tcc atg ctc acc gac ccc tcc cac att acg gcg gag acg      5929
Val Leu Thr Ser Met Leu Thr Asp Pro Ser His Ile Thr Ala Glu Thr
                1365                1370                1375 gct aag cgt agg ctg gcc agg gga tct ccc ccc tcc ttg gcc agc tca      5977
Ala Lys Arg Arg Leu Ala Arg Gly Ser Pro Pro Ser Leu Ala Ser Ser
                1380                1385                1390 tca gct agc cag ctg tct gcg cct tcc ttg aag gca aca tgc act acc      6025
Ser Ala Ser Gln Leu Ser Ala Pro Ser Leu Lys Ala Thr Cys Thr Thr
                1395                1400                1405 cgt cat gac tcc ccg gac gct gac ctc atc gag gcc aac ctc ctg tgg      6073
Arg His Asp Ser Pro Asp Ala Asp Leu Ile Glu Ala Asn Leu Leu Trp
                1410                1415                1420 cgg cag gag atg ggc ggg aac atc acc cgc gtg gag tca gag aat aag      6121
Arg Gln Glu Met Gly Gly Asn Ile Thr Arg Val Glu Ser Glu Asn Lys
1425                1430                1435                1440 gta gta att ttg gac tct ttc gag ccg ctc caa gcg gag gag gat gag      6169
Val Val Ile Leu Asp Ser Phe Glu Pro Leu Gln Ala Glu Glu Asp Glu
                1445                1450                1455 agg gaa gta tcc gtt ccg gcg gag atc ctg cgg agg tcc agg aaa ttc      6217
Arg Glu Val Ser Val Pro Ala Glu Ile Leu Arg Arg Ser Arg Lys Phe
                1460                1465                1470 cct cga gcg atg ccc ata tgg gca cgc ccg gat tac aac cct cca ctg      6265
Pro Arg Ala Met Pro Ile Trp Ala Arg Pro Asp Tyr Asn Pro Pro Leu
                1475                1480                1485 tta gag tcc tgg aag gac ccg gac tac gtc cct cca gtg gta cac ggg      6313
Leu Glu Ser Trp Lys Asp Pro Asp Tyr Val Pro Pro Val Val His Gly
                1490                1495                1500 tgt cca ttg ccg cct gcc aag gcc cct ccg ata cca cct cca cgg agg      6361
Cys Pro Leu Pro Pro Ala Lys Ala Pro Pro Ile Pro Pro Pro Arg Arg
1505                1510                1515                1520 aag agg acg gtt gtc ctg tca gaa tct acc gtg tct tct gcc ttg gcg      6409
Lys Arg Thr Val Val Leu Ser Glu Ser Thr Val Ser Ser Ala Leu Ala
                1525                1530                1535 gag ctc gcc aca aag acc ttc ggc agc tcc gaa tcg tcg gcc gtc gac      6457
Glu Leu Ala Thr Lys Thr Phe Gly Ser Ser Glu Ser Ser Ala Val Asp
                1540                1545                1550 agc ggc acg gca acg gcc tct cct gac cag ccc tcc gac gac ggc gac      6505
Ser Gly Thr Ala Thr Ala Ser Pro Asp Gln Pro Ser Asp Asp Gly Asp
                1555                1560                1565 gcg gga tcc gac gtt gag tcg tac tcc tcc atg ccc ccc ctt gag ggg      6553
Ala Gly Ser Asp Val Glu Ser Tyr Ser Ser Met Pro Pro Leu Glu Gly
                1570                1575                1580 gag ccg ggg gat ccc gat ctc agc gac ggg tct tgg tct acc gta agc      6601
Glu Pro Gly Asp Pro Asp Leu Ser Asp Gly Ser Trp Ser Thr Val Ser
1585                1590                1595                1600 gag gag gct agt gag gac gtc gtc tgc tgc tcg atg tcc tac aca tgg      6649
Glu Glu Ala Ser Glu Asp Val Val Cys Cys Ser Met Ser Tyr Thr Trp
                1605                1610                1615 aca ggc gcc ctg atc acg cca tgc gct gcg gag gaa acc aag ctg ccc      6697
Thr Gly Ala Leu Ile Thr Pro Cys Ala Ala Glu Glu Thr Lys Leu Pro
                1620                1625                1630 atc aat gca ctg agc aac tct ttg ctc cgt cac cac aac ttg gtc tat      6745
Ile Asn Ala Leu Ser Asn Ser Leu Leu Arg His His Asn Leu Val Tyr
                1635                1640                1645 gct aca aca tct cgc agc gca agc ctg cgg cag aag aag gtc acc ttt      6793
Ala Thr Thr Ser Arg Ser Ala Ser Leu Arg Gln Lys Lys Val Thr Phe
                1650                1655                1660 gac aga ctg cag gtc ctg gac gac cac tac cgg gac gtg ctc aag gag      6841
Asp Arg Leu Gln Val Leu Asp Asp His Tyr Arg Asp Val Leu Lys Glu
                1665                1670                1675                1680
```

```
atg aag gcg aag gcg tcc aca gtt aag gct aaa ctt cta tcc gtg gag    6889
Met Lys Ala Lys Ala Ser Thr Val Lys Ala Lys Leu Leu Ser Val Glu
            1685                1690                1695 gaa gcc tgt aag ctg acg ccc cca cat tcg gcc aga tct aaa ttt ggc    6937
Glu Ala Cys Lys Leu Thr Pro Pro His Ser Ala Arg Ser Lys Phe Gly
        1700                1705                1710 tat ggg gca aag gac gtc cgg aac cta tcc agc aag gcc gtt aac cac    6985
Tyr Gly Ala Lys Asp Val Arg Asn Leu Ser Ser Lys Ala Val Asn His
            1715                1720                1725 atc cgc tcc gtg tgg aag gac ttg ctg gaa gac act gag aca cca att    7033
Ile Arg Ser Val Trp Lys Asp Leu Leu Glu Asp Thr Glu Thr Pro Ile
        1730                1735                1740 gac acc acc atc atg gca aaa aat gag gtt ttc tgc gtc caa cca gag    7081
Asp Thr Thr Ile Met Ala Lys Asn Glu Val Phe Cys Val Gln Pro Glu
1745                1750                1755                1760 aag ggg ggc cgc aag cca gct cgc ctt atc gta ttc cca gat ttg ggg    7129
Lys Gly Gly Arg Lys Pro Ala Arg Leu Ile Val Phe Pro Asp Leu Gly
                1765                1770                1775 gtt cgt gtg tgc gag aaa atg gcc ctt tac gat gtg gtc tcc acc ctc    7177
Val Arg Val Cys Glu Lys Met Ala Leu Tyr Asp Val Val Ser Thr Leu
            1780                1785                1790 cct cag gcc gtg atg ggc tct tca tac gga ttc caa tac tct cct gga    7225
Pro Gln Ala Val Met Gly Ser Ser Tyr Gly Phe Gln Tyr Ser Pro Gly
        1795                1800                1805 cag cgg gtc gag ttc ctg gtg aat gcc tgg aaa gcg aag aaa tgc cct    7273
Gln Arg Val Glu Phe Leu Val Asn Ala Trp Lys Ala Lys Lys Cys Pro
    1810                1815                1820 atg ggc ttc gca tat gac acc cgc tgt ttt gac tca acg gtc act gag    7321
Met Gly Phe Ala Tyr Asp Thr Arg Cys Phe Asp Ser Thr Val Thr Glu
1825                1830                1835                1840 aat gac atc cgt gtt gag gag tca atc tac caa tgt tgt gac ttg gcc    7369
Asn Asp Ile Arg Val Glu Glu Ser Ile Tyr Gln Cys Cys Asp Leu Ala
                1845                1850                1855 ccc gaa gcc aga cag gcc ata agg tcg ctc aca gag cgg ctt tac atc    7417
Pro Glu Ala Arg Gln Ala Ile Arg Ser Leu Thr Glu Arg Leu Tyr Ile
            1860                1865                1870 ggg ggc ccc ctg act aat tct aaa ggg cag aac tgc ggc tat cgc cgg    7465
Gly Gly Pro Leu Thr Asn Ser Lys Gly Gln Asn Cys Gly Tyr Arg Arg
        1875                1880                1885 tgc cgc gcg agc ggt gta ctg acg acc agc tgc ggt aat acc ctc aca    7513
Cys Arg Ala Ser Gly Val Leu Thr Thr Ser Cys Gly Asn Thr Leu Thr
    1890                1895                1900 tgt tac ttg aag gcc gct gcg gcc tgt cga gct gcg aag ctc cag gac    7561
Cys Tyr Leu Lys Ala Ala Ala Ala Cys Arg Ala Ala Lys Leu Gln Asp
1905                1910                1915                1920 tgc acg atg ctc gta tgc gga gac gac ctt gtc gtt atc tgt gaa agc    7609
Cys Thr Met Leu Val Cys Gly Asp Asp Leu Val Val Ile Cys Glu Ser
                1925                1930                1935 gcg ggg acc caa gag gac gag gcg agc cta cgg gcc ttc acg gag gct    7657
Ala Gly Thr Gln Glu Asp Glu Ala Ser Leu Arg Ala Phe Thr Glu Ala
            1940                1945                1950 atg act aga tac tct gcc ccc cct ggg gac ccg ccc aaa cca gaa tac    7705
Met Thr Arg Tyr Ser Ala Pro Pro Gly Asp Pro Pro Lys Pro Glu Tyr
        1955                1960                1965 gac ttg gag ttg ata aca tca tgc tcc tcc aat gtg tca gtc gcg cac    7753
Asp Leu Glu Leu Ile Thr Ser Cys Ser Ser Asn Val Ser Val Ala His
    1970                1975                1980 gat gca tct ggc aaa agg gtg tac tat ctc acc cgt gac ccc acc acc    7801
Asp Ala Ser Gly Lys Arg Val Tyr Tyr Leu Thr Arg Asp Pro Thr Thr
1985                1990                1995                2000
```

| | | | | | | | | | | | | | | | | |
|---|---|---|---|---|---|---|---|---|---|---|---|---|---|---|---|---|
| ccc | ctt | gcg | cgg | gct | gcg | tgg | gag | aca | gct | aga | cac | act | cca | gtc | aat | 7849 |
| Pro | Leu | Ala | Arg | Ala | Ala | Trp | Glu | Thr | Ala | Arg | His | Thr | Pro | Val | Asn | |
| | | | | 2005 | | | | 2010 | | | | | 2015 | | | |
| tcc | tgg | cta | ggc | aac | atc | atc | atg | tat | gcg | ccc | acc | ttg | tgg | gca | agg | 7897 |
| Ser | Trp | Leu | Gly | Asn | Ile | Ile | Met | Tyr | Ala | Pro | Thr | Leu | Trp | Ala | Arg | |
| | | | 2020 | | | | | 2025 | | | | | 2030 | | | |
| atg | atc | ctg | atg | act | cat | ttc | ttc | tcc | atc | ctt | cta | gct | cag | gaa | caa | 7945 |
| Met | Ile | Leu | Met | Thr | His | Phe | Phe | Ser | Ile | Leu | Leu | Ala | Gln | Glu | Gln | |
| | | | | 2035 | | | | | 2040 | | | | 2045 | | | |
| ctt | gaa | aaa | gcc | cta | gat | tgt | cag | atc | tac | ggg | gcc | tgt | tac | tcc | att | 7993 |
| Leu | Glu | Lys | Ala | Leu | Asp | Cys | Gln | Ile | Tyr | Gly | Ala | Cys | Tyr | Ser | Ile | |
| | 2050 | | | | | 2055 | | | | 2060 | | | | | | |
| gag | cca | ctt | gac | cta | cct | cag | atc | att | caa | cga | ctc | cac | ggc | ctt | agc | 8041 |
| Glu | Pro | Leu | Asp | Leu | Pro | Gln | Ile | Ile | Gln | Arg | Leu | His | Gly | Leu | Ser | |
| 2065 | | | | 2070 | | | | | 2075 | | | | 2080 | | | |
| gca | ttt | tca | ctc | cat | agt | tac | tct | cca | ggt | gag | atc | aat | agg | gtg | gct | 8089 |
| Ala | Phe | Ser | Leu | His | Ser | Tyr | Ser | Pro | Gly | Glu | Ile | Asn | Arg | Val | Ala | |
| | | | | 2085 | | | | 2090 | | | | | 2095 | | | |
| tca | tgc | ctc | agg | aaa | ctt | ggg | gta | ccg | ccc | ttg | cga | gtc | tgg | aga | cat | 8137 |
| Ser | Cys | Leu | Arg | Lys | Leu | Gly | Val | Pro | Pro | Leu | Arg | Val | Trp | Arg | His | |
| | | | 2100 | | | | | 2105 | | | | | 2110 | | | |
| cgg | gcc | aga | agt | gtc | cgc | gct | agg | cta | ctg | tcc | cag | ggg | ggg | agg | gct | 8185 |
| Arg | Ala | Arg | Ser | Val | Arg | Ala | Arg | Leu | Leu | Ser | Gln | Gly | Gly | Arg | Ala | |
| | | | 2115 | | | | | 2120 | | | | | 2125 | | | |
| gcc | act | tgt | ggc | aag | tac | ctc | ttc | aac | tgg | gca | gta | agg | acc | aag | ctc | 8233 |
| Ala | Thr | Cys | Gly | Lys | Tyr | Leu | Phe | Asn | Trp | Ala | Val | Arg | Thr | Lys | Leu | |
| | | | 2130 | | | | | 2135 | | | | | 2140 | | | |
| aaa | ctc | act | cca | atc | ccg | gct | gcg | tcc | cag | ttg | gat | tta | tcc | agc | tgg | 8281 |
| Lys | Leu | Thr | Pro | Ile | Pro | Ala | Ala | Ser | Gln | Leu | Asp | Leu | Ser | Ser | Trp | |
| 2145 | | | | 2150 | | | | | 2155 | | | | 2160 | | | |
| ttc | gtt | gct | ggt | tac | agc | ggg | gga | gac | ata | tat | cac | agc | ctg | tct | cgt | 8329 |
| Phe | Val | Ala | Gly | Tyr | Ser | Gly | Gly | Asp | Ile | Tyr | His | Ser | Leu | Ser | Arg | |
| | | | | 2165 | | | | 2170 | | | | | 2175 | | | |
| gcc | cga | ccc | cgc | tgg | ttc | atg | tgg | tgc | cta | ctc | cta | ctt | tct | gta | ggg | 8377 |
| Ala | Arg | Pro | Arg | Trp | Phe | Met | Trp | Cys | Leu | Leu | Leu | Leu | Ser | Val | Gly | |
| | | | 2180 | | | | | 2185 | | | | | 2190 | | | |
| gta | ggc | atc | tat | cta | ctc | ccc | aac | cga | tga | acggggagct | | aaacactcca | | | | 8427 |
| Val | Gly | Ile | Tyr | Leu | Leu | Pro | Asn | Arg | | | | | | | | |
| | | | 2195 | | | | 2200 | | | | | | | | | |

| | | | | |
|---|---|---|---|---|
| ggccaatagg | ccatcctgtt | ttttccctt | tttttttc | tttttttt | 8487 |
| ttttttttt | ttttctcctt | tttttttcct | ctttttttcc | tttttcttcc | tttggtggct | 8547 |
| ccatcttagc | cctagtcacg | gctagctgtg | aaaggtccgt | gagccgcttg | actgcagaga | 8607 |
| gtgctgatac | tggcctctct | gcagatcaag | t | | | 8638 |

<210> SEQ ID NO 26
<211> LENGTH: 7
<212> TYPE: DNA
<213> ORGANISM: Hepatitis C virus

<400> SEQUENCE: 26 gccagcc                                                                    7

<210> SEQ ID NO 27
<211> LENGTH: 6
<212> TYPE: RNA
<213> ORGANISM: Hepatitis C virus

<400> SEQUENCE: 27 gccagc                                                                     6

```
<210> SEQ ID NO 28
<211> LENGTH: 14
<212> TYPE: DNA
<213> ORGANISM: Hepatitis C virus

<400> SEQUENCE: 28
cgcgcccaga tgtt                                                       14

<210> SEQ ID NO 29
<211> LENGTH: 6
<212> TYPE: DNA
<213> ORGANISM: E.coli

<400> SEQUENCE: 29 gaattc                                                                 6
```